US006962969B2

(12) United States Patent
Blaschuk et al.

(10) Patent No.: US 6,962,969 B2
(45) Date of Patent: Nov. 8, 2005

(54) COMPOUNDS AND METHODS FOR MODULATING NONCLASSICAL CADHERIN-MEDIATED FUNCTIONS

(75) Inventors: Orest W. Blaschuk, Westmount (CA); James Matthew Symonds, Ottawa (CA); Barbara J. Gour, Kemptville (CA)

(73) Assignee: Adherex Technologies, Inc., Ottawa (CA)

( * ) Notice: Subject to any disclaimer, the term of this patent is extended or adjusted under 35 U.S.C. 154(b) by 0 days.

(21) Appl. No.: 10/006,869

(22) Filed: Dec. 3, 2001

(65) Prior Publication Data

US 2003/0082166 A1 May 1, 2003

Related U.S. Application Data

(63) Continuation of application No. 09/187,859, filed on Nov. 6, 1998, now Pat. No. 6,358,920, which is a continuation-in-part of application No. 09/073,040, filed on May 5, 1998, now Pat. No. 6,472,367.

(51) Int. Cl.$^7$ .......................... A61K 38/12; G01N 33/53
(52) U.S. Cl. ........................................ 530/317; 435/7.1
(58) Field of Search ................................ 530/300, 317; 435/7.1

(56) References Cited

U.S. PATENT DOCUMENTS

| | | | |
|---|---|---|---|
| 5,585,351 A | 12/1996 | Ranscht | 514/12 |
| 5,597,725 A | 1/1997 | Suzuki | 435/328 |
| 5,610,281 A | 3/1997 | Brenner et al. | 530/388.85 |
| 5,639,634 A | 6/1997 | Suzuki | 435/69.1 |
| 5,643,781 A | 7/1997 | Suzuki | 435/325 |
| 5,646,250 A | 7/1997 | Suzuki | 530/350 |
| 5,663,300 A | 9/1997 | Suzuki | 530/350 |
| 5,708,143 A | 1/1998 | Suzuki | 530/350 |
| 5,811,514 A | 9/1998 | Bard et al. | 530/324 |
| 5,916,771 A | 6/1999 | Hori et al. | 435/69.6 |
| 6,031,072 A | 2/2000 | Blaschuk et al. | 530/317 |

FOREIGN PATENT DOCUMENTS

| | | |
|---|---|---|
| GB | 2282379 A | 4/1995 |
| WO | WO 91/04745 | 4/1991 |
| WO | WO 94/11401 | 5/1994 |
| WO | WO 96/27387 | 9/1996 |
| WO | WO 98/02452 | 1/1998 |
| WO | WO 98/25946 | 6/1998 |
| WO | WO 00/02917 | 1/2000 |

OTHER PUBLICATIONS

Cilnis et al. Genetic conservation of Highlands J viruses. Virology. 1996. vol. 218, pp. 343–351.*
Reobroek et al. Cloning and functional expression of Dfurin2, a subtilisin–like proprotein processing enzyme of Drosophila melanogaster with multiple repeats of a cysteine motif. J. Biol. Chem. Aug. 25, 1992. vol. 267, No. 24, pp. 17206–17215.*

Albelda et al., "Adhesion Molecules and Inflammatory Injury," *FASEB J.* 8(8):504–512, 1994.
Berndorff et al., "Liver–Intestine Cadherin: Molecular Cloning and Characterization of a Novel $Ca^{2+}$–dependent Cell Adhesion Molecule Expressed in Liver and Intestine," *The Journal of Cell Biology* 125(6): 1353–1369, 1994.
Blaschuk et al., "E–cadherin, estrogens, and cancer: is there a connection?," *The Canadian Journal of Oncology* 4(4): 291–301, 1994.
Busselmakers et al., "The role of OB–cadherin in human prostate cancer," *Proceedings of the American Association for Cancer Research*, vol. 39, New Orleans, LA, Mar., 1998, p. 500.
Edgington, "How Sweet It Is: Selectin–Mediating Drugs," *Bio/Technology* 10(4): 383–389, 1992.
Fredette and Ranscht, "T–Cadherin Expression Delineates Specific Regions of the Developing Motor Axon–Hindlimb Projection Pathway," *The Journal of Neuroscience* 14(12): 7331–7346, 1994.
Getsios et al., "Regulated Expression of Cadherin–6 and Cadherin–11 in the Glandular Epithelial and Stromal Cells of the Human Endometrium," *Developmental Dynamics* 211:238–247, 1998.
Grillner and Matsushima, "The Neural Network Underlying Locomotion in Lamprey—Synaptic and Cellular Mechanisms," *Neuron* 7:1–15, 1991.
Inoue et al., "Cadherin–6 in the Developing Mouse Brain: Expression Along Restricted Connection Systems and Synaptic Localization Suggest a Potential Role in Neuronal Circuitry," *Developmental Dynamics* 211:338–351, 1998.
Kahan, "Immunosuppressive Therapy," *Current Opinion in Immunology* 4(5): 553–560, 1992.
Kawamura et al., "cDNA Cloning and Expression of a Novel Human Desmocollin," *The Journal of Biological Chemistry* 269(42): 26295–26302, 1994.
King et al., "Cloning of the cDNA (DSC1) Coding for Human Type 1 Desmocollin and Its Assignment to Chromosome 18," *Genomics* 18: 185–194, 1993.
King et al., "The Desmocollins of Human Foreskin Epidermis: Identification and Chromosomal Assignment of a Third Gene and Expression Patterns of the Three Isoforms," *J. Invest. Dermatol.* 105:314–321, 1995.

(Continued)

*Primary Examiner*—Marjorie A. Moran
(74) *Attorney, Agent, or Firm*—Seed IP Law Group PLLC

(57) ABSTRACT

Modulating agents for inhibiting or enhancing nonclassical cadherin mediated cell adhesion are provided. The modulating agents comprise one or more of: (a) a peptide sequence that is at least 50% identical to a nonclassical cadherin CAR sequence; (b) a non-peptide mimetic of a nonclassical cadherin CAR sequence; (c) a substance, such as an antibody or antigen-binding fragment thereof, that specifically binds a nonclassical cadherin CAR sequence; and/or (d) a polynucleotide encoding a polypeptide that comprises a nonclassical cadherin CAR sequence or analogue thereof. Methods for using such modulating agents for modulating nonclassical cadherin-mediated cell adhesion in a variety of contexts are also provided.

14 Claims, 23 Drawing Sheets

OTHER PUBLICATIONS

Koch et al., "Complete amino acid sequence of the epidermal desmoglein precursor polypeptide and identification of a second type of desmoglein gene," *European Journal of Cell Biology 55:* 200–208, 1991.

Kohmura et al., "Diversity Revealed by a Novel Family of Cadherins Expressed in Neurons at a Synaptic Complex," *Neuron 20:*1137–1151, 1998.

Lutz et al., "Antibody Recognition of Peptide Sequences from the Cell–Cell Adhesion Proteins: N– and E–cadherins," *Peptide Research 9*(5): 233–239, 1996.

Matsuyoshi and Imamura, "Multiple Cadherins Are Expressed in Human Fibroblasts," *Biochemical And Biophysical Research Communications 235:* 355–358, 1997.

Munro et al., "Characterization of Cadherins Expressed by murine Thymocytes," *Cellular Immunology 169:* 309–312, 1996.

Munro and Blaschuk, *Cell Adhesion and Invasion in Cancer Metastasis,* P. Brodt (ed.), RG Landes Co., Austin, Texas, 1996, Chapter 3, "The Structure, Function, and Regulation of Cadherins," pp. 17–34.

Nakagawa and Takeichi, "Neural crest cell–cell adhesion controlled by sequential and subpopulation–specific expression of novel cadherins," *Development 121:* 1321–1332, 1995.

Navarro et al., "Differential Localization of VE– and N–Cadherins in Human Endothelial Cells: VE–Cadherin Competes with N–Cadherin for Junctional Localization," *The Journal of Cell Biology 140*(6): 1475–1484, 1998.

Okazaki et al., "Molecular Cloning and Characterization of OB–Cadherin, a New Member of Cadherin Family Expressed in Osteoblasts," *The Journal of Biological Chemistry 269*(16): 12092–12098, 1994.

Parker et al., "Desmosomal Glycoproteins II and III. Cadherin–Like Junctional Molecules Generated By Alternative Splicing," *The Journal of Biological Chemistry 266*(16): 10438–10445, 1991.

Ranscht and Bronner–Fraser, "T–cadherin expression alternates with migrating neural crest cells in the trunk of the avian embryo," *Development 111:* 15–22, 1991.

Ranscht and Dours–Zimmermann, "T–Cadherin, a Novel Cadherin Cell Adhesion Molecule in the Nervous System Lacks the Conserved Cytoplasmic Region," *Neuron 7:* 391–402, 1991.

Redies and Takeichi, "Cadherins in the Developing Central Nervous System: An Adhesive Code for Segmental and Functional Subdivisions," *Developmental Biology 180:* 413–423, 1996.

Sacristán et al., "T–Cadherin 2: Molecular Characterization, Function in Cell Adhesion, and Coexpression With T–Cadherin and N–Cadherin," *Journal of Neuroscience Research, 34:* 664–680, 1993.

Sano et al., "Protcadherins: a large family of cadherin–related molecules in central nervous system," *The EMBO Journal 12*(6): 2249–2256, 1993.

Shibata et al., "Identification of Human Cadherin–14, a Novel Neurally Specific Type II Cadherin, by Protein Interaction Cloning," *The Journal of Biological Chemistry 272*(8): 5236–5240, 1997.

Shibata et al., "Simultaneous expression of cadherin–11 in signet–ring cell carcinoma and stromal cells of diffuse–type gastric cancer," *Cancer Letters 99:* 147–153, 1996.

Shimazui et al., "Complex Cadherin Expression in the Renal Cell Carcinoma," *Cancer Research 56:*3234–3237, 1996.

Shimoyama et al., "Isolation and Sequence Analysis of Human Cadherin–6 Complementary DNA for the Full Coding Sequence and Its Expression in Human Carcinoma Cells," *Cancer Research 55:*2206–2211, 1995.

Shimoyama et al., "Molecular Cloning and Characterization of a Novel Human Classic Cadherin Homologous with Mouse Muscle Cadherin," *The Journal of Biological Chemistry 273*(16): 10011–10018, 1998.

Simmonneau et al., "Cadherin 11 Expression Marks the Mesenchymal Phenotype: Towards New Functions for Cadherins?," *Cell Adhesion and Communication 3:* 115–130, 1995.

Slootstra et al., "Structural Aspects of Antibody–Antigen Interaction Revealed Through Small Random Peptide Libraries," *Molecular Diversity I:* 87–96, 1995.

Sugimoto et al., "Molecular Cloning and Characterization of a Newly Identified Member of the Cadherin Family, PB–cadherin," *The Journal of Biological Chemistry 271*(19): 11548–11556, 1996.

Suzuki et al., "Diversity of the cadherin family: evidence for eight new cadherins in nervous tissue," *Cell Regulation 2:* 261–270, 1991.

Tanihara et al., "Cloning of Five Human Cadherins Clarifies Characteristic Features of Cadherin Extracellular Domain and Provides Further Evidence for Two Structurally Different Types of Cadherin," *Cell Adhesion and Communications 2:* 15–26, 1994.

Tkachuk et al., "Identification of an atypical lipoprotein–binding protein from human aortic smooth muscle as T–cadherin," *FEBS Letters 421:* 208–212, 1998.

Vestal and Ranscht, "Glycosyl Phosphatidylinositol–anchored T–Cadherin Mediates Calcium–dependent, Homophilic Cell Adhesion," *The Journal of Cell Biology 119*(2): 451–461, 1992.

Ward and Mulligan, "Blocking of Adhesion Molecules In Vivo as Anti–Inflammatory Therapy," *Therapeutic Immunology 1:* 165–171, 1994.

Wheeler et al., "Desmosomal glycoprotein DGI, a component of intercellular desmosome junctions, is related to the cadherin family of cell adhesion molecules," *Proc. Natl. Acad. Sci. USA 88:* 4796–4800, 1991.

* cited by examiner

Human G W V W N Q F F V I E E Y T G P D P V L V G R L H S D I D S G D G N I K Y I L S G E G A G
Mouse G W V W N Q F F V I E E Y T G P D P V L V G R L H S D I D S G D G N I K Y I L S G E G A G Human T I F V I D D K S G N I H A T K T L D R E E R A Q Y T L M A Q A V D R D T N R P L E P P S
Mouse T I F V I D D K S G N I H A T K T L D R E E R A Q Y T L M A Q A V D R D T N R P L E P P S Human E F I V K V Q D I N D N P P E F
Mouse E F I V K V Q D I N D N P P E F

*Fig. 3*

N-Ac-CIFVIDDKSGC-NH$_2$

N-Ac-IFVIDDKSG-NH$_2$

N-Ac-<u>CDDKC</u>-NH$_2$

N-Ac-<u>CDDKSC</u>-NH$_2$

N-Ac-<u>CIDDKC</u>-NH$_2$

N-Ac-<u>CIDDKSC</u>-NH$_2$

N-Ac-<u>CIDDKSGC</u>-NH$_2$

N-Ac-<u>CVIDDKSGC</u>-NH$_2$

Control

Control

H-VFRVDAETGD-OH

H-VFRVDAETGD-OH

N-Ac-VFRVDAETGD-NH$_2$

N-Ac-VFRVDAETGD-NH$_2$

N-Ac-CDADC-NH₂

N-Ac-CDAEC-NH₂

N-Ac-CDANC-NH₂

N-Ac-CNRNC-NH₂

N-Ac-CDDTC-NH₂

N-Ac-CDEKC-NH₂

N-Ac-<u>CDELC</u>-NH$_2$

N-Ac-<u>CDENC</u>-NH$_2$

N-Ac-<u>CDETC</u>-NH$_2$

N-Ac-<u>CDKFC</u>-NH$_2$

N-Ac-<u>CDLVC</u>-NH$_2$

N-Ac-<u>CDPKC</u>-NH$_2$

N-Ac-CDPSC-NH$_2$

N-Ac-CDPVC-NH$_2$

N-Ac-CDSGC-NH$_2$

N-Ac-CDSNC-NH$_2$

N-Ac-CDSSC-NH$_2$

N-Ac-CDSVC-NH$_2$

N-Ac-CEAQC-NH$_2$

N-Ac-CEEFC-NH$_2$

N-Ac-CEEYC-NH$_2$

N-Ac-CEKDC-NH$_2$

N-Ac-CEPKC-NH$_2$

N-Ac-CERDC-NH$_2$

N-Ac-CESEC-NH₂

N-Ac-CNDVC-NH₂

N-Ac-CNEKC-NH₂

N-Ac-CNENC-NH₂

N-Ac-CNKDC-NH₂

N-Ac-CNNKC-NH₂

COMPOUNDS AND METHODS FOR MODULATING NONCLASSICAL CADHERIN-MEDIATED FUNCTIONS

CROSS-REFERENCE TO RELATED APPLICATION

This application is a continuation of U.S. patent application Ser. No. 09/187,859, filed Nov. 6, 1998, now issued as U.S. Pat. No. 6,358,920, which is a continuation-in-part of U.S. patent application Ser. No. 09/073,040, filed May 5, 1998, now U.S. Pat. No. 6,472,367.

TECHNICAL FIELD

The present invention relates generally to methods for modulating nonclassical cadherin-mediated functions, and more particularly to the use of modulating agents derived from nonclassical cadherin cell adhesion recognition sequences for inhibiting or enhancing functions mediated by nonclassical cadherins.

BACKGROUND OF THE INVENTION

Cadherins are a rapidly expanding superfamily of calcium-dependent cell adhesion molecules (CAMs) (for review, see Munro et al., In: Cell Adhesion and Invasion in Cancer Metastasis, P. Brodt, ed., pp. 17–34, RG Landes Co., Austin Tex., 1996). All cadherins appear to be membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity.

There are many different types of cadherins. The most extensively studied group of cadherins is known as the classical, or type I, cadherins. Classical cadherins have been shown to regulate epithelial, endothelial, neural and cancer cell adhesion, with different cadherins expressed on different cell types. All classical cadherins have a similar structure. As illustrated in FIG. 1A, classical cadherins are composed of five extracellular domains (EC1–EC5), a single hydrophobic domain (TM) that transverses the plasma membrane (PM), and two cytoplasmic domains (CP1 and CP2). The calcium binding motifs DXNDN (SEQ ID NO:1), DXD and LDRE (SEQ ID NO:2) are interspersed throughout the extracellular domains, and each 110 amino acid region that contains such motifs is considered a cadherin repeat The first extracellular domain (EC1) contains the cell adhesion recognition (CAR) sequence, HAV (His-Ala-Val), along with flanking sequences on either side of the CAR sequence that play a role in conferring specificity. Synthetic peptides containing the HAV sequence and antibodies directed against such peptides have been shown to inhibit classical cadherin-dependent processes (Munro et al., supra; Blaschuk et al., J. Mol. Biol. 211:679–82, 1990; Blaschuk et al., Develop. Biol. 139:227–29, 1990; Alexander et al., J. Cell. Physiol. 156:610–18, 1993).

Cadherins that contain calcium binding motifs within extracellular domain cadherin repeats, but do not contain an HAV CAR sequence, are considered to be nonclassical cadherins (illustrated in FIGS. 1B to 1AA). To date, nine groups of nonclassical cadherins have been identified (types II–X). These cadherins are also membrane glycoproteins. Type II, or atypical, cadherins include OB-cadherin (cadherin-11; see Getsios et al., Developmental Dynamics 211:238–247, 1998; Simonneau et al., Cell Adhesion and Communication 3:115–130, 1995; Okazaki et al., J. Biological Chemistry 269:12092–12098, 1994), cadherin-5 (VE-cadherin; see Navarro et al., J. Cell Biology 140:1475–1484, 1998), cadherin-6 (K-cadherin; see Shimoyama et al., Cancer Research 55:2206–2211, 1995; Shimazui et al., Cancer Research 56:3234–3237, 1996; Inoue et al., Developmental Dynamics 211:338–351, 1998; Getsios et al., Developmental Dynamics 211:238–247, 1998), cadherin-7 (see Nakagawa et al., Development 121:1321–1332, 1995), cadherin-8 (see Suzuki et al., Cell Regulation 2:261–270, 1991), cadherin-12 (Br-cadherin; see Tanihara et al., Cell Adhesion and Communication 2:15–26, 1994), cadherin-14 (see Shibata et al., J. Biological Chemistry 272:5236–5240, 1997), cadherin-15 (M-cadherin; see Shimoyama et al., J. Biological Chemistry 273:10011–10018, 1998), and PB-cadherin (see Sugimoto et al., J. Biological Chemistry 271:11548–11556, 1996). For a general review of atypical cadherins, see Redies and Takeichi, Developmental Biology 180:413–423, 1996 and Suzuki et al., Cell Regulation 2:261–270, 1991.

Types III–X include LI-cadherin (type III; see Berndorff et al., J. Cell Biology 125:1353–1369, 1994). T-cadherin (type IV; see Ranscht, U.S. Pat. No. 5,585,351; Tkachuk et al., FEBS Lett. 421:208–212, 1998; Ranscht et al., Neuron 7:391–402, 1991; Sacristan et al., J. Neuroscience Research 34:664–680, 1993; Vestal and Ranscht, J. Cell Biology 119:451–461, 1992; Fredette and Ranscht, J. Neuroscience 14:7331–7346, 1994; Ranscht and Bronner-Fraser, Development 111:15–22, 1991), protocadherins (type V; e.g., protocadherins 42, 43 and 68; see Sano et al., EMBO J. 12:2249–2256, 1993; GenBank Accession Number AF029343), desmocollins (type VI; e.g., desmocollins 1, 2, 3 and 4; see King et al., Genomics 18:185–194, 1993; Parker et al., J. Biol. Chem. 266:10438–10445, 1991; King et al., J. Invest. Dermatol. 105:314–321, 1995; Kawamura et al., J. Biol. Chem. 269:26295–26302, 1994), desmogleins (type VII; e.g., desmogleins 1 and 2; see Wheeler et al., Proc. Natl. Acad. Sci. USA 88:4796–4800; Koch et al., Eur. J. Cell. Biol. 55:200–208, 1991), and cadherin-related neuronal receptors (type X; see Kohmura et al., Neuron 20:1137–1151, 1998).

Most studies of nonclassical cadherins have focused on atypical or type II cadherins. The structure of these cadherins is similar to that of the type I cadherins, but they do not contain the CAR sequence, HAV (FIG. 1B). Furthermore, functions mediated by the atypical cadherins may be diverse. OB-cadherin, which is also known as cadherin-11, is an atypical cadherin (Getsios et al., Developmental Dynamics 211:238–247, 1998; Okazaki et al., J. Biol. Chem. 269:12092–98, 1994; Suzuki et al., Cell Regulation 2:261–70, 1991; Munro et al., supra). This cadherin can promote cell adhesion through homophilic interactions. Recent studies have shown that OB-cadherin is not expressed by well-differentiated, poorly invasive cancer cells, whereas it is expressed by invasive cancer cells (et al., Cancer Res. 56:3234–37, 1996; Shibata et al., Cancer Letters 99:147–53, 1996). OB-cadherin levels are also high in stromal cells and osteoblasts (Shibata et al., Cancer Letters 99:147–53, 1996; Simonneau et al., Cell Adhes. Commun. 3:115–30, 1995; Matsuyoshi and Imamura, Biochem. Biophys. Res. Commun. 23:355–58, 1997; Okazaki et al., J. Biol. Chem. 269:12092–98, 1994). Collectively, these observations have led to the hypothesis that OB-cadherin may mediate the interaction between malignant tumor cells and other cell types, such as stromal cells and osteoblasts, thus facilitating tumor cell invasion and metastasis.

OB-cadherin is expressed in certain specific cell types. In some invasive cancer cells, OB-cadherin is not only found at sites of cell-cell contact, but also in lamellopodia-like projections which do not interact with other cells. These observations suggest that OB-cadherin may also play a role in modulating cell-substrate interactions. In adipocytes, OB-cadherin is the only known expressed cadherin. OB-cadherin is therefore likely to mediate adhesion between adipocytes, and it is likely to be an important regulator of adipogenesis. Another cell type that expresses OB-cadherin is the pericyte (also known as the peri-endothelial cell). Pericytes are contractile cells which are similar to smooth muscle cells. They encircle the endothelial cells of blood vessels. Pericytes are involved in maintaining the structural integrity of blood vessels (Hanahan, Science 277:48–50, 1997; Lindahl et al., Science 277:242–245, 1997). Loss of pericytes causes blood vessels to regress.

Other atypical cadherins appear to have different functions. For example, cadherin-5 (also referred to as VE-cadherin) appears to be involved in endothelial cell adhesion and cadherin-6 (also referred to as K-cadherin) may be involved in embryonic kidney cell adhesion and is up-regulated in kidney cancer. Cadherin-15 also appears to play a role in the terminal differentiation of muscle cells.

Notwithstanding these recent advances, nonclassical cadherin function remains poorly understood at the biological and molecular levels. Accordingly, there is a need in the art for identifying sequences involved in modulating nonclassical cadherin-dependent functions, such as cell adhesion, and for the development of methods employing such sequences to inhibit processes such as cancer cell adhesion, invasion and metastasis. The present invention fulfills these needs and further provides other related advantages.

SUMMARY OF THE INVENTION

Briefly stated, this invention provides compositions and methods for modulating nonclassical cadherin-mediated functions, such as cancer cell adhesion, invasion, and metastasis. Within certain aspects, modulating agents capable of modulating (i.e., inhibiting or enhancing) one or more functions mediated by a nonclassical cadherin are provided. Such modulating agents generally: (a) comprise a peptide sequence that is at least 50% identical to a nonclassical cadherin CAR sequence; (b) modulate a function mediated by the nonclassical cadherin, such that the modulating agent: (i) detectably inhibits a function that is modulated by the nonclassical cadherin; or (ii) detectably enhances adhesion of cells that express the nonclassical cadherin; and (c) contain no more than 85, and preferably no more than 50, consecutive amino acid residues present within the nonclassical cadherin. Certain modulating agents comprise a nonclassical cadherin CAR sequence and are 3–16 amino acid residues in length.

For certain modulating agents as provided above, the nonclassical cadherin CAR sequence has the formula:

Aaa-Phe-Baa-Ile/Leu/Val-Asp/Asn/Glu-Caa-Daa-
Ser/Thr/Asn-Gly (SEQ ID NO:3)

wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine or asparagine. For other modulating agents as described above, the nonclassical cadherin CAR sequence consists of at least three consecutive amino acid residues, and preferably at least five consecutive amino acid residues, of a nonclassical cadherin, wherein the consecutive amino acids are present within a region of the nonclassical cadherin having the formula recited above. Other modulating agents may comprise at least nine consecutive amino acid residues of a nonclassical cadherin, wherein the nine consecutive amino acid residues comprise a region having a formula as recited above.

Within certain specific embodiments, a modulating agent as described above is a peptide ranging in size from 3 to 50, preferably from 4 to 16, amino acid residues.

Within other embodiments, a modulating agent comprises a nonclassical cadherin CAR sequence that is present within a cyclic peptide. Such cyclic peptides may have the formula:

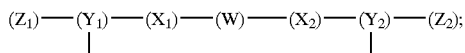

wherein W is a tripeptide selected from the group consisting of EEY, DDK, EAQ, DAE, NEN, ESE, DSG, DEN, EPK, DAN, EEF, NDV, DET, DPK, DDT, DAN, DKF, DEL, DAD, NNK, DLV, NRD, DPS, NQK, NRN, NKD, EKD, ERD, DPV, DSV, DLY, DSN, DSS, DEK and NEK; wherein $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; wherein $Y_1$ and $Y_2$ are independently selected from the group consisting of amino acid residues, and wherein a covalent bond is formed between residues $Y_1$ and $Y_2$; and wherein $Z_1$ and $Z_2$ are optional, and if present, are independently selected from the group consisting of amino acid residues and combinations thereof in which the residues are linked by peptide bonds.

Within other aspects of the present invention, polynucleotides encoding a modulating agent as described above are provided, along with expression vectors comprising such a polynucleotide and host cells transformed or transfected with such an expression vector.

The present invention further provides modulating agents that comprise an antibody or antigen-binding fragment thereof that specifically binds to a nonclassical cadherin CAR sequence and modulates a nonclassical cadherin-mediated function, wherein the nonclassical cadherin CAR sequence has the formula:

Aaa-Phe-Baa-Ile/Leu/Val-Asp/Asn/Glu-Caa-Daa-
Ser/Thr/Asn-Gly (SEQ ID NO:3)

wherein Aaa, Baa, Caa and Daa are independently selected amino acid residues; Ile/Leu/Val is an amino acid that is selected from the group consisting of isoleucine, leucine and valine, Asp/Asn/Glu is an amino acid that is selected from the group consisting of aspartate, asparagine and glutamate; and Ser/Thr/Asn is an amino acid that is selected from the group consisting of serine, threonine and asparagine; and wherein the modulating agent inhibits or enhances a function mediated by the nonclassical cadherin. Within specific embodiments, the nonclassical cadherin CAR sequence may be any of the sequences recited below.

Within further aspects, the present invention provides modulating agents comprising a non-peptide mimetic of any one of the nonclassical cadherin CAR sequences provided above.

Within certain specific embodiments, a modulating agent as provided herein may comprise: (a) one or more OB-cadherin CAR sequences selected from the group consisting of DDK, IDDK (SEQ ID NO:4051) DDKS (SEQ ID NO:73), VIDDK (SEQ ID NO:74), IDDKS (SEQ ID NO:75), VIDDKS (SEQ ID NO:76), DDKSG (SEQ ID NO:77), IDDKSG (SEQ ID NO:78), VIDDKSG (SEQ ID NO:79), FVIDDK (SEQ ID NO:80), FVIDDKS (SEQ ID NO:81), FVIDDKSG (SEQ ID NO:82), IFVIDDK (SEQ ID NO:83), IFVIDDKS (SEQ ID NO:84), IFVIDDKSG (SEQ ID NO:85), EEY, IEEY (SEQ ID NO:86), EEYT (SEQ ID NO:87), VIEEY (SEQ ID NO:88), IEEYT (SEQ ID NO:89), VIEEYT (SEQ ID NO:90), EEYTG (SEQ ID NO:91), IEEYTG (SEQ ID NO:92), VIEEYTG (SEQ ID NO:93), FVIEEY (SEQ ID NO:94), FVIEEYT (SEQ ID NO:95), FVIEEYTG (SEQ ID NO:96), FFVIEEY (SEQ ID NO:97), FFVIEEYT (SEQ ID NO:98), FFVIEEYTG (SEQ ID NO:99), EAQ, VEAQ (SEQ ID NO:100), EAQT (SEQ ID NO:101), SVEAQ (SEQ ID NO:102), VEAQT (SEQ ID NO:103), SVEAQT (SEQ ID NO:104), EAQTG (SEQ ID NO:105), VEAQTG (SEQ ID NO:106), SVEAQTG (SEQ ID NO:107), FSVEAQ (SEQ ID NO:108), FSVEAQT (SEQ ID NO:109), FSVEAQTG (SEQ ID NO:110), YFSVEAQ (SEQ ID NO:111), YFSVEAQT (SEQ ID NO:112) and YFSVEAQTG (SEQ ID NO:113); or (b) an analogue of any of the foregoing sequences that differs in one or more substitutions, deletions, additions and/or insertions such that that ability of the analogue to modulate an OB-cadherin-mediated function is not substantially diminished. For example, the agent may comprise a linear peptide having the sequence N-Ac-IFVIDDKSG-NH$_2$ (SEQ ID NO:85), N-Ac-FFVIEEYTG-NH$_2$ (SEQ ID NO:99) or N-Ac-YFSVEAQTG-NH$_2$ (SEQ ID NO:113). The OB-cadherin CAR sequence may, but need not, be present within a cyclic peptide.

Within certain specific embodiments, a modulating agent as provided herein may comprise: (a) one or more cadherin-5 CAR sequences selected from the group consisting of DAE, VDAE (SEQ ID NO:114), DAET (SEQ ID NO:115), RVDAE (SEQ ID NO:116), VDAET (SEQ ID NO:117), RVDAET (SEQ ID NO:118), DAETG (SEQ ID NO:119), VDAETG (SEQ ID NO:120), RVDAETG (SEQ ID NO:121), FRVDAE (SEQ ID NO:122), FRVDAET (SEQ ID NO:123), FRVDAETG (SEQ ID NO:124), VFRVDAE (SEQ ID NO:125), VFRVDAET (SEQ ID NO:126) and VFRVDAETG (SEQ ID NO:127); or (b) an analogue of any of the foregoing sequences that differs in one or more substitutions, deletions, additions and/or insertions such that that ability of the analogue to modulate a cadherin-5-mediated function is not substantially diminished. For example, the agent may comprise a linear peptide having the sequence N-Ac-VFRVDAETG-NH$_2$ (SEQ ID NO:127). The cadherin-5 CAR sequence may, but need not, be present within a cyclic peptide.

Within certain specific embodiments, a modulating agent as provided herein may comprise: (a) one or more cadherin-6 CAR sequences selected from the group consisting of NEN, INEN (SEQ ID NO128), NENT (SEQ ID NO:129), IINEN (SEQ ID NO:130), INENT (SEQ ID NO:131), IINENT (SEQ ID NO:132), NENTG (SEQ ID NO:133), INENTG (SEQ ID NO:134), IINENTG (SEQ ID NO:135), FIINEN (SEQ ID NO:136), FIINENT (SEQ ID NO:137), FIINENTG (SEQ ID NO:138), LFIINEN (SEQ ID NO:139), LFIINENT (SEQ ID NO:140), LFIINENTG (SEQ ID NO:141), EEY, EEYT (SEQ ID NO:142) EEYTG (SEQ ID NO:143), LEEY (SEQ ID NO:144), LEEYT (SEQ ID NO:145), LEEYTG (SEQ ID NO:146), LLEEY (SEQ ID NO:147), LLEEYTG (SEQ ID NO:148), FLLEEY (SEQ ID NO:149), FLLEEYT (SEQ ID NO:150), FLLEEYTG (SEQ ID NO:151), FFLLEEY (SEQ ID NO:152), FFLLEEYT (SEQ ID NO:153), FFLLEEYTG (SEQ ID NO:154), ESE, ESET (SEQ ID NO:155), ESETG (SEQ ID NO:156), VESE (SEQ ID NO:157), VSEST (SEQ ID NO:158), VESETG (SEQ ID NO:159), SVESE (SEQ ID NO:160), SVESET (SEQ ID NO:161), SVESETG (SEQ ID NO:162), FSVESE (SEQ ID NO:163), FSVESET (SEQ ID NO:164), FSVESETG (SEQ ID NO:165), YFSVESE (SEQ ID NO:166), YFSVESET (SEQ ID NO:167), YFSVESETG (SEQ ID NO:168), DSG, DSGN (SEQ ID NO:169), DSGNG (SEQ ID NO:170), IDSG (SEQ ID NO:171), IDSGN (SEQ ID NO:172), IDSGNG (SEQ ID NO:173), NIDSG (SEQ ID NO:174), NIDSGN (SEQ ID NO:175), NIDSGNG (SEQ ID NO:176), FNIDSG (SEQ ID NO:177), FNIDSGN (SEQ ID NO:178), FNIDSGNG (SEQ ID NO:179), IFNIDSG (SEQ ID NO:180), IFNIDSGN (SEQ ID NO:181) and IFNIDSGNG (SEQ ID NO:182); or (b) an analogue of any of the foregoing sequences that differs in one or more substitutions, deletions, additions and/or insertions such that that ability of the analogue to modulate a cadherin-6-mediated function is not substantially diminished. For example, the agent may comprise a linear peptide having the sequence N-Ac-FFLLEEYTG-NH$_2$ (SEQ ID NO:154), N-Ac-LFIINENTG-NH$_2$ (SEQ ID NO:141), N-Ac-YFSVESETG-NH$_2$ (SEQ ID NO:168) or N-Ac-IFNIDSGNG-NH$_2$ (SEQ ID NO:187). The cadherin-6 CAR sequence may, but need not, be present within a cyclic peptide.

Within certain specific embodiments, a modulating agent as provided herein may comprise: (a) one or more cadherin-7 CAR sequences selected from the group consisting of DEN, IDEN (SEQ ID NO:183), DENT (SEQ ID NO:184), IIDEN (SEQ ID NO:185), IDENT (SEQ ID NO:186), IIDENT (SEQ ID NO:187), DENTG (SEQ ID NO:188), IDENTG (SEQ ID NO:189), IIDENTG (SEQ ID NO:190), FIIDEN (SEQ ID NO:191), FIIDENT (SEQ ID NO:192), FIIDENTG (SEQ ID NO:193), IFIIDEN (SEQ ID NO:194), IFIIDENT (SEQ ID NO:195), IFIIDENTG (SEQ ID NO:196), EPK, EPKT (SEQ ID NO:197), EPKTG (SEQ ID NO:198), VEPK (SEQ ID NO:199), VEPKT (SEQ ID NO:200), VEPKTG (SEQ ID NO:201), SVEPK (SEQ ID NO:202), SVEPKT (SEQ ID NO:203), SVEPKTG (SEQ ID NO:204), FSVEPK (SEQ ID NO:205) FSVEPKT (SEQ ID NO:206), FSVEPKTG (SEQ ID NO:207), YFSVEPK (SEQ ID NO:208), YFSVEPKT (SEQ ID NO:209), YFSVEPKTG (SEQ ID NO:210), DAN, DANS (SEQ ID NO:211), DANSG (SEQ ID NO:212), IDAN (SEQ ID NO:213), IDANS (SEQ ID NO:214), IDANSG (SEQ ID NO:215), NIDAN (SEQ ID NO:216), NIDANS (SEQ ID NO:217), NIDANSG (SEQ ID NO:218), FNIDAN (SEQ ID NO:219), FNIDANS (SEQ ID NO:220), FNIDANSG (SEQ ID NO:221), YFNIDAN (SEQ ID NO:222), YFNIDANS (SEQ ID NO:223) and YFNIDANSG (SEQ ID NO:224); or (b) an analogue of any of the foregoing sequences that differs in one or more substitutions, deletions, additions and/or insertions such that that ability of the analogue to modulate a cadherin-7-mediated function is not substantially diminished. For example, the agent may comprise a linear peptide having the sequence N-Ac-IFIIDENTG-NH$_2$ (SEQ ID NO:196), N-Ac-YFSVEPKTG-NH$_2$ (SEQ ID NO:210) or N-Ac-YFNIDANSG-NH$_2$ (SEQ ID NO:224). The cadherin-7 CAR sequence may, but need not, be present within a cyclic peptide.

Within certain specific embodiments, a modulating agent as provided herein may comprise: (a) one or more cadherin-8 CAR sequences selected from the group consisting of NDV, INDV (SEQ ID NO:225), NDVT (SEQ ID NO:226), QINDV (SEQ ID NO:227), INDVT (SEQ ID NO:228), QINDVT (SEQ ID NO:229), NDVTG (SEQ ID NO:230), INDVTG (SEQ ID NO:231), QINDVTG (SEQ ID NO:232), FQINDV (SEQ ID NO:233), FQINDVT (SEQ ID NO:234), FQINDVTG (SEQ ID NO:235), IFQINDV (SEQ ID NO:236), IFQINDVT (SEQ ID NO:237), IFQINDVTG (SEQ ID NO:238), EEF, EFS (SEQ ID NO:239), EEFSG (SEQ ID NO:240), LEEF (SEQ ID NO:241), LEEFS (SEQ ID NO:242), LEEFSG (SEQ ID NO:240), VLEEF (SEQ ID NO:244), VLEEFS (SEQ ID NO:245), VLEEFSG (SEQ ID NO:247), FVLEEF (SEQ ID NO:247), FVLEEFS (SEQ ID NO:248), FVLEEFSG (SEQ ID NO:249), MFVLEEF (SEQ ID NO:250), MFVLEEFS (SEQ ID NO:251) and MFVLEEFSG (SEQ ID NO:252): or (b) an analogue of any of the foregoing sequences that differs in one or more substitutions, deletions, additions and/or insertions such that that ability of the analogue to modulate a cadherin-8-mediated function is not substantially diminished. For example, the agent may comprise a linear peptide having the sequence N-Ac-MFVLEEFSG-NH$_2$ (SEQ ID NO:252) or N-Ac-IFQINDVTG-NH$_2$ (SEQ ID NO:238). The cadherin-8 CAR sequence may, but need not, be present within a cyclic peptide.

Within certain specific embodiments, a modulating agent as provided herein may comprise: (a) one or more cadherin-12 CAR sequences selected from the group consisting of DET, IDET (SEQ ID NO:253), DETT (SEQ ID NO:254), TIDET (SEQ ID NO:255), IDETT (SEQ ID NO:256), TIDETT (SEQ ID NO:257), DETTG (SEQ ID NO:258), IDETTG (SEQ ID NO:259), TIDETTG (SEQ ID NO:260), FTIDET (SEQ ID NO:261), FTIDETT (SEQ ID NO:262), FTIDETTG (SEQ ID NO:263), VFTIDET (SEQ ID NO:264), VFTIDETT (SEQ ID NO:265), VFTIDETTG (SEQ ID NO:266), DPK, DPKT (SEQ ID NO:267), DPKTG (SEQ ID NO:268), IDPK (SEQ ID NO:269), IDPKT (SEQ ID NO:270), IDPKTG (SEQ ID NO:271), SIDPK (SEQ ID NO:272), SIDPKT (SEQ ID NO:273), SIDPKTG (SEQ ID NO:274), FSIDPK (SEQ ID NO:275), FSIDPKT (SEQ ID NO:276), FSIDPKTG (SEQ ID NO:277), YFSIDPK (SEQ ID NO:278), YFSIDPKT (SEQ ID NO:279) and YFSIDPKTG (SEQ ID NO:280); or (b) an analogue of any of the foregoing sequences that differs in one or more substitutions, deletions, additions and/or insertions such that that ability of the analogue to modulate a cadherin-12-mediated function is not substantially diminished. For example, the agent may comprise a linear peptide having the sequence N-Ac-VFTIDETTG-NH$_2$ (SEQ ID NO:266) or N-Ac-YFSIDPKTG-NH$_2$ (SEQ ID NO:280). The cadherin-12 CAR sequence may, but need not, be present within a cyclic peptide.

Within certain specific embodiments, a modulating agent as provided herein may comprise: (a) one or more cadherin-14 CAR sequences selected from the group consisting of DDT, IDDT (SEQ ID NO:281), DDTT (SEQ ID NO:282), IIDDT (SEQ ID NO:283), IDDTT (SEQ ID NO:284), IIDDTT (SEQ ID NO:285), DDTTG (SEQ ID NO:286), IDDTTG (SEQ ID NO:287), IIDDTTG (SEQ ID NO:288), FIIDDT (SEQ ID NO:289), FIIDDTT (SEQ ID NO:290), FIIDDTTG (SEQ ID NO:291), IFIIDDT (SEQ ID NO:292), IFIIDDTT (SEQ ID NO:293), IFIIDDTTG (SEQ ID NO:294), DPK, DPKT (SEQ ID NO:295), DPKTG (SEQ ID NO:296), VDPK (SEQ ID NO:297), VDPKT (SEQ ID NO:298), VDPKTG (SEQ ID NO:299), SVDPK (SEQ ID NO:300), SVDPKT (SEQ ID NO:301), SVDPKTG (SEQ ID NO:302), FSVDPK (SEQ ID NO:303), FSVDPKT (SEQ ID NO:304), FSVDPKTG (SEQ ID NO:305), YFSVDPK (SEQ ID NO:306), YFSVDPKT (SEQ ID NO:307), YFSVDPKTG (SEQ ID NO:308), DAN, DANT (SEQ ID NO:309), DANTG (SEQ ID NO:310), IDANT (SEQ ID NO:311), IDANTG (SEQ ID NO:312), NIDANT (SEQ ID NO:313), NIDANTG (SEQ ID NO:314), FNIDANT (SEQ ID NO:315), FNIDANTG (SEQ ID NO:316), FFNIDAN (SEQ ID NO:317), FFNIDANT (SEQ ID NO:318) and FFNIDANTG (SEQ ID NO:319); or (b) an analogue of any of the foregoing sequences that differs in one or more substitutions, deletions, additions and/or insertions such that that ability of the analogue to modulate a cadherin-14-mediated function is not substantially diminished. For example, the agent may comprise a linear peptide having the sequence N-Ac-IFIIDDTTG-NH$_2$ (SEQ ID NO:294), N-Ac-YFSVDPKTG-NH$_2$ (SEQ ID NO:308) or N-Ac-FFNIDANTG-NH$_2$ (SEQ ID NO:319). The cadherin-14 CAR sequence may, but need not, be present within a cyclic peptide.

Within certain specific embodiments, a modulating agent as provided herein may comprise: (a) one or more cadherin-15 CAR sequences selected from the group consisting of DKF, IDKF (SEQ ID NO:320), DKFT (SEQ ID NO:321), SIDKF (SEQ ID NO:322), IDKFT (SEQ ID NO:323), SIDKFT (SEQ ID NO:324), DKFTG (SEQ ID NO:325), IDKFTG (SEQ ID NO:326), SIDKFTG (SEQ ID NO:327), FSIDKF (SEQ ID NO:328), FSIDKFT (SEQ ID NO:329), FSIDKFTG (SEQ ID NO:330), VFSIDKF (SEQ ID NO:331), VFSIDKFT (SEQ ID NO:332), VFSIDKFTG (SEQ ID NO:333), DEL, DELT (SEQ ID NO:334), DELTG (SEQ ID NO:335), IDEL (SEQ ID NO:336), IDELT (SEQ ID NO:337), IDELTG (SEQ ID NO:338), SIDEL (SEQ ID NO:339), SIDELT (SEQ ID NO:340), SIDELTG (SEQ ID NO:341), FSIDEL (SEQ ID NO:342), FSIDELT (SEQ ID NO:343), FSIDELTG (SEQ ID NO:344), LFSIDEL (SEQ ID NO:345), LFSIDELT (SEQ ID NO:346) and LFSIDELTG (SEQ ID NO:347); or (b) an analogue of any of the foregoing sequences that differs in one or more substitutions, deletions, additions and/or insertions such that that ability of the analogue to modulate a cadherin-15-mediated function is not substantially diminished. For example, the agent may comprise a linear peptide having the sequence N-Ac-VFSIDKFTG-NH$_2$ (SEQ ID NO:333) or N-Ac-LFSIDELTG-NH$_2$ (SEQ ID NO:347). The cadherin-15 CAR sequence may, but need not, be present within a cyclic peptide.

Within certain specific embodiments, a modulating agent as provided herein may comprise: (a) one or more T-cadherin CAR sequences selected from the group consisting of NEN, INEN (SEQ ID NO:348), NENT (SEQ ID NO:349), RINEN (SEQ ID NO:350), INENT (SEQ ID NO:351), RINENT (SEQ ID NO:352), NENTG (SEQ ID NO:353), INENTG (SEQ ID NO:354), RINENTG (SEQ ID NO:355), FRINEN (SEQ ID NO:356), FRINENT (SEQ ID NO:357), FRINENTG (SEQ ID NO:358), IFRINEN (SEQ ID NO:359), IFRINENT (SEQ ID NO:360) and IFRINENTG (SEQ ID NO:361); or (b) an analogue of any of the foregoing sequences that differs in one or more substitutions, deletions, additions and/or insertions such that ability of the analogue to modulate a T-cadherin-mediated function is not substantially diminished. For example, the agent may comprise a linear peptide having the sequence N-Ac-IFRINENTG-NH$_2$ (SEQ ID NO:361). The T-cadherin CAR sequence may, but need not, be present within a cyclic peptide.

Within certain specific embodiments, a modulating agent as provided herein may comprise: (a) one or more PB-cadherin CAR sequences selected from the group consisting of EEY, EEYT (SEQ ID NO:362), EEYTG (SEQ ID NO:363), VEEY (SEQ ID NO:364), VEEYT (SEQ ID NO:365), VEEYTG (SEQ ID NO:366), VVEEY (SEQ ID NO:367), VVEEYT (SEQ ID NO:368), VVEEYTG (SEQ ID NO:369), FVVEEY (SEQ ID NO:370), FVEEYT (SEQ ID NO:371), FVEEYTG (SEQ ID NO:372), FFVVEEY (SEQ ID NO:373), FFVVEEYT (SEQ ID NO:374), FFVVEEYTG (SEQ ID NO:375), DEL, DELT (SEQ ID NO:376), DELTG (SEQ ID NO:377), IDEL (SEQ ID NO:378), IDELT (SEQ ID NO:379), IDELTG (SEQ ID NO:380), LIDEL (SEQ ID NO:381), LIDELT (SEQ ID NO:382), LIDELTG (SEQ ID NO:383), FLIDEL (SEQ ID NO:384), FLIDELT (SEQ ID NO:385), FLIDELTG (SEQ ID NO:386), IFLIDEL (SEQ ID NO:387), IFLIDELT (SEQ ID NO:388), IFLIDELTG (SEQ ID NO:389), DPK, DPKT (SEQ ID NO:390), DPKTG (SEQ ID NO:391), VDPK (SEQ ID NO:392), VDPKT (SEQ ID NO:393), VDPKTG (SEQ ID NO:394), TVDPK (SEQ ID NO:395), TVDPKT (SEQ ID NO:396), TVDPKTG (SEQ ID NO:397), FTVDPK (SEQ ID NO:398), FTVDPKT (SEQ ID NO:399), FTVDPKTG (SEQ ID NO:400), HFTVDPK (SEQ ID NO:401), HFTVDPKT (SEQ ID NO:402), HFTVDPKTG (SEQ ID NO:403), DAD, DADT (SEQ ID NO:404), DADTG (SEQ ID NO:405), IDAD (SEQ ID NO:406), IDADT (SEQ ID NO:407), IDADTG (SEQ ID NO:408), DIDAD (SEQ ID NO:409), DIDADT (SEQ ID NO:410), DIDADTG (SEQ ID NO:411), FDIDAD (SEQ ID NO:419), FDIDADT (SEQ ID NO:413), FDIDADTG (SEQ ID NO:414), IFDIDAD (SEQ ID NO:415), IFDIDADT (SEQ ID NO:416) and IFDIDADTG (SEQ ID NO:417); or (b) an analogue of any of the foregoing sequences that differs in one or more substitutions deletions, additions and/or insertions such that that ability of the analogue to modulate a PB-cadherin-mediated function is not substantially diminished. For example, the agent may comprise a linear peptide having the sequence N-Ac-FFVVEEYTG-NH$_2$ (SEQ ID NO:375), N-Ac-IFLIDELTG-NH$_2$ (SEQ ID NO:389), N-Ac-HFTVDPKTG-NH$_2$ (SEQ ID NO:403) or N-Ac-IFDIDADTG-NH$_2$ (SEQ ID NO:417). The PB-cadherin CAR sequence may, but need not, be present within a cyclic peptide.

Within certain specific embodiments, a modulating agent as provided herein may comprise: (a) one or more LI-cadherin CAR sequences selected from the group consisting of NNK, NNKT (SEQ ID NO:418), NNKTG (SEQ ID NO:419), INNK (SEQ ID NO:420), INNKT (SEQ ID NO:421), INNKTG (SEQ ID NO:422), QINNK (SEQ ID NO:423), QINNKT (SEQ ID NO:424), QINNKTG (SEQ ID NO:425), FQINNK (SEQ ID NO:426), FQINNKT (SEQ ID NO:427), FQINNKTG (SEQ ID NO:428), YFQINNK (SEQ ID NO:429), YFQINNKT (SEQ ID NO:430) and YFQINNKTG (SEQ ID NO:431); or (b) an analogue of any of the foregoing sequences that differs in one or more substitution, deletions, additions and/or insertions such that that ability of the analogue to modulate a LI-cadherin-mediated function is not substantially diminished. For example, the agent may comprise a linear peptide having the sequence N-Ac-YFQINNKTG-NH$_2$ (SEQ ID NO:431). The LI-cadherin CAR sequence may, but need not, be present within a cyclic peptide.

Within certain specific embodiments, a modulating agent as provided herein may comprise: (a) one or more protocadherin CAR sequences selected from the group consisting of DLV, DLVT (SEQ ID NO:432), DLVTG (SEQ ID NO:433), LDLV (SEQ ID NO:434), LDLVT (SEQ ID NO:435), LDLVTG (SEQ ID NO:436), ALDLV (SEQ ID NO:437), ALDLVT (SEQ ID NO:438), ALDLVTG (SEQ ID NO:439), FALDLV (SEQ ID NO:440), FALDLVT (SEQ ID NO:441), FALDLVTG (SEQ ID NO:442), LFALDLV (SEQ ID NO:443), LFALDLVT (SEQ ID NO:444), LFALDLVTG (SEQ ID NO:445), NRD, NRDN (SEQ ID NO:446), NRDNG (SEQ ID NO:447), INRD (SEQ ID NO:448), INRDN (SEQ ID NO:449), INRDNG (SEQ ID NO:450), TINRD (SEQ ID NO:451), TINRDN (SEQ ID NO:452), TINRDNG (SEQ ID NO:453), FTINRD (SEQ ID NO:454), FTINRDN (SEQ ID NO:455), FTINRDNG (SEQ ID NO:456), YFTINRD (SEQ ID NO:457), YFTINRDN (SEQ ID NO:458), YFTINRDNG (SEQ ID NO:459), DPK, DPKT (SEQ ID NO:460), DPKTG (SEQ ID NO:461), IDPK (SEQ ID NO:462), IDPKT (SEQ ID NO:463), IDPKTG (SEQ ID NO:464), SIDPK (SEQ ID NO:465), SIDPKT (SEQ ID NO:466), SIDPKTG (SEQ ID NO:467), FSIDPK (SEQ ID NO:468), FSIDPKT (SEQ ID NO:469), FSIDPKTG (SEQ ID NO:470), LFSIDPK (SEQ ID NO:471), LFSIDPKT (SEQ ID NO:472), LFSIDPKTG (SEQ ID NO:473), DPS, DPSS (SEQ ID NO:474), DPSSG (SEQ ID NO:475), IDPS (SEQ ID NO:476), IDPSS (SEQ ID NO:477), IDPSSG (SEQ ID NO:478), EIDPS (SEQ ID NO:479), EIDPSS (SEQ ID NO:480), EIDPSSG (SEQ ID NO:481), FEIDPS (SEQ ID NO:482), FEIDPSS (SEQ ID NO:483), FEIDPS (SEQ ID NO:484), FEIDPSS (SEQ ID NO:485), FEIDPSSG (SEQ ID NO:486), LFEIDPS (SEQ ID NO:487), LFEIDPSS (SEQ ID NO:488) and LFEIDPSSG (SEQ ID NO:489); or (b) an analogue of any of the foregoing sequences that differs in one or more substitutions, deletions, additions and/or insertions such that that ability of the analogue to modulate a protocadherin-mediated function is not substantially diminished. For example, the agent may comprise a linear peptide having the sequence N-Ac-LFALDLVTG-NH$_2$ (SEQ ID NO:445), N-Ac-YFTINRDNG-NH$_2$ (SEQ ID NO:459), N-Ac-LFSIDPKTG-NH$_2$ (SEQ ID NO:473) or N-Ac-LFEIDPSSG-NH$_2$ (SEQ ID NO:489). The protocadherin CAR sequence may, but need not, be present within a cyclic peptide.

Within certain specific embodiments, a modulating agent as provided herein comprises: (a) one or more desmoglein CAR sequences selected from the group consisting of NQK, NQKT (SEQ ID NO:490), NQKTG (SEQ ID NO:491), INQK (SEQ ID NO:492), INQKT (SEQ ID NO:493), INQKTG (SEQ ID NO:494), VINQK (SEQ ID NO:495), VINQKT (SEQ ID NO:496), VINQKTG (SEQ ID NO:497), FVINQK (SEQ ID NO:498), FVINQKT (SEQ ID NO:499), FVINQKTG (SEQ ID NO:500), IFVINQK (SEQ ID NO:501), IFVINQKT (SEQ ID NO:502), IFVINQKTG (SEQ ID NO:503), NRN, NRNT (SEQ ID NO:504), NRNTG (SEQ ID NO:505), INRN (SEQ ID NO:506), INRNT (SEQ ID NO:507), INRNTG (SEQ ID NO:508), IINRN (SEQ ID NO:509), IINRNT (SEQ ID NO:510), IINRNTG (SEQ ID NO:511), FIINRN (SEQ ID NO:512), FIINRNT (SEQ ID NO:513), FIINRNTG (SEQ ID NO:514), MFIINRN (SEQ ID NO:515), MFIINRNT (SEQ ID NO:516), MFIINRNTG (SEQ ID NO:517), NKD, NKDT (SEQ ID NO:518), NKDTG (SEQ ID NO:519), LNKD (SEQ ID NO:520), LNKDT (SEQ ID NO:521), LNKDTG (SEQ ID NO:522), YLNKD (SEQ ID NO:523), YLNKDT (SEQ ID NO:524), YLNKDTG (SEQ ID NO:525), FYLNKD (SEQ ID NO:526), FYLNKDT (SEQ ID NO:527), FYLNKDTG (SEQ ID NO:528), VFYLNKD (SEQ ID NO:529), VFYLNKDT (SEQ ID NO:530) and VFYLNKDTG (SEQ ID NO:531); or (b) an analogue of any of the foregoing sequences that differs in one or more substitutions, deletions, additions and/or insertions such that that ability of the analogue to modulate a desmoglein-mediated function is not substantially diminished. For example, the agent may comprise a linear peptide having the sequence N-Ac-IFVINQKTG-NH$_2$ (SEQ ID NO:503), N-Ac-MFIINRNTG-NH$_2$ (SEQ ID NO:517) or N-Ac-VFYLNKDTG-NH$_2$ (SEQ ID NO:531). The desmoglein CAR sequence may, but need not, be present within a cyclic peptide.

Within certain specific embodiments, a modulating agent as provided herein may comprise: (a) one or more desmocollin CAR sequences selected from the group consisting of EKD, EKDT (SEQ ID NO:532), EKDTG (SEQ ID NO:533), IEKD (SEQ ID NO:534), IEKDT (SEQ ID NO:535), IEKDTG (SEQ ID NO:536), YIEKD (SEQ ID NO:537), YIEKDT (SEQ ID NO:538), YIEKDTG (SEQ ID NO:539), FYIEKD (SEQ ID NO:540), FYIEKDT (SEQ ID NO:541), FYIEKDTG (SEQ ID NO:542), LFYIEKD (SEQ ID NO:543), LFYIEKDT (SEQ ID NO:544), LFYIEKDTG (SEQ ID NO:545), ERD, ERDT (SEQ ID NO:546), ERDTG (SEQ ID NO:547), VERD (SEQ ID NO:548), VERDT (SEQ ID NO:549), VERDTG (SEQ ID NO:550), YVERD (SEQ ID NO:551), YVERDT (SEQ ID NO:552), YVERDTG (SEQ ID NO:553), FYVERD (SEQ ID NO:554), FYVERDT (SEQ ID NO:555), FYVERDTG (SEQ ID NO:556), LFYVERD (SEQ ID NO:557), LFYVERDT (SEQ ID NO:558), LFYVERDTG (SEQ ID NO:559), IERD (SEQ ID NO:560), IERDT (SEQ ID NO:561), IERDTG (SEQ ID NO:562), YIERD (SEQ ID NO:563), YIERDT (SEQ ID NO:564), YIERDTG (SEQ ID NO:565), FYIERD (SEQ ID NO:566), FYIERDT (SEQ ID NO:567), FYIERDTG (SEQ ID NO:568), LFYIERD (SEQ ID NO:569), LFYIERDT (SEQ ID NO:570) and LFYIERDTG (SEQ ID NO:571); or (b) an analogue of any of the foregoing sequences that differs in one or more substitutions, deletions, additions and/or insertions such that that ability of the analogue to modulate a desmocollin-mediated function is not substantially diminished. For example, the agent may comprise a linear peptide having the sequence N-Ac-LFYIEKDTG-NH$_2$ (SEQ ID NO:545), N-Ac-LFYVERDTG-$NH_2$ (SEQ ID NO:559) or N-Ac-LFYIERDTG-$NH_2$ (SEQ ID NO:571). The desmocollin CAR sequence may, but need not, be present within a cyclic peptide.

Within certain specific embodiments, a modulating agent as provided herein comprises: (a) one or more cadherin-related neuronal receptor (cnr) CAR sequences selected from the group consisting of DPV, DPVS (SEQ ID NO:572), DPVSG (SEQ ID NO:573), IDPV (SEQ ID NO:574), IDPVS (SEQ ID NO:575), IDPVSG (SEQ ID NO:576), HIDPV (SEQ ID NO:577), HIDPVS (SEQ ID NO:578), HIDPVSG (SEQ ID NO:579) FHIDPV (SEQ ID NO:580), FHIDPVS (SEQ ID NO:581), FHIDPVSG (SEQ ID NO:582), KFHIDPV (SEQ ID NO:583), KFHIDPVS (SEQ ID NO:584), KFHIDPVSG (SEQ ID NO:585), DAD, DADT (SEQ ID NO:586), DADTG (SEQ ID NO:587), IDAD (SEQ ID NO:588), IDADT (SEQ ID NO:589), IDADTG (SEQ ID NO:590), SIDAD (SEQ ID NO:591), SIDADT (SEQ ID NO:592), SIDADTG (SEQ ID NO:593), FSIDAD (SEQ ID NO:594), FSIDADT (SEQ ID NO:595), FSIDADTG (SEQ ID NO:596), QFSIDAD (SEQ ID NO:597), QFSIDADT (SEQ ID NO:598), QFSIDADTG (SEQ ID NO:599), DSV, DSVS (SEQ ID NO:600), DSVSG (SEQ ID NO:601), IDSV (SEQ ID NO:602), IDSVS (SEQ ID NO:603), IDSVSG (SEQ ID NO:604), HIDSV (SEQ ID NO:605), HIDSVS (SEQ ID NO:606), HIDSVSG (SEQ ID NO:607), FHIDSV (SEQ ID NO:608), FHIDSVS (SEQ ID NO:609), FHIDSVSG (SEQ ID NO:610), TFHIDSV (SEQ ID NO:611), TFHIDSVS (SEQ ID NO:612), TFHIDSVSG (SEQ ID NO:613), DSN, DSNS (SEQ ID NO:614), DSNSG (SEQ ID NO:615), IDSN (SEQ ID NO:616), IDSNS (SEQ ID NO:617), IDSNSG (SEQ ID NO:618), NIDSN (SEQ ID NO:619), NIDSNS (SEQ ID NO:620), NIDSNSG (SEQ ID NO:621), FNIDSN (SEQ ID NO:622), FNIDSNS (SEQ ID NO:623), FNIDSNSG (SEQ ID NO:624), AFNIDSN (SEQ ID NO:625), AFNIDSNS (SEQ ID NO:626), AFNIDSNSG (SEQ ID NO:627), DSS, DSSS (SEQ ID NO:628), DSSSG (SEQ ID NO:629), IDSS (SEQ ID NO:630), IDSSS (SEQ ID NO:631), IDSSSG (SEQ ID NO:632), TIDSS (SEQ ID NO:633), TIDSSS (SEQ ID NO:634), TIDSSSG (SEQ ID NO:635), FTIDSS (SEQ ID NO:636), FTIDSSS (SEQ ID NO:637), FTIDSSSG (SEQ ID NO:638), KFTIDSS (SEQ ID NO:639), KFTIDSSS (SEQ ID NO:640), KFTIDSSSG (SEQ ID NO:641), DEK, DEKN (SEQ ID NO:642), DEKNG (SEQ ID NO:643), LDEK (SEQ ID NO:644), LDEKN (SEQ ID NO:645), LDEKNG (SEQ ID NO:646), TLDEK (SEQ ID NO:647), TLDEKN (SEQ ID NO:648), TLDEKNG (SEQ ID NO:649), FTLDEK (SEQ ID NO:650), FTLDEKN (SEQ ID NO:651), FTLDEKNG (SEQ ID NO:652), LFTLDEK (SEQ ID NO:653), LFTLDEKN (SEQ ID NO:654), LFTLDEKNG (SEQ ID NO:655), NEK, NEKT (SEQ ID NO:656), NEKTG (SEQ ID NO:657), INEK (SEQ ID NO:658), INEKT (SEQ ID NO:659), INEKTG (SEQ ID NO:660), LINEK (SEQ ID NO:661), LINEKT (SEQ ID NO:662), LINEKTG (SEQ ID NO:663), FLINEK (SEQ ID NO:664), FLINEKT (SEQ ID NO:665), FLINEKTG (SEQ ID NO:666), KFLINEK (SEQ ID NO:667), KFLINEKT (SEQ ID NO:668) and KFLINEKTG (SEQ ID NO:4052); or (b) an analogue of any of the foregoing sequences that differs in one or more substitutions, deletions, additions and/or insertions such that that ability of the analogue to modulate a cadherin-related neuronal receptor-mediated function is not substantially diminished. For example, the agent may comprise a linear peptide having the sequence N-Ac-KFHIDPVSG-$NH_2$ (SEQ ID NO:585), N-Ac-QFSIDADTG-$NH_2$ (SEQ ID NO:599), N-Ac-TFHIDSVSG-$NH_2$ (SEQ ID NO:613), N-Ac-AFNIDSNSG-$NH_2$ (SEQ ID NO:627), N-Ac-KFTIDSSSG-$NH_2$ (SEQ ID NO:641), N-Ac-LFTLDEKNG-$NH_2$ (SEQ ID NO:655) or N-Ac-KFLINEKTG-$NH_2$ (SEQ ID NO:4052). The cnr CAR sequence may, but need not, be present within a cyclic peptide.

Any of the above modulating agents may, within certain embodiments, be linked to one or more of a drug, detectable marker, targeting agent or support material. Alternatively, or in addition, a modulating agent as described above, may further comprise one or more of: (a) a CAR sequence that is specifically recognized by an adhesion molecule other than the particular nonclassical cadherin; and/or (b) an antibody or antigen-binding fragment thereof that specifically binds to a CAR sequence that is specifically recognized by an adhesion molecule other than the nonclassical cadherin. For example, such an adhesion molecule may be a classical cadherin, integrin, occludin, claudin, N-CAM, fibronectin, laminin or other extracellular matrix protein. In addition, or alternatively, a modulating agent may comprise a CAR sequence from a different non-classical cadherin, such that multiple non-classical cadherin CAR sequences are linked together within the modulating agent.

Within other aspects, the present invention provides pharmaceutical compositions comprising a modulating agent as described above in combination with a pharmaceutically acceptable carrier. Within such compositions, the modulating agent may, but need not, be present within a sustained-release formulation. Such compositions may, within certain embodiments, further comprise a drug and/or a modulator of cell adhesion that comprises one or more of: (a) a CAR sequence that is specifically recognized by an adhesion molecule other than the nonclassical cadherin; and/or (b) an antibody or antigen-binding fragment thereof that specifically binds to a CAR sequence that is specifically recognized by an adhesion molecule other than the nonclassical cadherin.

The present invention further provides, within other aspects, methods for modulating one or more nonclassical cadherin-mediated functions. Such methods generally comprise contacting a nonclassical cadherin-expressing cell with a modulating agent as described above. Suitable cells include, but are not limited to, epithelial cells, endothelial cells, neural cells, tumor cells and lymphocytes. Within such methods, the modulating agent may, but need not, be present within a pharmaceutical composition as recited above.

Within certain aspects, methods are provided for inhibiting adhesion of nonclassical cadherin-expressing cells in a mammal, comprising administering to a mammal a modulating agent as provided above that inhibits cell adhesion mediated by the nonclassical cadherin. Such modulating agents should inhibit cell adhesion with an activity that is not substantially diminished relative to the activity of the nonclassical cadherin in soluble form, within a cell adhesion assay such as the assays provided herein.

Within further aspects, the present invention provides methods for enhancing the delivery of a drug through the skin of a mammal, comprising contacting epithelial cells of a mammal with a drug and a modulating agent as described above, wherein the step of contacting is performed under conditions and for a time sufficient to allow passage of the drug across the epithelial cells, and wherein the modulating agent inhibits nonclassical cadherin-mediated cell adhesion. Such modulating agents may pass into the blood stream of the mammal. Within certain embodiments, the modulating agent is linked to the drug. The step of contacting may, but need not, be performed via a skin patch comprising the modulating agent and the drug, and such skin patches are further provided herein. Preferred modulating agents for use within such methods are those that inhibit cell adhesion mediated by OB-cadherin, cadherin-5, a desmoglein and/or a desmocollin, as described herein.

Methods are further provided for facilitating blood sampling in a mammal, comprising contacting epithelial cells of a mammal with a modulating agent as described above, wherein the modulating agent inhibits nonclassical cadherin-mediated cell adhesion, and wherein the step of contacting is performed under conditions and for a time sufficient to allow passage of one or more blood components across the epithelial cells. Preferred modulating agents for use within such methods are those that inhibit cell adhesion mediated by OB-cadherin, cadherin-5, a desmoglein and/or a desmocollin, as described herein. The step of contacting may be performed via a skin patch comprising the modulating agent, and (optionally) a reagent for detecting a blood component of interest, and such kits are specifically provided herein. Within certain embodiments, the epithelial cells are skin cells or are gum cells.

Within further aspects, methods are provided for enhancing the delivery of a drug to a tumor in a mammal, comprising administering to a mammal a modulating agent as described above, wherein the modulating agent inhibits nonclassical cadherin-mediated cell adhesion. Suitable tumors include, but are not limited to, bladder tumors, ovarian tumors, breast tumors, stomach tumors and kidney tumors, and the modulating agent may be administered locally to the tumor or may be administered systemically. Preferred modulating agents for use within such methods are those that inhibit cell adhesion mediated by OB-cadherin, cadherin-5, cadherin-6, a desmoglein and/or a desmocollin, as described herein.

Within other aspects, the present invention provides methods for treating cancer and/or inhibiting metastasis in a mammal, comprising administering to a mammal a modulating agent as described above, wherein the modulating agent inhibits cadherin-mediated cell adhesion. The mammal may be afflicted with a cancer such as a carcinoma, leukemia or melanoma, and the modulating agent may be administered to the tumor or systemically. Preferred modulating agents for use within such methods are those that inhibit cell adhesion mediated by OB-cadherin, cadherin-5, cadherin-6, a desmoglein and/or a desmocollin, as described herein.

Within other aspects, methods are provided for inhibiting angiogenesis in a mammal, comprising administering to a mammal a modulating agent as described above, wherein the modulating agent inhibits nonclassical cadherin-mediated cell adhesion. Preferred modulating agents for use within such methods are those that inhibit cell adhesion mediated by cadherin-5, as described herein.

The present invention further provides, within other aspects, methods for inducing apoptosis in a nonclassical cadherin-expressing cell, comprising contacting a nonclassical cadherin-expressing cell with a modulating agent as described above, wherein the modulating agent inhibits nonclassical cadherin-mediated cell adhesion.

In further aspects, methods are provided for preventing or treating obesity in a mammal, comprising administering to a mammal a modulating agent as described above, wherein the modulating agent inhibits an OB-cadherin and/or cadherin-5 mediated function.

Methods are further provided for stimulating blood vessel regression, comprising administering to a mammal a modulating agent as described above, wherein the modulating agent inhibits an OB-cadherin and/or cadherin-5 mediated function.

The present invention further provides, within other aspects, methods for enhancing drug delivery to the central nervous system of a mammal, comprising administering to a mammal a modulating agent as described above, wherein the modulating agent inhibits a nonclassical cadherin-mediated function. Preferably, the modulating agent inhibits an OB-cadherin and/or cadherin-5 mediated function.

The present invention further provides, in other aspects, methods for enhancing and/or directing neurite outgrowth, comprising contacting a neuron with a modulating agent as described above, wherein the modulating agent enhances a nonclassical cadherin-mediated function. Preferably, the modulating agent enhances a function mediated by cadherin-7, cadherin-8, cadherin-12, cadherin-14, cadherin-15, T-cadherin, PB-cadherin, a protocadherin and/or a cnr.

Methods are also provided, within further aspects, for treating a demyelinating neurological disease such as multiple sclerosis in a mammal, comprising administering to a mammal a modulating agent as described above. Within certain embodiments, the modulating agent is administered by implantation with Schwann cells, oligodendrocyte progenitor cells and/or oligodendrocytes. Preferably, the modulating agent enhances a function mediated by cadherin-7, cadherin-8, cadherin-12, cadherin-14, cadherin-15, T-cadherin, PB-cadherin, a protocadherin and/or a cnr.

Methods are further provided for increasing vasopermeability in a mammal, comprising administering to a mammal a modulating agent as described above, wherein the modulating agent inhibits a nonclassical cadherin-mediated function. Preferably, the modulating agent inhibits OB-cadherin and/or cadherin-5 mediated cell adhesion.

Within other aspects, the present invention provides methods for enhancing adhesion of nonclassical cadherin-expressing cells, comprising contacting nonclassical cadherin-expressing cells with a modulating agent as described above, wherein the modulating agent enhances nonclassical cadherin-mediated cell adhesion, wherein the step of contacting is performed under conditions and for a time sufficient to detectably enhance adhesion of the cells. Within certain embodiments, modulating agents for use within such methods are linked to a support molecule or a solid support.

Within related aspects, the present invention provides methods for facilitating wound healing and/or reducing scar tissue in a mammal, comprising contacting a wound in a mammal with a modulating agent as described above, wherein the modulating agent enhances cadherin-mediated cell adhesion. Preferably, the modulating agent enhances OB-cadherin, cadherin-5, desmoglein and/or desmocollin mediated cell adhesion. Within certain embodiments, modulating agents for use within such methods are linked to a support molecules or a solid support.

Methods are also provided, within other aspects, for enhancing adhesion of foreign tissue implanted within a mammal, comprising contacting a site of implantation of foreign tissue in a mammal with a modulating agent as described above, wherein the modulating agent enhances nonclassical cadherin-mediated cell adhesion. Such foreign tissue may be a skin graft or organ implant. Within certain embodiments, the modulating agent is linked to a support material. Preferably, the modulating agent enhances OB-cadherin, cadherin-5, desmoglein and/or desmocollin mediated cell adhesion. Within certain embodiments, modulating agents for use within such methods are linked to a support molecules or a solid support.

Within further aspects, the present invention provides methods for inhibiting synaptic stability in a mammal, comprising administering to a mammal a modulating agent as described above, wherein the modulating agent inhibits a cnr-mediated function.

Within further aspects, methods are provided for modulating the immune system of a mammal, comprising administering to a mammal a modulating agent as described above, wherein the modulating agent inhibits a nonclassical cadherin-mediated function. Preferably, the modulating agent inhibits OB-cadherin, cadherin-5, cadherin-6 and/or cadherin-8 mediated cell adhesion.

Within other aspects, the present invention provides methods for preventing pregnancy in a mammal, comprising administering to a mammal a modulating agent as described above, wherein the modulating agent inhibits a nonclassical cadherin-mediated function. Preferably, the modulating agent inhibits OB-cadherin or cadherin-5 mediated cell adhesion.

The present invention further provides methods for detecting the presence of nonclassical cadherin-expressing cells in a sample, comprising: (a) contacting a sample with an antibody or antigen-binding fragment thereof that binds to a nonclassical CAR sequence as described above under conditions and for a time sufficient to allow formation of an antibody-cadherin complex; and (b) detecting the level of antibody-cadherin complex, and therefrom detecting the presence of nonclassical cadherin expressing cells in a sample. The antibody may be linked to a support material or a detectable marker such as a fluorescent marker. In certain embodiments, the step of detecting is performed using fluorescence activated cell sorting.

Kits for detecting the presence of cadherin-expressing cells in a sample are also provided. Such kits may comprise: (a) an antibody or antigen-binding fragment thereof that specifically binds to a nonclassical cadherin CAR sequence; and (b) a detection reagent.

Within other aspects, the present invention provides methods for identifying a compound capable of modulating a nonclassical cadherin-mediated function, comprising: (a) contacting an antibody or antigen-binding fragment thereof that specifically binds to a nonclassical cadherin CAR sequence as described above with a test compound; and (b) detecting the level of antibody or fragment that binds to the test compound, and therefrom identifying a compound capable of modulating cadherin-mediated cell adhesion.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 2 provides the amino acid sequences of representative mammalian nonclassical cadherin extracellular domains, as indicated (SEQ ID NOs 4–43). Calcium binding motifs are shown in bold, and representative CAR sequences are shown in bold and underlined.

FIG. 3 provides the amino acid sequences of representative mammalian OB-cadherin EC1 domains: human OB-cadherin (SEQ ID NO:44) and mouse OB-cadherin (SEQ ID NO:45).

FIG. 5A shows the cells 24 hours after exposure to 100 µl water/1 ml culture medium (magnification 200×). FIGS. 5B and 5C show the cells 24 hours after exposure to 100 µL of a solution containing 10 mg/mL N-Ac-IFVIDDKSG-NH$_2$ (SEQ ID NO:85) per 1 mL culture medium (magnifications of 200× and 100×, respectively). Arrows indicate rounded cells.

FIGS. 6C and 6D show the cells in the presence of 75 µg/mL of a similar peptide without the terminal functional groups. Cells were incubated with peptide for 60 minutes, fixed and immunolabeled with monoclonal antibodies directed against VE-cadherin, and were observed at 400× (A, C and E) and 1000× (B, D and F).

DETAILED DESCRIPTION OF THE INVENTION

Figure 1A:
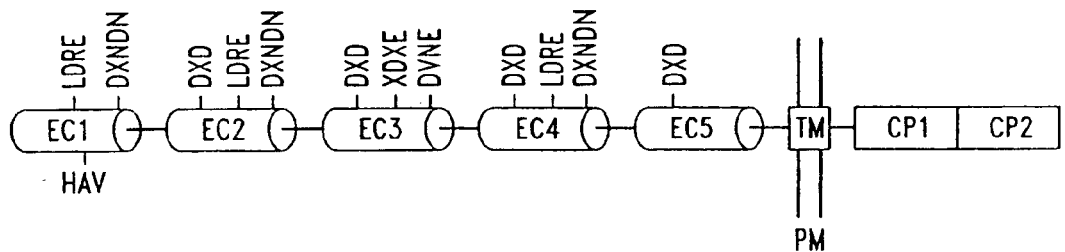
FIGS. 1A–1AA are diagrams depicting the structure of classical (FIG. 1A) and nonclassical cadherins (FIGS. 1B to 1AA). The extracellular domains are designated EC1–EC5 for most cadherins; EC1–EC7 for LI-cadherin and EC1–EC6 for protocadherins and cnr. The hydrophobic domain that transverses the plasma membrane (PM) is represented by TM, and the varying number of cytoplasmic domains are represented by CP. The calcium binding motifs for classical cadherins are shown in FIG. 1A by DXNDN (SEQ ID NO:1), DXD and LDRE (SEQ ID NO:2), and the calcium binding motifs for other cadherins are also indicated above the extracellular domains. Below the extracellular domains, the nine amino acid CAR sequences are shown.

As noted above, the present invention provides methods for modulating cadherin-mediated functions, such as cell adhesion. The present invention is based upon the identification of previously unknown cell adhesion recognition (CAR) sequences present in nonclassical cadherins. A modulating agent may generally comprise one or more nonclassical cadherin CAR sequences (or analogues or mimetics thereof), with or without one or more additional CAR sequences, as described below. Peptide CAR sequences may be present within a linear or cyclic peptide. Alternatively, or in addition, a modulating agent may comprise a polynucleotide encoding a peptide comprising one or more nonclassical cadherin CAR sequences and/or a modulating agent may comprise a substance (such as an antibody or antigen-binding fragment thereof) that specifically binds to a nonclassical cadherin CAR sequence.

In general, to modulate a nonclassical cadherin-mediated function, a cell that expresses a nonclassical cadherin is contacted with a modulating agent either in vivo or in vitro. Within certain aspects, the methods provided herein inhibit a nonclassical cadherin-mediated function. Such methods include, for example, methods for treating diseases or other conditions characterized by undesirable cell adhesion or for facilitating drug delivery to a specific tissue or tumor. Certain methods may inhibit cell adhesion (e.g., cancer cell adhesion), as well as cancer invasion and metastasis. Alternatively, a modulating agent may, such as when linked to a matrix or to another modulating agent via a linker, be used to enhance a nonclassical cadherin-mediated function, such as cell adhesion. Such conjugates may be used, for example, to facilitate wound healing or the adhesion of implants.

Modulating Agents

As noted above, the term "modulating agent," as used herein, refers to a molecule comprising at least one of the following components:

(a) a linear or cyclic peptide sequence that is at least 50% identical to a nonclassical cadherin CAR sequence (i.e., a nonclassical cadherin CAR sequence or an analogue thereof that retains at least 50% sequence identity);

(b) a mimetic (e.g. peptidomimetic or small molecule mimic) of a nonclassical cadherin CAR sequence;

(c) a substance, such as an antibody or antigen-binding fragment thereof, that specifically binds a nonclassical cadherin CAR sequence; and/or (d) a polynucleotide encoding a polypeptide that comprises a nonclassical cadherin CAR sequence or analogue thereof.

A modulating agent may consist entirely of one or more of the above elements, or may additionally comprise further peptide and/or non-peptide regions. Additional peptide regions may be derived from a nonclassical cadherin (preferably an extracellular domain that comprises a CAR sequence) and/or may be heterologous. Within certain preferred embodiments, a modulating agent contains no more than 85 consecutive amino acid residues, and preferably no more than 50 consecutive amino acid residues, present within a nonclassical cadherin.

A modulating agent is further capable of modulating a function mediated by a nonclassical cadherin. Such activity may generally be assessed using, for example, representative assays provided herein. Certain modulating agents inhibit an interaction between nonclassical cadherin molecules and/or between a nonclassical cadherin and a different adhesion molecule. For functions (e.g., cell adhesion) that are inhibited by a full length nonclassical cadherin, such a modulating agent may inhibit the function with an activity that is not substantially diminished relative to the full length nonclassical cadherin (i.e., the modulating agent inhibits the function at least as well as soluble cadherin, when contacted with cells that express the cadherin). For example, a modulating agent may be as effective as soluble cadherin in preventing and/or disrupting adhesion of cadherin-expressing cells. Alternatively, to enhance adhesion of nonclassical cadherin-expressing cells, a modulating agent may comprise an antibody or antigen-binding fragment thereof and/or multiple peptides or mimetics linked to a support material. Such modulating agents may function as a biological glue to bind nonclassical cadherin-expressing cells, and should result in a detectable enhancement of cell adhesion (preferably an enhancement that is at least as great as that observed for immobilized cadherin or antibody directed against the cadherin).

Figure 1B:
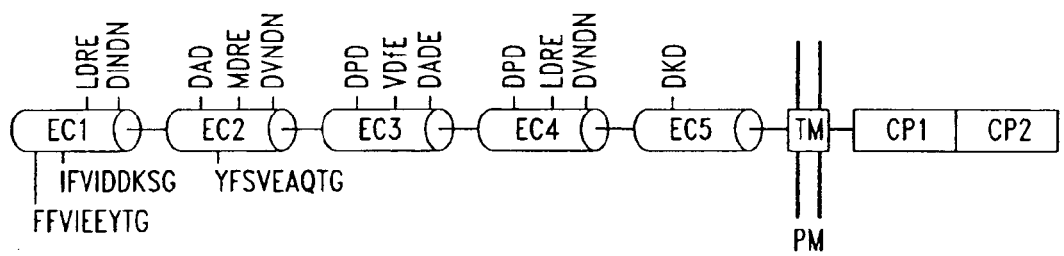
Figure 1C:
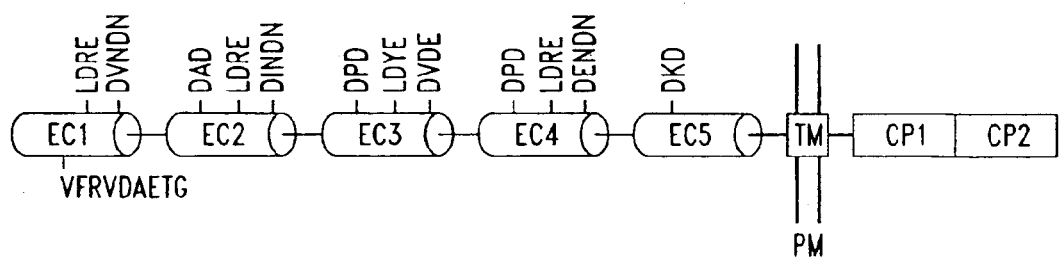
Figure 1D:
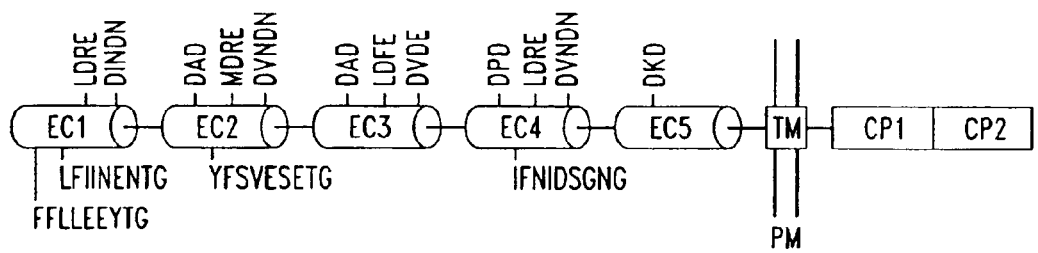
Figure 1E:
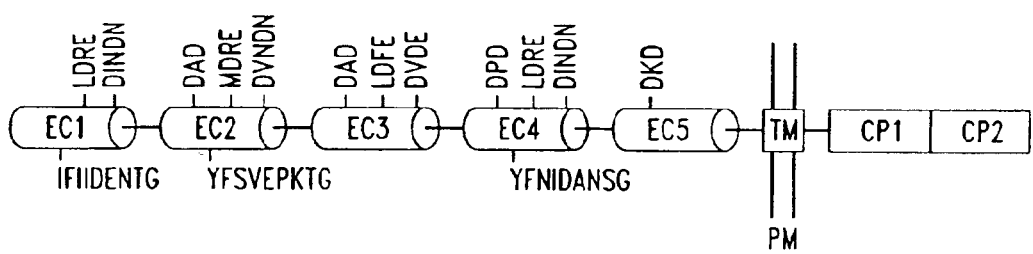
Figure 1F:
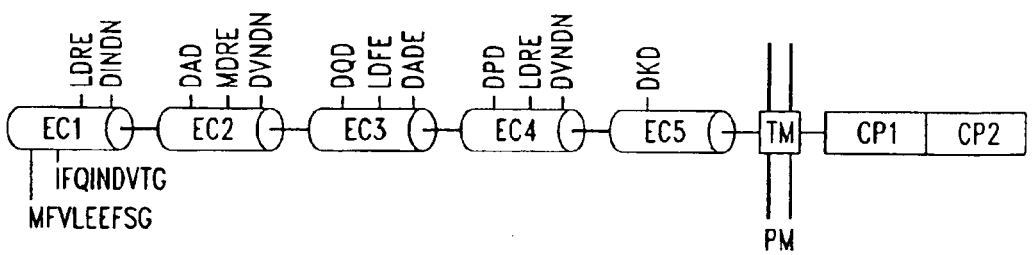
Figure 1G:
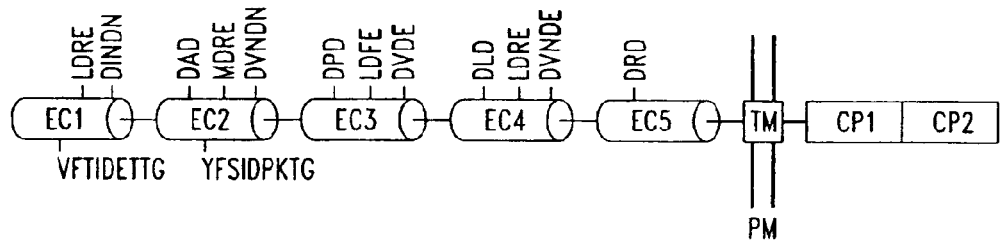
Figure 1H:
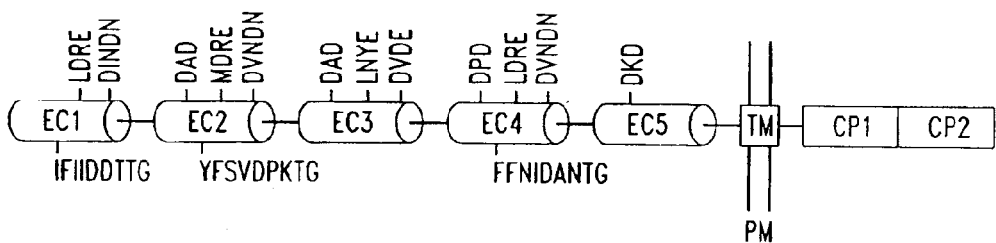
Figure 1I:
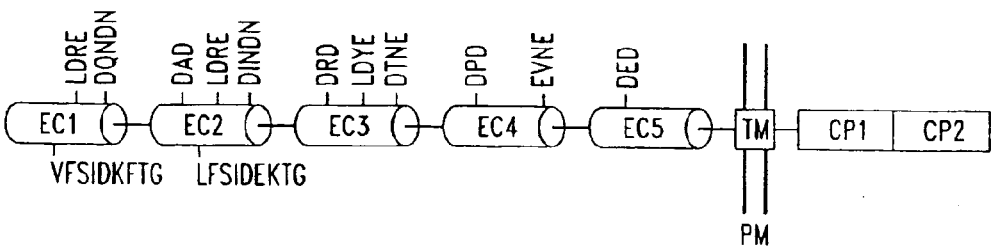
Figure 1J:
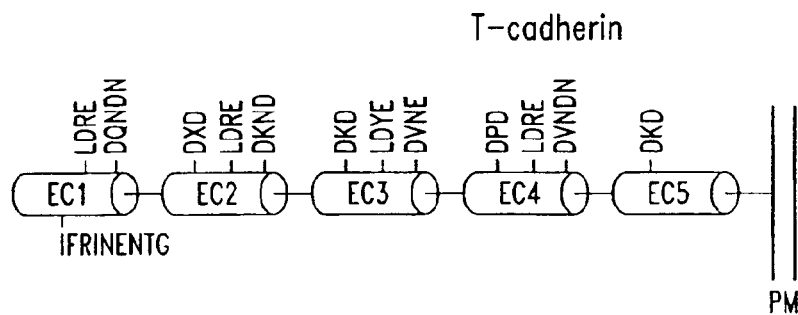
Figure 1K:
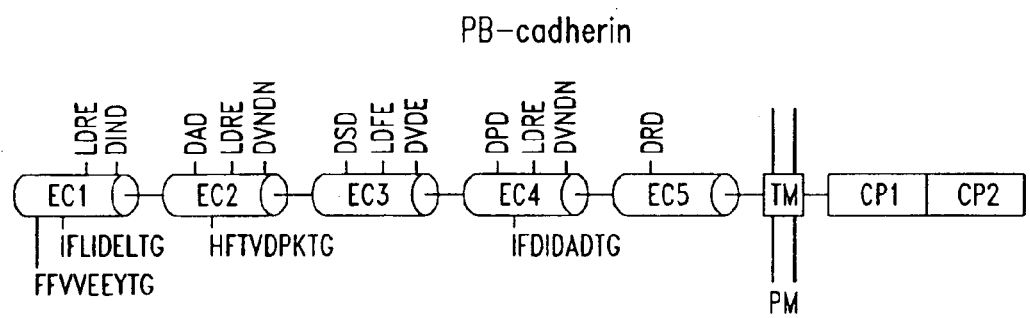
Figure 1L:
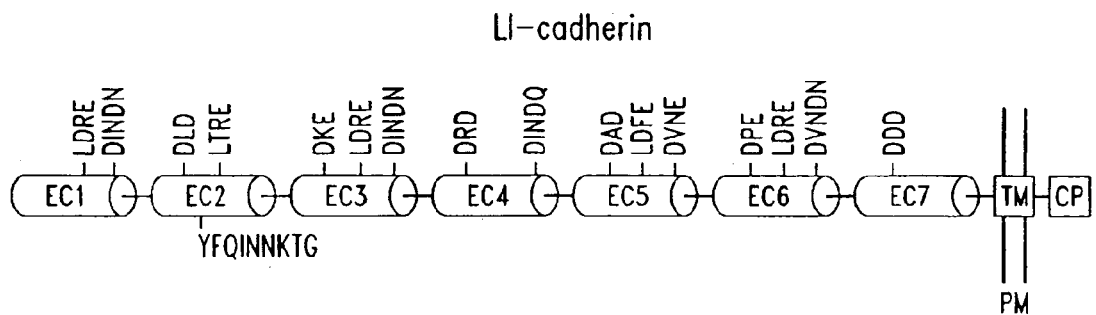
Figure 1M:
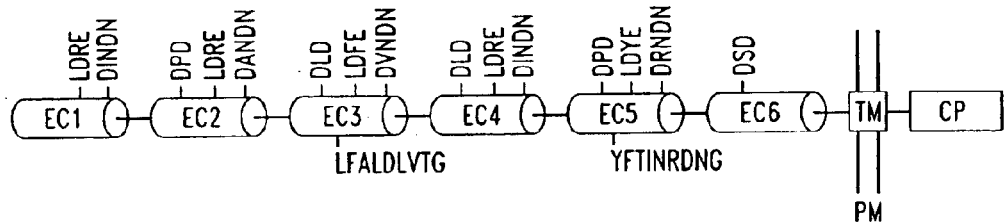
Figure 1N:
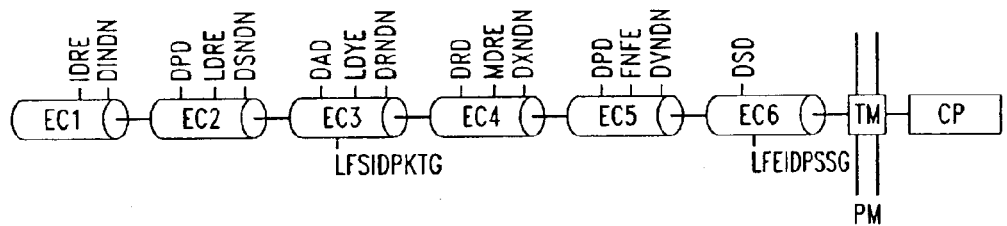
Figure 1O:
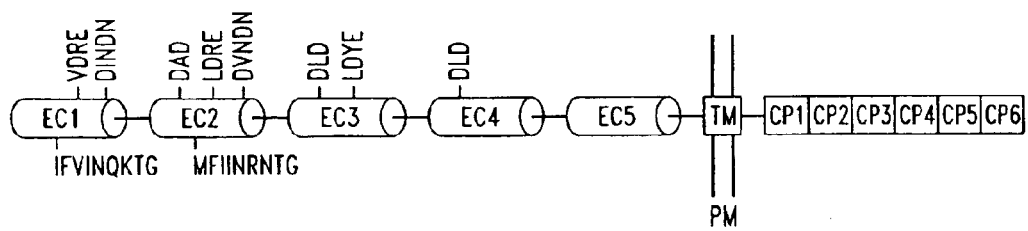
Figure 1P:
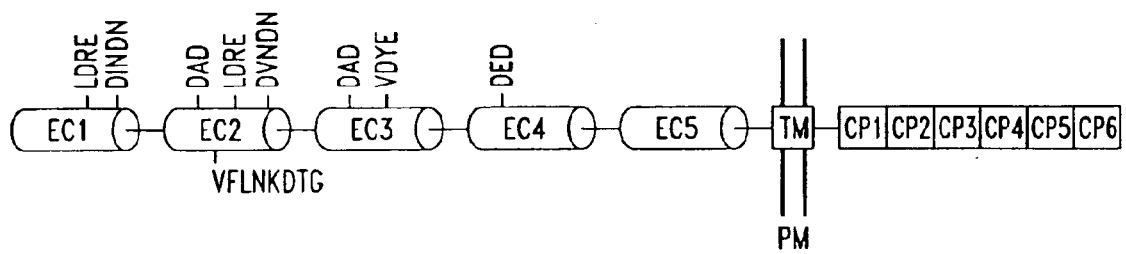
Figure 1Q:
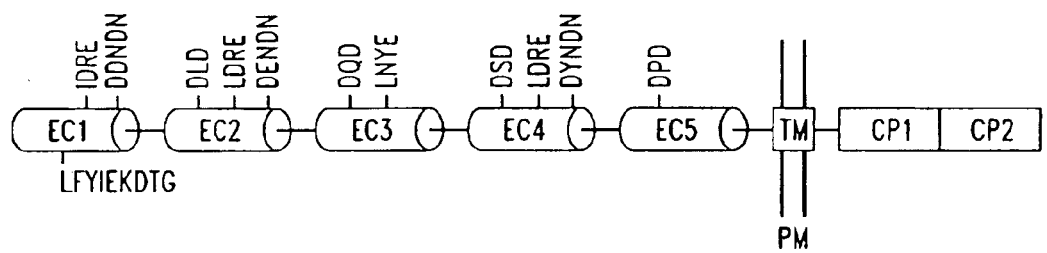
Figure 1R:
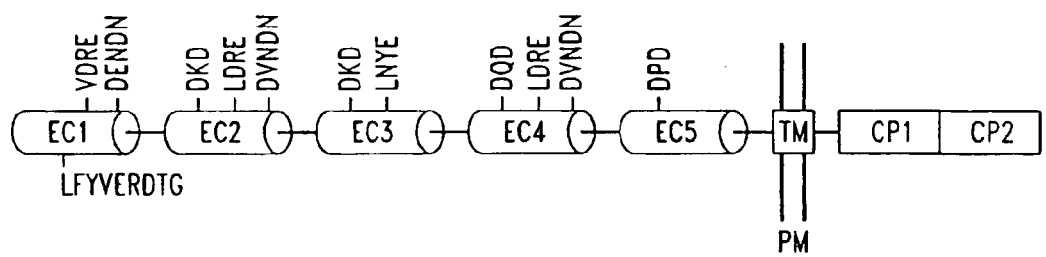
Figure 1S:
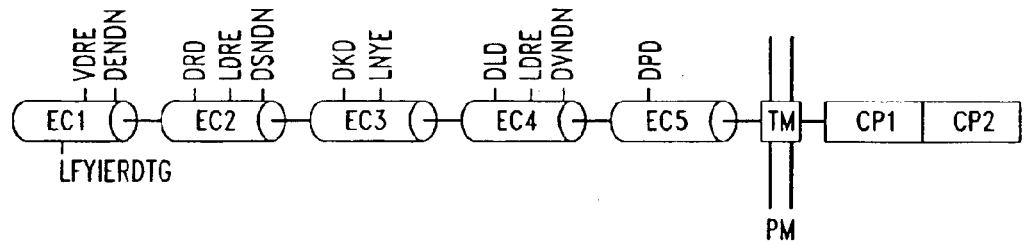
Figure 1T:
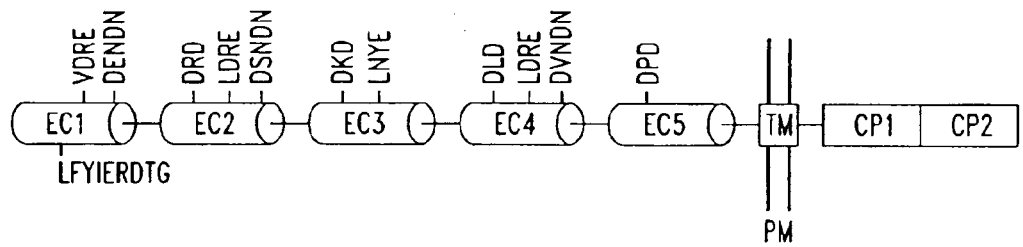
Figure 1U:
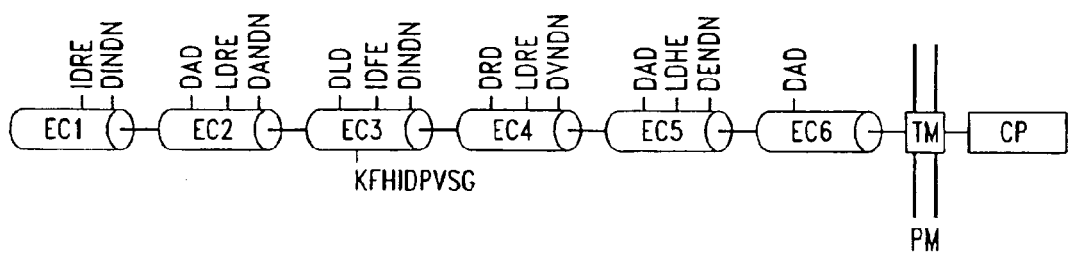
Figure 1V:
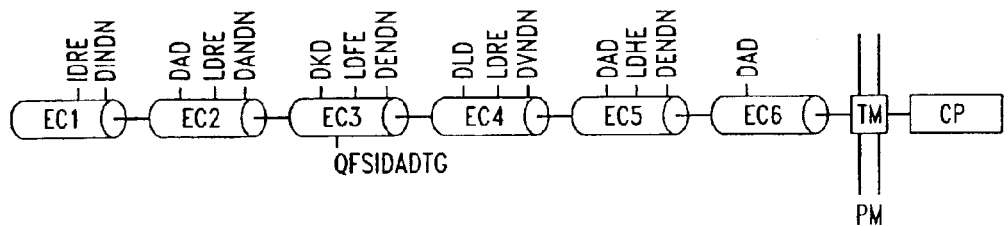
Figure 1W:
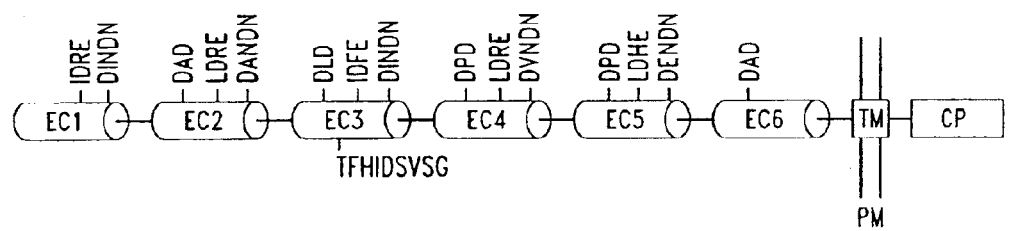
Figure 1X:
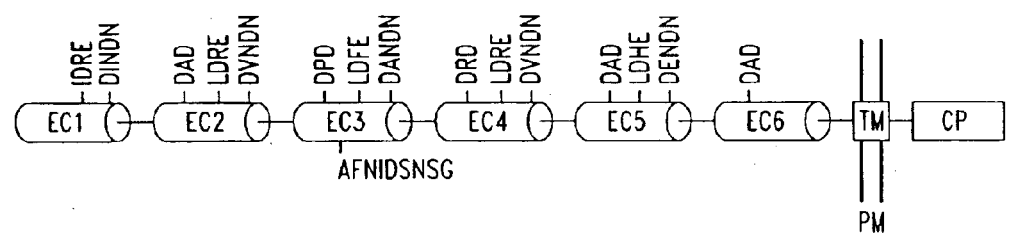
Figure 1Y:
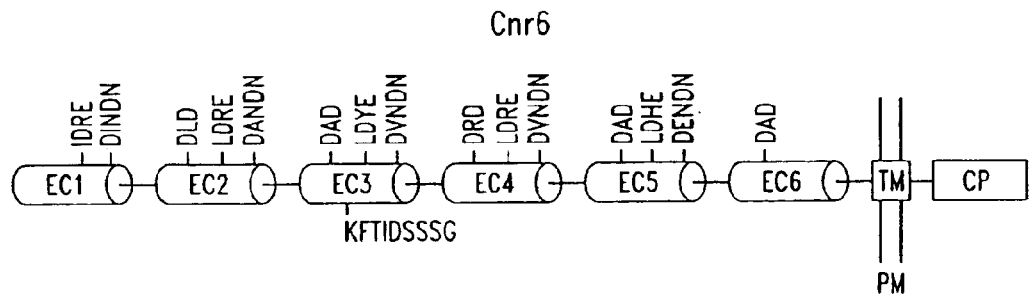
Figure 1Z:
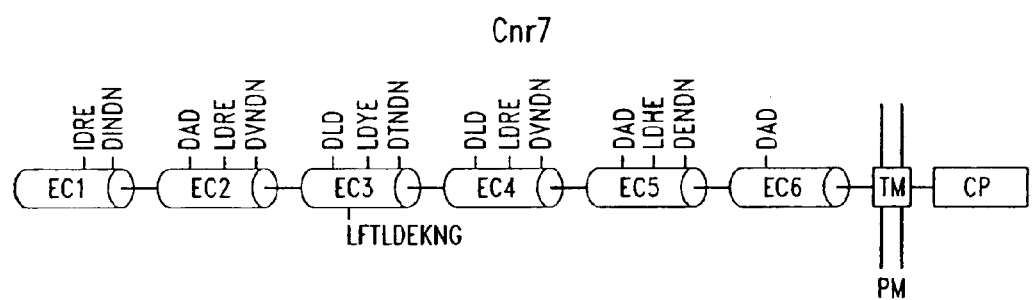
Figure 1A:
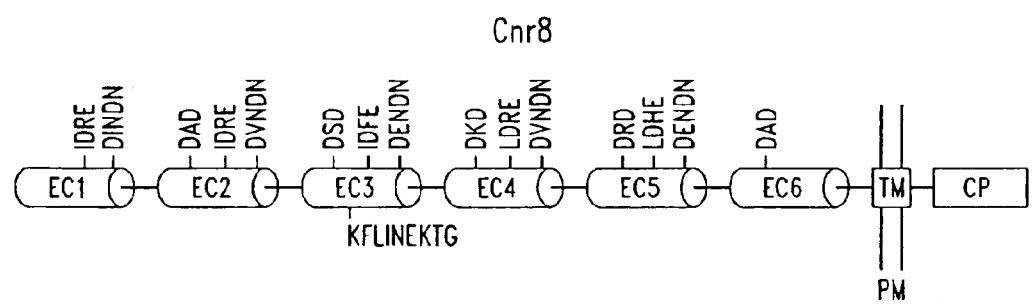
Figure 2B:
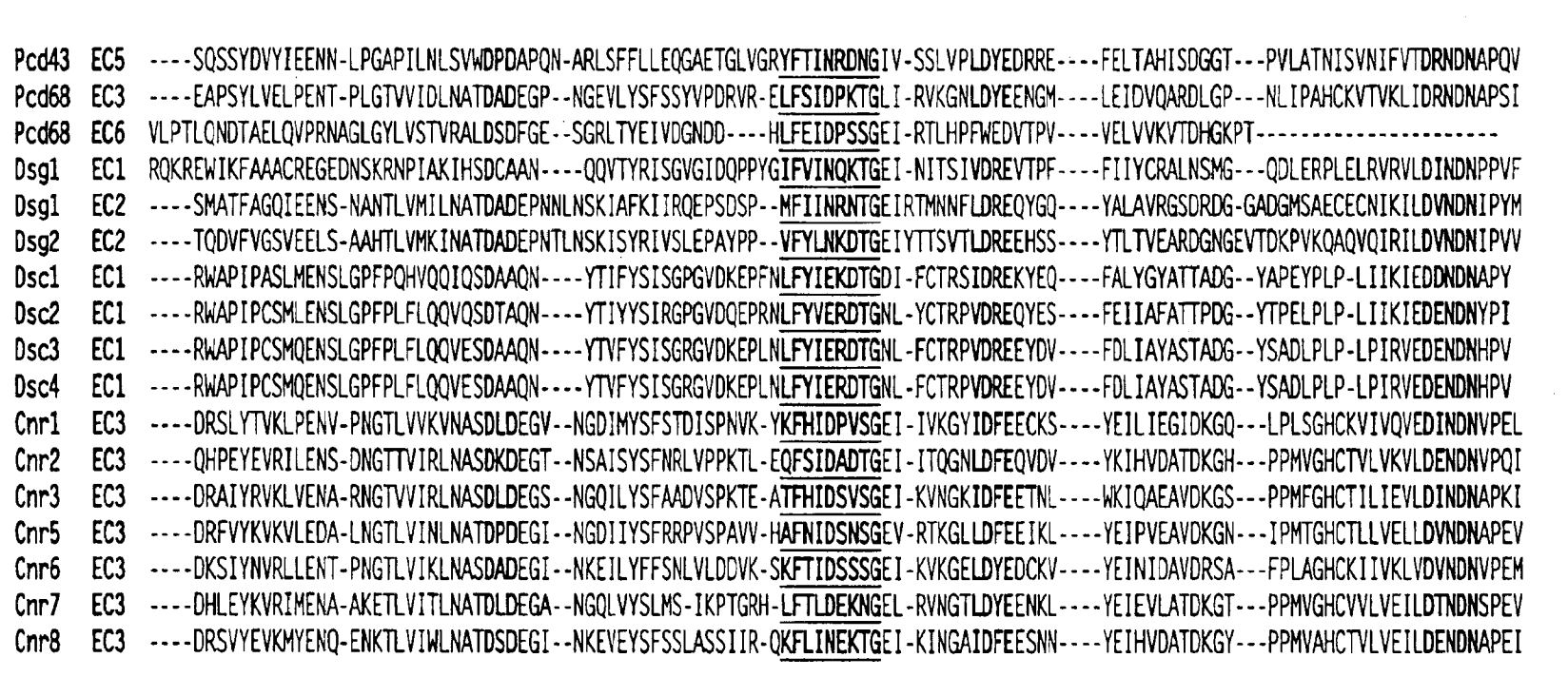

The term "nonclassical cadherin," as used herein, refers to a polypeptide that contains characteristic cadherin repeats, but does not contain an HAV CAR sequence. As used herein, a "cadherin repeat" refers to an amino acid sequence that is approximately 110 amino acid residues in length (generally 100 to 120 residues, preferably 105 to 115 residues), comprises an extracellular domain, and contains three calcium binding motifs (DXD, XDXE and DXXDX; SEQ ID NOS: 46 and 47 respectively) in the same order and in approximately the same position (see, e.g., FIG. 2). The presence of an extracellular domain may generally be determined using well known techniques, such as the presence of one or more of: a hydrophilic sequence, a region that is recognized by an antibody, a region that is cleaved by trypsin and/or a potential glycosylation site with the glycosylation motif Asn-X-Ser/Thr. The second calcium binding motif commonly has the sequence LDRE, although variants of this sequence with conservative substitutions are also observed, including MDRE (SEQ ID NO:65), LDFE (SEQ ID NO:66), LDYE (SEQ ID NO:67), IDRE (SEQ ID NO:68), VDRE (SEQ ID NO:69) and IDFE (SEQ ID NO:70). Within most cadherin repeats, the third calcium binding motif has the sequence [L,I,V]-X-[L,I,V]-X-D-X-N-D-[N,H]-X-P (SEQ ID NO:72), wherein residues indicated in brackets may be any one of the recited residues. A preferred third calcium binding motif has the sequence DXNDN (SEQ ID NO:1), although one or both of the D residues may be replaced by an E. Homology among cadherin repeats is generally at least 20%, preferably at least 30%, as determined by the ALIGN algorithm (Myers and Miller, *CABIOS* 4:11–17, 1988). Most cadherins comprise at least five cadherin repeats, along with a hydrophobic domain that transverses the plasma membrane and, optionally, one or more cytoplasmic domains, as shown in FIGS. 1B–1AA. Occasionally, however, a cadherin may substitute an extracellular domain that contains fewer than three calcium binding motifs for one or more of the cadherin repeats. For example, as shown in FIG. 2, the second extracellular domain of LI-cadherin comprises only the first calcium binding motif (DXD).

As noted above, atypical, or type II, cadherins include cadherin-5 (VE-cadherin), cadherin-6 (K-cadherin), cadherin-7, cadherin-8, cadherin-11 (OB-cadherin), cadherin-12, cadherin-14, cadherin-15 and PB-cadherin. Types III–X include LI-cadherin, T-cadherin, protocadherins (e.g., protocadherins 42, 43 and 68), desmocollins (e.g., desmocollins 1, 2, 3 and 4), desmogleins (e.g., desmogleins 1 and 2), and cadherin-related neuronal receptors. The sequence of various extracellular domains of each of these nonclassical cadherins is shown in FIG. 2, and SEQ ID NOs: 4–43.

A nonclassical cadherin CAR sequence, as used herein, is an amino acid sequence that is present within in a naturally occurring nonclassical cadherin and that is capable of detectably modulating a nonclassical cadherin-mediated function, such as cell adhesion, as described herein. In other words, contacting a nonclassical cadherin-expressing cell with a peptide comprising a CAR sequence results in a detectable change in a nonclassical cadherin-mediated function using at least one of the representative assays provided herein. CAR sequences are generally recognized in vivo by a nonclassical cadherin or other adhesion molecule (i.e., a molecule that mediates cell adhesion via a receptor on the cell surface), and are necessary for maximal heterophilic and/or homophilic interaction. CAR sequences may be of any length, but generally comprise at least three amino acid residues, preferably 4–16 amino acid residues, and more preferably 5–9 amino acid residues. A peptide modulating agent may comprise any number of amino acid residues, but preferred agents comprise 3–50 residues, preferably 4–16 residues.

It has been found, within the context of the present invention, that certain nonclassical cadherin CAR sequences share the consensus sequence:

Aaa-Phe-Baa-Ile/Leu/Val-Asp/Asn/Glu-Caa-Daa-
    Ser/Thr/Asn-Gly                          (SEQ ID NO:3)

Within the consensus sequence, Aaa, Baa, Caa and Daa indicate independently selected amino acid residues; "Ile/Leu/Val" indicates an amino acid that is isoleucine, leucine or valine; "Asp/Asn/Glu" indicates an amino acid that is aspartic acid, asparagine or glutamic acid; and "Ser/Thr/Asn" indicates an amino acid that is serine, threonine or asparagine. Representative nonclassical cadherin CAR sequences are provided within Table I. CAR sequences specifically provided herein further include portions of such representative CAR sequences, as well as longer polypeptides that comprise at least a portion of such sequences. Additional nonclassical cadherin CAR sequences may be identified based on sequence homology to the nonclassical cadherin CAR sequences provided herein, and based on the ability of a peptide comprising such a sequence to modulate a nonclassical cadherin-mediated function within a representative assay described herein. Within certain embodiments, a modulating agent comprises at least three consecutive residues, preferably at least five consecutive residues and more preferably at least seven consecutive residues, of a nonclassical cadherin CAR sequence that satisfies the above consensus sequence.

TABLE I

Representative Nonclassical Cadherin CAR Sequences

| Cadherin | CAR Sequence | |
|---|---|---|
| Human OB-cadherin EC1 | FFVIEEYTG | (SEQ ID NO: 99) |
| Human OB-cadherin EC1 | IFVIDDKSG | (SEQ ID NO: 85) |
| Human OB-cadherin EC2 | YFSVEAQTG | (SEQ ID NO: 113) |
| Human cadherin-5 EC1 | VFRVDAETG | (SEQ ID NO: 127) |
| Human cadherin-6 EC1 | FFLLEEYTG | (SEQ ID NO: 154) |
| Human cadherin-6 EC1 | LFIINENTG | (SEQ ID NO: 141) |
| Human cadherin-6 EC2 | YFSVESETG | (SEQ ID NO: 168) |

TABLE I-continued

Representative Nonclassical Cadherin CAR Sequences

| Cadherin | CAR Sequence | |
|---|---|---|
| Human cadherin-6 EC4 | IFNIDSGNG | (SEQ ID NO: 182) |
| Chicken cadherin-7 EC1 | IFIIDENTG | (SEQ ID NO: 196) |
| Chicken cadherin-7 EC2 | YFSVEPKTG | (SEQ ID NO: 210) |
| Chicken cadherin-7 EC4 | YFNIDANSG | (SEQ ID NO: 224) |
| Human cadherin-8 EC1 | MFVLEEFSG | (SEQ ID NO: 252) |
| Human cadherin-8 EC1 | IFQINDVTG | (SEQ ID NO: 238) |
| Human cadherin-12 EC1 | VFTIDETTG | (SEQ ID NO: 266) |
| Human cadherin-12 EC2 | YFSIDPKTG | (SEQ ID NO: 280) |
| Human cadherin-14 EC1 | IFIIDDTTG | (SEQ ID NO: 294) |
| Human cadherin-14 EC2 | YFSVDPKTG | (SEQ ID NO: 308) |
| Human cadherin-14 EC4 | FFNIDANTG | (SEQ ID NO: 319) |
| Human cadherin-15 EC1 | VFSIDKFTG | (SEQ ID NO: 333) |
| Human cadherin-15 EC2 | LFSIDELTG | (SEQ ID NO: 347) |
| Human T-cadherin EC1 | IFRINENTG | (SEQ ID NO: 361) |
| Rat PB-cadherin EC1 | FFVVEEYTG | (SEQ ID NO: 375) |
| Rat PB-cadherin EC1 | IFLIDELTG | (SEQ ID NO: 389) |
| Rat PB-cadherin EC2 | HFTVDPKTG | (SEQ ID NO: 403) |
| Rat PB-cadherin EC4 | IFDIDADTG | (SEQ ID NO: 417) |
| Human LI-cadherin EC2 | YFQINNKTG | (SEQ ID NO: 431) |
| Human protocadherin 43 EC3 | LFALDLVTG | (SEQ ID NO: 445) |
| Human protocadherin 43 EC5 | YFTINRDNG | (SEQ ID NO: 459) |
| Human protocadherin 68 EC3 | LFSIDPKTG | (SEQ ID NO: 473) |
| Human protocadherin 68 EC6 | LFEIDPSSG | (SEQ ID NO: 489) |
| Human desmoglein1 EC1 | IFVINQKTG | (SEQ ID NO: 503) |
| Human desmoglein1 EC2 | MFIINRNTG | (SEQ ID NO: 517) |
| Human desmoglein2 EC2 | VFYLNKDTG | (SEQ ID NO: 531) |
| Human desmocollin 1 EC1 | LFYIEKDTG | (SEQ ID NO: 545) |
| Human desmocollin 2 EC1 | LFYVERDTG | (SEQ ID NO: 559) |
| Human desmocollin 3/4 EC1 | LFYIERDTG | (SEQ ID NO: 571) |
| Mouse Cnr1 EC3 | KFHIDPVSG | (SEQ ID NO: 585) |
| Mouse Cnr2 EC3 | QFSIDADTG | (SEQ ID NO: 599) |
| Mouse Cnr3 EC3 | TFHIDSVSG | (SEQ ID NO: 613) |
| Mouse Cnr5 EC3 | AFNIDSNSG | (SEQ ID NO: 627) |
| Mouse Cnr6 EC3 | KFTIDSSSG | (SEQ ID NO: 641) |
| Mouse Cnr7 EC3 | LFTLDEKNG | (SEQ ID NO: 655) |
| Mouse Cnr8 EC3 | KFLINEKTG | (SEQ ID NO: 4052) |
| CONSENSUS | xFxidxxtG | (SEQ ID NO: 3) |
| | v n     s | |
| | l e     n | |

Nonclassical cadherin CAR sequences are generally physically located within the cadherin molecule in or near the binding site of an adhesion molecule (i.e., within 10 amino acids, and preferably within 5 amino acids). The location of a binding site may generally be determined using well known techniques, such as evaluating the ability of a portion of the nonclassical cadherin to bind to the same nonclassical cadherin or to another adhesion molecule. Any standard binding assay may be employed for such an evaluation. Recognition of a CAR sequence by the nonclassical cadherin or other adhesion molecule results in a measurable effect on an adhesion molecule function, such as cell adhesion. Peptides comprising a CAR sequence generally inhibit such a function unless linked, as described herein, to form an enhancer of adhesion molecule function.

Certain preferred nonclassical cadherin CAR sequences comprise 3–9 amino acid residues of a sequence provided in Table I. For example, a CAR sequence may comprise 3, 4 or 5 residues of a 9 amino acid sequence in Table I. For example, an OB cadherin CAR sequence generally comprises at least the sequence EEY, DDK or EAQ. Within certain embodiments, a CAR sequence may include at least residues 5–7 of a sequence in Table I.

Representative OB-cadherin CAR sequences comprise one or more of the peptide sequences DDK, IDDK (SEQ ID NO:4051) DDKS (SEQ ID NO:73), VIDDK (SEQ ID NO:74), IDDKS (SEQ ID NO:75), VIDDKS (SEQ ID NO:76), DDKSG (SEQ ID NO:77), IDDKSG (SEQ ID NO:78), VIDDKSG (SEQ ID NO:79), FVIDDK (SEQ ID NO:80), FVIDDKS (SEQ ID NO:81), FVIDDKSG (SEQ ID NO:82), IFVIDDK (SEQ ID NO:83), IFVIDDKS (SEQ ID NO:84), IFVIDDKSG (SEQ ID NO:85), EEY, IEEY (SEQ ID NO:86), EEYT (SEQ ID NO:87), VIEEY (SEQ ID NO:88), IEEYT (SEQ ID NO:89), VIEEYT (SEQ ID NO:90), EEYTG (SEQ ID NO:91), IEEYTG (SEQ ID NO:92), VIEEYTG (SEQ ID NO:93), FVIEEY (SEQ ID NO:94), FVIEEYT (SEQ ID NO:95), FVIEEYTG (SEQ ID NO:96), FFVIEEY (SEQ ID NO:97), FFVIEEYT (SEQ ID NO:98), FFVIEEYTG (SEQ ID NO:99), EAQ, VEAQ (SEQ ID NO:100), EAQT (SEQ ID NO:101), SVEAQ (SEQ ID NO:102), VEAQT (SEQ ID NO:103), SVEAQT (SEQ ID NO:104), EAQTG (SEQ ID NO:105), VEAQTG (SEQ ID NO:106), SVEAQTG (SEQ ID NO:107), FSVEAQ (SEQ ID NO:108), FSVEAQT (SEQ ID NO:109), FSVEAQTG (SEQ ID NO:110), YFSVEAQ (SEQ ID NO:111), YFSVEAQT (SEQ ID NO:112) or YFSVEAQTG (SEQ ID NO:113). Linear peptides having such sequences may be modified at the N- and/or C-termini, as in the peptides N-Ac-IFVIDDKSG-NH$_2$ (SEQ ID NO:85), N-Ac-FFVIEEYTG-NH$_2$ (SEQ ID NO:99) and N-Ac-YFSVEAQTG-NH$_2$ (SEQ ID NO:113).

Certain cadherin-5 CAR sequences comprise, for example, one or more of the peptide sequences: DAE, VDAE (SEQ ID NO:114), DAET (SEQ ID NO:115), RVDAE (SEQ ID NO:116), VDAET (SEQ ID NO:117), RVDAET (SEQ ID NO:118), DAETG (SEQ ID NO:119), VDAETG (SEQ ID NO:120), RVDAETG (SEQ ID NO:121), FRVDAE (SEQ ID NO:122), FRVDAET (SEQ ID NO:123), FRVDAETG (SEQ ID NO:124), VFRVDAE (SEQ ID NO:125), VFRVDAET (SEQ ID NO:126) or VFRVDAETG (SEQ ID NO:127). Linear peptides having such sequences may be modified at the N- and/or C-termini, as in the peptide N-Ac-VFRVDAETG-NH$_2$ (SEQ ID NO:127).

A cadherin-6 CAR sequence may comprise one or more of the sequences: NEN, INEN (SEQ ID NO:128), NENT (SEQ ID NO:129), IINEN (SEQ ID NO:130), INENT (SEQ ID NO:131), IINENT (SEQ ID NO:132), NENTG (SEQ ID NO:133), INENTG (SEQ ID NO:134), IINENTG (SEQ ID NO:135), FIINEN (SEQ ID NO:136), FIINENT (SEQ ID NO:137), FIINENTG (SEQ ID NO:138), LFIINEN (SEQ ID NO:139), LFIINENT (SEQ ID NO:140), LFIINENTG (SEQ ID NO:141), EEY, EEYT (SEQ ID NO:142), EEYTG (SEQ ID NO:143), LEEY (SEQ ID NO:144), LEEYT (SEQ ID NO:145), LEEYTG (SEQ ID NO:146), LLEEY (SEQ ID NO:147), LLEEYTG (SEQ ID NO:148), FLLEEY (SEQ ID NO:149), FLLEEYT (SEQ ID NO:150), FLLEEYTG (SEQ ID NO:151), FFLLEEY (SEQ ID NO:152), FFLLEEYT (SEQ ID NO:153), FFLLEEYTG (SEQ ID NO:154), ESE, ESET (SEQ ID NO:155), ESETG (SEQ ID NO:156), VESE (SEQ ID NO:157), VSEST (SEQ ID NO:158), VESETG (SEQ ID NO:159), SVESE (SEQ ID NO:160), SVESET (SEQ ID NO:161), SVESETG (SEQ ID NO:162), FSVESE (SEQ ID NO:163), FSVESET (SEQ ID NO:164), FSVESETG (SEQ ID NO:165), YFSVESE (SEQ ID NO:166), YFSVESET (SEQ ID NO:167), YFSVESETG (SEQ ID NO:168), DSG, DSGN (SEQ ID NO:169), DSGNG (SEQ ID NO:170), IDSG (SEQ ID NO:171), IDSGN (SEQ ID NO:172), IDSGNG (SEQ ID NO:173), NIDSG (SEQ ID NO:174), NIDSGN (SEQ ID NO:175), NIDSGNG (SEQ ID NO:176), FNIDSG (SEQ ID NO:177), FNIDSGN (SEQ ID NO:178), FNIDSGNG (SEQ ID NO:179), IFNIDSG (SEQ ID NO:180), IFNIDSGN (SEQ ID NO:181) or IFNIDSGNG (SEQ ID NO:182). Linear peptides having such sequences may be modified at the N- and/or C-termini, as in the peptides N-Ac-FFLLEEYTG-NH$_2$ (SEQ ID NO:154), N-Ac-LFIINENTG-NH$_2$ (SEQ ID NO:141), N-Ac-YFSVESETG-NH$_2$ (SEQ ID NO:168) and N-Ac-IFNIDSGNG-NH$_2$ (SEQ ID NO:182).

A cadherin-7 CAR sequence may comprise, for example, one or more of the sequences: DEN, IDEN (SEQ ID NO:183), DENT (SEQ ID NO:184), IIDEN (SEQ ID NO:185), IDENT (SEQ ID NO:186), IIDENT (SEQ ID NO:187), DENTG (SEQ ID NO:188), IDENTG (SEQ ID NO:189), IIDENTG (SEQ ID NO:190), FIIDEN (SEQ ID NO:191), FIIDENT (SEQ ID NO:192), FIIDENTG (SEQ ID NO:193), IFIIDEN (SEQ ID NO:194), IFIIDENT (SEQ ID NO:195), IFIIDENTG (SEQ ID NO:196), EPK, EPKT (SEQ ID NO:197), EPKTG (SEQ ID NO:198), VEPK (SEQ ID NO:199), VEPKT (SEQ ID NO:200), VEPKTG (SEQ ID NO:201), SVEPK (SEQ ID NO:202), SVEPKT (SEQ ID NO:203), SVEPKTG (SEQ ID NO:204), FSVEPK (SEQ ID NO:205), FSVEPKT (SEQ ID NO:206), FSVEPKTG (SEQ ID NO:207), YFSVEPK (SEQ ID NO:208), YFSVEPKT (SEQ ID NO:209), YFSVEPKTG (SEQ ID NO:210), DAN, DANS (SEQ ID NO:211), DANSG (SEQ ID NO:212), IDAN (SEQ ID NO:213), IDANS (SEQ ID NO:214), IDANSG (SEQ ID NO:215), NIDAN (SEQ ID NO:216), NIDANS (SEQ ID NO:217), NIDANSG (SEQ ID NO:218), FNIDAN (SEQ ID NO:219), FNIDANS (SEQ ID NO:220), FNIDANSG (SEQ ID NO:221), YFNIDAN (SEQ ID NO:222), YFNIDANS (SEQ ID NO:223) or YFNIDANSG (SEQ ID NO:224). Linear peptides having such sequences may be modified at the N- and/or C-termini, as in the peptides N-Ac-IFIIDENTG-NH$_2$ (SEQ ID NO:196), N-Ac-YFSVEPKTG-NH$_2$ (SEQ ID NO:210) and N-Ac-YFNIDANSG-NH$_2$ (SEQ ID NO:224).

A cadherin-8 CAR sequence may comprise, for example, one or more of the sequences: NDV, INDV (SEQ ID NO:225), NDVT (SEQ ID NO:226), QINDV (SEQ ID NO:227), INDVT (SEQ ID NO:228), QINDVT (SEQ ID NO:229), NDVTG (SEQ ID NO:230), INDVTG (SEQ ID NO:231), QINDVTG (SEQ ID NO:232), FQINDV (SEQ ID NO:233), FQINDVT (SEQ ID NO:234), FQINDVTG (SEQ ID NO:235), IFQINDV (SEQ ID NO:236), IFQINDVT (SEQ ID NO:237), IFQINDVTG (SEQ ID NO:238), EEF, EEFS (SEQ ID NO:239), EEFSG (SEQ ID NO:240), LEEF (SEQ ID NO:241), LEEFS (SEQ ID NO:242), LEEFSG (SEQ ID NO:243), VLEEF (SEQ ID NO:244), VLEEFS (SEQ ID NO:245), VLEEFSG (SEQ ID NO:247), FVLEEF (SEQ ID NO:247), FVLEEFS (SEQ ID NO:248), FVLEEFSG (SEQ ID NO:249), MFVLEEF (SEQ ID NO:250), MFVLEEFS (SEQ ID NO:251) or MFVLEEFSG (SEQ ID NO:252). Linear peptides having such sequences may be modified at the N- and/or C-termini, as in the peptides N-Ac-MFVLEEFSG-NH$_2$ (SEQ ID NO:252) and N-Ac-IFQINDVT-NH$_2$ (SEQ ID NO:238).

A cadherin-12 CAR sequence may comprise, for example, one or more of the sequences: DET, IDET (SEQ ID NO:253), DETT (SEQ ID NO:254), TIDET (SEQ ID NO:255), IDETT (SEQ ID NO:256), TIDETT (SEQ ID NO:257), DETTG (SEQ ID NO:258), IDETTG (SEQ ID NO:259), TIDETT (SEQ ID NO:260), FTIDET (SEQ ID NO:261), FTIDETT (SEQ ID NO:262), FTIDETTG (SEQ ID NO:263), VFTIDET (SEQ ID NO:264), VFTIDETT (SEQ ID NO:265), VFTIDETTG (SEQ ID NO:266), DPK, DPKT (SEQ ID NO:267), DPKTG (SEQ ID NO:268), IDPK (SEQ ID NO:269), IDPKT (SEQ ID NO:270), IDPKTG (SEQ ID NO:271), SIDPK (SEQ ID NO:272), SIDPKT (SEQ ID NO:273), SIDPKTG (SEQ ID NO:274), FSIDPK (SEQ ID NO:275), FSIDPKT (SEQ ID NO:276), FSIDPKTG (SEQ ID NO:277), YFSIDPK (SEQ ID NO:278), YFSIDPKT (SEQ ID NO:279) or YFSIDPKTG (SEQ ID NO:280). Linear peptides having such sequences may be modified at the N- and/or C-termini, as in the peptides N-Ac-VFTIDETTG-NH$_2$ (SEQ ID NO:266) and N-Ac-YFSIDPKTG-NH$_2$ (SEQ ID NO:280).

A cadherin-14 CAR sequence may comprise, for example, one or more of the sequences: DDT, IDDT (SEQ ID NO:281), DDTT (SEQ ID NO:282), IIDDT (SEQ ID NO:283), IDDTT (SEQ ID NO:284), IIDDTT (SEQ ID NO:285), DDTTG (SEQ ID NO:286), IDDTTG (SEQ ID NO:287), IIDDTTG (SEQ ID NO:288), FIIDDT (SEQ ID NO:289), FIIDDTT (SEQ ID NO:290), FIIDDTTG (SEQ ID NO:291), IFIIDDT (SEQ ID NO:292), IFIIDDTT (SEQ ID NO:293), IFIIDDTTG (SEQ ID NO:294), DPK, DPKT (SEQ ID NO:295), DPKTG (SEQ ID NO:296), VDPK (SEQ ID NO:297), VDPKT (SEQ ID NO:298), VDPKTG (SEQ ID NO:299), SVDPK (SEQ ID NO:300), SVDPKT (SEQ ID NO:301), SVDPKTG (SEQ ID NO:302), FSVDPK (SEQ ID NO:303), FSVDPKT (SEQ ID NO:304), FSVDPKTG (SEQ ID NO:305), YFSVDPK (SEQ ID NO:306), YFSVDPKT (SEQ ID NO:307), YFSVDPKTG (SEQ ID NO:308), DAN, DANT (SEQ ID NO:309), DANTG (SEQ ID NO:310), IDANT (SEQ ID NO:311), IDANTG (SEQ ID NO:312), NIDANT (SEQ ID NO:313), NIDANTG (SEQ ID NO:314), FNIDANT (SEQ ID NO:315), FNIDANTG (SEQ ID NO:316), FFNIDAN (SEQ ID NO:317), FFNIDANT (SEQ ID NO:318) or FFNIDANTG (SEQ ID NO:319). Linear peptides having such sequences may be modified at the N- and/or C-termini, as in the peptides N-Ac-IFIIDDTTG-NH$_2$ (SEQ ID NO:294), N-Ac-YFSVDPKTG-NH$_2$ (SEQ ID NO:308) and N-Ac-FFNIDANTG-NH$_2$ (SEQ ID NO:319).

A cadherin-15 CAR sequence may comprise, for example, one or more of the sequences: DKF, IDKF (SEQ ID NO:320), DKFT (SEQ ID NO:321), SIDKF (SEQ ID NO:322), IDKFT (SEQ ID NO:323), SIDKFT (SEQ ID NO:324), DKFTG (SEQ ID NO:325), IDKFTG (SEQ ID NO:326), SIDKFTG (SEQ ID NO:327), FSIDKF (SEQ ID NO:328), FSIDKFT (SEQ ID NO:329), FSIDKFTG (SEQ ID NO:330), VFSIDKF (SEQ ID NO:331), VFSIDKFT (SEQ ID NO:332), VFSIDKFTG (SEQ ID NO:333), DEL, DELT (SEQ ID NO:334), DELTG (SEQ ID NO:335), IDEL (SEQ ID NO:336), IDELT (SEQ ID NO:337), IDELTG (SEQ ID NO:338), SIDEL (SEQ ID NO:339), SIDELT (SEQ ID NO:340), SIDELTG (SEQ ID NO:341), FSIDEL (SEQ ID NO:342), FSIDELT (SEQ ID NO:343), FSIDELTG (SEQ ID NO:344), LFSIDEL (SEQ ID NO:345), LFSIDELT (SEQ ID NO:346) or LFSIDELTG (SEQ ID NO:347). Linear peptides having such sequences may be modified at the N- and/or C-termini, as in the peptides N-Ac-VFSIDKFTG-NH$_2$ (SEQ ID NO:333) and N-Ac-LFSIDELTG-NH$_2$ (SEQ ID NO:347).

A T-cadherin CAR sequence may comprise, for example, one or more of the sequences: NEN, INEN (SEQ ID NO:348), NENT (SEQ ID NO:349), RINEN (SEQ ID NO:350), INENT (SEQ ID NO:351), RINENT (SEQ ID NO:352), NENTG (SEQ ID NO:353), INENTG (SEQ ID NO:354), RINENTG (SEQ ID NO:355), FRINEN (SEQ ID NO:356), FRINENT (SEQ ID NO:357), FRINENTG (SEQ ID NO:358), IFRINEN (SEQ ID NO:359), IFRINENT (SEQ ID NO:360) or IFRINENTG (SEQ ID NO:361). Linear peptides having such sequences may be modified at the N- and/or C-termini, as in the peptide N-Ac-IFRINENTG-NH$_2$ (SEQ ID NO:361).

A PB-cadherin CAR sequence may comprise, for example, one or more of the sequences: EEY, EEYT (SEQ ID NO:362), EEYTG (SEQ ID NO:363), VEEY (SEQ ID NO:364), VEEYT (SEQ ID NO:365), VEEYTG (SEQ ID NO:366), VVEEY (SEQ ID NO:367), VVEEYT (SEQ ID NO:368), VVEEYTG (SEQ ID NO:369), FVVEEY (SEQ ID NO:370), FVEEYT (SEQ ID NO:371), FVEEYTG (SEQ ID NO:372), FFVVEEY (SEQ ID NO:373), FFVVEEYT (SEQ ID NO:374), FFVVEEYTG (SEQ ID NO:375), DEL, DELT (SEQ ID NO:376), DELTG (SEQ ID NO:377), IDEL (SEQ ID NO:378), IDELT (SEQ ID NO:379), IDELTG (SEQ ID NO:380), LIDEL (SEQ ID NO:381), LIDELT (SEQ ID NO:382), LIDELTG (SEQ ID NO:383), FLIDEL (SEQ ID NO:384), FLIDELT (SEQ ID NO:385), FLIDELTG (SEQ ID NO:386), IFLIDEL (SEQ ID NO:387), IFLIDELT (SEQ ID NO:388), IFLIDELTG (SEQ ID NO:389), DPK, DPKT (SEQ ID NO:390), DPKTG (SEQ ID NO:391), VDPK (SEQ ID NO:392), VDPKT (SEQ ID NO:393), VDPKTG (SEQ ID NO:394), TVDPK (SEQ ID NO:395), TVDPKT (SEQ ID NO:396), TVDPKTG (SEQ ID NO:397), FTVDPK (SEQ ID NO:398), FTVDPKT (SEQ ID NO:399), FTVDPKTG (SEQ ID NO:400), HFTVDPK (SEQ ID NO:401), HFTVDPKT (SEQ ID NO:402), HFTVDPKTG (SEQ ID NO:403), DAD, DADT (SEQ ID NO:404), DADTG (SEQ ID NO:405), IDAD (SEQ ID NO:406), IDADT (SEQ ID NO:407), IDADTG (SEQ ID NO:408), DIDAD (SEQ ID NO:409), DIDADT (SEQ ID NO:410), DIDADTG (SEQ ID NO:411), FDIDAD (SEQ ID NO:412), FDIDADT (SEQ ID NO:413), FDIDADTG (SEQ ID NO:414), IFDIDAD (SEQ ID NO:415), IFDIDADT (SEQ ID NO:416) and IFDIDADTG (SEQ ID NO:417). Linear peptides having such sequences may be modified at the N- and/or C-termini, as in the peptides N-Ac-FFVVEEYTG-NH$_2$ (SEQ ID NO:375), N-Ac-IFLIDELTG-NH$_2$ (SEQ ID NO:389), N-Ac-HFTVDPKTG-NH$_2$ (SEQ ID NO:403) and N-Ac-IFDIDADTG-NH$_2$ (SEQ ID NO:417).

A LI-cadherin CAR sequence may comprise, for example, one or more of the sequences: NNK, NNKT (SEQ ID NO:418), NNKTG (SEQ ID NO:419), INNK (SEQ ID NO:420), INNKT (SEQ ID NO:421), INNKTG (SEQ ID NO:422), QINNK (SEQ ID NO:423), QINNKT (SEQ ID NO:424), QINNKTG (SEQ ID NO:425), FQINNK (SEQ ID NO:426), FQINNKT (SEQ ID NO:427), FQINNKTG (SEQ ID NO:428), YFQINNK (SEQ ID NO:429), YFQINNKT (SEQ ID NO:430) or YFQINNKTG (SEQ ID NO:431). Linear peptides having such sequences may be modified at the N- and/or C-termini, as in the peptide N-Ac-YFQINNKTG-NH$_2$ (SEQ ID NO:431).

A protocadherin CAR sequence may comprise, for example, one or more of the sequences: DLV, DLVT (SEQ ID NO:432), DLVTG (SEQ ID NO:433), LDLV (SEQ ID NO:434), LDLVT (SEQ ID NO:435), LDLVTG (SEQ ID NO:436), ALDLV (SEQ ID NO:437), ALDLVT (SEQ ID NO:438), ALDLVTG (SEQ ID NO:439), FALDLV (SEQ ID NO:440), FALDLVT (SEQ ID NO:441), FALDLVTG (SEQ ID NO:442), LFALDLV (SEQ ID NO:443), LFALDLVT (SEQ ID NO:444), LFALDLVTG (SEQ ID NO:445), NRD, NRDN (SEQ ID NO:446), NRDNG (SEQ ID NO:447), INRD (SEQ ID NO:448), INRDN (SEQ ID NO:449), INRDNG (SEQ ID NO:450), TINRD (SEQ ID NO:451), TINRDN (SEQ ID NO:452), TINRDNG (SEQ ID NO:453), FTINRD (SEQ ID NO:454), FTINRDN (SEQ ID NO:455), FTINRDNG (SEQ ID NO:456), YFTINRD (SEQ ID NO:457), YFTINRDN (SEQ ID NO:458), YFTINRDNG (SEQ ID NO:459), DPK, DPKT (SEQ ID NO:460), DPKTG (SEQ ID NO:461), IDPK (SEQ ID NO:462), IDPKT (SEQ ID NO:463), IDPKTG (SEQ ID NO:464), SIDPK (SEQ ID NO:465), SIDPKT (SEQ ID NO:466), SIDPKTG (SEQ ID NO:467), FSIDPK (SEQ ID NO:468), FSIDPKT (SEQ ID NO:469), FSIDPKTG (SEQ ID NO:470), LFSIDPK (SEQ ID NO:471), LFSIDPKT (SEQ ID NO:472), LFSIDPKTG (SEQ ID NO:473), DPS, DPSS (SEQ ID NO:474), DPSSG (SEQ ID NO:475), IDPS (SEQ ID NO:476), IDPSS (SEQ ID NO:477), IDPSSG (SEQ ID NO:478), EIDPS (SEQ ID NO:479), EIDPSS (SEQ ID NO:480), EIDPSSG (SEQ ID NO:481), FEIDPS (SEQ ID NO:482), FEIDPSS (SEQ ID NO:483), FEIDPS (SEQ ID NO:484), FEIDPSS (SEQ ID NO:485), FEIDPSSG (SEQ ID NO:486), LFEIDPS (SEQ ID NO:487), LFEIDPSS (SEQ ID NO:488) or LFEIDPSSG (SEQ ID NO:489). Linear peptides having such sequences may be modified at the N- and/or C-termini, as in the peptides N-Ac-LFALDLVTG-NH$_2$ (SEQ ID NO:445), N-Ac-YFTINRDNG-NH$_2$ (SEQ ID NO:459), N-Ac-LFSIDPKTG-NH$_2$ (SEQ ID NO:473) and N-Ac-LFEIDPSSG-NH$_2$ (SEQ ID NO:489).

A desmoglein CAR sequence may comprise, for example, one or more of the sequences: NQK, NQKT (SEQ ID NO:490), NQKTG (SEQ ID NO:491), INQK (SEQ ID NO:492), INQKT (SEQ ID NO:493), INQKTG (SEQ ID NO:494), VINQK (SEQ ID NO:495), VINQKT (SEQ ID NO:496), VINQKTG (SEQ ID NO:497), FVINQK (SEQ ID NO:498), FVINQKT (SEQ ID NO:499), FVINQKTG (SEQ ID NO:500), IFVINQK (SEQ ID NO:501), IFVINQKT (SEQ ID NO:502), IFVINQKTG (SEQ ID NO:503), NRN, NRNT (SEQ ID NO:504), NRNTG (SEQ ID NO:505), INRN (SEQ ID NO:506), INRNT (SEQ ID NO:507), INRNTG (SEQ ID NO:508), IINRN (SEQ ID NO:509), IINRNT (SEQ ID NO:510), IINRNTG (SEQ ID NO:511), FIINRN (SEQ ID NO:512), FIINRNT (SEQ ID NO:513), FIINRNTG (SEQ ID NO:514), MFIINRN (SEQ ID NO:515), MFIINRNT (SEQ ID NO:516), MFIINRNTG (SEQ ID NO:517), NKD, NKDT (SEQ ID NO:518), NKDTG (SEQ ID NO:519), LNKD (SEQ ID NO:520), LNKDT (SEQ ID NO:521), LNKDTG (SEQ ID NO:522), YLNKD (SEQ ID NO:523), YLNKDT (SEQ ID NO:524), YLNKDTG (SEQ ID NO:525), FYLNKD (SEQ ID NO:526), FYLNKDT (SEQ ID NO:527), FYLNKDTG (SEQ ID NO:528), VFYLNKD (SEQ ID NO:529), VFYLNKDT (SEQ ID NO:530) or VFYLNKDTG (SEQ ID NO:531). Linear peptides having such sequences may be modified at the N- and/or C-termini, as in the peptides N-Ac-IFVINQKTG-NH$_2$ (SEQ ID NO:503), N-Ac-MFIINRNTG-NH$_2$ (SEQ ID NO:517) and N-Ac-VFYLNKDTG-NH$_2$ (SEQ ID NO:531).

A desmocollin CAR sequence may comprise, for example, one or more of the sequences EKD, EKDT (SEQ ID NO:532), EKDTG (SEQ ID NO:533), IEKD (SEQ ID NO:534), IEKDT (SEQ ID NO:535), IEKDTG (SEQ ID NO:536), YIEKD (SEQ ID NO:537), YIEKDT (SEQ ID NO:538), YIEKDTG (SEQ ID NO:539), FYIEKD (SEQ ID NO:540), FYIEKDT (SEQ ID NO:541), FYIEKDTG (SEQ ID NO:542), LFYIEKD (SEQ ID NO:543), LFYIEKDT (SEQ ID NO:544), LFYIEKDTG (SEQ ID NO:545), ERD, ERDT (SEQ ID NO:546), ERDTG (SEQ ID NO:547), VERD (SEQ ID NO:548), VERDT (SEQ ID NO:549), VERDTG (SEQ ID NO:550), YVERD (SEQ ID NO:551), YVERDT (SEQ ID NO:552), YVERDTG (SEQ ID NO:553), FYVERD (SEQ ID NO:554), FYVERDT (SEQ ID NO:555), FYVERDTG (SEQ ID NO:556), LFYVERD (SEQ ID NO:557), LFYVERDT (SEQ ID NO:558), LFYVERDTG (SEQ ID NO:559), IERD (SEQ ID NO:560), IERDT (SEQ ID NO:561), IERDTG (SEQ ID NO:562), YIERD (SEQ ID NO:563), YIERDT (SEQ ID NO:564), YIERDTG (SEQ ID NO:565), FYIERD (SEQ ID NO:566), FYIERDT (SEQ ID NO:567), FYIERDTG (SEQ ID NO:568), LFYIERD (SEQ ID NO:569), LFYIERDT (SEQ ID NO:570) or LFYIERDTG (SEQ ID NO:571). Linear peptides having such sequences may be modified at the N- and/or C-termini, as in the peptides N-Ac-LFYIEKDTG-NH$_2$ (SEQ ID NO:545), N-Ac-LFYVERDTG-NH$_2$ (SEQ ID NO:559) and N-Ac-LFYIERDTG-NH$_2$ (SEQ ID NO:571).

A cadherin-related neuronal receptor (cnr) CAR sequence may comprise, for example, one or more of the sequences: DPV, DPVS (SEQ ID NO:572), DPVSG (SEQ ID NO:573), IDPV (SEQ ID NO:574), IDPVS (SEQ ID NO:575), IDPVSG (SEQ ID NO:576), HIDPV (SEQ ID NO:577), HIDPVS (SEQ ID NO:578), HIDPVSG (SEQ ID NO:579), FHIDPV (SEQ ID NO:580), FHIDPVS (SEQ ID NO:581), FHIDPVSG (SEQ ID NO:582), KFHIDPV (SEQ ID NO:583), KFHIDPVS (SEQ ID NO:584), KFHIDPVSG (SEQ ID NO:585) DAD, DADT (SEQ ID NO:586), DADTG (SEQ ID NO:587), IDAD (SEQ ID NO:588), IDADT (SEQ ID NO:589), IDADTG (SEQ ID NO:590), SIDAD (SEQ ID NO:591), SIDADT (SEQ ID NO:592), SIDADTG (SEQ ID NO:593), FSIDAD (SEQ ID NO:594), FSIDADT (SEQ ID NO:595), FSIDADTG (SEQ ID NO:596), QFSIDAD (SEQ ID NO:597), QFSIDADT (SEQ ID NO:598), QFSIDADTG (SEQ ID NO:599), DSV, DSVS (SEQ ID NO:600), DSVSG (SEQ ID NO:601), IDSV (SEQ ID NO:602), IDSVS (SEQ ID NO:603), IDSVSG (SEQ ID NO:604), HIDSV (SEQ ID NO:605), HIDSVS (SEQ ID NO:606), HIDSVSG (SEQ ID NO:607), FHIDSV (SEQ ID NO:608), FHIDSVS (SEQ ID NO:609), FHIDSVSG (SEQ ID NO:610), TFHIDSV (SEQ ID NO:611), TFHIDSVS (SEQ ID NO:612), TFHIDSVSG (SEQ ID NO:613), DSN, DSNS (SEQ ID NO:614), DSNSG (SEQ ID NO:615), IDSN (SEQ ID NO:616), IDSNS (SEQ ID NO:617), IDSNSG (SEQ ID NO:618), NIDSN (SEQ ID NO:619), NIDSNS (SEQ ID NO:620), NIDSNSG (SEQ ID NO:621), FNIDSN (SEQ ID NO:622), FNIDSNS (SEQ ID NO:623), FNIDSNSG (SEQ ID NO:624), AFNIDSN (SEQ ID NO:625), AFNIDSNS (SEQ ID NO:626), AFNIDSNSG (SEQ ID NO:627), DSS, DSSS (SEQ ID NO:628), DSSSG (SEQ ID NO:629), IDSS (SEQ ID NO:630), IDSSS (SEQ ID NO:631), IDSSSG (SEQ ID NO:632), TIDSS (SEQ ID NO:633), TIDSSS (SEQ ID NO:634), TIDSSSG (SEQ ID NO:635), FTIDSS (SEQ ID NO:636), FTIDSSS (SEQ ID NO:637), FTIDSSSG (SEQ ID NO:638), KFTIDSS (SEQ ID NO:639), KFTIDSSS (SEQ ID NO:640), KFTIDSSSG (SEQ ID NO:641), DEK, DEKN (SEQ ID NO:642), DEKNG (SEQ ID NO:643), LDEK (SEQ ID NO:644), LDEKN (SEQ ID NO:645), LDEKNG (SEQ ID NO:646), TLDEK (SEQ ID NO:647), TLDEKN (SEQ ID NO:648), TLDEKNG (SEQ ID NO:649), FTDEK (SEQ ID NO:650), FTLDEKN (SEQ ID NO:651), FTLDEKNG (SEQ ID NO:652), LFTLDEK (SEQ ID NO:653), LFTLDEKN (SEQ ID NO:654), LFTLDEKNG (SEQ ID NO:655), NEK, NEKT (SEQ ID NO:656), NEKTG (SEQ ID NO:657), INEK (SEQ ID NO:658), INEKT (SEQ ID NO:659), INEKTG (SEQ ID NO:660), LINEK (SEQ ID NO:661), LINEKT (SEQ ID NO:662), LINEKTG (SEQ ID NO:663), FLINEK (SEQ ID NO:664), FLINEKT (SEQ ID NO:665), FLINEKTG (SEQ ID NO:666), KFLINEK (SEQ ID NO:667), KFLINEKT (SEQ ID NO:668) or KFLINEKTG (SEQ ID NO:4052). Linear peptides having such sequences may be modified at the N- and/or C-termini, as in the peptides N-Ac-KFHIDPVSG-NH$_2$ (SEQ ID NO:585), N-Ac-QFSIDADTG-NH$_2$ (SEQ ID NO:599), N-Ac-TFHIDSVSG-NH$_2$ (SEQ ID NO:613), N-Ac-AFNIDSNSG-NH$_2$ (SEQ ID NO:627), N-Ac-KFTIDSSSG-NH$_2$ (SEQ ID NO:641), N-Ac-LFTLDEKNG-NH$_2$ (SEQ ID NO:655) and N-Ac-KFLINEKTG-NH$_2$ (SEQ ID NO:4052).

Those of ordinary skill in the art will recognize that similar peptide sequences may be designed to modulate a function mediated by other cadherins, following identification of a CAR sequence as described herein.

It will be apparent that certain of the peptide sequences provided above may modulate a function mediated by multiple nonclassical cadherins. In general, peptides comprising a greater number of consecutive residues derived from a particular nonclassical cadherin have a greater specificity for that cadherin. In addition, further flanking sequences may be included to enhance specificity. Such flanking sequences may be identified based on the sequences provided in FIG. 2, or based on published sequences. To achieve specificity (i.e., modulation of a particular nonclassical cadherin function that is enhanced relative to the modulation of a function mediated by a different cadherin), the addition of 2 to 5 flanking residues (preferably at least one residue on either side of the CAR sequence) is generally sufficient. Specificity may be evaluated using assays for the ability to inhibit functions mediated by particular cadherins, as described herein.

As noted above, modulating agents as described herein may comprise an analogue or mimetic of a nonclassical cadherin CAR sequence. An analogue generally retains at least 50% identity to a native nonclassical cadherin CAR sequence, and modulates a nonclassical cadherin-mediated function as described herein. Such analogues preferably contain at least three consecutive residues of, and more preferably at least five consecutive residues of, a nonclassical cadherin CAR sequence. An analogue may contain any of a variety of amino acid substitutions, additions, deletions and/or modifications (e.g., side chain modifications). Preferred amino acid substitutions are conservative. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. The critical determining feature of a nonclassical cadherin CAR sequence analogue is the ability to modulate a nonclassical cadherin-mediated function, which may be evaluated using the representative assays provided herein.

A mimetic is a non-peptidyl compound that is conformationally similar to a nonclassical cadherin CAR sequence, such that it modulates a nonclassical cadherin-mediated function as described below. Such mimetics may be designed based on techniques that evaluate the three dimensional structure of the peptide. For example, Nuclear Magnetic Resonance spectroscopy (NMR) and computational techniques may be used to determine the conformation of a nonclassical cadherin CAR sequence. NMR is widely used for structural analyses of both peptidyl and non-peptidyl compounds. Nuclear Overhauser Enhancements (NOE's), coupling constants and chemical shifts depend on the conformation of a compound. NOE data provides the interproton distance between protons through space and can be used to calculate the lowest energy conformation for the nonclassical cadherin CAR sequence. This information can then be used to design mimetics of the preferred conformation. Linear peptides in solution exist in many conformations. By using conformational restriction techniques it is possible to fix the peptide in the active conformation. Conformational restriction can be achieved by i) introduction of an alkyl group such as a methyl which sterically restricts free bond rotation; ii) introduction of unsaturation which fixes the relative positions of the terminal and geminal substituents; and/or iii) cyclization, which fixes the relative positions of the sidechains. Mimetics may be synthesized where one or more of the amide linkages has been replaced by isosteres, substituents or groups which have the same size or volume such as —$CH_2NH$—, —CSNH—, —$CH_2S$—, —CH=CH—, —$CH_2CH_2$—, —CONMe— and others. These backbone amide linkages can also be part of a ring structure (e.g., lactam). Mimetics may be designed where one or more of the side chain functionalities of the nonclassical cadherin CAR sequence are replaced by groups that do not necessarily have the same size or volume, but have similar chemical and/or physical properties which produce similar biological responses. Other mimetics may be small molecule mimics, which may be readily identified from small molecule libraries, based on the three-dimensional structure of the CAR sequence. It should be understood that, within embodiments described below, an analogue or mimetic may be substituted for a nonclassical cadherin CAR sequence.

Modulating agents, or peptide portions thereof, may be linear or cyclic peptides. The term "cyclic peptide," as used herein, refers to a peptide or salt thereof that comprises (1) an intramolecular covalent bond between two non-adjacent residues and (2) at least one nonclassical cadherin CAR sequence or an analogue thereof. The intramolecular bond may be a backbone to backbone, side-chain to backbone or side-chain to side-chain bond (i.e., terminal functional groups of a linear peptide and/or side chain functional groups of a terminal or interior residue may be linked to achieve cyclization). Preferred intramolecular bonds include, but are not limited to, disulfide, amide and thioether bonds. One or more of any of the above nonclassical cadherin CAR sequences, or an analogue or mimetic thereof, may be incorporated into a cyclic peptide, with or without one or more other adhesion molecule binding sites. Additional adhesion molecule binding sites are described in greater detail below.

The size of a cyclic peptide ring generally ranges from 5 to about 15 residues, preferably from 5 to 10 residues. Additional residue(s) may be present on the N-terminal and/or C-terminal side of a nonclassical cadherin CAR sequence, and may be derived from sequences that flank a nonclassical cadherin CAR sequence, with or without amino acid substitutions and/or other modifications. Alternatively, additional residues present on one or both sides of the CAR sequence(s) may be unrelated to an endogenous sequence (e.g., residues that facilitate cyclization, purification or other manipulation and/or residues having a targeting or other function).

Within certain embodiments, a modulating agent may comprise a cyclic peptide that contains a nonclassical cadherin CAR sequence as provided in Table I (or a portion of such a CAR sequence). Certain cyclic peptides have the formula:

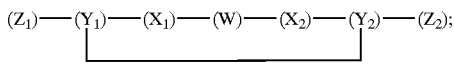

Within this formula, W is a tripeptide selected from the group consisting of EEY, DDK, EAQ, DAE, NEN, ESE, DSG, DEN, EPK, DAN, EEF, NDV, DET, DPK, DDT, DAN, DKF, DEL, DAD, NNK, DLV, NRD, DPS, NQK, NRN, NKD, EKD, ERD, DPV, DSV, DLY, DSN, DSS, DEK and NEK; $X_1$ and $X_2$ are optional, and if present, are independently selected from the group consisting of amino acid residues and combinations thereof in which the residues are linked by peptide bonds, and wherein $X_1$ and $X_2$ independently range in size from 0 to 10 residues, such that the sum of residues contained within $X_1$ and $X_2$ ranges from 1 to 12; $Y_1$ and $Y_2$ are independently selected from the group consisting of amino acid residues, and wherein a covalent bond is formed between residues $Y_1$ and $Y_2$; and $Z_1$ and $Z_2$ are optional, and if present, are independently selected from the group consisting of amino acid residues and combinations thereof in which the residues are linked by peptide bonds.

Cyclic peptides may comprise any of the above CAR sequence(s). Such cyclic peptides may be used as modulating agents without modification, or may be incorporated into a modulating agent.

For example, cyclic peptides may comprise any of the above OB-cadherin CAR sequence(s). Representative cyclic peptides include CDDKC (SEQ ID NO:669), CIDDKC (SEQ ID NO:670), CDDKSC (SEQ ID NO:671), CVIDDKC (SEQ ID NO:672), CIDDKSC (SEQ ID NO:673), CVIDDKSC (SEQ ID NO:674), CDDKSGC (SEQ ID NO:675), CIDDKSGC (SEQ ID NO:676), CVIDDKSGC (SEQ ID NO:677), CFVIDDKC (SEQ ID NO:678), CFVIDDKSC (SEQ ID NO:679), CFVIDDKSGC (SEQ ID NO:680), CIFVIDDKC (SEQ ID NO:681), CIFVIDDKSC (SEQ ID NO:682), CIFVIDDKSGC (SEQ ID NO:683), DDDKK (SEQ ID NO:684), DIDDKK (SEQ ID NO:685), DVIDDKK (SEQ ID NO:686), DFVIDDKK (SEQ ID NO:687), DIFVIDDKK (SEQ ID NO:688), EDDKK (SEQ ID NO:689), EIDDKK (SEQ ID NO:690), EVIDDKK (SEQ ID NO:691), EFVIDDKK (SEQ ID NO:692), EIFVIDDKK (SEQ ID NO:693), FVIDDK (SEQ ID NO:694), FVIDDKS (SEQ ID NO:695), FVIDDKSG (SEQ ID NO:696), KDDKD (SEQ ID NO:697), KIDDKD (SEQ ID NO:698), KDDKSD (SEQ ID NO:699), KVIDDKD (SEQ ID NO:700), KIDDKSD (SEQ ID NO:701), KVIDDKSD (SEQ ID NO:702), KDDKSGD (SEQ ID NO:703), KIDDKSGD (SEQ ID NO:704), KVIDDKSGD (SEQ ID NO:705), KFVIDDKD (SEQ ID NO:706), KFVIDDKSD (SEQ ID NO:707), KFVIDDKSGD (SEQ ID NO:708), KIFVIDDKD (SEQ ID NO:709), KIFVIDDKSD (SEQ ID NO:710), KIFVIDDKSGD (SEQ ID NO:711), VIDDK (SEQ ID NO:712), IDDKS (SEQ ID NO:713), VIDDKS (SEQ ID NO:714), VIDDKSG (SEQ ID NO:715), DDKSG (SEQ ID NO:716), IDDKSG (SEQ ID NO:717), IFVIDDK (SEQ ID NO:718), IFVIDDKS (SEQ ID NO:719), IFVIDDKSG (SEQ ID NO:720), KDDKE (SEQ ID NO:721), KIDDKE (SEQ ID NO:722), KDDKSE (SEQ ID NO:723), KVIDDKE (SEQ ID NO:724), KIDDKSE (SEQ ID NO:725), KVIDDKSE (SEQ ID NO:726), KDDKSGE (SEQ ID NO:727), KIDDKSGE (SEQ ID NO:728), KVIDDKSGE (SEQ ID NO:729), KFVIDDKE (SEQ ID NO:730), KFVIDDKSE (SEQ ID NO:731), KFVIDDKSGE (SEQ ID NO:732), KIFVIDDKE (SEQ ID NO:733), KIFVIDDKSE (SEQ ID NO:734), KIFVIDDKSGE (SEQ ID NO:735), CEEYC (SEQ ID NO:736), CIEEYC (SEQ ID NO:737), CEEYTC (SEQ ID NO:738), CVIEEYC (SEQ ID NO:739), CIEEYTC (SEQ ID NO:740), CVIEEYTC (SEQ ID NO:741), CEEYTGC (SEQ ID NO:742), CIEEYTGC (SEQ ID NO:743), CVIEEYTGC (SEQ ID NO:744), CFVIEEYC (SEQ ID NO:745), CFVIEEYTC (SEQ ID NO:746), CFVIEEYTGC (SEQ ID NO:747), CFFVIEEYC (SEQ ID NO:748), CFFVIEEYTC (SEQ ID NO:749), CFFVIEEYTGC (SEQ ID NO:750), KEEYD (SEQ ID NO:751), KIEEYD (SEQ ID NO:752), KEEYTD (SEQ ID NO:753), KVIEEYD (SEQ ID NO:754), KIEEYTD (SEQ ID NO:755), KVIEEYTD (SEQ ID NO:756), KEEYTGCD (SEQ ID NO:757), KIEEYTGD (SEQ ID NO:758), KVIEEYTGD (SEQ ID NO:759), KFVIEEYD (SEQ ID NO:760), KFVIEEYTD (SEQ ID NO:761), KFVIEEYTGD (SEQ ID NO:762), KFFVIEEYD (SEQ ID NO:763), KFFVIEEYTD (SEQ ID NO:764), KFFVIEEYTGD (SEQ ID NO:765), EEEYK (SEQ ID NO:766), EIEEYK (SEQ ID NO:767), EEEYTK (SEQ ID NO:768), EVIEEYK (SEQ ID NO:769), EIEEYTK (SEQ ID NO:770), EVIEEYTK (SEQ ID NO:771), EEEYTGK (SEQ ID NO:772), EIEEYTGK (SEQ ID NO:773), EVIEEYTGK (SEQ ID NO:774), EFVIEEYK (SEQ ID NO:775), EFVIEEYTK (SEQ ID NO:776), EFVIEEYTGK (SEQ ID NO:777), EFFVIEEYK (SEQ ID NO:778), EFFVIEEYTK (SEQ ID NO:779), EFFVIEEYTGK (SEQ ID NO:780), DCEEYK (SEQ ID NO:781), DIEEYCK (SEQ ID NO:782), DEEYTK (SEQ ID NO:783), DVIEEYK (SEQ ID NO:784), DIEEYTK (SEQ ID NO:785), DVIEEYTK (SEQ ID NO:786), DEEYTGK (SEQ ID NO:787), DIEEYTGK (SEQ ID NO:788), DVIEEYTGK (SEQ ID NO:789), DFVIEEYK (SEQ ID NO:790), DFVIEEYTK (SEQ ID NO:791), DFVIEEYTGK (SEQ ID NO:792), DFFVIEEYK (SEQ ID NO:793), DFFVIEEYTK (SEQ ID NO:794), DFFVIEEYTGK (SEQ ID NO:795), KEEYE (SEQ ID NO:796), KIEEYE (SEQ ID NO:797), KEEYTE (SEQ ID NO:798), KVIEEYE (SEQ ID NO:799), KIEEYTE (SEQ ID NO:800), KVIEEYTE (SEQ ID NO:801), KEEYTGE (SEQ ID NO:802), KIEEYTGE (SEQ ID NO:803), KVIEEYTGE (SEQ ID NO:804), KFVIEEYE (SEQ ID NO:805), KFVIEEYTE (SEQ ID NO:806), KFVIEEYTGE (SEQ ID NO:807), KFFVIEEYE (SEQ ID NO:808), KFFVIEEYTE (SEQ ID NO:809), KFFVIEEYTGE (SEQ ID NO:810), VIEEY (SEQ ID NO:811), IEEYT (SEQ ID NO:812), VIEEYT (SEQ ID NO:813), EEYTG (SEQ ID NO:814), IEEYTG (SEQ ID NO:815), VIEEYTG (SEQ ID NO:816), FVIEEY (SEQ ID NO:817), FVIEEYT (SEQ ID NO:818), FVIEEYTG (SEQ ID NO:819), FFVIEEY (SEQ ID NO:820), FFVIEEYT (SEQ ID NO:821), FFVIEEYTG (SEQ ID NO:822), CEAQC (SEQ ID NO:823), CVEAQC (SEQ ID NO:824), CEAQTC (SEQ ID NO:825), CSVEAQC (SEQ ID NO:826), CVEAQTC (SEQ ID NO:827), CSVEAQTC (SEQ ID NO:828), CEAQTGC (SEQ ID NO:829), CVEAQTGC (SEQ ID NO:830), CSVEAQTGC (SEQ ID NO:831), CFSVEAQC (SEQ ID NO:832), CFSVEAQTC (SEQ ID NO:833), CFSVEAQTGC (SEQ ID NO:834), CYFSVEAQC (SEQ ID NO:835), CYFSVEAQTC (SEQ ID NO:836), CYFSVEAQTGC (SEQ ID NO:837), KEAQD (SEQ ID NO:838), KVEAQD (SEQ ID NO:839), KEAQTD (SEQ ID NO:840), KSVEAQD (SEQ ID NO:841), KVEAQTD (SEQ ID NO:842), KSVEAQTD (SEQ ID NO:843), KEAQTGD (SEQ ID NO:844), KVEAQTGD (SEQ ID NO:845), KSVEAQTGD (SEQ ID NO:846), KFSVEAQD (SEQ ID NO:847), KFSVEAQTD (SEQ ID NO:848), KFSVEAQTGD (SEQ ID NO:849), KYFSVEAQD (SEQ ID NO:850), KYFSVEAQTD (SEQ ID NO:851), KYFSVEAQTGD (SEQ ID NO:852), EEAQK (SEQ ID NO:853), EVEAQK (SEQ ID NO:854), EEAQTK (SEQ ID NO:855), ESVEAQK (SEQ ID NO:856), EVEAQTK (SEQ ID NO:857), ESVEAQTK (SEQ ID NO:858), EEAQTGK (SEQ ID NO:859), EVEAQTGK (SEQ ID NO:860), ESVEAQTGK (SEQ ID NO:861), EFSVEAQK (SEQ ID NO:862), EFSVEAQTK (SEQ ID NO:863), EFSVEAQTGK (SEQ ID NO:864), EYFSVEAQK (SEQ ID NO:865), EYFSVEAQTK (SEQ ID NO:866), EYFSVEAQTGK (SEQ ID NO:867), DEAQK (SEQ ID NO:868), DVEAQK (SEQ ID NO:869), DEAQTK (SEQ ID NO:870), DSVEAQK (SEQ ID NO:871), DVEAQTK (SEQ ID NO:872), DSVEAQTK (SEQ ID NO:873), DEAQTGK (SEQ ID NO:874), DVEAQTGK (SEQ ID NO:875), DSVEAQTGK (SEQ ID NO:876), DFSVEAQK (SEQ ID NO:877), DFSVEAQTK (SEQ ID NO:878), DFSVEAQTGK (SEQ ID NO:879), DYFSVEAQK (SEQ ID NO:880), DYFSVEAQTK (SEQ ID NO:881), DYFSVEAQTGK (SEQ ID NO:882), KEAQE (SEQ ID NO:883), KVEAQE (SEQ ID NO:884), KEAQTE (SEQ ID NO:885), KSVEAQE (SEQ ID NO:886), KVEAQTE (SEQ ID NO:887), KSVEAQTE (SEQ ID NO:888), KEAQTGE (SEQ ID NO:889), KVEAQTGE (SEQ ID NO:890), KSVEAQTGE (SEQ ID NO:891), KFSVEAQE (SEQ ID NO:892), KFSVEAQTE (SEQ ID NO:893), KFSVEAQTGE (SEQ ID NO:894), KYFSVEAQE (SEQ ID NO:895), KYFSVEAQTE (SEQ ID NO:896), KYFSVEAQTGE (SEQ ID NO:897), SVEAQ (SEQ ID NO:898), VEAQT (SEQ ID NO:899), SVEAQT (SEQ ID NO:900), EAQTG (SEQ ID NO:901), VEAQTG (SEQ ID NO:902), SVEAQTG (SEQ ID NO:903), FSVEAQ (SEQ ID NO:904), FSVEAQT (SEQ ID NO:905), FSVEAQTG (SEQ ID NO:906), YFSVEAQ (SEQ ID NO:907), YFSVEAQT (SEQ ID NO:908) and YFSVEAQTG (SEQ ID NO:909). Within the context of the present invention, underlined sequences are cyclized using any suitable method, as described herein.

Similarly, cyclic peptides may comprise any of the above cadherin-5 CAR sequence(s). Representative cyclic peptides include: CDAEC (SEQ ID NO:910), CVDAEC (SEQ ID NO:911), CDAETC (SEQ ID NO:912), CRVDAEC (SEQ ID NO:913), CVDAETC (SEQ ID NO:914), CRVDAETC (SEQ ID NO:915), CDAETGC (SEQ ID NO:916), CCDAETGC (SEQ ID NO:917), CRVDAETGC (SEQ ID NO:918), CFRVDAEC (SEQ ID NO:919), CFRVDAETC (SEQ ID NO:920), CFRVDAETGC (SEQ ID NO:921), CVFRVDAEC (SEQ ID NO:922), CVFRVDAETC (SEQ ID NO:923), CVFRVDAETGC (SEQ ID NO:924), DDAEK (SEQ ID NO:925), DVDAEK (SEQ ID NO:926), DRVDAEK (SEQ ID NO:927), DFRVDAEK (SEQ ID NO:928), DVFRVDAEK (SEQ ID NO:929), EDAEK (SEQ ID NO:930), EVDAEK (SEQ ID NO:931), ERVDAEK (SEQ ID NO:932), EFRVDAEK (SEQ ID NO:933), EVFRVDAEK (SEQ ID NO:934), KDAED (SEQ ID NO:935), KVDAED (SEQ ID NO:936), KDAETD (SEQ ID NO:937), KRVDAED (SEQ ID NO:938), KVDAETD (SEQ ID NO:939), KRVDAETD (SEQ ID NO:940), KDAETGD (SEQ ID NO:941), KVDAETGD (SEQ ID NO:942), KRVDAETGD (SEQ ID NO:943), KFRVDAED (SEQ ID NO:944), KFRVDAETD (SEQ ID NO:945), KFRVDAETGD (SEQ ID NO:946), KVFRVDAED (SEQ ID NO:947), KVFRVDAETD (SEQ ID NO:948), KVFRVDAETGD (SEQ ID NO:949), VDAEK (SEQ ID NO:950), IDAES (SEQ ID NO:951), VDAES (SEQ ID NO:952), DAETG (SEQ ID NO:953), VDAETG (SEQ ID NO:954), KDAEE (SEQ ID NO:955), KVDAE (SEQ ID NO:956), KDAETE (SEQ ID NO:957), KRVDAE (SEQ ID NO:958), KVDAETE (SEQ ID NO:959), KRVDAETE (SEQ ID NO:960), KDAETGE (SEQ ID NO:961), KVDAETGE (SEQ ID NO:962), KRVDAETGE (SEQ ID NO:962), KFRVDAE (SEQ ID NO:964), KFRVDAETE (SEQ ID NO:965), KFRVDAETGE (SEQ ID NO:966), KVFRVDAE (SEQ ID NO:967), KVFRVDAETE (SEQ ID NO:968), KVFRVDAETGE (SEQ ID NO:969), VDAET (SEQ ID NO:970), VDAETG (SEQ ID NO:971), DAETG (SEQ ID NO:972), RVDAE (SEQ ID NO:973), RVDAET (SEQ ID NO:974), RVDAETG (SEQ ID NO:975), FRVDAE (SEQ ID NO:976), FRVDAET (SEQ ID NO:977), FRVDAETG (SEQ ID NO:978), VFRVDAE (SEQ ID NO:979), VFRVDAET (SEQ ID NO:980) and VFRVDAETG (SEQ ID NO:981).

Any cadherin-6 CAR sequence(s) may be formulated into a cyclic peptide. Representative cyclic peptides include: CNENC (SEQ ID NO:983), CINENC (SEQ ID NO:984), CNENTC (SEQ ID NO:985), CIINENC (SEQ ID NO:986), CINENTC (SEQ ID NO:987), CIINENTC (SEQ ID NO:988), CNENTGC (SEQ ID NO:989), CINENTGC (SEQ ID NO:990), CIINENTGC (SEQ ID NO:991), CFIINENC (SEQ ID NO:992), CFIINENTC (SEQ ID NO:993), CFIINENTGC (SEQ ID NO:994), CLFIINENC (SEQ ID NO:995), CLFIINENTC (SEQ ID NO:996), CLFIINENTGC (SEQ ID NO:997), DNENK (SEQ ID NO:998), DINENK (SEQ ID NO:999), DIINENK (SEQ ID NO:1000), DFIINENK (SEQ ID NO:1001), DLFIINENK (SEQ ID NO:1002), DNENTK (SEQ ID NO:982), DINENTK (SEQ ID NO:2883), DIINENTK (SEQ ID NO:2884), DFIINENTK (SEQ ID NO:2885), DLFIINENTK (SEQ ID NO:2946), DNENTGK (SEQ ID NO:2947), DINENTGK (SEQ ID NO:2948), DIINENTGK (SEQ ID NO:3009), DFIINENTGK (SEQ ID NO:3010), DLFIINENTGK (SEQ ID NO:3011), ENENTK (SEQ ID NO:3055), EINENTK (SEQ ID NO:3630), EIINENTK (SEQ ID NO:3736), EFIINENTK (SEQ ID NO:3842), ELFIINENTK (SEQ ID NO:3890), ENENTGK (SEQ ID NO:3891), EINENTGK (SEQ ID NO:3892), EIINENTGK (SEQ ID NO:3893), EFIINENTGK (SEQ ID NO:3894), ELFIINENTGK (SEQ ID NO:3895), ENENK (SEQ ID NO:1003), EINENK (SEQ ID NO:1004), EIINENK (SEQ ID NO:1005), EFIINENK (SEQ ID NO:1006), ELFIINENK (SEQ ID NO:1007), KNEND (SEQ ID NO:1008), KINEND (SEQ ID NO:1009), KNENTD (SEQ ID NO:1010), KIINEND (SEQ ID NO:1011), KINENTD (SEQ ID NO:1012), KIINENTD (SEQ ID NO:1013), KNENTGD (SEQ ID NO:1014), KINENTGD (SEQ ID NO:1015), KIINENTGD (SEQ ID NO:1016), KFIINEND (SEQ ID NO:1017), KFIINENTD (SEQ ID NO:1018), KFIINENTGD (SEQ ID NO:1019), KLFIINEND (SEQ ID NO:1020), KLFIINENTD (SEQ ID NO:1021), KLFIINENTGD (SEQ ID NO:1022), VNENT (SEQ ID NO:1023), INENT (SEQ ID NO:1024), IINENT (SEQ ID NO:1025), NENTG (SEQ ID NO:1026), INENTG (SEQ ID NO:1027), KNENE (SEQ ID NO:1028), KINENE (SEQ ID NO:1029), KNENTE (SEQ ID NO:1030), KIINENE (SEQ ID NO:1031), KINENTE (SEQ ID NO:1032), KIINENTE (SEQ ID NO:1033), KNENTGE (SEQ ID NO:1034), KINENTGE (SEQ ID NO:1035), KIINENTGE (SEQ ID NO:1036), KFIINENE (SEQ ID NO:1037), KFIINENTE (SEQ ID NO:1038), KFIINENTGE (SEQ ID NO:1039), KLFIINENE (SEQ ID NO:1040), KLFIINENTE (SEQ ID NO:1041), KLFIINENTGE (SEQ ID NO:1042), IINEN (SEQ ID NO:1043), FIINEN (SEQ ID NO:1044), FIINENT (SEQ ID NO:1045), FIINENTG (SEQ ID NO:1046), LFIINEN (SEQ ID NO:1047), LFIINENT (SEQ ID NO:1048), LFIINENTG (SEQ ID NO:1049), CEEYC (SEQ ID NO:1050), CEEYTC (SEQ ID NO:1051), CEEYTGC (SEQ ID NO:1052), CLEEYC (SEQ ID NO:1053), CLEEYTC (SEQ ID NO:1054), CLEEYTGC (SEQ ID NO:1055), CLLEEYC (SEQ ID NO:1056), CLLEEYTC (SEQ ID NO:1057), CFLLEEYC (SEQ ID NO:1058), CLLEEYTC (SEQ ID NO:1059), CFLLEEYTGC (SEQ ID NO:1060), CFFLLEEYC (SEQ ID NO:1061), CFFLLEEYTC (SEQ ID NO:1062), CFFLLEEYTGC (SEQ ID NO:1063), CESEC (SEQ ID NO:1064), CESETC (SEQ ID NO:1065), CESETGC (SEQ ID NO:1066), CVESEC (SEQ ID NO:1067), CVSESTC (SEQ ID NO:1068), CVESETGC (SEQ ID NO:1069), CSVESEC (SEQ ID NO:1070), CSVESETC (SEQ ID NO:1071), CSVESETGC (SEQ ID NO:1072), CFSVESEC (SEQ ID NO:1073), CFSVESETC (SEQ ID NO:1074), CFSVESETGC (SEQ ID NO:1075), CYFSVESEC (SEQ ID NO:1076), CYFSVESETC (SEQ ID NO:1077), CYFSVESETGC (SEQ ID NO:1078), CDSGC (SEQ ID NO:1079), CDSGNC (SEQ ID NO:1080), CDSGNGC (SEQ ID NO:1081), CIDSGC (SEQ ID NO:1082), CIDSGNC (SEQ ID NO:1083), CIDSGNGC (SEQ ID NO:1084), CNIDSGC (SEQ ID NO:1085), CNIDSGNC (SEQ ID NO:1086), CNIDSGNGC (SEQ ID NO:1087), CFNIDSGC (SEQ ID NO:1088), CFNIDSGNC (SEQ ID NO:1089), CFNIDSGNGC (SEQ ID NO:1090), CIFNIDSGC (SEQ ID NO:1091), CIFNIDSGNC (SEQ ID NO:1092), CIFNIDSGNGC (SEQ ID NO:1093), KEEYD (SEQ ID NO:1094), KLEEYD (SEQ ID NO:1095), KEEYTD (SEQ ID NO:1096), KEEYTGD (SEQ ID NO:1097), KLEEYTD (SEQ ID NO:1098), KLEEYTGD (SEQ ID NO:1099), KLLEEYD (SEQ ID NO:1100), KLLEEYTGD (SEQ ID NO:1101), KFLLEEYD (SEQ ID NO:1102), KLLEEYTD (SEQ ID NO:1103), KFLLEEYTGD (SEQ ID NO:1104), KFFLLEEYD (SEQ ID NO:1105), KFFLLEEYTD (SEQ ID NO:1106), KFFLLEEYTGD (SEQ ID NO:1107), KESED (SEQ ID NO:1108), KESETD (SEQ ID NO:1109), KESETGD (SEQ ID NO:1110), KVESED (SEQ ID NO:1111), KVSESTD (SEQ ID NO:1112), KVESETGD (SEQ ID NO:1113), KSVESED (SEQ ID NO:1114), KSVESETD (SEQ ID NO:1115), KSVESETGD (SEQ ID NO:1116), KFSVESED (SEQ ID NO:1117), KFSVESETD (SEQ ID NO:1118), KFSVESETGD (SEQ ID NO:1119), KYFSVESED (SEQ ID NO:1120), KYFSVESETD (SEQ ID NO:1121), KYFSVESETGD (SEQ ID NO:1122), KDSGD (SEQ ID NO:1123), KDSGND (SEQ ID NO:1124), KDSGNGD (SEQ ID NO:1125), KIDSGD (SEQ ID NO:1126), KIDSGND (SEQ ID NO:1127), KIDSGNGD (SEQ ID NO:1128), KNIDSGD (SEQ ID NO:1129), KNIDSGND (SEQ ID NO:1130), KNIDSGNGD (SEQ ID NO:1131), KFNIDSGD (SEQ ID NO:1132), KFNIDSGND (SEQ ID NO:1133), KFNIDSGNGD (SEQ ID NO:1134), KIFNIDSGD (SEQ ID NO:1135), KIFNIDSGND (SEQ ID NO:1136), KIFNIDSGNGD (SEQ ID NO:1137), EEEYK (SEQ ID NO:1138), EEEYTK (SEQ ID NO:1139), EEEYTGK (SEQ ID NO:1140), ELEEYK (SEQ ID NO:1141), EEEYTK (SEQ ID NO:1142), ELEEYTGK (SEQ ID NO:1143), ELLEEYK (SEQ ID NO:1144), ELLEEYTGK (SEQ ID NO:1145), EFLLEEYK (SEQ ID NO:1146), ELLEEYTK (SEQ ID NO:1147), EFLLEEYTGK (SEQ ID NO:1148), EFFLLEEYK (SEQ ID NO:1149), EFFLLEEYTK (SEQ ID NO:1150), EFFLLEEYTGK (SEQ ID NO:1151), EESEK (SEQ ID NO:1152), EESETK (SEQ ID NO:1153), EESETGK (SEQ ID NO:1154), EVESEK (SEQ ID NO:1155), EVSESTK (SEQ ID NO:1156), EVESETGK (SEQ ID NO:1157), ESVESEK (SEQ ID NO:1158), ESVESETK (SEQ ID NO:1159), ESVESETGK (SEQ ID NO:1160), EFSVESEK (SEQ ID NO:1161), EFSVESETK (SEQ ID NO:1162), EFSVESETGK (SEQ ID NO:1163), EYFSVESEK (SEQ ID NO:1164), EYFSVESETK (SEQ ID NO:1165), EYFSVESETGK (SEQ ID NO:1166), EDSGK (SEQ ID NO:1167), EDSGNK (SEQ ID NO:1168), EDSGNGK (SEQ ID NO:1169), EIDSGK (SEQ ID NO:1170), EIDSGNK (SEQ ID NO:1171), EIDSGNGK (SEQ ID NO:1172), ENIDSGK (SEQ ID NO:1173), ENIDSGNK (SEQ ID NO:1174), ENIDSGNGK (SEQ ID NO:1175), EFNIDSGK (SEQ ID NO:1176), EFNIDSGNK (SEQ ID NO:1177), EFNIDSGNGK (SEQ ID NO:1178), EIFNIDSGK (SEQ ID NO:1179), EIFNIDSGNK (SEQ ID NO:1180), EIFNIDSGNGK (SEQ ID NO:1181), DEEYK (SEQ ID NO:1182), DLEEYK (SEQ ID NO:1183), DLEEYTK (SEQ ID NO:1184), DLEEYTGK (SEQ ID NO:1185), DLLEEYK (SEQ ID NO:1186), DLLEEYTGK (SEQ ID NO:1187), DFLLEEYK (SEQ ID NO:1188), DLLEEYTK (SEQ ID NO:1189), DFLLEEYTGK (SEQ ID NO:1190), DFFLLEEYK (SEQ ID NO:1191), DFFLLEEYTK (SEQ ID NO:1192), DFFLLEEYTGK (SEQ ID NO:1193), DESEK (SEQ ID NO:1194), DESETK (SEQ ID NO:1195), DESETGK (SEQ ID NO:1196), DVESEK (SEQ ID NO:1197), DVSESTK (SEQ ID NO:1198), DVESETGK (SEQ ID NO:1199), DSVESEK (SEQ ID NO:1200), DSVESETK (SEQ ID NO:1201), DSVESETGK (SEQ ID NO:1202), DFSVESEK (SEQ ID NO:1203), DFSVESETK (SEQ ID NO:1204), DFSVESETGK (SEQ ID NO:1205), DYFSVESEK (SEQ ID NO:1206), DYFSVESETK (SEQ ID NO:1207), DYFSVESETGK (SEQ ID NO:1208), DDSGK (SEQ ID NO:1209), DDSGNK (SEQ ID NO:1210), DDSGNGK (SEQ ID NO:1211), DIDSGK (SEQ ID NO:1212), DIDSGNK (SEQ ID NO:1213), DIDSGNGK (SEQ ID NO:1214), DNIDSGK (SEQ ID NO:1215), DNIDSGNK (SEQ ID NO:1216), DNIDSGNGK (SEQ ID NO:1217), DFNIDSGK (SEQ ID NO:1218), DFNIDSGNK (SEQ ID NO:1219), DFNIDSGNGK (SEQ ID NO:1220), DIFNIDSGK (SEQ ID NO:1221), DIFNIDSGNK (SEQ ID NO:1222), DIFNIDSGNGK (SEQ ID NO:1223), KEEYE (SEQ ID NO:1224), KLEEYE (SEQ ID NO:1225), KLEEYTE (SEQ ID NO:1226), KLEEYTGE (SEQ ID NO:1227), KLLEEYE (SEQ ID NO:1228), KLLEEYTGE (SEQ ID NO:1229), KFLLEEYE (SEQ ID NO:1230), KLLEEYTE (SEQ ID NO:1231), KFLLEEYTGE (SEQ ID NO:1232), KFFLLEEYE (SEQ ID NO:1233), KFFLLEEYTE (SEQ ID NO:1234), KFFLLEEYTGE (SEQ ID NO:1235), KNENE (SEQ ID NO:1236), KNENTE (SEQ ID NO:1237), KINENTGE (SEQ ID NO:1238), KESEE (SEQ ID NO:1239), KESETE (SEQ ID NO:1240), KESETGE (SEQ ID NO:1241), KVESEE (SEQ ID NO:1242) KVSESTE (SEQ ID NO:1243), KVESETGE (SEQ ID NO:1244), KSVESEE (SEQ ID NO:1245), KSVESETE (SEQ ID NO:1246), KSVESETGE (SEQ ID NO:1247), KFSVESEE (SEQ ID NO:1248), KFSVESETE (SEQ ID NO:1249), KFSVESETGE (SEQ ID NO:1250), KYFSVESEE (SEQ ID NO:1251), KYFSVESETE (SEQ ID NO:1252), KYFSVESETGE (SEQ ID NO:1253), KDSGE (SEQ ID NO:1254), KDSGNE (SEQ ID NO:1255), KDSGNGE (SEQ ID NO:1256), KIDSGE (SEQ ID NO:1257), KIDSGNE (SEQ ID NO:1258), KIDSGNGE (SEQ ID NO:1259), KNIDSGE (SEQ ID NO:1260), KNIDSGNE (SEQ ID NO:1261), KNIDSGNGE (SEQ ID NO:1262), KFNIDSGE (SEQ ID NO:1263), KFNIDSGNE (SEQ ID NO:1264), KFNIDSGNGE (SEQ ID NO:1265), KIFNIDSGE (SEQ ID NO:1266), KIFNIDSGNE (SEQ ID NO:1267), KIFNIDSGNGE (SEQ ID NO:1268), LEEYT (SEQ ID NO:1269), LEEYTG (SEQ ID NO:1270), LLEEY (SEQ ID NO:1271), LLEEYTG (SEQ ID NO:1272), FLLEEY (SEQ ID NO:1273), LLEEYT (SEQ ID NO:1274), FLLEEYTG (SEQ ID NO:1275), FFLLEEY (SEQ ID NO:1276), FFLLEEYT (SEQ ID NO:1277), FFLLEEYTG (SEQ ID NO:1278), ESETG (SEQ ID NO:1279), VSEST (SEQ ID NO:1280), VESETG (SEQ ID NO:1281), SVESE (SEQ ID NO:1282), SVESET (SEQ ID NO:1283), SVESETG (SEQ ID NO:1284), FSVESE (SEQ ID NO:1285), FSVESET (SEQ ID NO:1286), FSVESETG (SEQ ID NO:1287), YFSVESE (SEQ ID NO:1288), YFSVESET (SEQ ID NO:1289), YFSVESETG (SEQ ID NO:1290), DSGNG (SEQ ID NO:1291), IDSGN (SEQ ID NO:1292), IDSGNG (SEQ ID NO:1293), NIDSG (SEQ ID NO:1294), NIDSGN (SEQ ID NO:1295), NIDSGNG (SEQ ID NO:1296), FNIDSG (SEQ ID NO:1297), FNIDSGN (SEQ ID NO:1298), FNIDSGNG (SEQ ID NO:1299), IFNIDSG (SEQ ID NO:1300), IFNIDSGN (SEQ ID NO:1301) and IFNIDSGNG (SEQ ID NO:1302).

Representative cyclic peptides comprising a cadherin-7 CAR sequence include: CDENC (SEQ ID NO:1303), CIDENC (SEQ ID NO:1304), CDENTC (SEQ ID NO:1305), CIIDENC (SEQ ID NO:1306), CIDENTC (SEQ ID NO:1307), CIIDENTC (SEQ ID NO:1308), CDENTGC (SEQ ID NO:1309), CIDENTGC (SEQ ID NO:1310), CIIDENTGC (SEQ ID NO:1311), CFIIDENC (SEQ ID NO:1312), CFIIDENTC (SEQ ID NO:1313), CFIIDENTGC (SEQ ID NO:1314), CIFIIDENC (SEQ ID NO:1315), CIFIIDENTC (SEQ ID NO:1316), CIFIIDENTGC (SEQ ID NO:1317), DDENK (SEQ ID NO:1319), DIDENK (SEQ ID NO:1320), DIIDENK (SEQ ID NO:1321), DFIIDENK (SEQ ID NO:1322), DIFIIDENK (SEQ ID NO:1323), DDENTK (SEQ ID NO:1318), DIDENTK (SEQ ID NO:1344), DIIDENTK (SEQ ID NO:3896), DFIIDENTK (SEQ ID NO:3897), DIFIIDENTK (SEQ ID NO:3898), DDENTGK (SEQ ID NO:3899), DIDENTGK (SEQ ID NO:3900), DIIDENTGK (SEQ ID NO:3901), DFIIDENTGK (SEQ ID NO:3902), DIFIIDENTGK (SEQ ID NO:3903), EDENTK (SEQ ID NO:3904), EIDENTK (SEQ ID NO:3905), EIIDENTK (SEQ ID NO:3906), EFIIDENTK (SEQ ID NO:3907), EIFIIDENTK (SEQ ID NO:3908), EDENTGK (SEQ ID NO:3909), EIDENTGK (SEQ ID NO:3910), EIIDENTGK (SEQ ID NO:3911), EFIIDENTGK (SEQ ID NO:3912), EIFIIDENTGK (SEQ ID NO:3913), EDENK (SEQ ID NO:1324), EIDENK (SEQ ID NO:1325), EIIDENK (SEQ ID NO:1326), EFIIDENK (SEQ ID NO:1327), EIFIIDENK (SEQ ID NO:1328), KDEND (SEQ ID NO:1329), KIDEND (SEQ ID NO:1330), KDENTD (SEQ ID NO:1331), KIIDEND (SEQ ID NO:1332), KIDENTD (SEQ ID NO:1333), KIIDENTD (SEQ ID NO:1334), KDENTGD (SEQ ID NO:1335), KIDENTGD (SEQ ID NO:1336), KIIDENTGD (SEQ ID NO:1337), KFIIDEND (SEQ ID NO:1338), KFIIDENTD (SEQ ID NO:1339), KFIIDENTGD (SEQ ID NO:1340), KIFIIDEND (SEQ ID NO:1341), KIFIIDENTD (SEQ ID NO:1342), KIFIIDENTGD (SEQ ID NO:1343), IDENT (SEQ ID NO:1345), IIDENT (SEQ ID NO:1346), DENTG (SEQ ID NO:1347), IDENTG (SEQ ID NO:1348) KDENE (SEQ ID NO:1349), KIDENE (SEQ ID NO:1350), KDENTE (SEQ ID NO:1351), KIIDENE (SEQ ID NO:1352), KIDENTE (SEQ ID NO:1353), KIIDENTE (SEQ ID NO:1354), KDENTGE (SEQ ID NO:1355), KIDENTGE (SEQ ID NO:1356), KIIDENTGE (SEQ ID NO:1357), KFIIDENE (SEQ ID NO:1358), KFIIDENTE (SEQ ID NO:1359), KFIIDENTGE (SEQ ID NO:1360), KIFIIDENE (SEQ ID NO:1361), KIFIIDENTE (SEQ ID NO:1362), KIFIIDENTGE (SEQ ID NO:1363), DDENTK (SEQ ID NO:1364), IIDEN (SEQ ID NO:1365), IIDENTG (SEQ ID NO:1366), FIIDEN (SEQ ID NO:1367), FIIDENT (SEQ ID NO:1368), FIIDENTG (SEQ ID NO:1369), IFIIDEN (SEQ ID NO:1370), IFIIDENT (SEQ ID NO:1371), IFIIDENTG (SEQ ID NO:1372), CEPKC (SEQ ID NO:1373), CEPKTC (SEQ ID NO:1374), CEPKTGC (SEQ ID NO:1375), CVEPKC (SEQ ID NO:1376), CVEPKTC (SEQ ID NO:1377), CVEPKTGC (SEQ ID NO:1378), CSVEPKC (SEQ ID NO:1379), CSVEPKTC (SEQ ID NO:1380), CSVEPKTGC (SEQ ID NO:1381), CFSVEPKC (SEQ ID NO:1382), CFSVEPKTC (SEQ ID NO:1383), CFSVEPKTGC (SEQ ID NO:1384), CYFSVEPKC (SEQ ID NO:1385), CYFSVEPKTC (SEQ ID NO:1386), CYFSVEPKTGC (SEQ ID NO:1387), CDANC (SEQ ID NO:1388), CDANSC (SEQ ID NO:1389), CDANSGC (SEQ ID NO:1390), CIDANC (SEQ ID NO:1391), CIDANSC (SEQ ID NO:1392), CIDANSGC (SEQ ID NO:1393), CNIDANC (SEQ ID NO:1394), CNIDANSC (SEQ ID NO:1395), CNIDANSGC (SEQ ID NO:1396), CFNIDANC (SEQ ID NO:1397), CFNIDANSC (SEQ ID NO:1398), CFNIDANSGC (SEQ ID NO:1399), CYFNIDANC (SEQ ID NO:1400), CYFNIDANSC (SEQ ID NO:1401), CYFNIDANSGC (SEQ ID NO:1402), EEPKK (SEQ ID NO:1403), EEPKTK (SEQ ID NO:1404), EEPKTGK (SEQ ID NO:1405), EVEPKK (SEQ ID NO:1406), EVEPKTK (SEQ ID NO:1407), EVEPKTGK (SEQ ID NO:1408), ESVEPKK (SEQ ID NO:1409), ESVEPKTK (SEQ ID NO:1410), ESVEPKTGK (SEQ ID NO:1411), EFSVEPKK (SEQ ID NO:1412), EFSVEPKTK (SEQ ID NO:1413), EFSVEPKTGK (SEQ ID NO:1414), EYFSVEPKK (SEQ ID NO:1415), EYFSVEPKTK (SEQ ID NO:1416), EYFSVEPKTGK (SEQ ID NO:1417), EDANK (SEQ ID NO:1418), EDANSK (SEQ ID NO:1419), EDANSGK (SEQ ID NO:1420), EIDANK (SEQ ID NO:1421), EIDANSK (SEQ ID NO:1422), EIDANSGK (SEQ ID NO:1423), ENIDANK (SEQ ID NO:1424), ENIDANSK (SEQ ID NO:1425), ENIDANSGK (SEQ ID NO:1426), EFNIDANK (SEQ ID NO:1427), EFNIDANSK (SEQ ID NO:1428), EFNIDANSGK (SEQ ID NO:1429), EYFNIDANK (SEQ ID NO:1430), EYFNIDANSK (SEQ ID NO:1431), EYFNIDANSGK (SEQ ID NO:1432), KDAND (SEQ ID NO:1433), KIDAND (SEQ ID NO:1434), KDANSD (SEQ ID NO:1435), KNIDAND (SEQ ID NO:1436), KIDANSD (SEQ ID NO:1437), KNIDANSD (SEQ ID NO:1438), KDANSGD (SEQ ID NO:1439), KIDANSGD (SEQ ID NO:1440), KNIDANSGD (SEQ ID NO:1441), KFNIDAND (SEQ ID NO:1442), KFNIDANSD (SEQ ID NO:1443), KFNIDANSGD (SEQ ID NO:1444), KYFNIDAND (SEQ ID NO:1445), KYFNIDANSD (SEQ ID NO:1446), KYFNIDANSGD (SEQ ID NO:1447), KEPKD (SEQ ID NO:1448), KEPKTD (SEQ ID NO:1449), KEPKTGD (SEQ ID NO:1450), KVEPKD (SEQ ID NO:1451), KVEPKTD (SEQ ID NO:1452), KVEPKTGD (SEQ ID NO:1453), KSVEPKD (SEQ ID NO:1454), KSVEPKTD (SEQ ID NO:1455), KSVEPKTGD (SEQ ID NO:1456), KFSVEPKD (SEQ ID NO:1457), KFSVEPKTD (SEQ ID NO:1458), KFSVEPKTGD (SEQ ID NO:1459), KYFSVEPKD (SEQ ID NO:1460), KYFSVEPKTD (SEQ ID NO:1461), KYFSVEPKTGD (SEQ ID NO:1462), KDAND (SEQ ID NO:1463), KDANSD (SEQ ID NO:1464), KDANSGD (SEQ ID NO:1465), KIDAND (SEQ ID NO:1466), KIDANSD (SEQ ID NO:1467), KIDANSGD (SEQ ID NO:1468), KNIDAND (SEQ ID NO:1469), KNIDANSD (SEQ ID NO:1470), KNIDANSGD (SEQ ID NO:1471), KFNIDAND (SEQ ID NO:1472), KFNIDANSD (SEQ ID NO:1473), KFNIDANSGD (SEQ ID NO:1474), KYFNIDAND (SEQ ID NO:1475), KYFNIDANSD (SEQ ID NO:1476), KYFNIDANSGD (SEQ ID NO:1477), DEPKK (SEQ ID NO:1478), DEPKTK (SEQ ID NO:1479), DEPKTGK (SEQ ID NO:1480), DVEPKK (SEQ ID NO:1481), DVEPKTK (SEQ ID NO:1482), DVEPKTGK (SEQ ID NO:1483), DSVEPKK (SEQ ID NO:1484), DSVEPKTK (SEQ ID NO:1485), DSVEPKTGK (SEQ ID NO:1486), DFSVEPKK (SEQ ID NO:1487), DFSVEPKTK (SEQ ID NO:1488), DFSVEPKTGK (SEQ ID NO:1489), DYFSVEPKK (SEQ ID NO:1490), DYFSVEPKTK (SEQ ID NO:1491), DYFSVEPKTGK (SEQ ID NO:1492), DDANK (SEQ ID NO:1493), DDANSK (SEQ ID NO:1494), DDANSGK (SEQ ID NO:1495), DIDANK (SEQ ID NO:1496), DIDANSK (SEQ ID NO:1497), DIDANSGK (SEQ ID NO:1498), DNIDANK (SEQ ID NO:1499), DNIDANSK (SEQ ID NO:1500), DNIDANSGK (SEQ ID NO:1501), DFNIDANK (SEQ ID NO:1502), DFNIDANSK (SEQ ID NO:1503), DFNIDANSGK (SEQ ID NO:1504), DYFNIDANK (SEQ ID NO:1505), DYFNIDANSK (SEQ ID NO:1506), DYFNIDANSGK (SEQ ID NO:1507), KDENE (SEQ ID NO:1508), KDENTE (SEQ ID NO:1509), KDENTGE (SEQ ID NO:1510), KIDENE (SEQ ID NO:1511), KIDENTE (SEQ ID NO:1512), KIDENTGE (SEQ ID NO:1513), KIIDENE (SEQ ID NO:1514), KIIDENTE (SEQ ID NO:1515), KIIDENTGE (SEQ ID NO:1516), KFIIDENE (SEQ ID NO:1517), KFIIDENTE (SEQ ID NO:1518), KFIIDENTGE (SEQ ID NO:1519), KIFIIDENE (SEQ ID NO:1520), KIFIIDENTE (SEQ ID NO:1521), KIFIIDENTGE (SEQ ID NO:1522), KEPKE (SEQ ID NO:1523), KEPKTE (SEQ ID NO:1524), KEPKTGE (SEQ ID NO:1525), KVEPKE (SEQ ID NO:1526), KVEPKTE (SEQ ID NO:1527), KVEPKTGE (SEQ ID NO:1528), KSVEPKE (SEQ ID NO:1529), KSVEPKTE (SEQ ID NO:1530), KSVEPKTGE (SEQ ID NO:1531), KFSVEPKE (SEQ ID NO:1532), KFSVEPKTE (SEQ ID NO:1533), KFSVEPKTGE (SEQ ID NO:1534), KYFSVEPKE (SEQ ID NO:1535), KYFSVEPKTE (SEQ ID NO:1536), KYFSVEPKTGE (SEQ ID NO:1537), KDANE (SEQ ID NO:1538), KDANSE (SEQ ID NO:1539), KDANSGE (SEQ ID NO:1540), KIDANE (SEQ ID NO:1541), KIDANSE (SEQ ID NO:1542), KIDANSGE (SEQ ID NO:1543), KNIDANE (SEQ ID NO:1544), KNIDANSE (SEQ ID NO:1545), KNIDANSGE (SEQ ID NO:1546), KFNIDANE (SEQ ID NO:1547), KFNIDANSE (SEQ ID NO:1548), KFNIDANSGE (SEQ ID NO:1549), KYFNIDANE (SEQ ID NO:1550), KYFNIDANSE (SEQ ID NO:1551), KYFNIDANSGE (SEQ ID NO:1552), DENTG (SEQ ID NO:1553), IDENT (SEQ ID NO:1554), IDENTG (SEQ ID NO:1555), IIDEN (SEQ ID NO:1556), IIDENT (SEQ ID NO:1557), IIDENTG (SEQ ID NO:1558), FIIDEN (SEQ ID NO:1559), FIIDENT (SEQ ID NO:1560), FIIDENTG (SEQ ID NO:1561), IFIIDEN (SEQ ID NO:1562), IFIIDENT (SEQ ID NO:1563), IFIIDENTG (SEQ ID NO:1564), EPKTG (SEQ ID NO:1565), VEPKT (SEQ ID NO:1566), VEPKTG (SEQ ID NO:1567), SVEPK (SEQ ID NO:1568), SVEPKT (SEQ ID NO:1569), SVEPKTG (SEQ ID NO:1570), FSVEPK (SEQ ID NO:1571), FSVEPKT (SEQ ID NO:1572), FSVEPKTG (SEQ ID NO:1573), YFSVEPK (SEQ ID NO:1574), YFSVEPKT (SEQ ID NO:1575), YFSVEPKTG (SEQ ID NO:1576), DANSG (SEQ ID NO:1577), IDANS (SEQ ID NO:1578), IDANSG (SEQ ID NO:1579), NIDAN (SEQ ID NO:1580), NIDANS (SEQ ID NO:1581), NIDANSG (SEQ ID NO:1582), FNIDAN (SEQ ID NO:1583), FNIDANS (SEQ ID NO:1584), FNIDANSG (SEQ ID NO:1585), YFNIDAN (SEQ ID NO:1586), YFNIDANS (SEQ ID NO:1587) and YFNIDANSG (SEQ ID NO:1588).

Representative cyclic peptides comprising a cadherin-8 CAR sequence include: CNDVC (SEQ ID NO:1589), CINDVC (SEQ ID NO:1590), CNDVTC (SEQ ID NO:1591), COINDVC (SEQ ID NO:1592), CINDVTC (SEQ ID NO:1593), CQINDVTC (SEQ ID NO:1594), CNDVTGC (SEQ ID NO:1595), CINDVTCC (SEQ ID NO:1596), CQINDVTGC (SEQ ID NO:1597), CFQINDVC (SEQ ID NO:1598), CFQINDVTC (SEQ ID NO:1599), CFQINDVTGC (SEQ ID NO:1600), CIFQINDVC (SEQ ID NO:1601), CIFQINDVTC (SEQ ID NO:1602), CIFQINDVTGC (SEQ ID NO:1603), DNDVK (SEQ ID NO:1604), DINDVK (SEQ ID NO:1605), DQINDVK (SEQ ID NO:1606), DFQINDVK (SEQ ID NO:1607), DIFQINDVK (SEQ ID NO:1608), DNDVTK (SEQ ID NO:3924), DINDVTK (SEQ ID NO:3925), DQINDVTK (SEQ ID NO:3926), DFQINDVTK (SEQ ID NO:3927), DIFQINDVTK (SEQ ID NO:3928), DNDVTGK (SEQ ID NO:3929), DINDVTGK (SEQ ID NO:3930), DQINDVTGK (SEQ ID NO:3931), DFQINDVTGK (SEQ ID NO:3932), DIFQINDVTGK (SEQ ID NO:3933), ENDVTK (SEQ ID NO:3914), EINDVTK (SEQ ID NO:3915), EQINDVTK (SEQ ID NO:3916), EFQINDVTK (SEQ ID NO:3917), EIFQINDVTK (SEQ ID NO:3918), ENDVTGK (SEQ ID NO:3919), EINDVTGK (SEQ ID NO:3920), EQINDVTGK (SEQ ID NO:3921), EFQINDVTGK (SEQ ID NO:3922), EIFQINDVTGK (SEQ ID NO:3923), ENDVK (SEQ ID NO:1609), EINDVK (SEQ ID NO:1610), EQINDVK (SEQ ID NO:1611), EFQINDVK (SEQ ID NO:1612), EIFQINDVK (SEQ ID NO:1613), KNDVD (SEQ ID NO:1614), KINDVD (SEQ ID NO:1615), KNDVTD (SEQ ID NO:1616), KQINDVD (SEQ ID NO:1617), KINDVTD (SEQ ID NO:1618), KQINDVTD (SEQ ID NO:1619), KNDVTGD (SEQ ID NO:1620), KINDVTGD (SEQ ID NO:1621), KQINDVTGD (SEQ ID NO:1622), KFQINDVD (SEQ ID NO:1623), KFQINDVTD (SEQ ID NO:1624), KFQINDVTGD (SEQ ID NO:1625), KIFQINDVD (SEQ ID NO:1626), KIFQINDVTD (SEQ ID NO:1627), KIFQINDVTGD (SEQ ID NO:1628), VNDVT (SEQ ID NO:1629), INDVT (SEQ ID NO:1630), QINDVT (SEQ ID NO:1631), NDVTG (SEQ ID NO:1632), INVTG (SEQ ID NO:1633), KNDVE (SEQ ID NO:1634), KINDVE (SEQ ID NO:1635), KNDVTE (SEQ ID NO:1636), KQINDVE (SEQ ID NO:1637), KINDVTE (SEQ ID NO:1638), KQINDVTE (SEQ ID NO:1639), KNDVTGE (SEQ ID NO:1640), KINDVTGE (SEQ ID NO:1641), KQINDVTGE (SEQ ID NO:1642), KFQINDVE (SEQ ID NO:1643), KFQINDVTE (SEQ ID NO:1644), KFQINDVTGE (SEQ ID NO:1645), KIFQINDVE (SEQ ID NO:1646), KIFQINDVTE (SEQ ID NO:1647), KIFQINDVTGE (SEQ ID NO:1648), CEEFC (SEQ ID NO:1649), CEEFSC (SEQ ID NO:1650), CEEFSGC (SEQ ID NO:1651), CLEEFC (SEQ ID NO:1652), CLEEFSC (SEQ ID NO:1653), CLEEFSGC (SEQ ID NO:1654), CVLEEFC (SEQ ID NO:1655), CVLEEFSC (SEQ ID NO:1656), CVLEEFSGC (SEQ ID NO:1657), CFVLEEFC (SEQ ID NO:1658), CFVLEEFSC (SEQ ID NO:1659), CFVLEEFSGC (SEQ ID NO:1660), CMFVLEEFC (SEQ ID NO:1661), CMFVLEEFSC (SEQ ID NO:1662), CMFVLEEFSGC (SEQ ID NO:1663), EEEFK (SEQ ID NO:1664), EEEFSK (SEQ ID NO:1665), EEEFSGK (SEQ ID NO:1666), ELEEFK (SEQ ID NO:1667), ELEEFSK (SEQ ID NO:1668), ELEEFSGK (SEQ ID NO:1669), EVLEEFK (SEQ ID NO:1670), EVLEEFSK (SEQ ID NO:1671), EVLEEFSGK (SEQ ID NO:1672), EFVLEEFK (SEQ ID NO:1673), EFVLEEFSK (SEQ ID NO:1674), EFVLEEFSGK (SEQ ID NO:1675), EMFVLEEFK (SEQ ID NO:1676) EMFVLEEFSK (SEQ ID NO:1677), EMFVLEEFSGK (SEQ ID NO:1678), KEEFD (SEQ ID NO:1679), KEEFSD (SEQ ID NO:1680), KEEFSGD (SEQ ID NO:1681), KLEEFD (SEQ ID NO:1682), KLEEFSD (SEQ ID NO:1683), KLEEFSGD (SEQ ID NO:1684), KVLEEFD (SEQ ID NO:1685), KVLEEFSD (SEQ ID NO:1686), KVLEEFSGD (SEQ ID NO:1687), KFVLEEFD (SEQ ID NO:1688), KFVLEEFSD (SEQ ID NO:1689), KFVLEEFSGD (SEQ ID NO:1690), KNIFVLEEFD (SEQ ID NO:1691), KMFVLEEFSD (SEQ ID NO:1692), KMFVLEEFSGD (SEQ ID NO:1693), DEEFK (SEQ ID NO:1694), DEEFSK (SEQ ID NO:1695), DEEFSGK (SEQ ID NO:1696), DLEEFK (SEQ ID NO:1697), DLEEFSK (SEQ ID NO:1698), DLEEFSGK (SEQ ID NO:1699), DVLEEFK (SEQ ID NO:1700), DVLEEFSK (SEQ ID NO:1701), DVLEEFSGK (SEQ ID NO:1702), DFVLEEFK (SEQ ID NO:1703), DFVLEEFSK (SEQ ID NO:1704), DFVLEEFSGK (SEQ ID NO:1705), DMFVLEEFK (SEQ ID NO:1706), DMFVLEEFSK (SEQ ID NO:1707), DMFVLEEFSGK (SEQ ID NO:1708), KEEFE (SEQ ID NO:1709), KEEFSE (SEQ ID NO:1710), KEEFSGE (SEQ ID NO:1711), KLEEFE (SEQ ID NO:1712), KLEEFSE (SEQ ID NO:1713), KLEEFSGE (SEQ ID NO:1714), KVLEEFE (SEQ ID NO:1715), KVLEEFSE (SEQ ID NO:1716), KVLEEFSGE (SEQ ID NO:1717), KFVLEEFE (SEQ ID NO:1718), KFVLEEFSE (SEQ ID NO:1719), KFVLEEFSGE (SEQ ID NO:1720), KMFVLEEFE (SEQ ID NO:1721), KMFVLEEFSE (SEQ ID NO:1722), KMFVLEEFSGE (SEQ ID NO:1723), EEFSG (SEQ ID NO:1724), LEEFS (SEQ ID NO:1725), LEEFSG (SEQ ID NO:1726) VLEEF (SEQ ID NO:1727), VLEEFS (SEQ ID NO:1728), VLEEFSG (SEQ ID NO:1729), FVLEEF (SEQ ID NO:1730), FVLEEFS (SEQ ID NO:1731), FVLEEFSG (SEQ ID NO:1732) MFVLEEF (SEQ ID NO:1733), MFVLEEFS (SEQ ID NO:1734) and MFVLEEFSG (SEQ ID NO:1735).

Representative cyclic peptides comprising a cadherin-12 CAR sequence include: CDETC (SEQ ID NO:1736), CIDETC (SEQ ID NO:1737), CDETTC (SEQ ID NO:1738), CTIDETC (SEQ ID NO:1739), CIDETTC (SEQ ID NO:1740), CTIDETTC (SEQ ID NO:1741), CDETTGC (SEQ ID NO:1742), CIDETTGC (SEQ ID NO:1743), CTIDETTGC (SEQ ID NO:1744), CFTIDETC (SEQ ID NO:1745), CFTIDETTC (SEQ ID NO:1746), CFTIDETTGC (SEQ ID NO:1747), CVFTIDETC (SEQ ID NO:1748), CVFTIDETTC (SEQ ID NO:1749), CVFTIDETTGC (SEQ ID NO:1750), DDETK (SEQ ID NO:1752), DIDETK (SEQ ID NO:1753), DTIDETK (SEQ ID NO:1754), DFTIDETK (SEQ ID NO:1755), DVFTIDETK (SEQ ID NO:1756), EDETK (SEQ ID NO:1757), EIDETK (SEQ ID NO:1758), ETIDETK (SEQ ID NO:1759), EFTIDETK (SEQ ID NO:1760), EVFTIDETK (SEQ ID NO:1761), KDETD (SEQ ID NO:1762), KIDETD (SEQ ID NO:1763), KDETTD (SEQ ID NO:1764), KTIDETD (SEQ ID NO:1765), KIDETTD (SEQ ID NO:1766), KTIDETTB (SEQ ID NO:1767), KDETTGD (SEQ ID NO:1768), KIDETTGD (SEQ ID NO:1769), KTIDETTGD (SEQ ID NO:1770), KFTIDETD (SEQ ID NO:1771), KFTIDETTD (SEQ ID NO:1772), KFTIDETTGD (SEQ ID NO:1773), KVFTIDETD (SEQ ID NO:1774), KVFTIDETTD (SEQ ID NO:1775), KVFTIDETTGD (SEQ ID NO:1776), DDETTK (SEQ ID NO:1751), DIDETTK (SEQ ID NO:1777), DTIDETTK (SEQ ID NO:3934), DFTIDETTK (SEQ ID NO:3935), DVFTIDETTK (SEQ ID NO:3936), DDETTGK (SEQ ID NO:3937), DIDETTGK (SEQ ID NO:3938), DTIDETTGK (SEQ ID NO:3939), DFTIDETTGK (SEQ ID NO:3940), DVFTIDETTGK (SEQ ID NO:3941), EDETTK (SEQ ID NO:3942), EIDETTK (SEQ ID NO:3943), ETIDETTK (SEQ ID NO:3944), EFTIDETTK (SEQ ID NO:3945), DVFTIDETTK (SEQ ID NO:3946), EDETTGK (SEQ ID NO:3947), EIDETTGK (SEQ ID NO:3948), ETIDETTGK (SEQ ID NO:3949), EFTIDETTGK (SEQ ID NO:3950), EVFTIDETTGK (SEQ ID NO:3951), IDETT (SEQ ID NO:1778), TIDETT (SEQ ID NO:1779), DETTG (SEQ ID NO:1780), IDETTG (SEQ ID NO:1781) KDETE (SEQ ID NO:1782), KIDETE (SEQ ID NO:1783), KDETTE (SEQ ID NO:1784), KTIDETE (SEQ ID NO:1785), KIDETTE (SEQ ID NO:1786), KTIDETTE (SEQ ID NO:1787), KDETTGE (SEQ ID NO:1788), KIDETTGE (SEQ ID NO:1789), KTIDETTGE (SEQ ID NO:1790), KFTIDETE (SEQ ID NO:1791), KFTIDETTE (SEQ ID NO:1792), KFTIDETTGE (SEQ ID NO:1793), KVFTIDETE (SEQ ID NO:1794), KIFTIDETTE (SEQ ID NO:1795), KVFTIDETTGE (SEQ ID NO:1796), CDPKC (SEQ ID NO:1797), CDPKTC (SEQ ID NO:1798), CDPKTGC (SEQ ID NO:1799), CIDPKC (SEQ ID NO:1800), CIDPKTC (SEQ ID NO:1801), CIDPKTGC (SEQ ID NO:1802), CSIDPKC (SEQ ID NO:1803), CSIDPKTC (SEQ ID NO:1804), CSIDPKTGC (SEQ ID NO:1805), CFSIDPKC (SEQ ID NO:1806), CFSIDPKTC (SEQ ID NO:1807), CFSIDPKTGC (SEQ ID NO:1808), CYFSIDPKC (SEQ ID NO:1809), CYFSIDPKTC (SEQ ID NO:1810), CYFSIDPKTGC (SEQ ID NO:1811), EDPKK (SEQ ID NO:1812), EDPKTK (SEQ ID NO:1813), EDPKTGK (SEQ ID NO:1814), EIDPKK (SEQ ID NO:1815), EIDPKTK (SEQ ID NO:1816), EIDPKTGK (SEQ ID NO:1817), ESIDPKK (SEQ ID NO:1818), ESIDPKTK (SEQ ID NO:1819), ESIDPKTGK (SEQ ID NO:1820), EFSIDPKK (SEQ ID NO:1821), EFSIDPKTK (SEQ ID NO:1822), EFSIDPKTGK (SEQ ID NO:1823), EYFSIDPKK (SEQ ID NO:1824), EYFSIDPKTK (SEQ ID NO:1825), EYFSIDPKTGK (SEQ ID NO:1826), KDPKD (SEQ ID NO:1827), KDPKTD (SEQ ID NO:1828), KDPKTGD (SEQ ID NO:1829), KIDPKD (SEQ ID NO:1830), KIDPKTD (SEQ ID NO:1831), KIDPKTGD (SEQ ID NO:1832), KSIDPKD (SEQ ID NO:1833), KSIDPKTD (SEQ ID NO:1834), KSIDPKTGD (SEQ ID NO:1835), KFSIDPKD (SEQ ID NO:1836), KFSIDPKTD (SEQ ID NO:1837), KFSIDPKTGD (SEQ ID NO:1838), KYFSIDPKD (SEQ ID NO:1839), KYFSIDPKTD (SEQ ID NO:1840), KYFSIDPKTGD (SEQ ID NO:1841), DDPKK (SEQ ID NO:1842), DDPKTK (SEQ ID NO:1843), DDPKTGK (SEQ ID NO:1844), DIDPKK (SEQ ID NO:1845), DIDPKTK (SEQ ID NO:1846), DIDPKTGK (SEQ ID NO:1847), DSIDPKK (SEQ ID NO:1848), DSIDPKTK (SEQ ID NO:1849), DSIDPKTGK (SEQ ID NO:1850), DFSIDPKK (SEQ ID NO:1851), DFSIDPKTK (SEQ ID NO:1852), DFSIDPKTGK (SEQ ID NO:1853), DYFSIDPKK (SEQ ID NO:1854), DYFSIDPKTK (SEQ ID NO:1855), DYFSIDPKTGK (SEQ ID NO:1856), KDPKE (SEQ ID NO:1857), KDPKTE (SEQ ID NO:1858), KDPKTGE (SEQ ID NO:1859), KIDPKE (SEQ ID NO:1860), KIDPKTE (SEQ ID NO:1861), KIDPKTGE (SEQ ID NO:1862), KSIDPKE (SEQ ID NO:1863), KSIDPKTE (SEQ ID NO:1864), KSIDPKTGE (SEQ ID NO:1865), KFSIDPKE (SEQ ID NO:1866), KFSIDPKTE (SEQ ID NO:1867), KFSIDPKTGE (SEQ ID NO:1868), KYFSIDPKE (SEQ ID NO:1869), KYFSIDPKTE (SEQ ID NO:1870), KYFSIDPKTGE (SEQ ID NO:1871), DPKTG (SEQ ID NO:1872), IDPKT (SEQ ID NO:1873), IDPKTG (SEQ ID NO:1874), SIDPK (SEQ ID NO:1875), SIDPKT (SEQ ID NO:1876), SIDPKTG (SEQ ID NO:1877), FSIDPK (SEQ ID NO:1878), FSIDPKT (SEQ ID NO:1879), FSIDPKTG (SEQ ID NO:1880), YFSIDPK (SEQ ID NO:1881), YFSIDPKT (SEQ ID NO:1882) and YFSIDPKTG (SEQ ID NO:1883).

Representative cyclic peptides comprising a cadherin-14 CAR sequence include: CDDTC (SEQ ID NO:1884), CIDDTC (SEQ ID NO:1885), CDDTTC (SEQ ID NO:1886), CIIDDTC (SEQ ID NO:1887), CIDDTTC (SEQ ID NO:1888), CIIDDTTC (SEQ ID NO:1889), CDDTTGC (SEQ ID NO:1890), CIDDTTGC (SEQ ID NO:1891), CIIDDTTGC (SEQ ID NO:1892), CFIIDDTC (SEQ ID NO:1893), CFIIDDTTC (SEQ ID NO:1894), CFIIDDTTGC (SEQ ID NO:1895), CIFIIDDTC (SEQ ID NO:1896), CIFIIDDTTC (SEQ ID NO:1897), CIFIIDDTTGC (SEQ ID NO:1898), EDDTTK (SEQ ID NO:1899), EIDDTTK (SEQ ID NO:3952), EIIDDTTK (SEQ ID NO:3953), EFIIDDTTK (SEQ ID NO:3954), EIFIIDDTTK (SEQ ID NO:3955), EDDTTGK (SEQ ID NO:3956), EIDDTTGK (SEQ ID NO:3957), EIIDDTTGK (SEQ ID NO:3958), EFIIDDTTGK (SEQ ID NO:3959), EIFIIDDTTGK (SEQ ID NO:3960), DDDTTK (SEQ ID NO:3961), DIDDTTK (SEQ ID NO:3962), DFIIDDTTK (SEQ ID NO:3963), DIFIIDDTTK (SEQ ID NO:3964), DDDTTGK (SEQ ID NO:3965), DIDDTTGK (SEQ ID NO:3966), DIIDDTTGK (SEQ ID NO:3967), DFIIDDTTGK (SEQ ID NO:3968), DIFIIDDTTGK (SEQ ID NO:3969), DDDTK (SEQ ID NO:1900), DIDDTNK (SEQ ID NO:1901), DIIDDTK (SEQ ID NO:1902), DFIIDDTK (SEQ ID NO:1903), DIFIIDDTK (SEQ ID NO:1904), EDDTK (SEQ ID NO:1905), EIDDTK (SEQ ID NO:1906), EIIDDTK (SEQ ID NO:1907), EFIIDDTK (SEQ ID NO:1908), EIFIIDDTK (SEQ ID NO:1909), KDDTD (SEQ ID NO:1910), KIDDTD (SEQ ID NO:1911), KDDTTD (SEQ ID NO:1912), KIIDDTD (SEQ ID NO:1913), KIDDTTD (SEQ ID NO:1914), KIIDDTTD (SEQ ID NO:1915), KDDTTGD (SEQ ID NO:1916), KIDDTTGD (SEQ ID NO:1917), KIIDDTTGD (SEQ ID NO:1918), KFHIIDDTD (SEQ ID NO:1919), KFIIDDTTD (SEQ ID NO:1920), KFIIDDTTGD (SEQ ID NO:1921), KIFIIDDTD (SEQ ID NO:1922), KIFIIDDTTD (SEQ ID NO:1923), KFIIDDTTGD (SEQ ID NO:1924), DDTT (SEQ ID NO:1925), IDDTT (SEQ ID NO:1926), IIDDTT (SEQ ID NO:1927), DDTTG (SEQ ID NO:1928), IDDTTG (SEQ ID NO:1929) KDDTE (SEQ ID NO:1930), KIDDTE (SEQ ID NO:1931), KDDTTE (SEQ ID NO:1932), KIIDDTE (SEQ ID NO:1933), KIDDTTE (SEQ ID NO:1934), KIIDDTTE (SEQ ID NO:1935), KDDTTGE (SEQ ID NO:1936), KIDDTTGE (SEQ ID NO:1937), KIIDDTTGE (SEQ ID NO:1938), KFIIDDTE (SEQ ID NO:1939), KFIIDDTTE (SEQ ID NO:1940), KFIIDDTTGE (SEQ ID NO:1941), KIFIIDDTE (SEQ ID NO:1942), KIFIIDDTTE (SEQ ID NO:1943), KIFIIDDTTGE (SEQ ID NO:1944), CDPKC (SEQ ID NO:1945), CVDPKC (SEQ ID NO:1946), CVDPKTC (SEQ ID NO:1947), CVDPKTGC (SEQ ID NO:1948), CSVDPKC (SEQ ID NO:1949), CSVDPKTC (SEQ ID NO:1950), CSVDPKTGC (SEQ ID NO:1951), CFSVDPKC (SEQ ID NO:1952), CFSVDPKTC (SEQ ID NO:1953), CFSVDPKTGC (SEQ ID NO:1954), CYFSVDPKC (SEQ ID NO:1955), CYFSVDPKTC (SEQ ID NO:1956), CYFSVDPKTGC (SEQ ID NO:1957), CDPKTC (SEQ ID NO:3970), CDPKTGC (SEQ ID NO:3971), CDANC (SEQ ID NO:1958), CDANTC (SEQ ID NO:1959), CDANTGC (SEQ ID NO:1960), CIDANTC (SEQ ID NO:1961), CIDANTGC (SEQ ID NO:1962), CNIDANTC (SEQ ID NO:1963), CNIDANTGC (SEQ ID NO:1964), CFNIDANTC (SEQ ID NO:1965), CFNIDANTGC (SEQ ID NO:1966), CFFNIDANC (SEQ ID NO:1967), CFFNIDANTC (SEQ ID NO:1968), CFFNIDANTGC (SEQ ID NO:1969), CIDANC (SEQ ID NO:3972), CNIDANC (SEQ ID NO:3973), CFNIDANC (SEQ ID NO:3974), EDPKK (SEQ ID NO:1970), EDPKTK (SEQ ID NO:1971), EDPKTGK (SEQ ID NO:1972), EVDPKK (SEQ ID NO:1973), EVDPKTK (SEQ ID NO:1974), EVDPKTGK (SEQ ID NO:1975), ESVDPKK (SEQ ID NO:1976), ESVDPKTK (SEQ ID NO:1977), ESVDPKTGK (SEQ ID NO:1978), EFSVDPKK (SEQ ID NO:1979), EFSVDPKTK (SEQ ID NO:1980), EFSVDPKTGK (SEQ ID NO:1981), EYFSVDPKK (SEQ ID NO:1982), EYFSVDPKTK (SEQ ID NO:1983), EYFSVDPKTGK (SEQ ID NO:1984), EDANK (SEQ ID NO:1985), EDANTK (SEQ ID NO:1986), EDANTGK (SEQ ID NO:1987), EIDANTK (SEQ ID NO:1988), EIDANTGK (SEQ ID NO:1989), ENIDANTK (SEQ ID NO:1990), ENIDANTGK (SEQ ID NO:1991), EFNIDANTK (SEQ ID NO:1992), EFNIDANTGK (SEQ ID NO:1993), EFFNIDANK (SEQ ID NO:1994), EFFNIDANTK (SEQ ID NO:1995), EFFNIDANTGK (SEQ ID NO:1996), EIDANK (SEQ ID NO:3975), ENIDANK (SEQ ID NO:3976), EFNIDANK (SEQ ID NO:3977), KVDPKD (SEQ ID NO:1997), KVDPKTD (SEQ ID NO:1998), KVDPKTGD (SEQ ID NO:1999), KSVDPKD (SEQ ID NO:2000), KSVDPKTD (SEQ ID NO:2001), KSVDPKTGD (SEQ ID NO:2002), KFSVDPKD (SEQ ID NO:2003), KFSVDPKTD (SEQ ID NO:2004), KFSVDPKTGD (SEQ ID NO:2005), KYFSVDPKD (SEQ ID NO:2006), KYFSVDPKTD (SEQ ID NO:2007), KYFSVDPKTGD (SEQ ID NO:2008), KDPKD (SEQ ID NO:3978), KDPKTD (SEQ ID NO:3979), KDPKTGD (SEQ ID NO:3980), KDAND (SEQ ID NO:3981), KIDAND (SEQ ID NO:3982), KNIDAND (SEQ ID NO:3983), KDANTD (SEQ ID NO:2009), KDANTGD (SEQ ID NO:2010), KIDANTD (SEQ ID NO:2011), KIDANTGD (SEQ ID NO:2012), KNIDANTD (SEQ ID NO:2013), KNIDANTGD (SEQ ID NO:2014), KFNIDANTD (SEQ ID NO:2015), KFNIDANTGD (SEQ ID NO:2016), KFFNIDAND (SEQ ID NO:2017), KFFNIDANTD (SEQ ID NO:2018), KFFNIDANTGD (SEQ ID NO:2019), DDPKK (SEQ ID NO:2020), DDPKTK (SEQ ID NO:2021), DDPKTGK (SEQ ID NO:2022), DVDPKK (SEQ ID NO:2023), DVDPKTK (SEQ ID NO:2024), DVDPKTGK (SEQ ID NO:2025), DSVDPKK (SEQ ID NO:2026), DSVDPKTK (SEQ ID NO:2027), DSVDPKTGK (SEQ ID NO:2028), DFSVDPKK (SEQ ID NO:2029), DFSVDPKTK (SEQ ID NO:2030), DFSVDPKTGK (SEQ ID NO:2031), DYFSVDPKK (SEQ ID NO:2032), DYFSVDPKTK (SEQ ID NO:2033), DYFSVDPKTGK (SEQ ID NO:2034), DDANK (SEQ ID NO:2035), DDANTK (SEQ ID NO:2036), DDANTGK (SEQ ID NO:2037), DIDANTK (SEQ ID NO:2038), DIDANTGK (SEQ ID NO:2039), DNIDANTK (SEQ ID NO:2040), DNIDANTGK (SEQ ID NO:2041), DFNIDANTC (SEQ ID NO:2042), DFNIDANTGK (SEQ ID NO:2043), DFFNIDANK (SEQ ID NO:2044), DFFNIDANTK (SEQ ID NO:2045), DFFNIDANTGK (SEQ ID NO:2046), DIDANK (SEQ ID NO:3984), DNIDANK (SEQ ID NO:3985), DFNIDANK (SEQ ID NO:3986), DFNIDANTK (SEQ ID NO:3987), KDPKE (SEQ ID NO:3988), KDPKTE (SEQ ID NO:3989), KDPKTGE (SEQ ID NO:3990), KVDPKE (SEQ ID NO:2047), KVDPKTE (SEQ ID NO:2048), KVDPKTGE (SEQ ID NO:2049), KSVDPKE (SEQ ID NO:2050), KSVDPKTE (SEQ ID NO:2051), KSVDPKTGE (SEQ ID NO:2052), KFSVDPKE (SEQ ID NO:2053), KFSVDPKTE (SEQ ID NO:2054), KFSVDPKTGE (SEQ ID NO:2055), KYFSVDPKE (SEQ ID NO:2056), KYFSVDPKTE (SEQ ID NO:2057), KYFSVDPKTGE (SEQ ID NO:2058), KDANE (SEQ ID NO:2059), KDANTE (SEQ ID NO:2060), KDANTGE (SEQ ID NO:2061), KIDANTE (SEQ ID NO:2062), KIDANTGE (SEQ ID NO:2063), KNIDANTE (SEQ ID NO:2064), KNIDANTGE (SEQ ID NO:2065), KFNIDANTE (SEQ ID NO:2066), KFNIDANTGE (SEQ ID NO:2067), KFFNIDANE (SEQ ID NO:2068), KFFNIDANTE (SEQ ID NO:2069), KFFNIDANTGE (SEQ ID NO:2070), KIDANE (SEQ ID NO:3991), KNIDANE (SEQ ID NO:3992), KFNIDANE (SEQ ID NO:3993), VDPKT (SEQ ID NO:2071), VDPKTG (SEQ ID NO:2072), SVDPK (SEQ ID NO:2073), SVDPKT (SEQ ID NO:2074), SVDPKTG (SEQ ID NO:2075), FSVDPK (SEQ ID NO:2076), FSVDPKT (SEQ ID NO:2077), FSVDPKTG (SEQ ID NO:2078), YFSVDPK (SEQ ID NO:2079), YFSVDPKT (SEQ ID NO:2080), YFSVDPKTG (SEQ ID NO:2081), DANTG (SEQ ID NO:2082), IDANT (SEQ ID NO:2083), IDANTG (SEQ ID NO:2084), NIDANT (SEQ ID NO:2085), NIDANTG (SEQ ID NO:2086), FNIDANT (SEQ ID NO:2087), FNIDANTG (SEQ ID NO:2088), FFNIDAN (SEQ ID NO:2089), FFNIDANT (SEQ ID NO:2090), and FFNIDANTG (SEQ ID NO:2091).

Representative cyclic peptides comprising a cadherin-15 CAR sequence include: CDKFC (SEQ ID NO:2092), CIDKFC (SEQ ID NO:2093), CDKFTC (SEQ ID NO:2094), CSIDKFC (SEQ ID NO:2095), CIDKFTC (SEQ ID NO:2096), CSIDKFTC (SEQ ID NO:2097), CDKFTGC (SEQ ID NO:2098), CIDKFTGC (SEQ ID NO:2099), CSIDKFTGC (SEQ ID NO:2100), CFSIDKFC (SEQ ID NO:2101), CFSIDKFTC (SEQ ID NO:2102), CFSIDKFTGC (SEQ ID NO:2103), CVFSIDKFC (SEQ ID NO:2104), CVFSIDKFTC (SEQ ID NO:2105), CVFSIDKFTGC (SEQ ID NO:2106), DDKFK (SEQ ID NO:2108), DIDKFK (SEQ ID NO:2109), DSIDKFK (SEQ ID NO:2110), DFSIDKFK (SEQ ID NO:2111), DVFSIDKFK (SEQ ID NO:2112), DDKFTK (SEQ ID NO:2107), DIDKFTK (SEQ ID NO:2133), DSIDKFTK (SEQ ID NO:3994), DFSIDKFTK (SEQ ID NO:3995), DVFSIDKFTK (SEQ ID NO:3996), DDKTGK (SEQ ID NO:3997), DIDKFTGK (SEQ ID NO:3998), DSIDKFTGK (SEQ ID NO:3999), DFSIDKFTGK (SEQ ID NO:4000), DVFSIDKFTGK (SEQ ID NO:4001), EDKFTK (SEQ ID NO:4002), EIDKFTK (SEQ ID NO:4003), ESIDKFTK (SEQ ID NO:4004), EFSIDKFTK (SEQ ID NO:4005), EVFSIDKFTK (SEQ ID NO:4006), EDKFTGK (SEQ ID NO:4007), EIDKFTGK (SEQ ID NO:4008), EFSIDKFTGK (SEQ ID NO:4009), EVFSIDKFTGK (SEQ ID NO:4010), EDKFK (SEQ ID NO:2113), EIDKFK (SEQ ID NO:2114), ESIDKFK (SEQ ID NO:2115), EFSIDKFK (SEQ ID NO:2116), EVFSIDKFK (SEQ ID NO:2117), KDKFD (SEQ ID NO:2118), KIDKFD (SEQ ID NO:2119), KDKFTD (SEQ ID NO:2120), KSIDKFD (SEQ ID NO:2121), KIDKFTD (SEQ ID NO:2122), KSIDKFTD (SEQ ID NO:2123), KDKFTGD (SEQ ID NO:2124), KIDKFTGD (SEQ ID NO:2125), KSIDKFTGD (SEQ ID NO:2126), KFSIDKFD (SEQ ID NO:2127), KFSIDKFTD (SEQ ID NO:2128), KFSIDKFTGD (SEQ ID NO:2129), KVFSIDKFD (SEQ ID NO:2130), KVFSIDKFTD (SEQ ID NO:2131), KVFSIDKFTGD (SEQ ID NO:2132), IDKFT (SEQ ID NO:2134), SIDKFT (SEQ ID NO:2135), DKFTG (SEQ ID NO:2136), IDKFTG (SEQ ID NO:2137) KDKFE (SEQ ID NO:2138), KIDKFE (SEQ ID NO:2139), KDKFTE (SEQ ID NO:2140), KSIDKFE (SEQ ID NO:2141), KIDKFTE (SEQ ID NO:2142), KSIDKFTE (SEQ ID NO:2143), KDKFTGE (SEQ ID NO:2144), KIDKFTGE (SEQ ID NO:2145), KSIDKFTGE (SEQ ID NO:2146), KFSIDKFE (SEQ ID NO:2147), KFSIDKFTE (SEQ ID NO:2148), KFSIDKFTGE (SEQ ID NO:2149), KVFSIDKFE (SEQ ID NO:2150), KIFSIDKFTE (SEQ ID NO:2151), KVFSIDKFTGE (SEQ ID NO:2152), CDELC (SEQ ID NO:2153), CDELTC (SEQ ID NO:2154), CDELTGC (SEQ ID NO:2155), CIDELC (SEQ ID NO:2156), CIDELTC (SEQ ID NO:2157), CIDELTGC (SEQ ID NO:2158), CSIDELC (SEQ ID NO:2159), CSIDELTC (SEQ ID NO:2160), CSIDELTGC (SEQ ID NO:2161), CFSIDELC (SEQ ID NO:2162), CFSIDELTC (SEQ ID NO:2163), CFSIDELTGC (SEQ ID NO:2164), CLFSIDELC (SEQ ID NO:2165), CLFSIDELTC (SEQ ID NO:2166), CLFSIDELTGC (SEQ ID NO:2167), EDELCK (SEQ ID NO:2168), EDELTK (SEQ ID NO:2169), EDELTGK (SEQ ID NO:2170), EIDELK (SEQ ID NO:2171), EIDELTK (SEQ ID NO:2172), EIDELTGK (SEQ ID NO:2173), ESIDELK (SEQ ID NO:2174), ESIDELTK (SEQ ID NO:2175), ESIDELTGK (SEQ ID NO:2176), EFSIDELK (SEQ ID NO:2177), EFSIDELTK (SEQ ID NO:2178), EFSIDELTGK (SEQ ID NO:2179), ELFSIDELK (SEQ ID NO:2180), ELFSIDELTK (SEQ ID NO:2181), ELFSIDELTGK (SEQ ID NO:2182), KDELD (SEQ ID NO:2183), KDELTD (SEQ ID NO:2184), KDELTGD (SEQ ID NO:2185), KIDELD (SEQ ID NO:2186), KIDELTD (SEQ ID NO:2187), KIDELTGD (SEQ ID NO:2188), KSIDELD (SEQ ID NO:2189), KSIDELTD (SEQ ID NO:2190), KSIDELTGD (SEQ ID NO:2191), KFSIDELD (SEQ ID NO:2192), KFSIDELTD (SEQ ID NO:2193), KFSIDELTGD (SEQ ID NO:2194), KLFSIDELD (SEQ ID NO:2195), KLFSIDELTD (SEQ ID NO:2196), KLFSIDELTGD (SEQ ID NO:2197), DDELK (SEQ ID NO:2198), DDELTK (SEQ ID NO:2199), DDELTGK (SEQ ID NO:2200), DIDELK (SEQ ID NO:2201), DIDELTK (SEQ ID NO:2202), DIDELTGK (SEQ ID NO:2203), DSIDELK (SEQ ID NO:2204), DSIDELTK (SEQ ID NO:2205), DSIDELTGK (SEQ ID NO:2206), DFSIDELK (SEQ ID NO:2207), DFSIDELTK (SEQ ID NO:2208), DFSIDELTGK (SEQ ID NO:2209), DLFSIDELK (SEQ ID NO:2210), DLFSIDELTK (SEQ ID NO:2211), DLFSIDELTGK (SEQ ID NO:2212), KDELE (SEQ ID NO:2213), KDELTE (SEQ ID NO:2214), KDELTGE (SEQ ID NO:2215), KIDELE (SEQ ID NO:2216), KIDELTE (SEQ ID NO:2217), KIDELTGE (SEQ ID NO:2218), KSIDELE (SEQ ID NO:2219), KSIDELTE (SEQ ID NO:2220), KSIDELTGE (SEQ ID NO:2221), KFSIDELE (SEQ ID NO:2222), KFSIDELTE (SEQ ID NO:2223), KFSIDELTGE (SEQ ID NO:2224), KLFSIDELE (SEQ ID NO:2225), KLFSIDELTE (SEQ ID NO:2226), KLFSIDELTGE (SEQ ID NO:2227), DELTG (SEQ ID NO:2228), IDELT (SEQ ID NO:2229), IDELTG (SEQ ID NO:2230), SIDEL (SEQ ID NO:2231), SIDELT (SEQ ID NO:2232), SIDELTG (SEQ ID NO:2233), FSIDEL (SEQ ID NO:2234), FSIDELT (SEQ ID NO:2235), FSIDELTG (SEQ ID NO:2236), LFSIDEL (SEQ ID NO:2237), LFSIDELT (SEQ ID NO:2238) and LFSIDELTG. (SEQ ID NO:2239).

Representative cyclic peptides comprising a T-cadherin CAR sequence include: CNENC (SEQ ID NO:2240), CINENC (SEQ ID NO:2241), CNENTC (SEQ ID NO:2242), CRINENC (SEQ ID NO:2243), CINENTC (SEQ ID NO:2244), CRINENTC (SEQ ID NO:2245), CNENTGC (SEQ ID NO:2246), CINENTGC (SEQ ID NO:2247), CRINENTGC (SEQ ID NO:2248), CFRINENC (SEQ ID NO:2249), CFRINENTC (SEQ ID NO:2250), CFRINENTGC (SEQ ID NO:2251), CIFRINENC (SEQ ID NO:2252), CIFRINENTC (SEQ ID NO:2253), CIFRINENTGC (SEQ ID NO:2254), DNENK (SEQ ID NO:2255), DINENK (SEQ ID NO:2256), DRINENK (SEQ ID NO:2257), DFRINENK (SEQ ID NO:2258), DIFRINENK (SEQ ID NO:2259), ENENK (SEQ ID NO:2260), EINENK (SEQ ID NO:2261), ERINENK (SEQ ID NO:2262), EFRINENK (SEQ ID NO:2263), EIFRINENK (SEQ ID NO:2264), KNEND (SEQ ID NO:2265), KINEND (SEQ ID NO:2266), KNENTD (SEQ ID NO:2267), KRINEND (SEQ ID NO:2268), KINENTD (SEQ ID NO:2269), KRINENTD (SEQ ID NO:2270), KINENTGD (SEQ ID NO:2271), KINENTGD (SEQ ID NO:2272), KRINENTGD (SEQ ID NO:2273), KFRINEND (SEQ ID NO:2274), KFRINENTD (SEQ ID NO:2275), KFRINENTGD (SEQ ID NO:2276), KIFRINEND (SEQ ID NO:2277), KIFRINENTD (SEQ ID NO:2278), KIFRINENTGD (SEQ ID NO:2279), DNENTK (SEQ ID NO:4011), DINENTK (SEQ ID NO:4012), DRINENTK (SEQ ID NO:4013), DFRINENTK (SEQ ID NO:4014), DIFRINENTK (SEQ ID NO:4015), DNENTGK (SEQ ID NO:4016), DINENTGK (SEQ ID NO:4017), DRINENTGK (SEQ ID NO:4018), DFRINENTGK (SEQ ID NO:4019), DIFRINENTGK (SEQ ID NO:4020), ENENTK (SEQ ID NO:4021), EINENTK (SEQ ID NO:4022), ERINENTK (SEQ ID NO:4023), EFRINENTK (SEQ ID NO:4024), EIFRINENTK (SEQ ID NO:4025), ENENTGK (SEQ ID NO:4026), EINENTGK (SEQ ID NO:4027), ERINENTGK (SEQ ID NO:4028), EFRINENTGK (SEQ ID NO:4029), EIFRINENTGK (SEQ ID NO:4030), VNENTG (SEQ ID NO:4031), RINENTG (SEQ ID NO:4032), FRINEN (SEQ ID NO:4033), FRINENT (SEQ ID NO:4034), FRINENTG (SEQ ID NO:4035), IFRINEN (SEQ ID NO:4036), IFRINENT (SEQ ID NO:4037), IFRINENTG (SEQ ID NO:4038), VNENT (SEQ ID NO:2280), INENT (SEQ ID NO:2281), RINENT (SEQ ID NO:2282), NENTG (SEQ ID NO:2283), INENTG (SEQ ID NO:2284) KNENE (SEQ ID NO:2285), KINENE (SEQ ID NO:2286), KINENTE (SEQ ID NO:2287), KRINENE (SEQ ID NO:2288), KINENTE (SEQ ID NO:2289), KRINENTE (SEQ ID NO:2290), KNENTGE (SEQ ID NO:2291), KINENTGE (SEQ ID NO:2292), KRINENTGE (SEQ ID NO:2293), KFRINENE (SEQ ID NO:2294), KFRINENTE (SEQ ID NO:2295), KFRINENTGE (SEQ ID NO:2296), KIFRINENE (SEQ ID NO:2297), KIFRINENTE (SEQ ID NO:2298) and KIFRINENTGE (SEQ ID NO:2299).

Representative cyclic peptides comprising a PB-cadherin CAR sequence include: CEEYC (SEQ ID NO:2300), CEEYTC (SEQ ID NO:2301), CEEYTG (SEQ ID NO:2302), CVEEYC (SEQ ID NO:2303), CVEEYTC (SEQ ID NO:2304), CVEEYTGC (SEQ ID NO:2305), CVVEEYC (SEQ ID NO:2306), CVVEEYTC (SEQ ID NO:2307), CVVEEYTGC (SEQ ID NO:2308), CFVVEEYC (SEQ ID NO:2309), CFVEEYTC (SEQ ID NO:2310), CFVEEYTGC (SEQ ID NO:2311), CFFVVEEYC (SEQ ID NO:2312), CFFVVEEYTC (SEQ ID NO:2313), CFFVVEEYTGC (SEQ ID NO:2314), CLIDELC (SEQ ID NO:2315), CLIDELTC (SEQ ID NO:2316), CLIDELTGC (SEQ ID NO:2317), CFLIDELC (SEQ ID NO:2318), CFLIDELTC (SEQ ID NO:2319), CFLIDELTGC (SEQ ID NO:2320), CIFLIDELC (SEQ ID NO:2321), CIFLIDELTC (SEQ ID NO:2322), CIFLIDELTGC (SEQ ID NO:2323), CDELC (SEQ ID NO:4039), CDELTC (SEQ ID NO:4040), CDELTGC (SEQ ID NO:4041), CIDELC (SEQ ID NO:4042), CIDELTC (SEQ ID NO:4043), CIDELTGC (SEQ ID NO:4044), CDPKC (SEQ ID NO:4045), CDPKTC (SEQ ID NO:4046), CDPKTGC (SEQ ID NO:4047), CVDPKC (SEQ ID NO:4048), CVDPKTC (SEQ ID NO:4049), CVDPKTGC (SEQ ID NO:4050), CTVDPKC (SEQ ID NO:2324), CTVDPKTC (SEQ ID NO:2325), CTVDPKTGC (SEQ ID NO:2326), CFTVDPKC (SEQ ID NO:2327), CFTVDPKTC (SEQ ID NO:2328), CFTVDPKTGC (SEQ ID NO:2329), CHFTVDPKC (SEQ ID NO:2330), CHFTVDPKTC (SEQ ID NO:2331), CHFTVDPKTGC (SEQ ID NO:2332), CDADC (SEQ ID NO:2333), CDADTC (SEQ ID NO:2334), CDADTGC (SEQ ID NO:2335), CIDADC (SEQ ID NO:2336), CIDADTC (SEQ ID NO:2337), CIDADTGC (SEQ ID NO:2338), CDIDADC (SEQ ID NO:2339), CDIDADTC (SEQ ID NO:2340), CDIDADTGC (SEQ ID NO:2341), CFDIDADC (SEQ ID NO:2342), CFDIDADTC (SEQ ID NO:2343), CFDIDADTGC (SEQ ID NO:2344), CIFDIDADC (SEQ ID NO:2345), CIFDIDADTC (SEQ ID NO:2346), CIFDIDADTGC (SEQ ID NO:2347), EEEYK (SEQ ID NO:2348), EEEYTK (SEQ ID NO:2349), EEEYTGK (SEQ ID NO:2350), EVEEYK (SEQ ID NO:2351), EVEEYTK (SEQ ID NO:2352), EVEEYTGK (SEQ ID NO:2353), EVVEEYK (SEQ ID NO:2354), EVVEEYTK (SEQ ID NO:2355), EVVEEYTGK (SEQ ID NO:2356), EFVVEEYK (SEQ ID NO:2357), EFVEEYTK (SEQ ID NO:2358), EFVEEYTGK (SEQ ID NO:2359), EFFVVEEYK (SEQ ID NO:2360), EFFVVEEYTK (SEQ ID NO:2361), EFFVVEEYTGK (SEQ ID NO:2362), EDELK (SEQ ID NO:2363), EDELTK (SEQ ID NO:2364), EDELTGK (SEQ ID NO:2365), EIDELK (SEQ ID NO:2366), EIDELTK (SEQ ID NO:2367), EIDELTGK (SEQ ID NO:2368), ELIDELK (SEQ ID NO:2369), ELIDELTK (SEQ ID NO:2370), ELIDELTGK (SEQ ID NO:2371), EFLIDELK (SEQ ID NO:2372), EFLIDELTK (SEQ ID NO:2373), EFLIDELTGK (SEQ ID NO:2374), EIFLIDELK (SEQ ID NO:2375), EIFLIDELTK (SEQ ID NO:2376), EIFLIDELTGK (SEQ ID NO:2377), EDPKK (SEQ ID NO:2378), EDPKTK (SEQ ID NO:2379), EDPKTGK (SEQ ID NO:2380), EVDPKK (SEQ ID NO:2381), EVDPKTK (SEQ ID NO:2382), EVDPKTGK (SEQ ID NO:2383), ETVDPKK (SEQ ID NO:2384), ETVDPKTK (SEQ ID NO:2385), ETVDPKTGK (SEQ ID NO:2386), EFTVDPKK (SEQ ID NO:2387), EFTVDPKTK (SEQ ID NO:2388), EFTVDPKTGK (SEQ ID NO:2389), EHFTVDPKK (SEQ ID NO:2390), EHFTVDPKTK (SEQ ID NO:2391), EHFTVDPKTGK (SEQ ID NO:2392), EDADK (SEQ ID NO:2393), EDADTK (SEQ ID NO:2394), EDADTGK (SEQ ID NO:2395), EIDADK (SEQ ID NO:2396), EIDADTK (SEQ ID NO:2397), EIDADTGK (SEQ ID NO:2398), EDIDADK (SEQ ID NO:2399), EDIDADTK (SEQ ID NO:2400), EDIDADTGK (SEQ ID NO:2401), EFDIDADK (SEQ ID NO:2402), EFDIDADTK (SEQ ID NO:2403), EFDIDADTGK (SEQ ID NO:2404), EIFDIDADK (SEQ ID NO:2405), EIFDIDADTK (SEQ ID NO:2406), EIFDIDADTGK (SEQ ID NO:2407), KEEYD (SEQ ID NO:2408), KEEYTD (SEQ ID NO:2409), KEEYTGD (SEQ ID NO:2410), KVEEYD (SEQ ID NO:2411), KVEEYTD (SEQ ID NO:2412), KVEEYTGD (SEQ ID NO:2413), KVVEEYD (SEQ ID NO:2414), KVVEEYTD (SEQ ID NO:2415), KVVEEYTGD (SEQ ID NO:2416), KFVVEEYD (SEQ ID NO:2417), KFVEEYTD (SEQ ID NO:2418), KFVEEYTGD (SEQ ID NO:2419), KFFVVEEYD (SEQ ID NO:2420), KFFVVEEYTD (SEQ ID NO:2421), KFFVVEEYTGD (SEQ ID NO:2422), KDELD (SEQ ID NO:2423), KDELTD (SEQ ID NO:2424), KDELTGD (SEQ ID NO:2425), KIDELD (SEQ ID NO:2426), KIDELTD (SEQ ID NO:2427), KIDELTGD (SEQ ID NO:2428), KLIDELD (SEQ ID NO:2429), KLIDELTD (SEQ ID NO:2430), KLIDELTGD (SEQ ID NO:2431), KFLIDELD (SEQ ID NO:2432), KFLIDELTD (SEQ ID NO:2433), KFLIDELTGD (SEQ ID NO:2434), KIFLIDELD (SEQ ID NO:2435), KIFLIDELTD (SEQ ID NO:2436), KIFLIDELTGD (SEQ ID NO:2437), KDPKD (SEQ ID NO:2438), KDPKTD (SEQ ID NO:2439), KDPKTGD (SEQ ID NO:2440), KVDPKD (SEQ ID NO:2441), KVDPKTD (SEQ ID NO:2442), KVDPKTGD (SEQ ID NO:2443), KTVDPKD (SEQ ID NO:2444), KTVDPKTD (SEQ ID NO:2445), KTVDPKTGD (SEQ ID NO:2446), KFTVDPKD (SEQ ID NO:2447), KFTVDPKTD (SEQ ID NO:2448), KFTVDPKTGD (SEQ ID NO:2449), KHFTVDPKD (SEQ ID NO:2450), KHFTVDPKTD (SEQ ID NO:2451), KHFTVDPKTGD (SEQ ID NO:2452), KDADD (SEQ ID NO:2453), KDADTD (SEQ ID NO:2454), KDADTGD (SEQ ID NO:2455), KIDADD (SEQ ID NO:2456), KIDADTD (SEQ ID NO:2457), KDADTGD (SEQ ID NO:2458), KDIDADD (SEQ ID NO:2459), KDIDADTD (SEQ ID NO:2460), KDIDADTGD (SEQ ID NO:2461), KFDIDADD (SEQ ID NO:2462), KFDIDADTD (SEQ ID NO:2463), KFDIDADTGD (SEQ ID NO:2464), KIFDIDADD (SEQ ID NO:2465), KIFDIDADTD (SEQ ID NO:2466), KIFDIDADTGD (SEQ ID NO:2467), DEEYK (SEQ ID NO:2468), DEEYTK (SEQ ID NO:2469), DEEYTGK (SEQ ID NO:2470), DVEEYK (SEQ ID NO:2471), DVEEYTK (SEQ ID NO:2472), DVEEYTGK (SEQ ID NO:2473), DVVEEYK (SEQ ID NO:2474), DVVEEYTK (SEQ ID NO:2475), DVVEEYTGK (SEQ ID NO:2476), DFVVEEYK (SEQ ID NO:2477), DFVEEYTK (SEQ ID NO:2478), DFVEEYTGK (SEQ ID NO:2479), DFFVVEEYK (SEQ ID NO:2480), DFFVVEEYTK, (SEQ ID NO:2481), DFFVVEEYTGK (SEQ ID NO:2482), DDELK (SEQ ID NO:2483), DDELTK (SEQ ID NO:2484), DDELTGK (SEQ ID NO:2485), DIDELK (SEQ ID NO:2486), DIDELTK (SEQ ID NO:2487), DIDELTGK (SEQ ID NO:2488), DLIDELK (SEQ ID NO:2489), DLIDELTK (SEQ ID NO:2490), DLIDELTGK (SEQ ID NO:2491), DFLIDELK (SEQ ID NO:2492), DFLIDELTK (SEQ ID NO:2493), DFLIDELTGK (SEQ ID NO:2494), DIFLIDELK (SEQ ID NO:2495), DIFLIDELTK (SEQ ID NO:2496), DIFLIDELTGK (SEQ ID NO:2497), DDPKK (SEQ ID NO:2498), DDPKTK (SEQ ID NO:2499), DDPKTGK (SEQ ID NO:2500), DVDPKK (SEQ ID NO:2501), DVDPKYK (SEQ ID NO:2502), DVTPKTGK (SEQ ID NO:2503), DTVDPKK (SEQ ID NO:2504), DTVDPKTK (SEQ ID NO:2505), DTVDPKTGK (SEQ ID NO:2506), DFTVDPKK (SEQ ID NO:2507), DFTVDPKTK (SEQ ID NO:2508), DFTVDPKTGK (SEQ ID NO:2509), DHFTVDPKK (SEQ ID NO:2510), DHFTVDPKTK (SEQ ID NO:2511), DHFTVDPKTGK (SEQ ID NO:2512), DDADK (SEQ ID NO:2513), DDADTK (SEQ ID NO:2514), DDADTGK (SEQ ID NO:2515), DIDADK (SEQ ID NO:2516), DIDADTK (SEQ ID NO:2517), DIDADTGK (SEQ ID NO:2518), DDIDADK (SEQ ID NO:2519), DDIDADTK (SEQ ID NO:2520), DDIDADTGK (SEQ ID NO:2521), DFDIDADK (SEQ ID NO:2522), DFDIDADTK (SEQ ID NO:2523), DFDIDADTGK (SEQ ID NO:2524), DIFDIDADK (SEQ ID NO:2525), DIFDIDADTK (SEQ ID NO:2526), DIFDIDADTGK (SEQ ID NO:2527), KEEYE (SEQ ID NO:2528), KEEYTE (SEQ ID NO:2529), KEEYTGE (SEQ ID NO:2530), KVEEYE (SEQ ID NO:2531), KVEEYTE (SEQ ID NO:2532), KVEEYTGE (SEQ ID NO:2533), KVVEEYE (SEQ ID NO:2534), KVVEEYTE (SEQ ID NO:2535), KVVEEYTGE (SEQ ID NO:2536), KFVVEEYE (SEQ ID NO:2537), KFVEEYTE (SEQ ID NO:2538), KFVEEYTGE (SEQ ID NO:2539), KFFVVEEYE (SEQ ID NO:2540), KFFVVEEYTE (SEQ ID NO:2541), KFFVVEEYTGE (SEQ ID NO:2542), KDELE (SEQ ID NO:2543), KDELTE (SEQ ID NO:2544), KDELTGE (SEQ ID NO:2545), KIDELE (SEQ ID NO:2546), KIDELTE (SEQ ID NO:2547), KIDELTGE (SEQ ID NO:2548), KLIDELE (SEQ ID NO:2549), KLIDELTE (SEQ ID NO:2550), KLIDELTGE (SEQ ID NO:2551), KFLIDELE (SEQ ID NO:2552), KFLIDELTE (SEQ ID NO:2553), KFLIDELTGE (SEQ ID NO:2554), KIFLIDELE (SEQ ID NO:2555), KIFLIDELTE (SEQ ID NO:2556), KIFLIDELTGE (SEQ ID NO:2557), KDPKE (SEQ ID NO:2558), KDPKTE (SEQ ID NO:2559), KDPKTGE (SEQ ID NO:2560), KVDPKE (SEQ ID NO:2561), KVDPKTE (SEQ ID NO:2562), KDPKTGE (SEQ ID NO:2563), KTVDPKE (SEQ ID NO:2564), KTVDPKTE (SEQ ID NO:2565), KTVDPKTGE (SEQ ID NO:2566), KFTVDPKE (SEQ ID NO:2567), KFTVDPKTE (SEQ ID NO:2568), KFTVDPKTGE (SEQ ID NO:2569), KHFTVDPKE (SEQ ID NO:2570), KHFTVDPKTE (SEQ ID NO:2571), KHFTVDPKTGE (SEQ ID NO:2572), KDADE (SEQ ID NO:2573), KDADTE (SEQ ID NO:2574), KDADTGE (SEQ ID NO:2575), KIDADE (SEQ ID NO:2576), KIDADTE (SEQ ID NO:2577), KIDADTGE (SEQ ID NO:2578), KDIDADE (SEQ ID NO:2579), KDIDADTE (SEQ ID NO:2580), KDIDADTGE (SEQ ID NO:2581), KFDIDADE (SEQ ID NO:2582), KFDIDADTE (SEQ ID NO:2583), KFDIDADTGE (SEQ ID NO:2584), KIFDIDADE (SEQ ID NO:2585), KIFDIDADTE (SEQ ID NO:2586), KIFDIDADTGE (SEQ ID NO:2587), VEEYT (SEQ ID NO:2588), VEEYTG (SEQ ID NO:2589), VVEEY (SEQ ID NO:2590), VVEEYT (SEQ ID NO:2591), VVEEYTG (SEQ ID NO:2592), FVVEEY (SEQ ID NO:2593), FVEEYT (SEQ ID NO:2594), FVEEYTG (SEQ ID NO:2595), FFVVEEY (SEQ ID NO:2596), FFVVEEYT (SEQ ID NO:2597), FFVVEEYTG (SEQ ID NO:2598), LIDEL (SEQ ID NO:2599), LIDELT (SEQ ID NO:2600), LIDELTG (SEQ ID NO:2601), FLIDEL (SEQ ID NO:2602), FLIDELT (SEQ ID NO:2603), FLIDELTG (SEQ ID NO:2604), IFLIDEL (SEQ ID NO:2605), IFLIDELT (SEQ ID NO:2606), IFLIDELTG (SEQ ID NO:2607), TVDPK (SEQ ID NO:2608), TVDPKT (SEQ ID NO:2609), TVDPKTG (SEQ ID NO:2610), FTVDPK (SEQ ID NO:2611), FTVDPKT (SEQ ID NO:2612), FTVDPKTG (SEQ ID NO:2613), HFTVDPK (SEQ ID NO:2614), HFTVDPKT (SEQ ID NO:2615), HFTVDPKTG (SEQ ID NO:2616), DADTG (SEQ ID NO:2617), IDADT (SEQ ID NO:2618), IDADTG (SEQ ID NO:2619), DIDAD (SEQ ID NO:2620), DIDADT (SEQ ID NO:2621), DIDADTG (SEQ ID NO:2622), FDIDAD (SEQ ID NO:2623), FDIDADT (SEQ ID NO:2624), FDIDADTG (SEQ ID NO:2625), IFDIDAD (SEQ ID NO:2626), IFDIDADT (SEQ ID NO:2627) and IFDIDADTG (SEQ ID NO:2628).

Representative cyclic peptides comprising a LI-cadherin CAR sequence include: CNNKC (SEQ ID NO:2629), CNNKTC (SEQ ID NO:2630), CNNKTGC (SEQ ID NO:2631), CINNKC (SEQ ID NO:2632), CINNKTC (SEQ ID NO:2633), CINNKTGC (SEQ ID NO:2634), CQINNKC (SEQ ID NO:2635), CQINNKTC (SEQ ID NO:2636), COINNKTGC (SEQ ID NO:2637), CFQINNKC (SEQ ID NO:2638), CFQINNKTC (SEQ ID NO:2639), CFQINNKTGC (SEQ ID NO:2640), CYFQINNKC (SEQ ID NO:2641), CYFQINNKTC (SEQ ID NO:2642), CYFQINNKTGC (SEQ ID NO:2643), ENNKK (SEQ ID NO:2644), ENNKTK (SEQ ID NO:2645), ENNKTGK (SEQ ID NO:2646), EINNKK (SEQ ID NO:2647), EINNKTK (SEQ ID NO:2648), EINNKTGK (SEQ ID NO:2649), EQINNKK (SEQ ID NO:2650), EQINNKTK (SEQ ID NO:2651), EQNNKTGK (SEQ ID NO:2652), EFQINNKK (SEQ ID NO:2653), EFQINNKTK (SEQ ID NO:2654), EFQINNKTGK (SEQ ID NO:2655), EYFQINNKK (SEQ ID NO:2656), EYFQINNKTK (SEQ ID NO:2657), EYFQINNKTGK (SEQ ID NO:2658), KNNKD (SEQ ID NO:2659), KNNKTD (SEQ ID NO:2660), KNNKTGD (SEQ ID NO:2661), KINNKD (SEQ ID NO:2662), KINNKTD (SEQ ID NO:2663), KINNKTGD (SEQ ID NO:2664), KQFNNKD (SEQ ID NO:2665), KQINNKTD (SEQ ID NO:2666), KQINNKTGD (SEQ ID NO:2667), KFQINNKD (SEQ ID NO:2668), KFQINNKTD (SEQ ID NO:2669), KFQINNKTGD (SEQ ID NO:2670), KYFQINNKD (SEQ ID NO:2671), KYFQINNKTD (SEQ ID NO:2672), KYFQINNKTGD (SEQ ID NO:2673), DNNKK (SEQ ID NO:2674), DNNKTK (SEQ ID NO:2675), DNNKTGK (SEQ ID NO:2676), DINNKK (SEQ ID NO:2677), DINNKTK (SEQ ID NO:2678), DINNKTGK (SEQ ID NO:2679), DQINNKK (SEQ ID NO:2680), DQINNKTK (SEQ ID NO:2681), DQINNKTGK (SEQ ID NO:2682), DFQINNKK (SEQ ID NO:2683), DFQINNKTK (SEQ ID NO:2684), DFQINNKTGK (SEQ ID NO:2685), DYFQINNKK (SEQ ID NO:2686), DYFQINNKTK (SEQ ID NO:2687), DYFQINNKTGK (SEQ ID NO:2688), KNNKE (SEQ ID NO:2689), KNNKTE (SEQ ID NO:2690), KNNKTGE (SEQ ID NO:2691), KINNKE (SEQ ID NO:2692), KINNKTE (SEQ ID NO:2693), KINNKTGE (SEQ ID NO:2694), KQINNKE (SEQ ID NO:2695), KQINNKTE (SEQ ID NO:2696), KQINNKTGE (SEQ ID NO:2697), KFQINNKE (SEQ ID NO:2698), KFQINNKTE (SEQ ID NO:2699), KFQINNKTGE (SEQ ID NO:2700), KYFQINNKE (SEQ ID NO:2701), KYFQINNKTE (SEQ ID NO:2702), KYFQINNKTGE (SEQ ID NO:2703), NNKTG (SEQ ID NO:2704), INNKT (SEQ ID NO:2705), INNKTG (SEQ ID NO:2706), QINNK (SEQ ID NO:2707), INNKT (SEQ ID NO:2708), QINNKTG (SEQ ID NO:2709), FQINNK (SEQ ID NO:2710), FQINNKT (SEQ ID NO:2711), FQINNKTG (SEQ ID NO:2712), YFQINNK (SEQ ID NO:2713), YFQINNKT (SEQ ID NO:2714) and YFQINNKTG (SEQ ID NO:2715)

Representative cyclic peptides comprising a protocadherin CAR sequence include: CDLVC (SEQ ID NO:2716), CDLVTC (SEQ ID NO:2717), CDLVTGC (SEQ ID NO:2718), CLDLVC (SEQ ID NO:2719), CLDLVTC (SEQ ID NO:2720), CLDLVTGC (SEQ ID NO:2721), CALDLVC (SEQ ID NO:2722), CALDLVTC (SEQ ID NO:2723), CALDLVTGC (SEQ ID NO:2724), CFALDLVC (SEQ ID NO:2725), CFALDLVTC (SEQ ID NO:2726), CFALDLVTGC (SEQ ID NO:2727), CLFALDLVC (SEQ ID NO:2728), CLFALDLVTC (SEQ ID NO:2729), CLFALDLVTGC (SEQ ID NO:2730), CNRDC (SEQ ID NO:2731), CNRDNC (SEQ ID NO:2732), CNRDNGC (SEQ ID NO:2733), CINRDC (SEQ ID NO:2734), CINRDNC (SEQ ID NO:2735), CINRDNGC (SEQ ID NO:2736), CTINRDC (SEQ ID NO:2737), CTINRDNC (SEQ ID NO:2738), CTINRDNGC (SEQ ID NO:2739), CFTINRDC (SEQ ID NO:2740), CFTINRDNC (SEQ ID NO:2741), CFTINRDNGC (SEQ ID NO:2742), CYFTINRDC (SEQ ID NO:2743), CYFTINRDNC (SEQ ID NO:2744), CYFTINRDNGC (SEQ ID NO:2745), CDPSC (SEQ ID NO:2746), CDPSSC (SEQ ID NO:2747), CDPSSGC (SEQ ID NO:2748), CIDPSC (SEQ ID NO:2749), CIDPSSC (SEQ ID NO:2750), CIDPSSGC (SEQ ID NO:2751), CEIDPSC (SEQ ID NO:2752), CEIDPSSC (SEQ ID NO:2753), CEIDPSSGC (SEQ ID NO:2754), CFEIDPSC (SEQ ID NO:2755), CFEIDPSSC (SEQ ID NO:2756), CEIDPSSGC (SEQ ID NO:2757), CFEIDPSC (SEQ ID NO:2758), CFEIDPSSC (SEQ ID NO:2759), CFEIDPSSGC (SEQ ID NO:2760), CLFEIDPSC (SEQ ID NO:2761), CLFEIDPSSC (SEQ ID NO:2762), CLFEIDPSSGC (SEQ ID NO:2763), EDLVK (SEQ ID NO:2764), EDLVTK (SEQ ID NO:2765), EDLVTGK (SEQ ID NO:2766), ELDLVK (SEQ ID NO:2767), ELDLVTK (SEQ ID NO:2768), ELDLVTGK (SEQ ID NO:2769), EALDLVK (SEQ ID NO:2770), EALDLVTK (SEQ ID NO:2771), EALDLVTGK (SEQ ID NO:2772), EFALDLVK (SEQ ID NO:2773), EFALDLVTK (SEQ ID NO:2774), EFALDLVTGK (SEQ ID NO:2775), ELFALDLVK (SEQ ID NO:2776), ELFALDLVTK (SEQ ID NO:2777), ELFALDLVTGK (SEQ ID NO:2778), ENRDK (SEQ ID NO:2779), ENRDNK (SEQ ID NO:2780), ENRDNGK (SEQ ID NO:2781), EINRDK (SEQ ID NO:2782), EINRDNK (SEQ ID NO:2783), EINRDNGK (SEQ ID NO:2784), ETINRDK (SEQ ID NO:2785), ETINRDNK (SEQ ID NO:2786), ETINRDNGK (SEQ ID NO:2787), EFTINRDK (SEQ ID NO:2788), EFTINRDNK (SEQ ID NO:2789), EFTINRDNGK (SEQ ID NO:2790), EYFTINRDK (SEQ ID NO:2791), EYFTINRDNK (SEQ ID NO:2792), EYFTINRDNGK (SEQ ID NO:2793), EDPKK (SEQ ID NO:2794), EDPKTK (SEQ ID NO:2795), EDPKTGK (SEQ ID NO:2796), EIDPKK (SEQ ID NO:2797), EIDPKTK (SEQ ID NO:2798), EIDPKTGK (SEQ ID NO:2799), ESIDPKK (SEQ ID NO:2800), ESIDPKTK (SEQ ID NO:2801), ESIDPKTGK (SEQ ID NO:2802), EFSIDPKK (SEQ ID NO:2803), EFSIDPKTK (SEQ ID NO:2804), EFSIDPKTGK (SEQ ID NO:2805), ELFSIDPKK (SEQ ID NO:2806), ELFSIDPKTK (SEQ ID NO:2807), ELFSIDPKTGK (SEQ ID NO:2808), EDPSK (SEQ ID NO:2809), EDPSSK (SEQ ID NO:2810), EDPSSGK (SEQ ID NO:2811), EIDPSK (SEQ ID NO:2812), EIDPSSK (SEQ ID NO:2813), EIDPSSGK (SEQ ID NO:2814), EEIDPSK (SEQ ID NO:2815), EEIDPSSK (SEQ ID NO:2816), EEIDPSSGK (SEQ ID NO:2817), EFEIDPSK (SEQ ID NO:2818), EFEIDPSSK (SEQ ID NO:2819), EEIDPSSGK (SEQ ID NO:2820), EFEIDPSK (SEQ ID NO:2821), EFEIDPSSK (SEQ ID NO:2822), EFEIDPSSGK (SEQ ID NO:2823), ELFEIDPSK (SEQ ID NO:2824), ELFEIDPSSK (SEQ ID NO:2825), ELFEIDPSSGK (SEQ ID NO:2826), KDLVD (SEQ ID NO:2827), KDLVTD (SEQ ID NO:2828), KDLVTGD (SEQ ID NO:2829), KLDLVD (SEQ ID NO:2830), KLDLVTD (SEQ ID NO:2831), KLDLVTGD (SEQ ID NO:2832), KALDLVD (SEQ ID NO:2833), KALDLVTD (SEQ ID NO:2834), KALDLVTGD (SEQ ID NO:2835), KFALDLVD (SEQ ID NO:2836), KFALDLVTD (SEQ ID NO:2837), KFALDLVTGD (SEQ ID NO:2838), KLFALDLVD (SEQ ID NO:2839), KLFALDLVTD (SEQ ID NO:2840), KLFALDLVTGD (SEQ ID NO:2841), KNRDD (SEQ ID NO:2842), KNRDND (SEQ ID NO:2843), KNRDNGD (SEQ ID NO:2844), KINRDD (SEQ ID NO:2845), KINRDND (SEQ ID NO:2846), KINRDNGD (SEQ ID NO:2847), KTINRDD (SEQ ID NO:2848), KTINRDND (SEQ ID NO:2849), KTINRDNGD (SEQ ID NO:2850), KFTINRDD (SEQ ID NO:2851), KFTINRDND (SEQ ID NO:2852), KFTINRDNGD (SEQ ID NO:2853), KYFTINRDD (SEQ ID NO:2854), KYFTDND (SEQ ID NO:2855), KYFTINRDNGD (SEQ ID NO:2856), KDPKD (SEQ ID NO:2857), KDPKTD (SEQ ID NO:2858), KDPKTGD (SEQ ID NO:2859), KIDPKD (SEQ ID NO:2860), KIDPKTD (SEQ ID NO:2861), KIDPKTGD (SEQ ID NO:2862), KSIDPKD (SEQ ID NO:2863), KSIDPKTD (SEQ ID NO:2864), KSIDPKTGD (SEQ ID NO:2865), KFSIDPKD (SEQ ID NO:2866), KFSIDPKTD (SEQ ID NO:2867), KFSIDPKTGD (SEQ ID NO:2868), KLFSIDPKD (SEQ ID NO:2869), KLFSIDPKTD (SEQ ID NO:2870), KLFSIDPKTGD (SEQ ID NO:2871), KDPSD (SEQ ID NO:2872), KDPSSD (SEQ ID NO:2873), KDPSSGD (SEQ ID NO:2874), KIDPSD (SEQ ID NO:2875), KIDPSSD (SEQ ID NO:2876), KIDPSSGD (SEQ ID NO:2877), KEIDPSD (SEQ ID NO:2878), KEIDPSSD (SEQ ID NO:2879), KEIDPSSGD (SEQ ID NO:2880), KFEIDPSD (SEQ ID NO:2881), KFEIDPSSD (SEQ ID NO:2882), KFEIDPSSGD (SEQ ID NO:2886), KLFEIDPSD (SEQ ID NO:2887), KLFEIDPSSD (SEQ ID NO:2888), KLFEIDPSSGD (SEQ ID NO:2889), KDLVE (SEQ ID NO:2890), KDLVTE (SEQ ID NO:2891), KDLVTGE (SEQ ID NO:2892), KLDLVE (SEQ ID NO:2893), KLDLVTE (SEQ ID NO:2894), KLDLVTGE (SEQ ID NO:2895), KALDLVE (SEQ ID NO:2896), KALDLVTE (SEQ ID NO:2897), KALDLVTGE (SEQ ID NO:2898), KFALDLVE (SEQ ID NO:2899), KFALDLVTE (SEQ ID NO:2900), KFALDLVTGE (SEQ ID NO:2901), KLFALDLVE (SEQ ID NO:2902), KLFALDLVTE (SEQ ID NO:2903), KLFALDLVTGE (SEQ ID NO:2904), KNRDE (SEQ ID NO:2905), KNRDNE (SEQ ID NO:2906), KNRDNGE (SEQ ID NO:2907), KINRDE (SEQ ID NO:2908), KINRDNE (SEQ ID NO:2909), KINRDNGE (SEQ ID NO:2910), KTINRDE (SEQ ID NO:2911), KTINRDNE (SEQ ID NO:2912), KTINRDNGE (SEQ ID NO:2913), KFTINRDE (SEQ ID NO:2914), KFTINRDNE (SEQ ID NO:2915), KFTINRDNGE (SEQ ID NO:2916), KYFTINRDE (SEQ ID NO:2917), KYFTINRDNE (SEQ ID NO:2918), KYFTINRDNGE (SEQ ID NO:2919), KDPKE (SEQ ID NO:2920), KDPKTE (SEQ ID NO:2921), KDPKTGE (SEQ ID NO:2922), KIDPKE (SEQ ID NO:2923), KIDPKTE (SEQ ID NO:2924), KIDPKTGE (SEQ ID NO:2925), KSIDPKE (SEQ ID NO:2926), KSIDPKTE (SEQ ID NO:2927), KSIDPKTGE (SEQ ID NO:2928), KFSIDPKE (SEQ ID NO:2929), KFSIDPKTE (SEQ ID NO:2930), KFSIDPKTGE (SEQ ID NO:2931), KLFSIDPKE (SEQ ID NO:2932), KLFSIDPKTE (SEQ ID NO:2933), KLFSIDPKTGE (SEQ ID NO:2934), KDPSE (SEQ ID NO:2935), KDPSSE (SEQ ID NO:2936), KDPSSGE (SEQ ID NO:2937), KIDPSE (SEQ ID NO:2938), KIDPSSE (SEQ ID NO:2939), KIDPSSGE (SEQ ID NO:2940), KEIDPSE (SEQ ID NO:2941), KEIDPSSE (SEQ ID NO:2942), KEIDPSSGE (SEQ ID NO:2943), KFEIDPSE (SEQ ID NO:2944), KFEIDPSSE (SEQ ID NO:2945), KFEIDPSSGE (SEQ ID NO:2949), KLFEIDPSE (SEQ ID NO:2950), KLFEIDPSSE (SEQ ID NO:2951), KLFEIDPSSGE (SEQ ID NO:2952), DDLVK (SEQ ID NO:2953), DDLVTK (SEQ ID NO:2954), DDLVTGK (SEQ ID NO:2955), DLDLVK (SEQ ID NO:2956), DLDLVTK (SEQ ID NO:2957), DLDLVTGK (SEQ ID NO:2958), DALDLVK (SEQ ID NO:2959), DALDLVTK (SEQ ID NO:2960), DALDLVTGK (SEQ ID NO:2961), DFALDLVK (SEQ ID NO:2962), DFALDLVTK (SEQ ID NO:2963), DFALDLVTGK (SEQ ID NO:2964), DLFALDLVK (SEQ ID NO:2965), DLFALDLVTK (SEQ ID NO:2966), DLFALDLVTGK (SEQ ID NO:2967), DNRDK (SEQ ID NO:2968), DNRDNK (SEQ ID NO:2969), DNRDNGK (SEQ ID NO:2970), DINRDK (SEQ ID NO:2971), DINRDNK (SEQ ID NO:2972), DINRDNGK (SEQ ID NO:2973), DTINRDK (SEQ ID NO:2974), DTINRDNK (SEQ ID NO:2975), DTINRDNGK (SEQ ID NO:2976), DFTINRDK (SEQ ID NO:2977), DFTINRDNK (SEQ ID NO:2978), DFTINRDNGK (SEQ ID NO:2979), DYFTINRDK (SEQ ID NO:2980), DYFTINRDNK (SEQ ID NO:2981), DYFTINRDNGK (SEQ ID NO:2982), DDPKK (SEQ ID NO:2983), DDPKTK (SEQ ID NO:2984), DDPKTGK (SEQ ID NO:2985), DIDPKK (SEQ ID NO:2986), DIDPKTK (SEQ ID NO:2987), DIDPKTGD (SEQ ID NO:2988), DSIDPKK (SEQ ID NO:2989), DSIDPKTK (SEQ ID NO:2990), DSIDPKTGK (SEQ ID NO:2991), DFSIDPKK (SEQ ID NO:2992), DFSIDPKTK (SEQ ID NO:2993), DFSIDPKTGK (SEQ ID NO:2994), DLFSIDPKK (SEQ ID NO:2995), DLFSIDPKTK (SEQ ID NO:2996), DLFSIDPKTGK (SEQ ID NO:2997), DDPSK (SEQ ID NO:2998), DDPSSK (SEQ ID NO:2999), DDPSSGK (SEQ ID NO:3000), DIDPSK (SEQ ID NO:3001), DIDPSSK (SEQ ID NO:3002), DIDPSSGK (SEQ ID NO:3003), DEIDPSK (SEQ ID NO:3004), DEIDPSSK (SEQ ID NO:3005), DEIDPSSGK (SEQ ID NO:3006), DFEIDPSK (SEQ ID NO:3007), DFEIDPSSK (SEQ ID NO:3008), DFEIDPSSGK (SEQ ID NO:3012), DLFEIDPSK (SEQ ID NO:3013), DLFEIDPSSK (SEQ ID NO:3014), DLFEIDPSSGK (SEQ ID NO:3015), DLVTG (SEQ ID NO:3016), LDLVT (SEQ ID NO:3017), LDLVTG (SEQ ID NO:3018), ALDLV (SEQ ID NO:3019), ALDLVT (SEQ ID NO:3020), ALDLVTG (SEQ ID NO:3021), FALDLV (SEQ ID NO:3022), FALDLVTC (SEQ ID NO:3023), FALDLVTG (SEQ ID NO:3024), LFALDLV (SEQ ID NO:3025), LFALDLVT (SEQ ID NO:3026), LFALDLVTG (SEQ ID NO:3027), NRDNG (SEQ ID NO:3028), INRDN (SEQ ID NO:3029), INRDNG (SEQ ID NO:3030), TINRD (SEQ ID NO:3031), TINRDN (SEQ ID NO:3032), TINRDNG (SEQ ID NO:3033), FTINRD (SEQ ID NO:3034), FTINRDN (SEQ ID NO:3035), FTINRDNG (SEQ ID NO:3036), YFTINRD (SEQ ID NO:3037), YFTINRDN (SEQ ID NO:3038), YFTINRDNG (SEQ ID NO:3039), DPKTG (SEQ ID NO:3040), IDPKT (SEQ ID NO:3041), IDPKTG (SEQ ID NO:3042), SIDPK (SEQ ID NO:3043), SIDPKT (SEQ ID NO:3044), SIDPKTG (SEQ ID NO:3045), FSIDPK (SEQ ID NO:3046), FSIDPKT (SEQ ID NO:3047), FSIDPKTG (SEQ ID NO:3048), LFSIDPK (SEQ ID NO:3049), LFSIDPKT (SEQ ID NO:3050), LFSIDPKTG (SEQ ID NO:3051), DPSSG (SEQ ID NO:3052), IDPSS (SEQ ID NO:3053), IDPSSG (SEQ ID NO:3054), EIDPSS (SEQ ID NO:3056), EIDPSSG (SEQ ID NO:3057), FEIDPS (SEQ ID NO:3058), FEIDPSS (SEQ ID NO:3059), EIDPSSG (SEQ ID NO:3060), FEIDPS (SEQ ID NO:3061), FEIDPSSG (SEQ ID NO:3062), LFEIDPS (SEQ ID NO:3063), LFEIDPSS (SEQ ID NO:3064) and LFEIDPSSG (SEQ ID NO:3065).

Representative cyclic peptides comprising a desmoglein CAR sequence include: CNQKC (SEQ ID NO:3066), CNQKTC (SEQ ID NO:3067), CNQKTGC (SEQ ID NO:3068), CINQKC (SEQ ID NO:3069), CINQKTC (SEQ ID NO:3070), CINQKTGC (SEQ ID NO:3071), CVINQKC (SEQ ID NO:3072), CVINQKTC (SEQ ID NO:3073), CVINQKTGC (SEQ ID NO:3074), CFVINQKC (SEQ ID NO:3075), CFVINQKTC (SEQ ID NO:3076), CFVINQKTGC (SEQ ID NO:3077), CIFVINQKC (SEQ ID NO:3078), CIFVINQKTC (SEQ ID NO:3079), CIFVINQKTGC (SEQ ID NO:3080), CNRNC (SEQ ID NO:3081), CNRNTC (SEQ ID NO:3082), CNRNTGC (SEQ ID NO:3083), CINRNC (SEQ ID NO:3084), CINRNTC (SEQ ID NO:3085), CINRNTGC (SEQ ID NO:3086), CIINRNC (SEQ ID NO:3087), CIINRNTC (SEQ ID NO:3088), CIINRNTGC (SEQ ID NO:3089), CFIINRNC (SEQ ID NO:3090), CFIINRNTC (SEQ ID NO:3091), CFIINRNTGC (SEQ ID NO:3092), CMFIINRNC (SEQ ID NO:3093), CMFIINRNTC (SEQ ID NO:3094), CMFIINRNTGC (SEQ ID NO:3095), CNKDC (SEQ ID NO:3096), CNKDTC (SEQ ID NO:3097), CNKDTGC (SEQ ID NO:3098), CLNKDC (SEQ ID NO:3099), CLNKDTC (SEQ ID NO:3100), CLNKDTGC (SEQ ID NO:3101), CYLNKDC (SEQ ID NO:3102), CYLNKDTC (SEQ ID NO:3103), CYLNKDTGC (SEQ ID NO:3104), CFYLNKDC (SEQ ID NO:3105), CFYLNKDTC (SEQ ID NO:3106), CFYLNKDTGC (SEQ ID NO:3107), CVFYLNKDC (SEQ ID NO:3108), CVFYLNKDTC (SEQ ID NO:3109), CVFYLNKDTGC (SEQ ID NO:3110), ENQKK (SEQ ID NO:3111), ENQKTK (SEQ ID NO:3112), ENQKTGK (SEQ ID NO:3113), EINQKK (SEQ ID NO:3114), EINQKTK (SEQ ID NO:3115), EINQKTGK (SEQ ID NO:3116), EVINQKK (SEQ ID NO:3117), EVINQKTK (SEQ ID NO:3118), EVINQKTGK (SEQ ID NO:3119), EFVINQKK (SEQ ID NO:3120), EFVINQKTK (SEQ ID NO:3121), EFVINQKTGK (SEQ ID NO:3122), EIFVINQKK (SEQ ID NO:3123), EIFVINQKTK (SEQ ID NO:3124), EIFVINQKTGK (SEQ ID NO:3125), ENRNK (SEQ ID NO:3126), ENRNTK (SEQ ID NO:3127), ENRINTK (SEQ ID NO:3128), EINRNK (SEQ ID NO:3129), EINRNTK (SEQ ID NO:3130), EINRNTGK (SEQ IDNO:3131), EIINRNK (SEQ ID NO:3132), EIINRNTK (SEQ ID NO:3133), EIINRNTGK (SEQ ID NO:3134), EFIINRNK (SEQ ID NO:3135), EFIINRNTK (SEQ ID NO:3136), EFIINRNTGK (SEQ ID NO:3137), EMFIINRNK (SEQ ID NO:3138), EMFIINRNTK (SEQ ID NO:3139), EMFIINRNTGK (SEQ ID NO:3140), ENKDK (SEQ ID NO:3141), ENKDTK (SEQ ID NO:3142), ENKDTGK (SEQ ID NO:3143), ELNKDK (SEQ ID NO:3144), ELNKDTK (SEQ ID NO:3145), ELNKDTGK (SEQ ID NO:3146), EYLNKDK (SEQ ID NO:3147), EYLNKDTK (SEQ ID NO:3148), EYLNKDTGK (SEQ ID NO:3149), EFYLNKDK (SEQ ID NO:3150), EFYLNKDTK (SEQ ID NO:3151), EFYLNKDTGK (SEQ ID NO:3152), EVFYLNKDK (SEQ ID NO:3153), EVFYLNKDTK (SEQ ID NO:3154), EVFYLNKDTGK (SEQ ID NO:3155), KINQKD (SEQ ID NO:3156), KNQKTD (SEQ ID NO:3157), KNQKTGD (SEQ ID NO:3158), KINQKD (SEQ ID NO:3159), KINQKTD (SEQ ID NO:3160), KINQKTGD (SEQ ID NO:3161), KVINQKD (SEQ ID NO:3162), KVINQKTD (SEQ ID NO:3163), KVINQKTGD (SEQ ID NO:3164), KFVINQKD (SEQ ID NO:3165), KFVINQKTD (SEQ ID NO:3166), KFVINQKTGD (SEQ ID NO:3167), KIFVINQKD (SEQ ID NO:3168), KIFVINQKTD (SEQ ID NO:3169), KIFVINQKTGD (SEQ ID NO:3170), KNRND (SEQ ID NO:3171), KNRNTD (SEQ ID NO:3172), KNRNTGD (SEQ ID NO:3173), KINRND (SEQ ID NO:3174), KINRNTD (SEQ ID NO:3175), KINRNTGD (SEQ ID NO:3176), KIINRND (SEQ ID NO:3177), KIINRNTD (SEQ ID NO:3178), KIINRNTGD (SEQ ID NO:3179), KFIINRND (SEQ ID NO:3180), KFIINRNTD (SEQ ID NO:3181), KFIINRNTGD (SEQ ID NO:3182), KMFIINRND (SEQ ID NO:3183), KMFIINRNTD (SEQ ID NO:3184), KMFIINRNTGD (SEQ ID NO:3185), KNKDD (SEQ ID NO:3186), KNKDTD (SEQ ID NO:3187), KNKDTGD (SEQ ID NO:3188), KLNKDD (SEQ ID NO:3189), KLNKDTD (SEQ ID NO:3190) KLNKDTGD (SEQ ID NO:3191), KYLNKDD (SEQ ID NO:3192), KYLNKDTD (SEQ ID NO:3193), KYLNKDTGD (SEQ ID NO:3194), KFYLNKDD (SEQ ID NO:3195), KFYLNKDTD (SEQ ID NO:3196), KFYLNKDTGD (SEQ ID NO:3197), KVFYLNKDD (SEQ ID NO:3198), KVFYLNKDTD (SEQ ID NO:3199), KVFYLNKDTGD (SEQ ID NO:3200), DNQKK (SEQ ID NO:3201), DNQKTK (SEQ ID NO:3202), DNQKTGK (SEQ ID NO:3203), DINQKK (SEQ ID NO:3204), DINQKTK (SEQ ID NO:3205), DINQKTGK (SEQ ID NO:3206), DVINQKK (SEQ ID NO:3207), DVINQKTK (SEQ ID NO:3208), DVINQKTGK (SEQ ID NO:3209), DFVINQKK (SEQ ID NO:3210), DFVINQKTK (SEQ ID NO:3211), DFVINQKTGK (SEQ ID NO:3212), DIFVINQKK (SEQ ID NO:3213), DIFVINQKTK (SEQ ID NO:3214), DIFVINQKTGK (SEQ ID NO:3215), DNRNK (SEQ ID NO:3216), DNRNTK (SEQ ID NO:3217), DNRNTGK (SEQ ID NO:3218), DINRNK (SEQ ID NO:3219), DINRNTK (SEQ ID NO:3220), DINRNTGK (SEQ ID NO:3221), DIINRNK (SEQ ID NO:3222), DIINRNTK (SEQ ID NO:3223), DIINRNTGK (SEQ ID NO:3224), DFIINRNK (SEQ ID NO:3225), DFIINRNTK (SEQ ID NO:3226), DFIINRNTGK (SEQ ID NO:3227), DMFIINRNK (SEQ ID NO:3228), DMFIINRNTK (SEQ ID NO:3229), DMFIINRNTGK (SEQ ID NO:3230), DNKDK (SEQ ID NO:3231), DNKDTK (SEQ ID NO:3232), DNKDTGK (SEQ ID NO:3233), DLNKDK (SEQ ID NO:3234), DLNKDTK (SEQ ID NO:3235), DLNKDTGK (SEQ ID NO:3236), DYLNKDK (SEQ ID NO:3237), DYLNKDTK (SEQ ID NO:3238), DYLNKDTGK (SEQ ID NO:3239), DFYLNKDK (SEQ ID NO:3240), DFYLNKDTK (SEQ ID NO:3241), DFYLNKDTGK (SEQ ID NO:3242), DVFYLNKDK (SEQ ID NO:3243), DVFYLNKDTK (SEQ ID NO:3244), DVFYLNKDTGK (SEQ ID NO:3245), KKNQKE (SEQ ID NO:3246), KNQKTE (SEQ ID NO:3247), KNQKTGE (SEQ ID NO:3248), KINQKE (SEQ ID NO:3249), KINQKTE (SEQ ID NO:3250), KINQKTGE (SEQ ID NO:3251), KVINQKE (SEQ ID NO:3252), KVINQKTE (SEQ ID NO:3253), KVINQKTGE (SEQ ID NO:3254), KFVINQKE (SEQ ID NO:3255), KFVINQKTE (SEQ ID NO:3256), KFVINQKTGE (SEQ ID NO:3257), KIFVINQKE (SEQ ID NO:3258), KIFVINQKTE (SEQ ID NO:3259), KIFVINQKTGE (SEQ ID NO:3260), KNRNE (SEQ ID NO:3261), KNRNTE (SEQ ID NO:3262), KNRNTGE (SEQ ID NO:3263), KINRNE (SEQ ID NO:3264), KINRNTE (SEQ ID NO:3265), KINRNTGE (SEQ ID NO:3266), KIINRNE (SEQ ID NO:3267), KIINRNTE (SEQ ID NO:3268), KIINRNTGE (SEQ ID NO:3269), KFIINRNE (SEQ ID NO:3270), KFIINRNTE (SEQ ID NO:3271), KFIINRNTGE (SEQ ID NO:3272), KMFIINRNE (SEQ ID NO:3273), KMFIINRNTE (SEQ ID NO:3274), KMFIINRNTGE (SEQ ID NO:3275), KNKDE (SEQ ID NO:3276), KNKDTE (SEQ ID NO:3277), KNKDTGE (SEQ ID NO:3278), KLNKDE (SEQ ID NO:3279), KLNKDTE (SEQ ID NO:3280), KLNKDTGE (SEQ ID NO:3281), KYLNKDE (SEQ ID NO:3282), KYLNKDTE (SEQ ID NO:3283), KYLNKDTGE (SEQ ID NO:3284), KFYLNKDE (SEQ ID NO:3285), KFYLNKDTE (SEQ ID NO:3286), KFYLNKDTGE (SEQ ID NO:3287), KVFYLNKDE (SEQ ID NO:3288), KVFYLNKDTE (SEQ ID NO:3289), KVFYLNKDTGE (SEQ ID NO:3290), NQKTG (SEQ ID NO:3291), INQKT (SEQ ID NO:3292), INQKTG (SEQ ID NO:3293), VINQK (SEQ ID NO:3294), VINQKT (SEQ ID NO:3295), VTNQKTG (SEQ ID NO:3296), FVINQK (SEQ ID NO:3297), FVINQKT (SEQ ID NO:3298), FVINQKTG (SEQ ID NO:3299), IFVINQK (SEQ ID NO:3300), IFVINQKT (SEQ ID NO:3301), IFVINQKTG (SEQ ID NO:3302), NRNTG (SEQ ID NO:3303), INRNT (SEQ ID NO:3304), INRNTG (SEQ ID NO:3305), IINRN (SEQ ID NO:3306), IINRNT (SEQ ID NO:3307), IINRNTG (SEQ ID NO:3308), FIINRN (SEQ ID NO:3309), FIINRNT (SEQ ID NO:3310), FIINRNTG (SEQ ID NO:3311), MFIINRN (SEQ ID NO:3312), MFIINRNT (SEQ ID NO:3313), MFIINRNTG (SEQ ID NO:3314), NKDTG (SEQ ID NO:3315), LNKDT (SEQ ID NO:3316), LNKDTG (SEQ ID NO:3317), YLNKD (SEQ ID NO:3318), YLNKDT (SEQ ID NO:3319), YLNKDTG (SEQ ID NO:3320), FYLNKD (SEQ ID NO:3321), FYLNKDT (SEQ ID NO:3322), FYLNKDTG (SEQ ID NO:3323), VFYLNKD (SEQ ID NO:3324), VFYLNKDT (SEQ ID NO:3325) and VFYLNKDTG (SEQ ID NO:3326).

Representative cyclic peptides comprising a desmocollin CAR sequence include: CEKDC (SEQ ID NO:3327), CEKDTC (SEQ ID NO:3328), CEKDTGC (SEQ ID NO:3329), CIEKDC (SEQ ID NO:3330), CIEKDTC (SEQ ID NO:3331), CIEKDTGC (SEQ ID NO:3332), CYIEKDC (SEQ ID NO:3333), CYIEKDTC (SEQ ID NO:3334), CYIEKDTGC (SEQ ID NO:3335), CFYIEKDC (SEQ ID NO:3336), CFYIEKDTC (SEQ ID NO:3337), CFYIEKDTGC (SEQ ID NO:3338), CLFYIEKDC (SEQ ID NO:3339), CLFYIEKDTC (SEQ ID NO:3340), CLFYIEKDTGC (SEQ ID NO:3341), CERDC (SEQ ID NO:3342), CERDTC (SEQ ID NO:3343), CERDTGC (SEQ ID NO:3344), CVERDC (SEQ ID NO:3345), CVERDTC (SEQ ID NO:3346), CVERDTGC (SEQ ID NO:3347), CYVERDC (SEQ ID NO:3348), CYVERDTC (SEQ ID NO:3349), CYVERDTGC (SEQ ID NO:3350), CFYVERDC (SEQ ID NO:3351), CFYVERDTC (SEQ ID NO:3352), CFYVERDTGC (SEQ ID NO:3353), CLFYVERDC (SEQ ID NO:3354), CLFYVERDTC (SEQ ID NO:3355), CLFYVERDTGC (SEQ ID NO:3356), CIERDC (SEQ ID NO:3357), CIERDTC (SEQ ID NO:3358), CIERDTGC (SEQ ID NO:3359), CYIERDC (SEQ ID NO:3360), CYIERDTC (SEQ ID NO:3361), CYIERDTGC (SEQ ID NO:3362), CFYIERDC (SEQ ID NO:3363), CFYIERDTC (SEQ ID NO:3364), CFYIERDTGC (SEQ ID NO:3365), CLFYIERDC (SEQ ID NO:3366), CLFYIERDTC (SEQ ID NO:3367), CLFYIERDTGC (SEQ ID NO:3368), EEKDK (SEQ ID NO:3369), EEKDTK (SEQ ID NO:3370), EEKDTGK (SEQ ID NO:3371), EIEKDK (SEQ ID NO:3372), EIEKDTK (SEQ ID NO:3373), EIEKDTGK (SEQ ID NO:3374), EYIEKDK (SEQ ID NO:3375), EYIEKDTK (SEQ ID NO:3376), EYIEKDTGK (SEQ ID NO:3377), EFYIEKDK (SEQ ID NO:3378), EFYIEKDTK (SEQ ID NO:3379), EFYIEKDTGK (SEQ ID NO:3380), ELFYIEKDK (SEQ ID NO:3381), ELFYIEKDTK (SEQ ID NO:3382), ELFYIEKDTGK (SEQ ID NO:3383), EERDK (SEQ ID NO:3384), EERDTK (SEQ ID NO:3385), EERDTGK (SEQ ID NO:3386), EVERDK (SEQ ID NO:3387), EVERDTK (SEQ ID NO:3388), EVERDTGK (SEQ ID NO:3389), EYVERDK (SEQ ID NO:3390), YVERDTK (SEQ ID NO:3391), EYVERDTGK (SEQ ID NO:3392), EFYVERDK (SEQ ID NO:3393), EFYVERDTK (SEQ ID NO:3394), EFYVERDTGK (SEQ ID NO:3395), ELFYVERDK (SEQ ID NO:3396), ELFYVERDTK (SEQ ID NO:3397), ELFYVERDTGK (SEQ ID NO:3398), EIERDK (SEQ ID NO:3399), EIERDTK (SEQ ID NO:3400), EIERDTGK (SEQ ID NO:3401), EYIERDK (SEQ ID NO:3402), EYIERDTK (SEQ ID NO:3403), EYIERDTGK (SEQ ID NO:3404), EFYIERDK (SEQ ID NO:3405), EFYIERDTK (SEQ ID NO:3406), EFYIERDTGK (SEQ ID NO:3407), ELFYIERDK (SEQ ID NO:3408), ELFYIERDTK (SEQ ID NO:3409), ELFYIERDTGK (SEQ ID NO:3410), KEKDD (SEQ ID NO:3411), KEKDTD (SEQ ID NO:3412), KEKDTGD (SEQ ID NO:3413), KIEKDD (SEQ ID NO:3414), KIEKDTD (SEQ ID NO:3415), KIEKDTGD (SEQ ID NO:3416), KYIEKDD (SEQ ID NO:3417), KYIEKDTD (SEQ ID NO:3418), KYIEKDTGD (SEQ ID NO:3419), KFYIEKDD (SEQ ID NO:3420), KFYIEKDTD (SEQ ID NO:3421), KFYIEKDTGD (SEQ ID NO:3422), KLFYIEKDD (SEQ ID NO:3423), KLFYIEKDTD (SEQ ID NO:3424), KLFYIEKDTGD (SEQ ID NO:3425), KERDD (SEQ ID NO:3426), KERDTD (SEQ ID NO:3427), KERDTGD (SEQ ID NO:3428), KVERDD (SEQ ID NO:3429), KVERDTD (SEQ ID NO:3430), KVERDTGD (SEQ ID NO:3431), KYVERDD (SEQ ID NO:3432), KYVERDTD (SEQ ID NO:3433), KYVERDTGD (SEQ ID NO:3434), KFYVERDD (SEQ ID NO:3435), KFYVERDTD (SEQ ID NO:3436), KFYVERDTGD (SEQ ID NO:3437), KLFYVERDD (SEQ ID NO:3438), KLFYVERDTD (SEQ ID NO:3439), KLFYVERDTGD (SEQ ID NO:3440), KIERDD (SEQ ID NO:3441), KIERDTD (SEQ ID NO:3442), KIERDTGD (SEQ ID NO:3443), KYIERD (SEQ ID NO:3444), KYIERDTD (SEQ ID NO:3445), KYIERDTGD (SEQ ID NO:3446), KFYIERDD (SEQ ID NO:3447), KFYIERDTD (SEQ ID NO:3448), KFYIERDTGD (SEQ ID NO:3449), KLFYIERDD (SEQ ID NO:3450), KLFYIERDTD (SEQ ID NO:3451), KLFYIERDTGD (SEQ ID NO:3452), DEKDK (SEQ ID NO:3453), DEKDTK (SEQ ID NO:3454), DEKDTGK (SEQ ID NO:3455), DIEKDK (SEQ ID NO:3456), DIEKDTK (SEQ ID NO:3457), DIEKDTGK (SEQ ID NO:3458), DYIEKDK (SEQ ID NO:3459), DYIEKDTK (SEQ ID NO:3460), DYIEKDTGK (SEQ ID NO:3461), DFYIEKDK (SEQ ID NO:3462), DFYIEKDTK (SEQ ID NO:3463), DFYIEKDTGK (SEQ ID NO:3464), DLFYIEKDK (SEQ ID NO:3465), DLFYIEKDTK (SEQ ID NO:3466), DLFYIEKDTGK (SEQ ID NO:3467), DERDK (SEQ ID NO:3468), DERDTK (SEQ ID NO:3469), DERDTGK (SEQ ID NO:3470), DVERDK (SEQ ID NO:3471), DVERDTK (SEQ ID NO:3472), DVERDTGK (SEQ ID NO:3473), DYVERDK (SEQ ID NO:3474), DYVERDTK (SEQ ID NO:3475), DYVERDTGK (SEQ ID NO:3476), DFYVERDK (SEQ ID NO:3477), DFYVERDTK (SEQ ID NO:3478), DFYVERDTGK (SEQ ID NO:3479), DLFYVERDK (SEQ ID NO:3480), DLFYVERDTK (SEQ ID NO:3481), DLFYVERDTGK (SEQ ID NO:3482), DIERDK (SEQ ID NO:3483), DIERDTK (SEQ ID NO:3484), DIERDTGK (SEQ ID NO:3485), DYIERDK (SEQ ID NO:3486), DYIERDTK (SEQ ID NO:3487), DYIERDTGK (SEQ ID NO:3488), DFYIERDK (SEQ ID NO:3489), DFYIERDTK (SEQ ID NO:3490), DFYIERDTGK (SEQ ID NO:3491), DLFYIERDK (SEQ ID NO:3492), DLFYIERDTK (SEQ ID NO:3493), DLFYIERDTGK (SEQ ID NO:3494), KEKDE (SEQ ID NO:3495), KEKDTE (SEQ ID NO:3496), KEKDTGE (SEQ ID NO:3497), KIEKDE (SEQ ID NO:3498), KIEKDTE (SEQ ID NO:3499), KIEKDTGE (SEQ ID NO:3500), KYIEKDE (SEQ ID NO:3501), KYIEKDTE (SEQ ID NO:3502), KYIEKDTGE (SEQ ID NO:3503), KFYIEKDE (SEQ ID NO:3504), KFYIEKDTE (SEQ ID NO:3505), KFYIEKDTGE (SEQ ID NO:3506), KLFYIEKDE (SEQ ID NO:3507), KLFYIEKDTE (SEQ ID NO:3508), KLFYIEKDTGE (SEQ ID NO:3509), KERDE (SEQ ID NO:3510), KERDTE (SEQ ID NO:3511), KERDTGE (SEQ ID NO:3512), KVERDE (SEQ ID NO:3513), KVERDTE (SEQ ID NO:3514), KVERDTGE (SEQ ID NO:3515), KYVERDE (SEQ ID NO:3516), KYVERDTE (SEQ ID NO:3517), KYVERDTGE (SEQ ID NO:3518), KFYVERDE (SEQ ID NO:3519), KFYVERDTE (SEQ ID NO:3520), KFYVERDTGE (SEQ ID NO:3521), KLFYVERDE (SEQ ID NO:3522), KLFYVERDTE (SEQ ID NO:3523), KLFYVERDTGE (SEQ ID NO:3524), KIERDE (SEQ ID NO:3525), KIERDTE (SEQ ID NO:3526), KIERDTGE (SEQ ID NO:3527), KYIERDE (SEQ ID NO:3528), KYIERDTE (SEQ ID NO:3529), KYIERDTGE (SEQ ID NO:3530), KFYIERDE (SEQ ID NO:3531), KFYIERDTE (SEQ ID NO:3532), KFYIERDTGE (SEQ ID NO:3533), KLFYIERDE (SEQ ID NO:3534), KLFYIERDTE (SEQ ID NO:3535), KLFYIERDTGE (SEQ ID NO:3536), EKDTG (SEQ ID NO:3537), IEKDT (SEQ ID NO:3538), IEKDTG (SEQ ID NO:3539), YIEKD (SEQ ID NO:3540), YIEKDT (SEQ ID NO:3541), YIEKDTG (SEQ ID NO:3542), FYIEKD (SEQ ID NO:3543), FYIEKDT (SEQ ID NO:3544), FYIEKDTG (SEQ ID NO:3545), LFYIEKD (SEQ ID NO:3546), LFYIEKDT (SEQ ID NO:3547), LFYIEKDTG (SEQ ID NO:3548), ERDTG (SEQ ID NO:3549), VERDT (SEQ ID NO:3550), VERDTG (SEQ ID NO:3551), YVERD (SEQ ID NO:3552), YVERDT (SEQ ID NO:3553), YVERDTG (SEQ ID NO:3554), FYVERD (SEQ ID NO:3555), FYVERDT (SEQ ID NO:3556), FYVERDTG (SEQ ID NO:3557), LFYVERD (SEQ ID NO:3558), LFYVERDT (SEQ ID NO:3559), LFYVERDTG (SEQ ID NO:3560), IERDT (SEQ ID NO:3561), IERDTG (SEQ ID NO:3562), YIERD (SEQ ID NO:3563), YIERDT (SEQ ID NO:3564), YIERDTG (SEQ ID NO:3565), FYIERD (SEQ ID NO:3566), FYIERDT (SEQ ID NO:3567), FYIERDTG (SEQ ID NO:3568), LFYIERD (SEQ ID NO:3569), LFYIERDT (SEQ ID NO:3570) and LFYIERDTG (SEQ ID NO:3571).

Representative cyclic peptides comprising a cnr CAR sequence include: CDPVC (SEQ ID NO:3572), CDPVSC (SEQ ID NO:3573), CDPVSGC (SEQ ID NO:3574), CIDPVC (SEQ ID NO:3575), CIDPVSC (SEQ ID NO:3576), CIDPVSGC (SEQ ID NO:3577), CHIDPVC (SEQ ID NO:3578), CHIDPVSC (SEQ ID NO:3579), CHIDPVSGC (SEQ ID NO:3580), CFHIDPVC (SEQ ID NO:3581), CFHIDPVSC (SEQ ID NO:3582), CFHIDPVSGC (SEQ ID NO:3583), CKFHIDPVC (SEQ ID NO:3584), CKFHIDPVSC (SEQ ID NO:3585), CKFHIDPVSGC (SEQ ID NO:3586), CDADC (SEQ ID NO:3587), CDADTC (SEQ ID NO:3588), CDADTGC (SEQ ID NO:3589), CIDADTC (SEQ ID NO:3590), CIDADC (SEQ ID NO:3591), CIDADTGC (SEQ ID NO:3592), CSIDADC (SEQ ID NO:3593), CSIDADTC (SEQ ID NO:3594), CSIDADTGC (SEQ ID NO:3595), CFSIDADC (SEQ ID NO:3596), CFSIDADTC (SEQ ID NO:3597), CFSIDADTGC (SEQ ID NO:3598), COFSIDADC (SEQ ID NO:3599), COFSIDADTC (SEQ ID NO:3600), CQFSIDADTGC (SEQ ID NO:3601), CDSVC (SEQ ID NO:3602), CDSVSC (SEQ ID NO:3603), CDSVSGC (SEQ ID NO:3604), CIDSVC (SEQ ID NO:3605), CIDSVSC (SEQ ID NO:3606), CIDSVSGC (SEQ ID NO:3607), CHIDSVC (SEQ ID NO:3608), CHIDSVSC (SEQ ID NO:3609), CHIDSVSGC (SEQ ID NO:3610), CFHIDSVC (SEQ ID NO:3611), CFHIDSVSC (SEQ ID NO:3612), CFHIDSVSGC (SEQ ID NO:3613), CTFHIDSVC (SEQ ID NO:3614), CTFHIDSVSC (SEQ ID NO:3615), CTFHIDSVSGC (SEQ ID NO:3616), CDSNC (SEQ ID NO:3617), CDSNSC (SEQ ID NO:3618), CDSNSGC (SEQ ID NO:3619), CIDSNC (SEQ ID NO:3620), CIDSNSC (SEQ ID NO:3621), CIDSNSGC (SEQ ID NO:3622), CNIDSNC (SEQ ID NO:3623), CNIDSNSC (SEQ ID NO:3624), CNIDSNSGC (SEQ ID NO:3625), CFNIDSNC (SEQ ID NO:3626), CFNIDSNSC (SEQ ID NO:3627), CFNIDSNSGC (SEQ ID NO:3628), CAFNIDSNC (SEQ ID NO:3629), CAFNIDSNSC (SEQ ID NO:3631), CAFNIDSNSGC (SEQ ID NO:3632), CDSSC (SEQ ID NO:3633), CDSSSC (SEQ ID NO:3634), CDSSSGC (SEQ ID NO:3635), CIDSSC (SEQ ID NO:3636), CIDSSSC (SEQ ID NO:3637), CIDSSSGC (SEQ ID NO:3638), CTIDSSC (SEQ ID NO:3639), CTIDSSSC (SEQ ID NO:3640), CTIDSSSGC (SEQ ID NO:3641), CFTIDSSC (SEQ ID NO:3642), CFTIDSSSC (SEQ ID NO:3643), CFTIDSSSGC (SEQ ID NO:3644), CKFTIDSSC (SEQ ID NO:3645), CKFTIDSSSC (SEQ ID NO:3646), CKFTIDSSSGC (SEQ ID NO:3647), CDEKC (SEQ ID NO:3648), CDEKNC (SEQ ID NO:3649), CDEKNGC (SEQ ID NO:3650), CLDEKC (SEQ ID NO:3651), CLDEKNC (SEQ ID NO:3652), CLDEKNGC (SEQ ID NO:3653), CTLDEKC (SEQ ID NO:3654), CTLDEKNC (SEQ ID NO:3655), CTLDEKNGC (SEQ ID NO:3656), CFTLDEKC (SEQ ID NO:3657), CFTLDEKNC (SEQ ID NO:3658), CFTLDEKNGC (SEQ ID NO:3659), CLFTLDEKC (SEQ ID NO:3660), CLFTLDEKNC (SEQ ID NO:3661), CLFTLDEKNGC (SEQ ID NO:3662), CNEKC (SEQ ID NO:3663), CNEKTC (SEQ ID NO:3664), CNEKTGC (SEQ ID NO:3665), CINEKC (SEQ ID NO:3666), CINEKTC (SEQ ID NO:3667), CINEKTGC (SEQ ID NO:3668), CLINEKC (SEQ ID NO:3669), CLINEKTC (SEQ ID NO:3670), CLINEKTGC (SEQ ID NO:3671), CFLINEKC (SEQ ID NO:3672), CFLINEKRC (SEQ ID NO:3673), CFLINEKTGC (SEQ ID NO:3674), CKFLINEKC (SEQ ID NO:3675), CKFLINEKTC (SEQ ID NO:3676), CKFLINEKTGC (SEQ ID NO:3677), EDPVK (SEQ ID NO:3678), EDPVSK (SEQ ID NO:3679), EDPVSGK (SEQ ID NO:3680), EIDPVK (SEQ ID NO:3681), EIDPVSK (SEQ ID NO:3682), EIDPVSGK (SEQ ID NO:3683), EHIDPVK (SEQ ID NO:3684), EHIDPVSK (SEQ ID NO:3685), EHIDPVSGK (SEQ ID NO:3686), EFHIDPVK (SEQ ID NO:3687), EFHIDPVSK (SEQ ID NO:3688), EFHIDPVSGK (SEQ ID NO:3689), EKFHIDPVK (SEQ ID NO:3690), EKFHIDPVSK (SEQ ID NO:3691), EKFHIDPVSGK (SEQ ID NO:3692), EDADK (SEQ ID NO:3693), EDADTK (SEQ ID NO:3694), EDADTGK (SEQ ID NO:3695), EIDADK (SEQ ID NO:3696), EIDADTK (SEQ ID NO:3697), EIDADTGK (SEQ ID NO:3698), ESIDADK (SEQ ID NO:3699), ESIDADTK (SEQ ID NO:3700), ESIDADTGK (SEQ ID NO:3701), EFSIDADK (SEQ ID NO:3702), EFSIDADTK (SEQ ID NO:3703), EFSIDADTGK (SEQ ID NO:3704), EQFSIDADK (SEQ ID NO:3705), EQFSIDADTK (SEQ ID NO:3706), EQFSIDADTGK (SEQ ID NO:3707), EDSVK (SEQ ID NO:3708), EDSVSK (SEQ ID NO:3709), EDSVSGK (SEQ ID NO:3710), EIDSVK (SEQ ID NO:3711), EIDSVSK (SEQ ID NO:3712), EIDSVSGK (SEQ ID NO:3713), EHIDSVK (SEQ ID NO:3714), EHIDSVSK (SEQ ID NO:3715), EHIDSVSGK (SEQ ID NO:3716), EFHIDSVK (SEQ ID NO:3717), EFHIDSVSK (SEQ ID NO:3718), EFHIDSVSGK (SEQ ID NO:3719), ETFHIDSVK (SEQ ID NO:3720), ETFHIDSVSK (SEQ ID NO:3721), ETFHIDSVSGK (SEQ ID NO:3722), EDSNK (SEQ ID NO:3723), EDSNSK (SEQ ID NO:3724), EDSNSGK (SEQ ID NO:3725), EIDSNK (SEQ ID NO:3726), EIDSNSK (SEQ ID NO:3727), EIDSNSGK (SEQ ID NO:3728), ENIDSNK (SEQ ID NO:3729), ENIDSNSK (SEQ ID NO:3730), ENIDSNSGK (SEQ ID NO:3731), EFNIDSNK (SEQ ID NO:3732), EFNIDSNSK (SEQ ID NO:3733), EFNIDSNSGK (SEQ ID NO:3734), EAFNIDSNK (SEQ ID NO:3735), EAFNIDSNSK (SEQ ID NO:3737), EAFNIDSNSGK (SEQ ID NO:3738), EDSSK (SEQ ID NO:3739), EDSSSK (SEQ ID NO:3740), EDSSSGK (SEQ ID NO:3741), EIDSSK (SEQ ID NO:3742), EIDSSSK (SEQ ID NO:3743), EIDSSSGK (SEQ ID NO:3744), ETIDSSK (SEQ ID NO:3745), ETIDSSSK (SEQ ID NO:3746), ETIDSSSGK (SEQ ID NO:3747), EFTIDSSK (SEQ ID NO:3748), EFTIDSSSK (SEQ ID NO:3749), EFTIDSSSGK (SEQ ID NO:3750), EKFTIDSSK (SEQ ID NO:3751), EKFTIDSSSK (SEQ ID NO:3752), EKFTIDSSSGK (SEQ ID NO:3753), EDEKK (SEQ ID NO:3754), EDEKNK (SEQ ID NO:3755), EDEKNGK (SEQ ID NO:3756), ELDEKK (SEQ ID NO:3757), ELDEKNK (SEQ ID NO:3758), ELDEKNGK (SEQ ID NO:3759), ETLDEKK (SEQ ID NO:3760), ETLDEKNK (SEQ ID NO:3761), ETLDEKNGK (SEQ ID NO:3762), EFTLDEKK (SEQ ID NO:3763), EFTLDEKNK (SEQ ID NO:3764), EFTLDEKNGK (SEQ ID NO:3765), ELFTLDEKK (SEQ ID NO:3766), ELFTLDEKNK (SEQ ID NO:3767), ELFTLDEKNGK (SEQ ID NO:3768), ENEKK (SEQ ID NO:3769), ENEKTK (SEQ ID NO:3770), ENEKTGK (SEQ ID NO:3771), EINEKK (SEQ ID NO:3772), EINEKTK (SEQ ID NO:3773), EINEKTGK (SEQ ID NO:3774), ELINEKK (SEQ ID NO:3775), ELINEKTK (SEQ ID NO:3776), ELINEKTGK (SEQ ID NO:3777), EFLINEKK (SEQ ID NO:3778), EFLINEKTK (SEQ ID NO:3779), EFLINEKTGK (SEQ ID NO:3780), EKFLINEKK (SEQ ID NO:3781), EKFLINEKTK (SEQ ID NO:3782), EKFLINEKTGK (SEQ ID NO:3783), KDPVD (SEQ ID NO:3784), KDPVSD (SEQ ID NO:3785), KDPVSGD (SEQ ID NO:3786), KIDPVD (SEQ ID NO:3787), KIDPVSD (SEQ ID NO:3788), KIDPVSGD (SEQ ID NO:3789), KHIDPVD (SEQ ID NO:3790), KHIDPVSD (SEQ ID NO:3791), KHIDPVSGD (SEQ ID NO:3792), KFHIDPVD (SEQ ID NO:3793), KFHIDPVSD (SEQ ID NO:3794), KFHIDPVSGD (SEQ ID NO:3795), KKFHIDPVD (SEQ ID NO:3796), KKFHIDPVSD (SEQ ID NO:3797), KKFHIDPVSGD (SEQ ID NO:3798), KDADD (SEQ ID NO:3799), KDADTD (SEQ ID NO:3800), KDADTGD (SEQ ID NO:3801), KIDADD (SEQ ID NO:3802), KIDADTD (SEQ ID NO:3803), KIDADTGD (SEQ ID NO:3804), KSIDADD (SEQ ID NO:3805), KSIDADTD (SEQ ID NO:3806), KSIDADTGD (SEQ ID NO:3807), KFSIDADD (SEQ ID NO:3808), KFSIDADTD (SEQ ID NO:3809), KFSIDADTGD (SEQ ID NO:3810), KQFSIDADD (SEQ ID NO:3811), KQFSIDADTD (SEQ ID NO:3812), KQFSIDADTGD (SEQ ID NO:3813), KDSVD (SEQ ID NO:3814), KDSVSD (SEQ ID NO:3815), KDSVSGD (SEQ ID NO:3816), KIDSVD (SEQ ID NO:3817), KIDSVSD (SEQ ID NO:3818), KIDSVSGD (SEQ ID NO:3819), KHIDSVD (SEQ ID NO:3820), KHIDSVSD (SEQ ID NO:3821), KHIDSVSGD (SEQ ID NO:3822), KFHIDSVD (SEQ ID NO:3823), KFHIDSVSD (SEQ ID NO:3824), KFHIDSVSGD (SEQ ID NO:3825), KTFHIDSVD (SEQ ID NO:3826), KTFHIDSVSD (SEQ ID NO:3827), KTFHIDSVSGD (SEQ ID NO:3828), KDSND (SEQ ID NO:3829), KDSNSD (SEQ ID NO:3830), KDSNSGD (SEQ ID NO:3831), KIDSND (SEQ ID NO:3832), KIDSNSD (SEQ ID NO:3833), KIDSNSGD (SEQ ID NO:3834), KNIDSND (SEQ ID NO:3835), KNIDSNSD (SEQ ID NO:3836), KNIDSNSGD (SEQ ID NO:3837), KFNIDSND (SEQ ID NO:3838), KFNIDSNSD (SEQ ID NO:3839), KFNIDSNSGD (SEQ ID NO:3840), KAFNIDSND (SEQ ID NO:3841), KAFNIDSNSD (SEQ ID NO:3843), KAFNIDSNSGD (SEQ ID NO:3844), KDSSD (SEQ ID NO:3845), KDSSSD (SEQ ID NO:3846), KDSSSGD (SEQ ID NO:3847), KIDSSD (SEQ ID NO:3848), KIDSSSD (SEQ ID NO:3849), KIDSSSGD (SEQ ID NO:3850), KTIDSSD (SEQ ID NO:3851), KTIDSSSD (SEQ ID NO:3852), KTIDSSSGD (SEQ ID NO:3853), KFTIDSSD (SEQ ID NO:3854), KFTIDSSSD (SEQ ID NO:3855), KFTIDSSSGD (SEQ ID NO:3856), KKFTIDSSD (SEQ ID NO:3857), KKFTIDSSSD (SEQ ID NO:3858), KKFTIDSSSGD (SEQ ID NO:3859), KDEKD (SEQ ID NO:3860), KDEKND (SEQ ID NO:3861), KDEKNGD (SEQ ID NO:3862), KLDEKD (SEQ ID NO:3863), KLDEKND (SEQ ID NO:3864), KLDEKNGD (SEQ ID NO:3865), KTLDEKD (SEQ ID NO:3866), KTLDEKND (SEQ ID NO:3867), KTLDEKNGD (SEQ ID NO:3868), KFTLDEKD (SEQ ID NO:3869), KFTLDEKND (SEQ ID NO:3870), KFTLDEKNGD (SEQ ID NO:3871), KLFTLDEKD (SEQ ID NO:3872), KLFTLDEKND (SEQ ID NO:3873), KLFTLDEKNGD (SEQ ID NO:3874), KNEKD (SEQ ID NO:3875), KNEKTD (SEQ ID NO:3876), KNEKTGD (SEQ ID NO:3877), KINEKD (SEQ ID NO:3878), KINEKTD (SEQ ID NO:3879), KINEKTGD (SEQ ID NO:3880), KLINEKD (SEQ ID NO:3881), KLINEKTD (SEQ ID NO:3882), KLINEKTGD (SEQ ID NO:3883), KFLINEKD (SEQ ID NO:3884), KFLINEKTD (SEQ ID NO:3885), KFLINEKTGD (SEQ ID NO:3886), KKFLINEKD (SEQ ID NO:3887), KKFLINEKTD (SEQ ID NO:3888) and KKFLINEKTGD (SEQ ID NO:3889).

As noted above, certain preferred modulating agents comprise a peptide (containing a nonclassical cadherin CAR sequence or an analogue thereof) in which at least one terminal amino acid residue is modified (e.g., the N-terminal amino group is modified by, for example, acetylation or alkoxybenzylation and/or an amide or ester is formed at the C-terminus). It has been found, within the context of the present invention, that the addition of at least one such group to a linear or cyclic peptide modulating agent may improve the ability of the agent to modulate a nonclassical cadherin-mediated function. Certain preferred modulating agents contain modifications at the N- and C-terminal residues, such as N-Ac-IFVIDDKSG-NH$_2$ (SEQ ID NO:85), which modulates OB-cadherin mediated functions. Other CAR sequences provided herein are also preferably modified by the addition of one or more terminal groups.

The present invention further contemplates nonclassical cadherin CAR sequences from other organisms. Such CAR sequences may be identified based upon sequence similarity to the sequences provided herein, and the ability to modulate a nonclassical cadherin-mediated function such as may be confirmed as described herein.

Figure 4A:
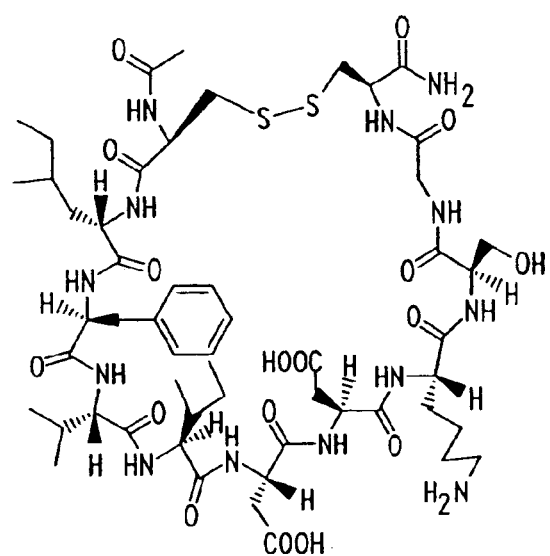
FIGS. 4A–4C provide structures of representative modulating agents (SEQ ID NOS: 85, 669–674, 676, 677, 683, 697 and 717).
Figure 4A:
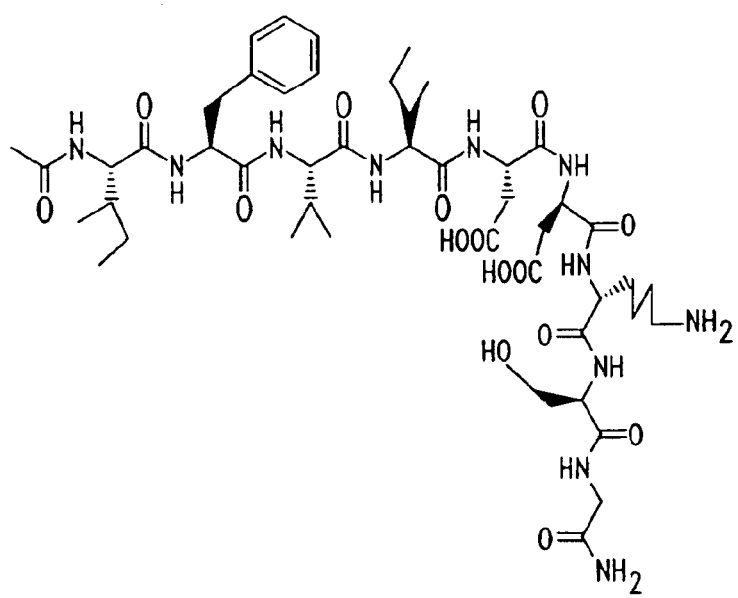
Figure 4B:
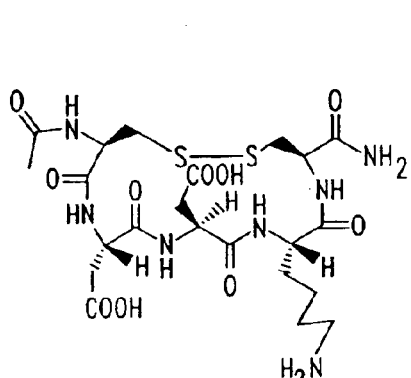
Figure 4B:
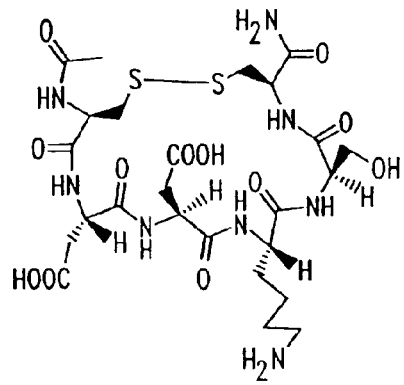
Figure 4B:
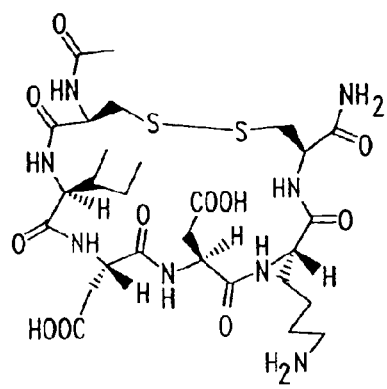
Figure 4B:
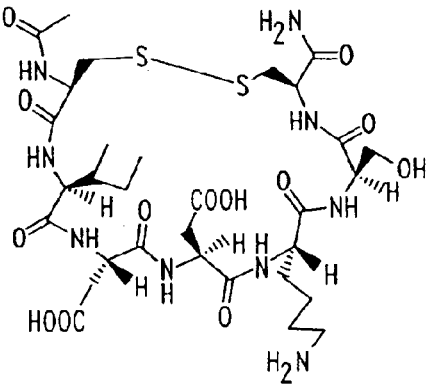
Figure 4B:
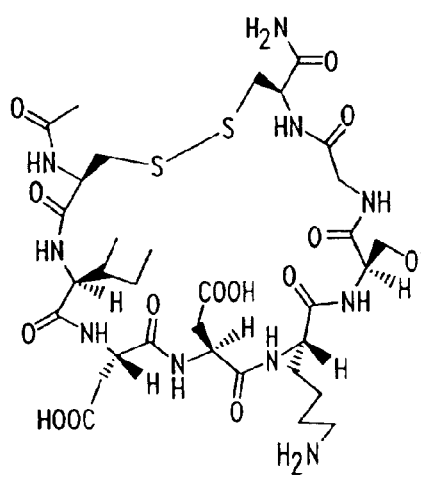
Figure 4B:
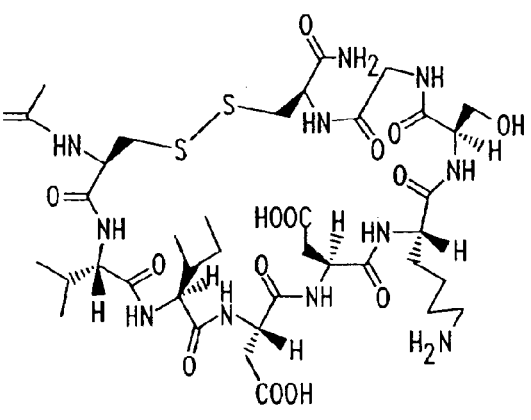
Figure 4C:
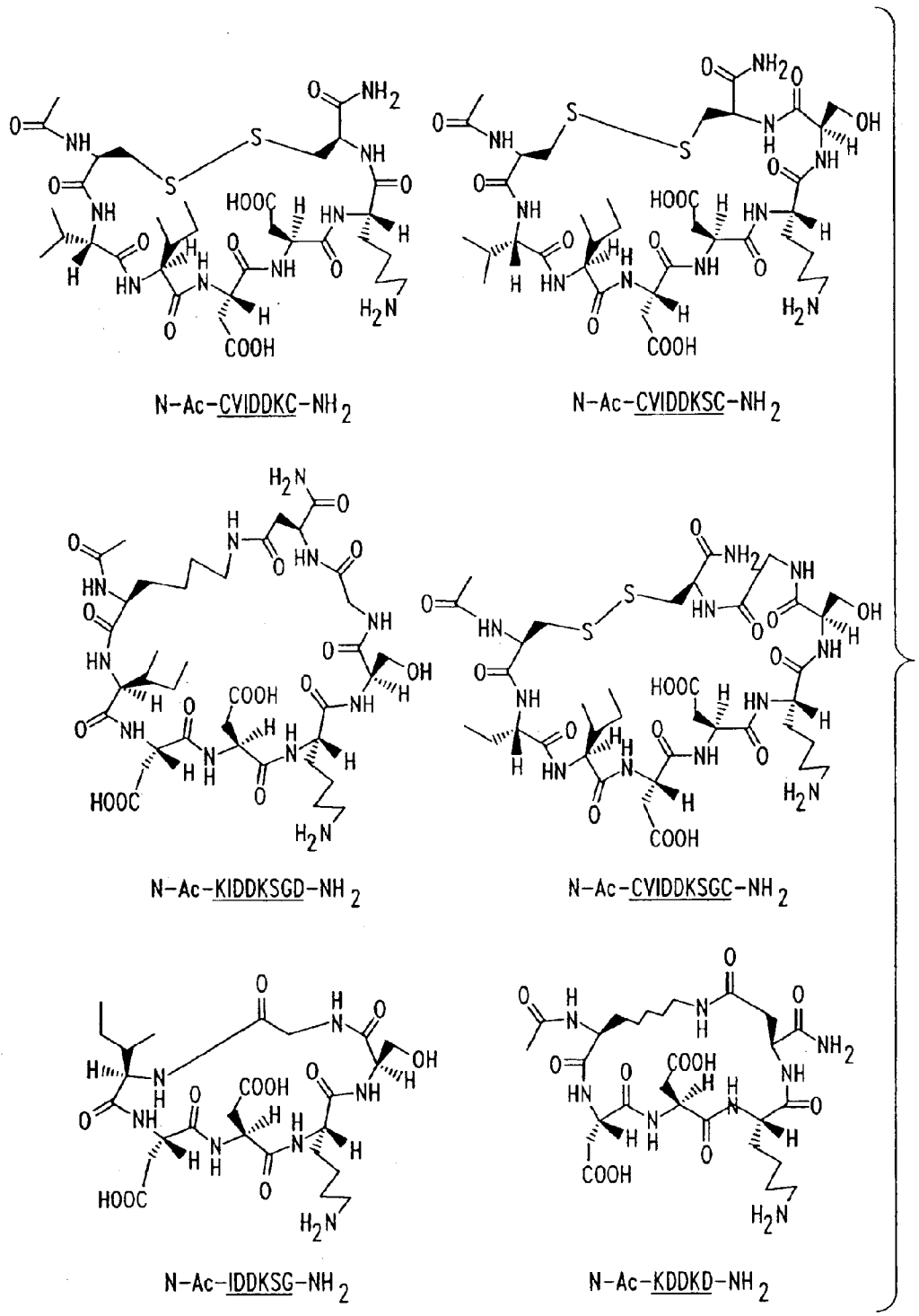

Within certain embodiments, as discussed below, cyclic peptides that contain small CAR sequences (e.g., three residues without significant flanking sequences) are preferred for modulating nonclassical cadherin-mediated functions. Such peptides may contain an N-acetyl group and a C-amide group (e.g., the 5-residue ring N-Ac-CDDKC-NH$_2$ (SEQ ID NO:669) or N-Ac-KDDKD-NH$_2$ (SEQ ID NO:697), for modulating OB-cadherin mediated functions). Small cyclic peptides may generally be used to specifically modulate adhesion of cancer and/or other cell types by topical administration or by systemic administration, with or without linking a targeting agent to the peptide, as discussed below. Certain representative cyclic peptides comprising an OB-cadherin CAR sequence are shown in FIGS. 4A–4C. Other representative cyclic peptides comprising a nonclassical cadherin CAR sequence are shown in FIGS. 7A–7F.

Within embodiments in which inhibition of a nonclassical cadherin-interaction is desired, a modulating agent may contain one nonclassical cadherin CAR sequence, or multiple CAR sequences that are adjacent to one another (i.e., without intervening sequences) or in close proximity (i.e., separated by peptide and/or non-peptide linkers to give a distance between the nonclassical CAR sequences that ranges from about 0.1 to 400 nm). A linker may be any molecule (including peptide and/or non-peptide sequences) that does not contain a CAR sequence and that can be covalently linked to at least two peptide sequences. Using a linker, CAR sequence-containing peptides and other peptide or protein sequences may be joined end-to-end (i.e., the linker may be covalently attached to the carboxyl or amino group of each peptide sequence), and/or via side chains. One linker that can be used for such purposes is (H$_2$N(CH$_2$)

$_n$CO$_2$H), or derivatives thereof, where n ranges from 1 to 4. Other linkers that may be used will be apparent to those of ordinary skill in the art. Peptide and non-peptide linkers may generally be incorporated into a modulating agent using any appropriate method known in the art.

Within embodiments in which enhancement of cell adhesion mediated by a nonclassical cadherin is desired, a modulating agent may contain multiple nonclassical cadherin CAR sequences, or antibodies that specifically bind to such sequences, joined by linkers as described above. For enhancers of cadherin function, the linker distance should generally be 400–10,000 nm. One linker that can be used for such purposes is (H$_2$N(CH$_2$)$_n$CO$_2$H)$_m$, or derivatives thereof, where n ranges from 1 to 10 and m ranges from 1 to 4000. For example, if glycine (H$_2$NCH$_2$CO$_2$H) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Enhancement of cell adhesion may also be achieved by attachment of multiple modulating agents to a support material, as discussed further below.

A modulating agent as described herein may additionally comprise one or more CAR sequences for one or more different adhesion molecules (including, but not limited to, other CAMs) and/or one or more substances, such as antibodies or fragments thereof, that bind to such sequences. Linkers may, but need not, be used to separate such CAR sequence(s) and/or antibody sequence(s) from the CAR sequence(s) and/or each other. Such modulating agents may generally be used within methods in which it is desirable to simultaneously disrupt a function mediated by multiple adhesion molecules. As used herein, an "adhesion molecule" is any molecule that mediates cell adhesion via a receptor on a cell's surface. Adhesion molecules include cell adhesion proteins (e.g., other members of the cadherin gene superfamily, such as N-cadherin and E-cadherin); integrins; extracellular matrix proteins such as laminin, fibronectin, collagens, vitronectin, entactin and tenascin; and members of the immunoglobulin supergene family, such as N-CAM. Preferred CAR sequences for inclusion within a modulating agent include the classical cadherin CAR sequence His-Ala-Val (HAV); Arg-Gly-Asp (RGD), which is bound by integrins (see Cardarelli et al., *J. Biol. Chem.* 267:23159–64, 1992); Tyr-Ile-Gly-Ser-Arg (YIGSR; SEQ ID NO:48), which is bound by α6β1 integrin; KYSFNYDGSE (SEQ ID NO:49), which is bound by N-CAM; the N-CAM heparin sulfate-binding site IWKHKGRDVILKKDVRF (SEQ ID NO:50); the putative claudin CAR sequence IYSY (SEQ ID NO:51) and/or the occludin CAR sequence LYHY (SEQ ID NO:52). Using linkers, such modulating agents may form linear or branched structures. Within one embodiment, modulating agents having a branched structure comprise four different CAR sequences, such as IFVIDDKSG (SEQ ID NO:85), RGD, YIGSR (SEQ ID NO:48) and HAV. Bi-functional modulating agents that comprise a nonclassical cadherin CAR sequence joined via a linker to a classical cadherin CAR sequence are also preferred for certain embodiments. As noted above, linkers preferably produce a distance between CAR sequences ranging from 0.1 to 10,000 nm, more preferably ranging from 0.1–400 nm. A separation distance between recognition sites may generally be determined according to the desired function of the modulating agent.

The total number of CAR sequences (including the nonclassical cadherin CAR sequence, with or without other CAR sequences derived from one or more different adhesion molecules) present within a modulating agent may range from 1 to a large number, such as 100, preferably from 1 to 10, and more preferably from 1 to 5. Peptide modulating agents comprising multiple CAR sequences typically contain from 6 (e.g., DDK-HAV) to about 1000 amino acid residues, preferably from 6 to 50 residues. When non-peptide linkers are employed, each CAR sequence of the modulating agent is present within a peptide that generally ranges in size from 3 to 50 residues in length, preferably from 4 to 25 residues, and more preferably from 5 to 15 residues.

As noted above, modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations, and the corresponding D-amino acids are designated by a lower case one letter symbol.

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solution or solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

In solution phase synthesis, a wide variety of coupling methods and protecting groups may be used (see Gross and Meienhofer, eds., "The Peptides: Analysis, Synthesis, Biology," Vol. 1–4 (Academic Press, 1979); Bodansky and Bodansky, "The Practice of Peptide Synthesis," 2d ed. (Springer Verlag, 1994)). In addition, intermediate purification and linear scale up are possible. Those of ordinary skill in the art will appreciate that solution synthesis requires consideration of main chain and side chain protecting groups and activation method. In addition, careful segment selection is necessary to minimize racemization during segment condensation. Solubility considerations are also a factor.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

Acetylation of the N-terminus can be accomplished by reacting the final peptide with acetic anhydride before cleavage from the resin. C-amidation is accomplished using an appropriate resin such as methylbenzhydrylamine resin using the Boc technology.

Following synthesis of a linear peptide, with or without N-acetylation and/or C-amidation, cyclization may be achieved if desired by any of a variety of techniques well known in the art. Within one embodiment, a bond may be generated between reactive amino acid side chains. For example, a disulfide bridge may be formed from a linear peptide comprising two thiol-containing residues by oxidizing the peptide using any of a variety of methods. Within one such method, air oxidation of thiols can generate disulfide linkages over a period of several days using either basic or neutral aqueous media. The peptide is used in high dilution to minimize aggregation and intermolecular side reactions. This method suffers from the disadvantage of being slow but has the advantage of only producing $H_2O$ as a side product. Alternatively, strong oxidizing agents such as $I_2$ and $K_3Fe(CN)_6$ can be used to form disulfide linkages. Those of ordinary skill in the art will recognize that care must be taken not to oxidize the sensitive side chains of Met, Tyr, Trp or His. Cyclic peptides produced by this method require purification using standard techniques, but this oxidation is applicable at acid pHs. Oxidizing agents also allow concurrent deprotection/oxidation of suitable S-protected linear precursors to avoid premature, nonspecific oxidation of free cysteine.

DMSO, unlike $I_2$ and $K_3Fe(CN)_6$, is a mild oxidizing agent which does not cause oxidative side reactions of the nucleophilic amino acids mentioned above. DMSO is miscible with $H_2O$ at all concentrations, and oxidations can be performed at acidic to neutral pHs with harmless byproducts. Methyltrichlorosilane-diphenylsulfoxide may alternatively be used as an oxidizing agent, for concurrent deprotection/oxidation of S-Acm, S-Tacm or S-t-Bu of cysteine without affecting other nucleophilic amino acids. There are no polymeric products resulting from intermolecular disulfide bond formation. Suitable thiol-containing residues for use in such oxidation methods include, but are not limited to, cysteine, β,β-dimethyl cysteine (penicillamine or Pen), β,β-tetramethylene cysteine (Tmc), β,β-pentamethylene cysteine (Pmc), β-mercaptopropionic acid (Mpr), β,β-pentamethylene-β-mercaptopropionic acid (Pmp), 2-mercaptobenzene, 2-mercaptoaniline and 2-mercaptoproline. Peptides containing such residues are illustrated by the following representative formulas, in which the nonclassical cadherin is OB-cadherin, the underlined portion is cyclized, N-acetyl groups are indicated by N-Ac and C-terminal amide groups are represented by —NH$_2$:

i) (SEQ ID NO:669)
N-Ac-<u>Cys</u>-<u>Asp</u>-<u>Asp</u>-<u>Lys</u>-<u>Cys</u>-NH$_2$ ii) (SEQ ID NO:676)
N-Ac-<u>Cys</u>-<u>Ile</u>-<u>Asp</u>-<u>Asp</u>-<u>Lys</u>-<u>Ser</u>-<u>Gly</u>-<u>Cys</u>-NH$_7$ iii) (SEQ ID NO:670)
N-Ac-<u>Cys</u>-<u>Ile</u>-<u>Asp</u>-<u>Asp</u>-<u>Lys</u>-<u>Cys</u>-NH$_2$ iv) (SEQ ID NO:671)
N-Ac-<u>Cys</u>-<u>Asp</u>-<u>Asp</u>-<u>Lys</u>-<u>Ser</u>-<u>Cys</u>-NH$_2$ v) (SEQ ID NO:673)
N-Ac-<u>Cys</u>-<u>Ile</u>-<u>Asp</u>-<u>Asp</u>-<u>Lys</u>-<u>Ser</u>-<u>Cys</u>-NH$_2$ vi) (SEQ ID NO:671)
N-Ac-<u>Cys</u>-<u>Asp</u>-<u>Asp</u>-<u>Lys</u>-<u>Ser</u>-<u>Cys</u>-OH vii) (SEQ ID NO:673)
H-<u>Cys</u>-<u>Ile</u>-<u>Asp</u>-<u>Asp</u>-<u>Lys</u>-<u>Ser</u>-<u>Cys</u>-NH$_2$ viii) (SEQ ID NO:71)
N-Ac-<u>Cys</u>-<u>Asp</u>-<u>Asp</u>-<u>Lys</u>-<u>Pen</u>-NH$_2$ ix) (SEQ ID NO:680)
N-Ac-<u>Cys</u>-<u>Phe</u>-<u>Val</u>-<u>Ile</u>-<u>Asp</u>-<u>Asp</u>-<u>Lys</u>-<u>Ser</u>-<u>Gly</u>-<u>Cys</u>-NH$_2$ -continued x) (SEQ ID NO:683)
N-Ac-<u>Cys</u>-<u>Ile</u>-<u>Phe</u>-<u>Val</u>-<u>Ile</u>-<u>Asp</u>-<u>Asp</u>-<u>Lys</u>-<u>Ser</u>-<u>Gly</u>-<u>Cys</u>-NH$_2$ xi) (SEQ ID NO:53)
N-Ac-Ile-<u>Tmc</u>-<u>Val</u>-<u>Ile</u>-<u>Asp</u>-<u>Asp</u>-<u>Lys</u>-<u>Ser</u>-<u>Cys</u>-Glu-NH$_2$ xii) (SEQ ID NO:54)
N-Ac-IIe-<u>Pmc</u>-<u>Val</u>-<u>Ile</u>-<u>Asp</u>-<u>Asp</u>-<u>Lys</u>-<u>Ser</u>-<u>Gly</u>-<u>Cys</u>-NH$_2$ xiii) (SEQ ID NO:55)
<u>Mpr</u>-<u>Val</u>-<u>Ile</u>-<u>Asp</u>-<u>Asp</u>-<u>Lys</u>-<u>Ser</u>-<u>Gly</u>-<u>Cys</u>-NH$_2$ xiv) (SEQ ID NO:56)
<u>Pmp</u>-<u>Val</u>-<u>Ile</u>-<u>Asp</u>-<u>Asp</u>-<u>Lys</u>-<u>Ser</u>-<u>Gly</u>-<u>Cys</u>-NH$_2$ xv)

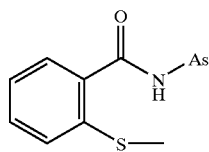

xvi)

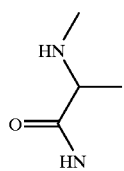

It will be readily apparent to those of ordinary skill in the art that, within each of these representative formulas, any of the above thiol-containing residues may be employed in place of one or both of the thiol-containing residues recited. Similar formulas comprising different nonclassical cadherin CAR sequences may be generated by those of ordinary skill in the art, based on the CAR sequences provided herein.

Within another embodiment, cyclization may be achieved by amide bond formation. For example, a peptide bond may be formed between terminal functional groups (i.e., the amino and carboxy termini of a linear peptide prior to cyclization). One such cyclic peptide comprising an OB-cadherin CAR sequence is <u>IDDKSG</u> (SEQ ID NO:717) with or without an N-terminal acetyl group and/or a C-terminal amide. Within another such embodiment, the linear peptide comprises a D-amino acid (e.g., <u>DDKsS</u>; SEQ ID NO:57). Alternatively, cyclization may be accomplished by linking one terminus and a residue side chain or using two side chains, as in <u>KDDKD</u> (SEQ ID NO:697) or <u>KIDDKSGD</u> (SEQ ID NO:704), with or without an N-terminal acetyl group and/or a C-terminal amide. Residues capable of forming a lactam bond include lysine, ornithine (Orn), α-amino adipic acid, m-aminomethylbenzoic acid, α,β-diaminopropionic acid, glutamate or aspartate.

Methods for forming amide bonds are well known in the art and are based on well established principles of chemical reactivity. Within one such method, carbodiimide-mediated lactam formation can be accomplished by reaction of the carboxylic acid with DCC, DIC, EDAC or DCCI, resulting in the formation of an O-acylurea that can be reacted immediately with the free amino group to complete the cyclization. The formation of the inactive N-acylurea, resulting from O→N migration, can be circumvented by converting the O-acylurea to an active ester by reaction with an N-hydroxy compound such as 1-hydroxybenzotriazole, 1-hydroxysuccinimide, 1-hydroxynorbornene carboxamide or ethyl 2-hydroximino-2-cyanoacetate. In addition to minimizing O→N migration, these additives also serve as catalysts during cyclization and assist in lowering racemization. Alternatively, cyclization can be performed using the azide method, in which a reactive azide intermediate is generated from an alkyl ester via a hydrazide. Hydrazinolysis of the terminal ester necessitates the use of a t-butyl group for the protection of side chain carboxyl functions in the acylating component. This limitation can be overcome by using diphenylphosphoryl acid (DPPA), which furnishes an azide directly upon reaction with a carboxyl group. The slow reactivity of azides and the formation of isocyanates by their disproportionation restrict the usefulness of this method. The mixed anhydride method of lactam formation is widely used because of the facile removal of reaction by-products. The anhydride is formed upon reaction of the carboxylate anion with an alkyl chloroformate or pivaloyl chloride. The attack of the amino component is then guided to the carbonyl carbon of the acylating component by the electron donating effect of the alkoxy group or by the steric bulk of the pivaloyl chloride t-butyl group, which obstructs attack on the wrong carbonyl group. Mixed anhydrides with phosphoric acid derivatives have also been successfully used. Alternatively, cyclization can be accomplished using activated esters. The presence of electron withdrawing substituents on the alkoxy carbon of esters increases their susceptibility to aminolysis. The high reactivity of esters of p-nitrophenol, N-hydroxy compounds and polyhalogenated phenols has made these "active esters" useful in the synthesis of amide bonds. The last few years have witnessed the development of benzotriazolyloxytris-(dimethylamino) phosphonium hexafluorophosphonate (BOP) and its congeners as advantageous coupling reagents. Their performance is generally superior to that of the well established carbodiimide amide bond formation reactions.

Within a further embodiment, a thioether linkage may be formed between the side chain of a thiol-containing residue and an appropriately derivatized α-amino acid. By way of example, a lysine side chain can be coupled to bromoacetic acid through the carbodiimide coupling method (DCC, EDAC) and then reacted with the side chain of any of the thiol containing residues mentioned above to form a thioether linkage. In order to form dithioethers, any two thiol containing side-chains can be reacted with dibromoethane and diisopropylamine in DMF. Examples of thiol-containing linkages are shown below:

i
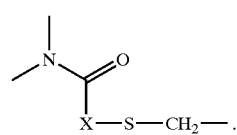

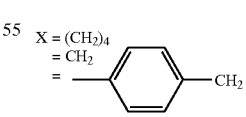

ii
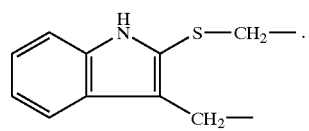

Cyclization may also be achieved using $\delta_1,\delta_1$-Ditryptophan (i.e., Ac-Trp-Gly-Gly-Trp-OMe) (SEQ ID NO:58), as shown below:

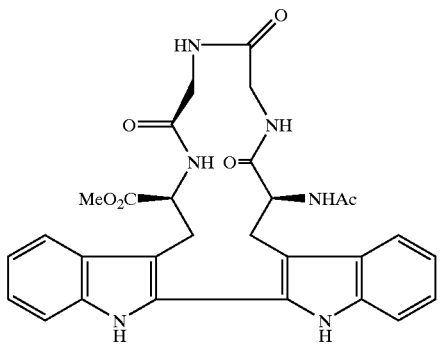

Representative structures of cyclic peptides comprising OB-cadherin CAR sequences are provided in FIGS. 4A–4C. The structures and formulas recited herein are provided solely for the purpose of illustration, and are not intended to limit the scope of the cyclic peptides described herein.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of a nonclassical cadherin or other adhesion molecule, or may encode a peptide comprising a nonclassical cadherin analogue or an antibody fragment that specifically binds to a nonclassical cadherin CAR sequence. Such DNA sequences may be prepared based on known cDNA or genomic sequences, or from sequences isolated by screening an appropriate library with probes designed based on the sequences of known nonclassical cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, polynucleotides may also function as modulating agents. In general, such polynucleotides should be formulated to permit expression of a polypeptide modulating agent following administration to a mammal. Such formulations are particularly useful for therapeutic purposes, as described below. Those of ordinary skill in the art will appreciate that there are many ways to achieve expression of a polynucleotide within a mammal, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transfected cells) and/or a targeting moiety, such as a gene that encodes a ligand for a receptor on a specific target cell, to render the vector target specific. Targeting may also be accomplished using an antibody, by methods known to those of ordinary skill in the art. Other formulations for polynucleotides for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

As noted above, a modulating agent may additionally, or alternatively, comprise a substance such as an antibody or antigen-binding fragment thereof, that specifically binds to a nonclassical cadherin CAR sequence. As used herein, a substance is said to "specifically bind" to a nonclassical cadherin CAR sequence (with or without flanking amino acids) if it reacts at a detectable level with a peptide containing that sequence, and does not react detectably with peptides containing a different CAR sequence or a sequence in which the order of amino acid residues in the cadherin CAR sequence and/or flanking sequence is altered. Such antibody binding properties may generally be assessed using an ELISA, which may be readily performed by those of ordinary skill in the art and is described, for example, by Newton et al., *Develop. Dynamics* 197:1–13, 1993.

Polyclonal and monoclonal antibodies may be raised against a nonclassical cadherin CAR sequence using conventional techniques. See, e.g., Harlow and Lane, *Antibodies: A Laboratory Manual*, Cold Spring Harbor Laboratory, 1988. In one such technique, an immunogen comprising the CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for a nonclassical cadherin sequence may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation and extraction. Antibodies having the desired activity may generally be identified using immunofluorescence analyses of tissue sections, cell or other samples where the target cadherin is localized.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628–29).

Evaluation of Modulating Agent Activity

Modulating agents as described above are capable of modulating one or more nonclassical cadherin-mediated functions. An initial screen for such activity may be performed by evaluating the ability of a modulating agent to bind to a nonclassical cadherin using any binding assay known to those of ordinary skill in the art. For example, a Pharmacia Biosensor machine may be used, as discussed in Jonsson et al., *Biotechniques* 11:520–27, 1991. For example, a modulating agent may comprise a CAR sequence that binds to a nonclassical cadherin. A specific example of a technology that measures the interaction of peptides with molecules can be found in Williams et al., *J. Biol. Chem.* 272, 22349–22354, 1997. Alternatively, real-time BIA (Biomolecular Interaction Analysis) uses the optical phenomenon surface plasmon resonance to monitor biomolecular interactions. The detection depends upon changes in the mass concentration of macromolecules at the biospecific interface, which in turn depends upon the immobilization of test molecule or peptide (referred to as the ligand) to the surface of a Biosensor chip, followed by binding of the interacting molecule (referred to as the analyte) to the ligand. Binding to the chip is measured in real-time in arbitrary units of resonance (RU).

By way of example, surface plasmon resonance experiments may be carried out using a BIAcore X™ Biosensor (Pharmacia Ltd., BIAcore, Uppsala, Sweden). Parallel flow cells of CM 5 sensor chips may be derivatized, using the amine coupling method, with streptavidin (200 $\mu$g/ml) in 10 mM Sodium Acetate, pH 4.0, according to the manufacturer's protocol. Approximately 2100–2600 resonance units (RU) of ligand may be immobilized, corresponding to a concentration of about 2.1–2.6 ng/mm$^2$. The chips may then coated be with nonclassical cadherin derivatized to biotin. Any non-specifically bound protein is removed.

To determine binding, test analytes (e.g., peptides containing the nonclassical cadherin CAR sequence) may be placed in running buffer and passed simultaneously over test and control flow cells. After a period of free buffer flow, any analyte remaining bound to the surface may be removed with, for example, a pulse of 0.1% SDS bringing the signal back to baseline. Specific binding to the derivatized sensor chips may be determined automatically by the system by subtraction of test from control flow cell responses. In general, a modulating agent binds to a nonclassical cadherin at a detectable level within such as assay. The level of binding is preferably at least that observed for the full length nonclassical cadherin under similar conditions.

The ability to modulate a nonclassical cadherin-mediated function may be evaluated using any of a variety of in vitro assays designed to measure the effect of the peptide on a response that is generally mediated by the nonclassical cadherin. As noted above, modulating agents may be capable of enhancing or inhibiting a nonclassical cadherin-mediated function.

Certain nonclassical cadherins are associated with adhesion of particular cell types (e.g., cancer cells). The ability of an agent to modulate cell adhesion may generally be evaluated in vitro by assaying the effect on adhesion between appropriate cells. In general, a modulating agent is an inhibitor of cell adhesion if contact of the test cells with the modulating agent results in a discernible disruption of cell adhesion. Modulating agents that enhance cell adhesion (e.g., agents comprising multiple nonclassical cadherin CAR sequences and/or nonclassical cadherin CAR sequences linked to a support material) are considered to be modulators of cell adhesion if they are capable of promoting cell adhesion, as judged by plating assays to assess cell adhesion to a modulating agent attached to a support material, such as tissue culture plastic.

Within certain cell adhesion assays, the addition of a modulating agent to cells that express a nonclassical cadherin results in disruption of cell adhesion. A "nonclassical cadherin-expressing cell," as used herein, may be any type of cell that expresses a nonclassical cadherin at a detectable level, using standard techniques such as immunocytochemical protocols (e.g., Blaschuk and Farookhi, *Dev. Biol.* 136:564-567, 1989). For example, such cells may be plated under standard conditions that, in the absence of modulating agent, permit cell adhesion. In the presence of modulating agent (e.g., 1 mg/mL), disruption of cell adhesion may be determined visually within 24 hours, by observing retraction of the cells from one another and the substratum.

Suitable cells for use within such assays may be any of a variety of cells that express the nonclassical cadherin of interest. Certain cells express one or more cadherins endogenously. For example, OB-cadherin-expressing cells include stromal, osteoblast and/or cancer cells. Cadherin-5 is expressed by endothelial cells, and cadherin-6 expression is associated with, for example, kidney tumor cells. Accordingly, such cell types may be used to assess the effect of modulating agents directed against OB-cadherin or cadherin-5 CAR sequences. In general, MDCK cells or keratinocytes may be used to evaluate desmocollin- or desmoglein-mediated cell adhesion. Neural cells may be used to evaluate protocadherin, cnr, PB-cadherin and type II cadherin function. It will be apparent that other cells may also be used within such assays, provided that the cells express the nonclassical cadherin of interest.

Alternatively, cells that do not naturally express a cadherin may be used within such assays. Such cells may be stably transfected with a polynucleotide (e.g., a cDNA) encoding a cadherin of interest, such that the cadherin is expressed on the surface of the cell. Expression of the cadherin may be confirmed by assessing adhesion of the transfected cells, in conjunction with immunocytochemical techniques using antibodies directed against the cadherin of interest. The stably transfected cells that aggregate, as judged by light microscopy, following transfection express sufficient levels of the nonclassical cadherin. Preferred cells for use in such assays include L cells, which do not detectably adhere and do not express any cadherin (Nagafuchi et al., *Nature* 329:341–343, 1987). Following transfection of L cells with a cDNA encoding a cadherin, aggregation is observed. Modulating agents that detectably inhibit such aggregation may be used to modulate functions mediated by the nonclassical cadherin. Such assays have been used for numerous nonclassical cadherins, including OB-cadherin (Okazaki et al., *J. Biol. Chem.* 269:12092–98, 1994), cadherin-5 (Breier et al., *Blood* 87:630–641, 1996), cadherin-6 (Mbalaviele et al., *J. Cell. Biol.* 141:1467–1476, 1998), cadherin-8 (Kido et al., *Genomics* 48:186–194, 1998), cadherin-15 (Shimoyama et al., *J. Biol. Chem.* 273:10011–10018, 1998), PB-cadherin (Sugimoto et al., *J. Biol. Chem.* 271:11548–11556, 1996), LI-cadherin (Kreft et al., *J. Cell. Biol.* 136:1109–1121, 1997), protocadherin 42 and 43 (Sano et al., *EMBO J.* 12:2249–2256, 1993) and desmosomal cadherins (Marcozzi et al., *J. Cell. Sci.* 111:495–509, 1998). It will be apparent to those of ordinary skill in the art that assays may be performed in a similar manner for other nonclassical cadherins.

Transfection of cells for use in cell adhesion assays may be performed using standard techniques and published cadherin sequences. For example, sequences of nonclassical cadherins may be found within references cited herein and in the GenBank database. GenBank accession numbers for certain nonclassical cadherins include: X59796 (human cadherin-5); D31784 (human cadherin-6); D42150 (chicken cadherin-7); L34060 (human cadherin-8); L34056 (human OB cadherin); L34057 (human cadherin-12); U59325 (human cadherin-14); D83542 (human cadherin-15); D83348 and D88349 (rat PB-cadherin); X83228 (human LI-cadherin); L34058 (human T cadherin); L11373 (human protocadherin 43); AF029343 (human protocadherin 68); X56654 (human desmoglein 1); Z26317 and S64273 (human desmoglein 2); X72925 (human desmocollin 1); X56807 (human desmocollin 2); X83929 (human desmocollin 3); D17427 (human desmocollin 4); D86916 (mouse cadherin-related neuronal receptor 1); D86917 (mouse cadherin-related neuronal receptor 2); AB008178 (mouse cadherin-related neuronal receptor 3); AB008180 (mouse cadherin-related neuronal receptor 5); AB008181 (mouse cadherin-related neuronal receptor 6); AB008182 (mouse cadherin-related neuronal receptor 7); AB008183 (mouse cadherin-related neuronal receptor 8).

By way of example, an assay for evaluating a modulating agent for the ability to inhibit an OB-cadherin mediated function may employ MDA-231 human breast cancer cells. According to a representative procedure, the cells may be plated at 10–20,000 cells per 35 mm tissue culture flasks containing DMEM with 5% FCS and sub-cultured periodically (Sommers et al., *Cell Growth Diffn* 2:365–72, 1991). Cells may be harvested and replated in 35 mm tissue culture flasks containing 1 mm coverslips and incubated until 50–65% confluent (24–36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 2% paraformaldehyde for 30 minutes and then washed three times with PBS. Coverslips can be mounted and viewed by phase contrast microscopy.

In the absence of modulating agent, MDA-231 cells display an epithelial-like morphology and are well attached to the substratum. MDA-231 cells that are treated with a modulating agent that disrupts OB-cadherin mediated cell adhesion may assume a round shape and become loosely attached to the substratum within 48 hours of treatment with 1 mg/mL of modulating agent.

It will be apparent that similar assays may be performed to assess a modulating agent for the ability to inhibit cell adhesion mediated by other nonclassical cadherins, using cells appropriate for the nonclassical cadherin of interest. In general, a modulating agent that is derived from a particular nonclassical cadherin CAR sequence (i.e., comprises such a CAR sequence, or an analog or mimetic thereof, or an antibody that specifically recognizes such a CAR sequence) and that modulates adhesion of a cell that expresses the same nonclassical cadherin is considered to modulate a function mediated by the nonclassical cadherin.

Other assays may be used to assess the effect of a modulating agent on specific nonclassical cadherin-mediated functions. For example, modulating agents that inhibit interactions of certain nonclassical cadherins (e.g., OB-cadherin, cadherin-5, desmogleins and desmocollins) may enhance skin permeability. This ability may be assessed by evaluating, for example, the effect of a modulating agent on permeability of adherent epithelial and/or endothelial cell layers (e.g., human skin). Such skin may be derived from a natural source or may be synthetic. Human abdominal skin for use in such assays may generally be obtained from humans at autopsy within 24 hours of death. Briefly, a modulating agent (e.g., 500 μg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58–68, 1978; Franz, *J. Invest. Dermatol.* 64:190–195, 1975). The penetration of the markers through the skin may be assessed at, for example, 6, 12, 24, 36, and 48 hours after the start of the experiment. In general, a modulating agent that enhances the permeability of human skin results in a statistically significant increase in the amount of marker in the receptor compartment after 6–48 hours in the presence of 500 μg/mL modulating agent.

Certain other nonclassical cadherins (e.g., cadherin-7, cadherin-8, cadherin-12, cadherin-14, cadherin-15, T-cadherin, PB-cadherin, protocadherins and cnrs) may be involved in mediating neurite growth. Agents that modulate such a function may be evaluated using a neurite outgrowth assay. Within one such assay, neurons may be cultured on a monolayer of cells (e.g., 3T3 cells) that express a nonclassical cadherin. Neurons grown on such cells (under suitable conditions and for a sufficient period of time) extend neurites that are typically, on average, twice as long as neurites extended from neurons cultured on 3T3 cells that do not express the nonclassical cadherin. Briefly, monolayers of control 3T3 fibroblasts and 3T3 fibroblasts that express a nonclassical cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2%FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent may inhibit or enhance such neurite outgrowth. Under the conditions described above, the presence of 500 μg/mL of a modulating agent that disrupts neural cell adhesion should result in a decrease in the mean neurite length by at least 50%, relative to the length in the absence of modulating agent or in the presence of a negative control peptide. Alternatively, the presence of 500 μg/mL of a modulating agent that enhances neural cell adhesion should result in an increase in the mean neurite length by at least 50%.

Transfection of cells for use in a neurite outgrowth assay may be performed using standard techniques and published cadherin sequences. For example, sequences of nonclassical cadherins may be found within references cited herein and in the GenBank database. GenBank accession numbers for these cadherins are recited above.

Certain modulating agents (e.g., peptides that contain VE-cadherin and/or OB-cadherin CAR sequences, or analogues or mimetics thereof) may inhibit angiogenesis. The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327–343, 1995). Briefly, a modulating agent may be embedded in a mesh composed of vitrogen at one or more concentrations (e.g., ranging from about 1 to 100 µg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 33 µg/mesh.

A myoblast fusion assay may be used as a functional assay for agents that modulate cadherin-15 function. Cadherin-15 has been shown to mediate the fusion of muscle cells into mature muscle fibers in vitro. Briefly, to perform such an assay, myoblasts may be grown in a dish, differentiation is induced, and modulating agent is added. The effect on fusion is then evaluated. In general, a modulating agent that inhibits cadherin-15 function results in a statistically significant decrease in myoblast fusion in the presence of 1 mg/mL modulating agent. Such assays may be performed as described by Pouliot et al., *Dev. Biol.* 141:292–298, 1990.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an HAV or RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multifunctional linkers.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than the particular nonclassical cadherin. Such modulators may generally be prepared as described above, using one or more CAR sequences and/or antibodies thereto. Such compositions are particularly useful for situations in which it is desirable to inhibit cell adhesion mediated by multiple cell adhesion molecules, such as other members of the cadherin gene superfamily such as the classical cadherins (e.g., N-cadherin and E-cadherin); integrins; occludin; claudins; N-CAM and/or extracellular matrix proteins such as laminin, fibronectin, collagens, vitronectin, entactin and tenascin.

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antipsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a calorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain about 10 ng/ml to 5 mg/ml, preferably from about 10 $\mu$g to 2 mg/mL modulating agent. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agnet Methods of Use

In general, the modulating agents and compositions described herein may be used for modulating a function, such as cell adhesion, of nonclassical cadherin-expressing cells. Such modulation may be performed in vitro and/or in vivo, preferably in a mammal such as a human, using any method that contacts the nonclassical cadherin-expressing cell with the modulating agent. As noted above, modulating agents for purposes that involve the disruption of nonclassical cadherin-mediated cell adhesion may comprise a nonclassical cadherin CAR sequence, multiple nonclassical cadherin CAR sequences in close proximity and/or a substance (such as an antibody or an antigen-binding fragment thereof) that recognizes a nonclassical cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the nonclassical cadherin CAR sequence by linkers. As noted above, such linkers may or may not comprise one or more amino acids. For enhancing cell adhesion, a modulating agent may contain multiple nonclassical cadherin CAR sequences derived from either a particular nonclassical cadherin or antibodies (or fragments), preferably separated by linkers, and/or may be linked to a single molecule or to a support material as described above. When it is desirable to also enhance cell adhesion mediated by other adhesion molecules, a modulating agent may additionally comprise one or more CAR sequences bound by such adhesion molecules (and/or antibodies or fragments thereof that bind such sequences), preferably separated from each other and from the nonclassical cadherin CAR sequence by linker.

Certain methods involving the disruption of cell adhesion as described herein have an advantage over prior techniques in that they block tumor cell adhesion. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, methods are provided in which cell adhesion is diminished. In one such aspect, the present invention provides methods for reducing unwanted cellular adhesion in a mammal by administering a modulating agent as described herein. Unwanted cellular adhesion can occur, for example, between tumor cells, between tumor cells and normal cells or between normal cells as a result of surgery, injury, chemotherapy, disease, inflammation or other condition jeopardizing cell viability or function. Certain preferred modulating agents for use within such methods comprise one or more of the nonclassical CAR sequences provided herein. In one particularly preferred embodiment, a modulating agent is further capable of disrupting cell adhesion mediated by multiple adhesion molecules. Such an agent may comprise, in addition to one or more nonclassical cadherin CAR sequences, CAR sequences such as the classical cadherin CAR sequence HAV sequence, an RGD sequence, which is bound by integrins, the occludin CAR sequence LYHY (SEQ ID NO:52); and/or the putative claudin CAR sequence IYSY (SEQ ID NO:51), preferably separated from the nonclassical cadherin CAR sequence via a linker. Alternatively, separate modulators of cell adhesion mediated by other adhesion molecules may be administered in conjunction with the modulating agent(s), either within the same pharmaceutical composition or separately.

Topical administration of the modulating agent(s) is generally preferred, but other means may also be employed. Preferably, a fluid composition for topical administration (comprising, for example, physiological saline) comprises an amount of modulating agent as described above, and more preferably from 10 μg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Certain modulating agents as provided herein may be used to facilitate transdermal drug delivery. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Certain preferred modulating agents for use within such methods comprise a CAR sequence (or an analogue or mimetic thereof) of OB-cadherin, cadherin-5, a desmoglein or a desmocollin. Multifunctional modulating agents comprising multiple nonclassical cadherin CAR sequences may also be used. Such modulating agents may also, or alternatively, comprise the classical cadherin CAR sequence HAV, the fibronectin CAR sequence RGD, which is recognized by integrins, and/or the occludin CAR sequence LYHY (SEQ ID NO:52). Alternatively, a separate modulator of cell adhesion may be administered in conjunction with the modulating agent(s), either within the same pharmaceutical composition or separately.

Contact may be achieved by direct application of the modulating agent, generally within a composition formulated as a cream or gel, or using any of a variety of skin contact devices for transdermal application (such as those described in European Patent Application No. 566,816 A; U.S. Pat. Nos. 5,613,958; 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, modulating agents as described herein may be used to increase the permeability of endothelial and epithelial cell layers, thereby facilitating sampling of the blood compartment by passive diffusion. Such methods permit the detection and/or measurement of the levels of specific molecules circulating in the blood. In general, to sample the blood compartment, it is necessary to perturb adhesion between the epithelial cells (keratinocytes) and the endothelial cells of the microvasculature. Using currently available techniques, only small, uncharged molecules may be detected across skin in vivo. The methods described herein are not subject to the same degree of limitation. Accordingly, a wide variety of blood components may be sampled across epithelial and endothelial cell layers. Such sampling may be achieved across any such cell layers, including skin and gums.

For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

To facilitate sampling of blood in a patient, a modulating agent as described above for enhancing drug delivery is contacted with the skin surface. Modulating agent(s) and reagents for assaying blood components may, but need not, be contained within the same composition or skin patch. In general, the amount of modulating agent administered via the skin may vary as described above. Such levels may be achieved by appropriate adjustments to the device used, or by applying a cream formulated as described above. Transfer of the blood component across the skin may be predicted based on in vitro studies using, for example, a Franz cell apparatus, and evaluated in vivo by appropriate means that will be apparent to those of ordinary skill in the art.

Kits for sampling blood component via, for example, the skin or gums of a mammal, are also provided within the present invention. Such kits generally comprise a device for transdermal application (i.e., skin patch) in combination with, or impregnated with, one or more modulating agents. A reagent for detection of a blood component may additionally be included within such kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt functions mediated by OB-cadherin, cadherin-5, cadherin-6, a desmoglein and/or a desmocollin, and may further disrupt E-cadherin and/or N-cadherin mediated cell adhesion. For example, such a modulating agent may comprise a CAR sequence (or analogue or mimetic thereof) derived from one or more of the above cadherins, as described above. A modulating agent may further comprise an E- and/or N-cadherin CAR sequence (e.g. HAV, SHAVSS (SEQ ID NO:59), AHAVDI (SEQ ID NO:60) or a analogue of such a sequence). Bi-functional modulating agents that comprise the nonclassical cadherin CAR sequence with either flanking E-cadherin-specific sequences or flanking N-cadherin-specific sequences joined via a linker to the nonclassical cadherin CAR sequence are also preferred. Preferably, the peptide portion(s) of a modulating agent comprises 6–16 amino acids, since longer peptides are difficult to dissolve in aqueous solution and are more likely to be degraded by peptidases.

In one particularly preferred embodiment, a modulating agent is capable of disrupting cell adhesion mediated by multiple adhesion molecules. For example, a single branched modulating agent (or multiple agents linked to a single molecule or support material) may disrupt adhesion mediated by a nonclassical cadherin, as well as E-cadherin, N-cadherin, occludin, claudin and integrin mediated cell adhesion. Such agents serve as multifunctional disrupters of cell adhesion. Alternatively, a separate modulator may be administered in conjunction with the modulating agent(s), either within the same pharmaceutical composition or separately. Preferred antibody modulating agents include Fab fragments directed against a nonclassical or classical cadherin CAR sequence, as described above. A Fab fragment may be incorporated into a modulating agent or may be present within a separate modulator that is administered concurrently.

Preferably, the modulating agent and the drug are formulated within the same composition or drug delivery device prior to administration. In general, a modulating agent may enhance drug delivery to any tumor (e.g., breast tumor, stomach tumor, ovarian tumor or kidney tumor), and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., breast tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., taxol for breast cancer). In general, the amount of modulating agent administered varies with the method of administration and the nature of the tumor, within the typical ranges provided above, preferably ranging from about 1 µg/mL to about 2 mg/mL, and more preferably from about 10 µg/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Modulating agents for use within such methods include those designed to disrupt functions mediated by OB-cadherin, cadherin-5, cadherin-6, a desmoglein and/or a desmocollin, and may further disrupt E-cadherin, N-cadherin and/or integrin mediated cell adhesion. For example, such a modulating agent may comprise a CAR sequence (or analogue or mimetic thereof) derived from one or more of the above cadherins, as described above, optionally in combination with a sequence such as HAV, SHAVSS (SEQ ID NO:59), AHAVDI (SEQ ID NO:68), RGD, YIGSR (SEQ ID NO:48) or a derivative of such a sequence. Preferably, the peptide portion(s) of such modulating agents comprise 6–16 amino acids. Preferred antibody modulating agents include Fab fragments directed against a nonclassical or classical cadherin CAR sequence. The Fab fragments may be either incorporated into a modulating agent or may be present within a separate modulator that is administered concurrently.

A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above.

Preferably, the tumor is a breast tumor, stomach tumor or kidney tumor. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g. CEA or PSA).

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

Within further aspects, the present invention provides methods for inhibiting angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for inhibition of angiogenesis include those that modulate functions mediated by cadherin-5, such as those that comprises a cadherin-5 CAR sequence or analogue or mimetic thereof. In addition, a modulating agent for use in inhibiting angiogenesis may comprise the sequence RGD, which is recognized by integrins, an OB-cadherin CAR sequence (e.g., DKK), the classical cadherin CAR sequence HAV, and/or the occludin CAR sequence LYHY (SEQ ID NO:52), separated from the cadherin-5 sequence via a linker. Alternatively, a separate modulator of classical cadherin-, integrin- or occludin-mediated cell adhesion may be administered in conjunction with the modulating agent(s), either within the same pharmaceutical composition or separately. The ability of a modulating agent to inhibit angiogenesis may be evaluated as described above.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in a nonclassical cadherin-expressing cell. In general, patients afflicted with cancer may benefit from such treatment. Modulating agents for use within such methods may modulate functions mediated any nonclassical cadherin(s). Such agents may comprise, for example, a CAR sequence of such a cadherin, or an analogue or mimetic thereof. In addition, such agents may comprise a sequence such as HAV, SHAVSS (SEQ ID NO:59), AHAVDI (SEQ ID NO:60), RGD, YIGSR (SEQ ID NO:48) or an analogue of such a sequence. Preferably, the peptide portion(s) of such modulating agents comprise 6–16 amino acids. Preferred antibody modulating agents include Fab fragments directed against a nonclassical or classical cadherin CAR sequence. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

Within a related aspect, the present invention provides methods for treating obesity in a mammal, by using modulating agents that disrupt OB-cadherin function to inhibit adipocyte adhesion. Alternatively, modulating agents that inhibit angiogenesis as described herein may be used to inhibit fat cell growth. Modulating agents as described herein may be administered alone, or in combination with other agents, which may comprise, for example, a cadherin-5 CAR sequence, HAV, SHAVSS (SEQ ID NO:59), AHAVDI (SEQ ID NO:60), RGD or an analogue of such a sequence. Preferably the peptide portion(s) of such modulating agents comprise 6–16 amino acids. The use of Fab fragments directed against an OB-cadherin, cadherin-5 or N-cadherin CAR sequence is also preferred. A modulating agent may be administered alone (e.g., via the skin) or within a pharmaceutical composition. Injection or topical administration as described above may be preferred. In other instances, the composition may be administered systemically.

In another embodiment, methods are provided for causing the regression of blood vessels for the treatment of conditions such as cancer, psoriasis, arthritis, and age-related macular degeneration. Cancer tumors are solid masses of cells, growing out of control, which require nourishment via blood vessels. The formation of new capillaries is a prerequisite for tumor growth and the emergence of metastases. Administration of the modulating agents described herein may disrupt blood vessels and cause them to regress, thereby providing effective therapy for patients afflicted with diseases such as cancer. Certain preferred modulating agents for use within such methods comprise, in addition to a nonclassical cadherin CAR sequence (preferably an OB-cadherin or cadherin-5 CAR sequence), a sequence such as HAV and RGD, or an analogue of such a sequence. Preferably, the peptide portion(s) of such modulating agents comprise 6–16 amino acids. Preferred antibody modulating agents include Fab fragments directed against the nonclassical cadherin CAR sequence, with or without Fab fragments directed against one or more classical cadherin CAR sequences. The Fab fragments may be either incorporated into a modulating agent or within a separate modulator that is administered concurrently. Administration may be topical, via injection or by other means, and the addition of a targeting agent may be beneficial, particularly when the administration is systemic. Suitable modes of administration and dosages depend upon the location and nature of the pericytes for which disruption of cell adhesion is desired but, in general, dosages may vary as described above. The effectiveness of the cancer treatment or inhibition of metastasis may be evaluated using well known clinical observations such as the level of serum markers (e.g., CEA or PSA). The addition of a targeting agent may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumor to maintain growth and microscopically by an absence of nerves at the periphery of the tumor.

Within another aspect, the present invention provides methods for enhancing drug delivery to the central nervous system (CNS) of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Modulating agents for enhancing drug delivery to the central nervous system include those agents that disrupt functions mediated by OB-cadherin or cadherin-5. Certain preferred modulating agents for use within such methods are relatively small cyclic peptides (e.g., a ring size of 4–10 residues; preferably 5–7 residues). Also preferred are multi-functional modulating agents comprising a nonclassical cadherin CAR sequence and an N-cadherin CAR sequence, the putative claudin CAR sequence IYSY (SEQ ID NO:51) and/or occludin CAR sequence, preferably joined by a linker. Alternatively, a separate modulator of N-cadherin, claudin and/or occludin-mediated cell adhesion may be administered in conjunction with the modulating agent(s), either within the same pharmaceutical composition or separately. Modulating agents may further comprise antibodies or Fab fragments directed against the N-cadherin CAR sequence FHLRAHAVDINGNQV-NH$_2$ (SEQ ID NO:61). Fab fragments directed against the occludin CAR sequence GVNPTAQSSGSLYGSQIYALCNQFYT-PAATGLYVDQYLYHYCVVDPQE (SEQ ID NO:62) may also be employed, either incorporated into the modulating agent or administered concurrently as a separate modulator. In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

The present invention also provides, within further aspects, methods for enhancing and/or directing neurological growth. In one such aspect, neurite outgrowth may be enhanced and/or directed by contacting a neuron with one or more modulating agents. Modulating agents for enhancing and/or directing neurological growth include those agents that disrupt functions mediated by one or more of cadherin-7, cadherin-8, cadherin-12, cadherin-14, cadherin-1, T-cadherin, PB cadherin, a protocadherin and/or a cadherin-related neuronal receptor. Preferred modulating agents for use within such methods are linked to a polymeric matrix or other support and/or contain multiple CAR sequences separated by one or more linkers. In addition, a modulating agent comprising the cadherin CAR sequence HAV, RGD and/or YIGSR (SEQ ID NO:48), which are bound by integrins, and/or the N-CAM CAR sequence KYSFNYDGSE (SEQ ID NO:63) may further facilitate neurite outgrowth. Modulating agents comprising antibodies, or fragments thereof, may be used within this aspect of the present invention without the use of linkers or support materials. In addition, Fab fragments directed against the N-CAM CAR sequence KYSFNYDGSE (SEQ ID NO:63) or the N-cadherin CAR sequence FHLRAHAVDINGNQV-NH$_2$ (SEQ ID NO:61) may be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

Within another aspect, one or more modulating agents may be used for therapy of a demyelinating neurological disease in a mammal. There are a number of demyelinating diseases, such as multiple sclerosis, characterized by oligodendrocyte death. Modulating agents for treating and/or preventing such diseases include those agents that disrupt functions mediated by one or more of cadherin-7, cadherin-8, cadherin-12, cadherin-14, cadherin-15, T-cadherin, PB cadherin, a protocadherin and/or a cnr. Modulating agents may further comprise HAV, RGD and/or YIGSR (SEQ ID NO:48), which are bound by integrins, and/or the N-CAM CAR sequence KYSFNYDGSE (SEQ ID NO:63). Such agents, when implanted with Schwann cells into the central nervous system, may facilitate Schwann cell migration and permit the practice of Schwann cell replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Suitable amounts of modulating agent generally range as described above, preferably from about 10 μg/mL to about 1 mg/mL. Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelinforming oligodendrocytes and contribute to repair of demyelinated axons (see e.g., Groves et al., *Nature* 362:453–55, 1993; Baron-Van Evercooren et al., *Glia* 16:147–64, 1996). OPs can be isolated using routine techniques known in the art (see e.g., Milner and French-Constant, *Development* 120:3497–3506, 1994), from many regions of the CNS including brain, cerebellum, spinal cord, optic nerve and olfactory bulb. Substantially greater yields of OP'bs are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS.

OPs can be expanded in vitro if cultured as "homotypic aggregates" or "spheres" (Avellana-Adalid et al. *J. Neurosci. Res.* 45:558–70, 1996). Spheres (sometimes called "oligospheres" or "neurospheres") are formed when OPs are grown in suspension in the presence of growth factors such as PDGF and FGF. OPs can be harvested from spheres by mechanical dissociation and used for subsequent transplantation or establishment of new spheres in culture. Alternatively, the spheres themselves may be transplanted, providing a "focal reservoir" of OPs (Avellana-Adalid et al, *J. Neurosci. Res.* 45:558–70, 1996).

An alternative source of OP may be spheres derived from CNS stem cells. Recently, Reynolds and Weiss, *Dev. Biol.* 165:1–13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1–13, 1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy. Neurosphere grafts may be implanted directly into the central nervous system along with the modulating agent(s) using standard techniques.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573–79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14, 1994) or the location and extent of lesions using $T_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by zadolinium enhanced images.

The present invention also provides methods for increasing vasopermeability in a mammal by administering one or more modulating agents or pharmaceutical compositions. Modulating agents as described herein that decrease OB-cadherin and/or cadherin-5 mediate cell adhesion may be used to increase vascular permeability. Certain preferred modulating agents for use within such methods further inhibit N-cadherin, claudin and or occludin mediated adhesion. Such agents may comprise, in addition to an OB-cadherin and/or cadherin-5 CAR sequence, a sequence such as LYHY (the occludin CAR sequence; SEQ ID NO:52), IYSY (the putative claudin CAR sequence; SEQ ID NO:51) HAV and RGD, or an analogue of such a sequence. Preferably, the peptide portion(s) of such modulating agents comprise 6–16 amino acids. Preferred antibody modulating agents include Fab fragments directed against one or more of the OB-cadherin, cadherin-5, classical cadherin, claudin and/or occludin CAR sequences. The Fab fragments may be either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

In certain other aspects, the present invention provides methods for enhancing adhesion of nonclassical cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising either HAV or RGD sequences may be attached to the same matrix, preferably in an alternating pattern). Such matrices may be used in contexts in which it is desirable to enhance adhesion mediated by multiple cell adhesion molecules. Alternatively, the modulating agent itself may comprise multiple nonclassical cadherin CAR sequences or antibodies (or fragments thereof), separated by linkers as described above. Either way, the modulating agent(s) function as a "biological glue" to bind multiple nonclassical cadherin-expressing cells within a variety of contexts.

Within one such aspect, modulating agents comprising the nonclassical cadherin CAR sequence and/or multiple modulating agents linked to a single molecule or support material may be used to facilitate wound healing and/or reduce scar tissue in a mammal. Peptides that may be linked to a support, and/or to one another via a linker, to generate a suitable modulating agent include, but are not limited to, one or more nonclassical cadherin CAR sequences, or analogues or mimetics thereof. Suitable nonclassical CAR sequences include OB-cadherin, cadherin-5, desmoglein and/or desmocollin CAR sequences. Such nonclassical CAR sequences may be used in combination with one or more classical cadherin CAR sequences, including HAV, SHAVSS (SEQ ID NO:59), AKVDI (SEQ ID NO:60), or an analogue of such a sequence. Preferred antibody modulating agents include Fab fragments directed against either the nonclassical cadherin or E-cadherin CAR sequences. Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multifunctional modulating agents comprising a nonclassical cadherin sequence, a classical cadherin CAR sequence (HAV), and the CAR sequence bound by certain integrins (ROD) may also be used as potent stimulators of wound healing and/or to reduce scar tissue. Alternatively, one or more separate modulators of classical cadherin- or integrin-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Within a further aspect, modulating agents as described herein may be used for controlled inhibition of synaptic stability, resulting in increased synaptic plasticity. Within this aspect, administration of one or more modulating agents that inhibit cnr-mediated cell adhesion may be advantageous for repair processes within the brain, as well as learning and memory, in which neural plasticity is a key early event in the remodeling of synapses. In addition, a preferred modulating agent may comprise one or more additional CAR sequences, such as HAV, RGD and/or the N-CAM CAR sequence KYSFNYDGSE (SEQ ID NO:63). As noted above, such additional sequence(s) may be separated from the nonclassical CAR sequence via a linker. Alternatively, a separate modulator of cell adhesion mediated by a different adhesion molecule may be administered in conjunction with the modulating agent(s), either within the same pharmaceutical composition or separately. For such aspects, administration may be via encapsulation into a delivery vehicle such as a liposome, using standard techniques, and injection into, for example, the carotid artery. Alternatively, a modulating agent may be linked to a disrupter of the blood-brain barrier. In-general dosages range as described above.

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies. Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-T cells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Preferred modulating agents for use within such methods include those that disrupt OB-cadherin, cadherin-5, cadherin-6 and/or cadherin-8 mediated cell adhesion. In addition, a preferred modulating agent may comprise one or more additional CAR sequences, such as HAV, RGD, LYHY (SEQ ID NO:52) and/or KYSFNYDGSE (SEQ ID NO:63). As noted above, such additional sequence(s) may be separated from a nonclassical CAR sequence via a linker. Alternatively, a separate modulator of classical cadherin-, occludin-, integrin- and/or N-CAM-mediated cell adhesion may be administered in conjunction with the modulating agent(s), either within the same pharmaceutical composition or separately.

Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of OB-cadherin function prevents the adhesion of trophoblasts and their subsequent fusion to form syncitiotrophoblasts, whereas disruption of cadherin-5 function prevents angiogenesis. In one embodiment, one or more modulating agents may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include those comprising an OB-cadherin and/or cadherin-5 CAR sequence, or analogue or mimetic thereof. In addition, a preferred modulating agent may comprise additional CAR sequences, such as HAV and/or RGD. As noted above, such additional sequences may be separated from the nonclassical CAR sequence via a linker. Alternatively, a separate modulator of classical cadherin- and/or integrin-mediated cell adhesion may be administered in conjunction with the modulating agent(s), either within the same pharmaceutical composition or separately.

Suitable methods for incorporation into a contraceptive device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

Other aspects of the present invention provide methods that employ antibodies raised against the nonclassical CAR sequences for diagnostic and assay purposes. Assays typically involve using an antibody to detect the presence or absence of a nonclassical cadherin (free or on the surface of a cell), or proteolytic fragments containing one or more EC domains in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing an extracellular domain and encompassing a CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of a nonclassical cadherin in a sample is a two-antibody sandwich assay. This assay may be performed by first contacting an antibody that has been immobilized on a solid support, commonly the well of a microtiter plate, with the biological sample, such that the nonclassical cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and or wash solutions, to be used in the immunoassay.

Within further aspects, modulating agents or antibodies (or fragments thereof) may be used to facilitate cell identification and sorting in vitro or imaging in vivo, permitting the selection of cells expressing the nonclassical cadherin (or different nonclassical cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating nonclassical cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate OB-cadherin-mediated cell adhesion.

The following examples are offered by way of illustration and not by way of limitation.

EXAMPLES

Example 1

Preparation of Representative Modulating Agents

This Example illustrates the solid phase synthesis of representative peptide modulating agents.

The peptides were synthesized on a 431A Applied Biosystems peptide synthesizer using p-Hydroxymethylphenoxymethyl polystyrene (HMP) resin and standard Fmoc chemistry. After synthesis and deprotection, the peptides were de-salted on a Sephadex G-10 column and lyophilized. The peptides were analyzed for purity by analytical HPLC, and in each case a single peak was observed. Peptides were made as stock solutions at 10 to 25 mg/mL in dimethylsulfoxide (DMSO) or water and stored at −20° C. before use.

Example 2

Disruption of Human Breast Cancer Cell Adhesion

This Example illustrates the ability of a representative linear peptide comprising an OB-cadherin CAR sequence to disrupt human breast epithelial cell adhesion.

Figure 5A:
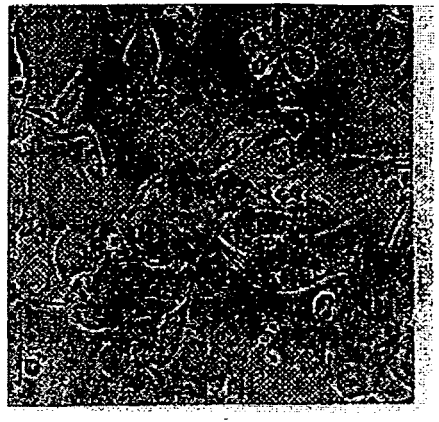
FIGS. 5A–5C are photographs showing cultures of human breast cancer cells in the presence (FIGS. 5B and 5C) and absence (FIG. 5A) of a representative linear peptide modulating agent.
Figure 5B:
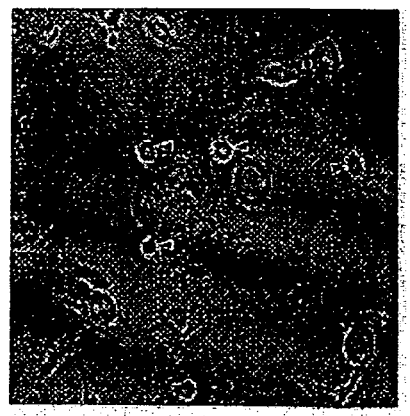
Figure 5C:

MDA-MB-231 human breast cancer cells (Lombardi Cancer Research Center, Washington, D.C.) were used in these experiments. They express cadherin-11 (also known as OB-cadherin) but not N-cadherin or E-cadherin. The cells were plated (~50,000 cells) on glass coverslips and cultured for 24 hours in DMEM containing 5% serum. Peptides (N-Ac-IFVIDDKSG-NH$_2$ (SEQ ID NO:85) and H-IFVIDDKSG-OH (SEQ ID NO:85)) were dissolved in sterile water (10 mg/ml), and 100 µl of each peptide stock solution was added to 1 ml of DMEM containing 5% serum. Control cells had 100 µl of water added to the medium. Cells were monitored by phase contrast microscopy. After 24 hours cells were fixed in formaldehyde. After 24 hours, neither the peptide H-IFVIDDKSG-OH (SEQ ID NO:85) nor water had an effect on cell morphology (FIG. 5A). The cells treated with either water or H-IFVIDDKSG-OH (SEQ ID NO:85) remained flattened and well-attached to the substratum. In contrast, the cells treated with N-Ac-IFVIDDKSG-NH$_2$ (SEQ ID NO:85) rounded up from each other and were not well-attached to the substratum (FIGS. 5A and 5B; arrows indicate rounded cells). These results demonstrate that the peptide N-Ac-FVIDDKSG-NH$_2$ (SEQ ID NO:85) interferes with cell adhesion. The amino acid sequence of this peptide is identical to that which is found in the first extracellular domain of OB-cadherin.

Example 3

Disruption of Endothelial Cell Adhesion Using Peptide Modulating Agents with a Cadherin-5 CAR Sequence This Example illustrates the ability of a representative linear peptide comprising a cadherin-5 CAR sequence to disrupt endothelial cell adhesion.

Human umbilical vein endothelial cells were cultured using standard procedures (see Ichikawa et al., *Amer. J. Physiol.* 273 (*Gastrointest. Liver Physiol.* 36):3642–6347, 1997). Cells were maintained in EGM (Clonetics, San Diego, Calif.) and used at P2 for all experiments. Endothelial identity was established by Dil-LDL and factor VIII staining.

The cells were cultured on glass coverslips. Monolayers were exposed to peptides at a concentration of 75 µg/mL for 60 minutes. The cells were then fixed with 95% ethanol for 30 minutes at 4° C., followed by acetone for one minute and left to air dry at room temperature. Primary antibody for VE-cadherin (Immunotech, Marseilles, France; 1:250) was added for one hour at 37° C. Coverslips were then washed with 0.1% milk/PBS solution three times for five minutes each. Secondary antibody (1:250), goat anti-rabbit FITC (Zymed, San Francisco, Calif.) was incubated at 37° C. for one hour. Coverslips were again washed with 0.1% milk/PBS solution three times for five minutes each. Coverslips were mounted with anti-quenching solution (1 mg/mL phenylenediamine (Sigma, St. Louis, Mo.) in 50% glycerol, 50% PBS). All photographs were taken at 400× and 1000× with exposure times of 12 seconds.

Figure 6A:
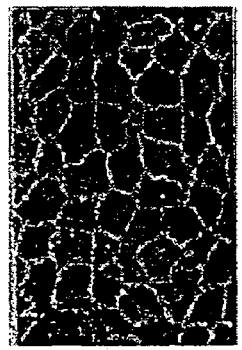
FIGS. 6A–6F are photographs showing human umbilical vein endothelial cells in the presence (FIGS. 6E and 6F) and absence (FIGS. 6A and 6B) of 75 µg/mL of a representative linear peptide modulating agent N-Ac-VFRVDAETGD-NH$_2$ (SEQ ID NO:64).
Figure 6B:
Figure 6C:
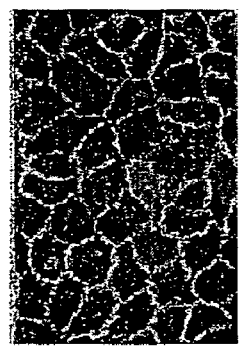
Figure 6D:
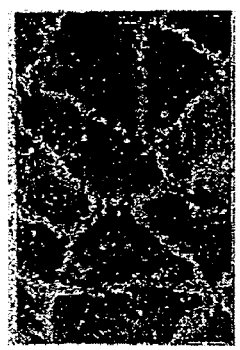
Figure 6E:
Figure 6F:
Figure 7A:
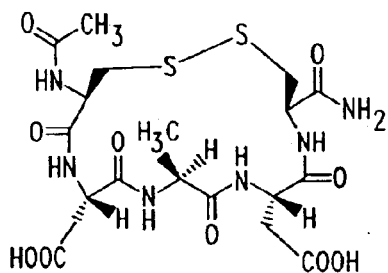
FIGS. 7A–7F provide further structures of representative modulating agents (SEQ ID NOS: 736, 823, 910, 983, 1050, 1064, 1079, 1303, 1373, 1388, 1589, 1649, 1736, 1797, 1884, 1945, 1958, 2092, 2153, 2240, 2300, 2333, 2629, 2716, 2746, 2731, 3066, 3081, 3096, 3327, 3342, 3572, 3587, 3602, 3617, 3633, 3648, 3663, 4039, 1045).
Figure 7A:
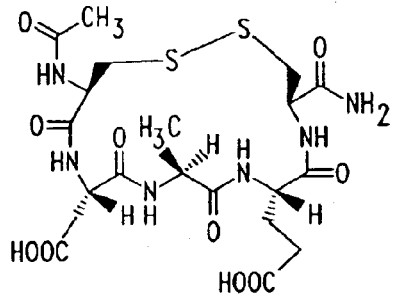
Figure 7A:
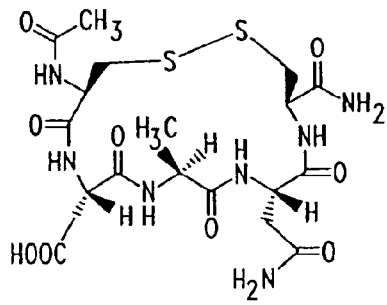
Figure 7A:
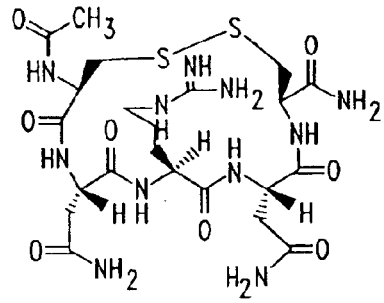
Figure 7A:
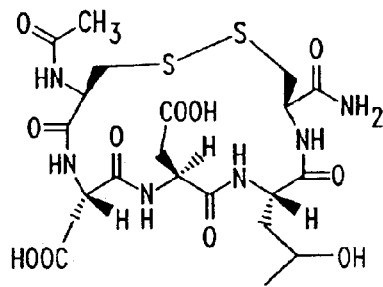
Figure 7A:
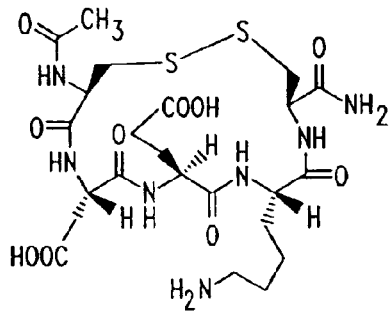
Figure 7B:
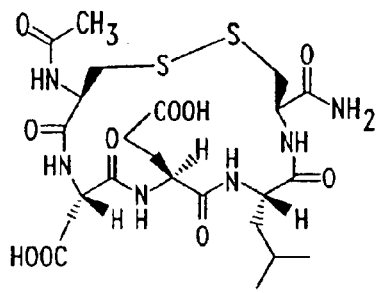
Figure 7B:
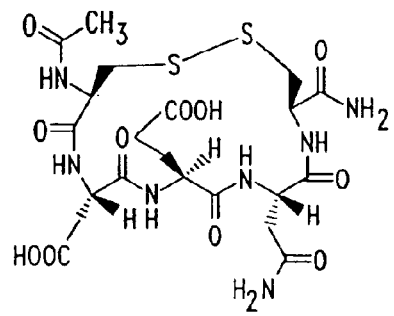
Figure 7B:
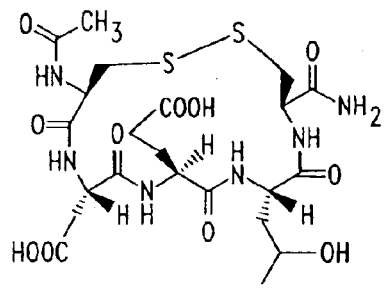
Figure 7B:
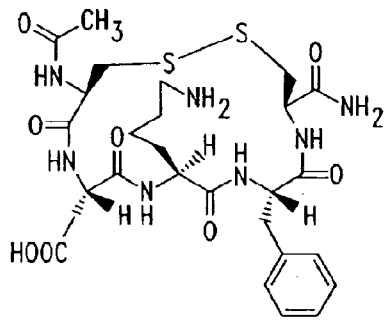
Figure 7B:
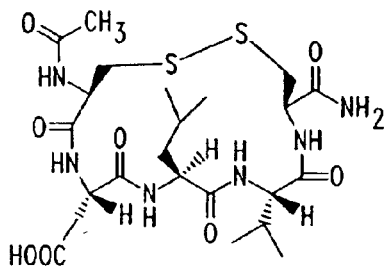
Figure 7B:
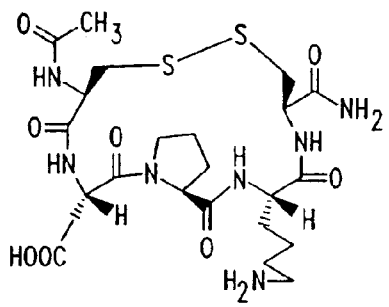
Figure 7C:
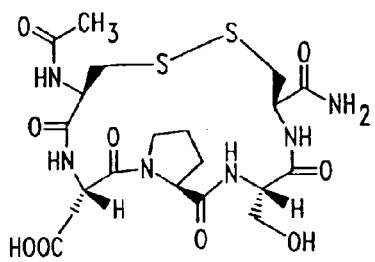
Figure 7C:
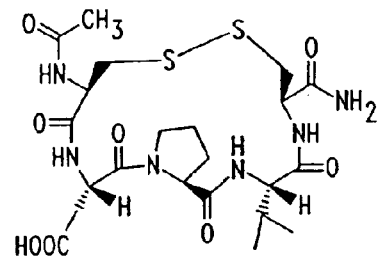
Figure 7C:
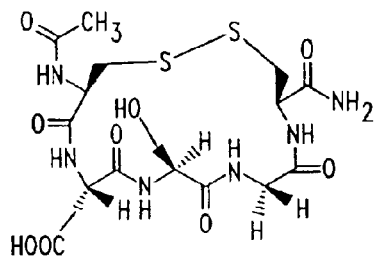
Figure 7C:
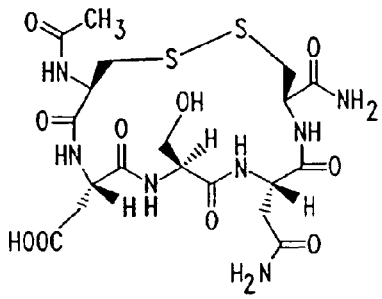
Figure 7C:
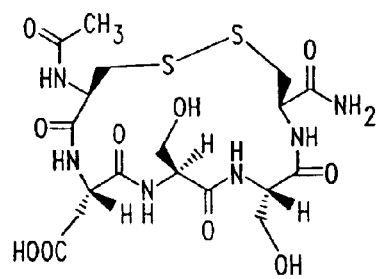
Figure 7C:
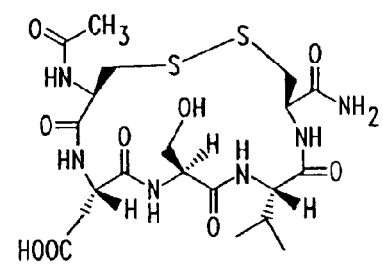
Figure 7D:
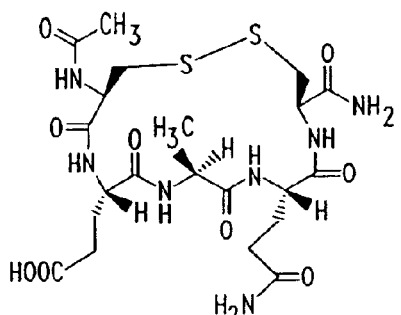
Figure 7D:
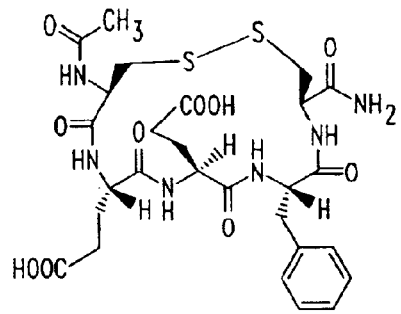
Figure 7D:
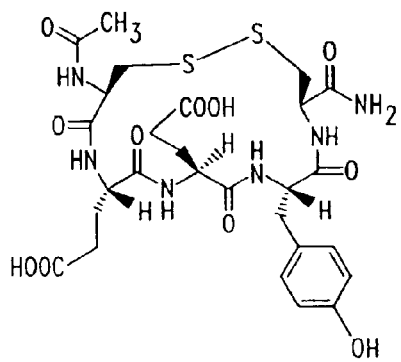
Figure 7D:
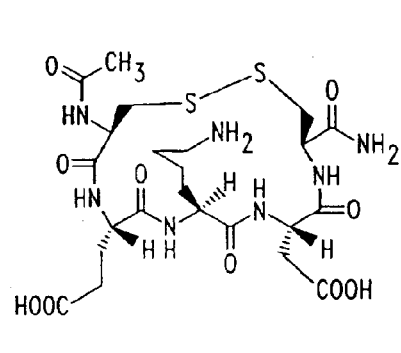
Figure 7D:
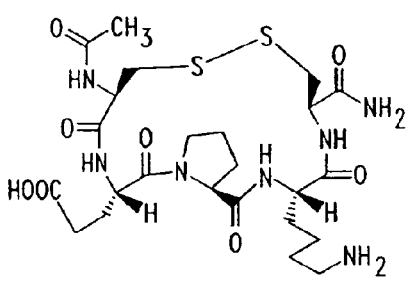
Figure 7D:
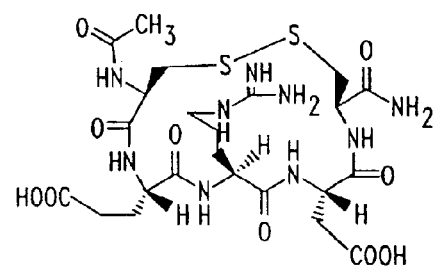
Figure 7E:
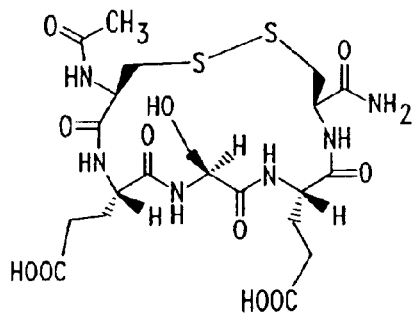
Figure 7E:
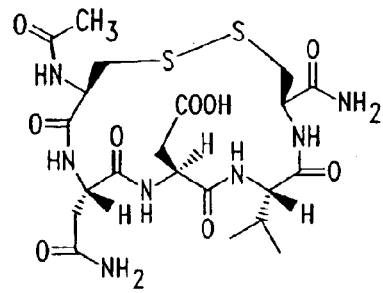
Figure 7E:
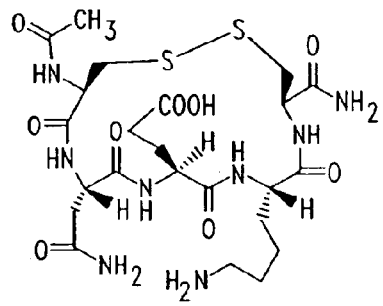
Figure 7E:
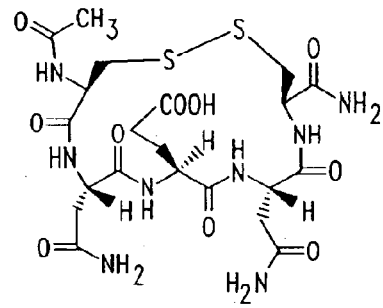
Figure 7E:
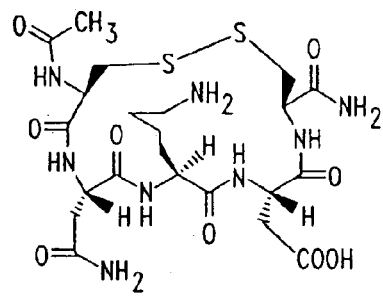
Figure 7E:
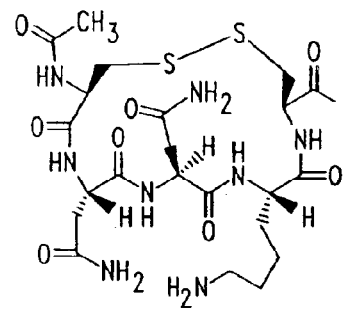
Figure 7F:
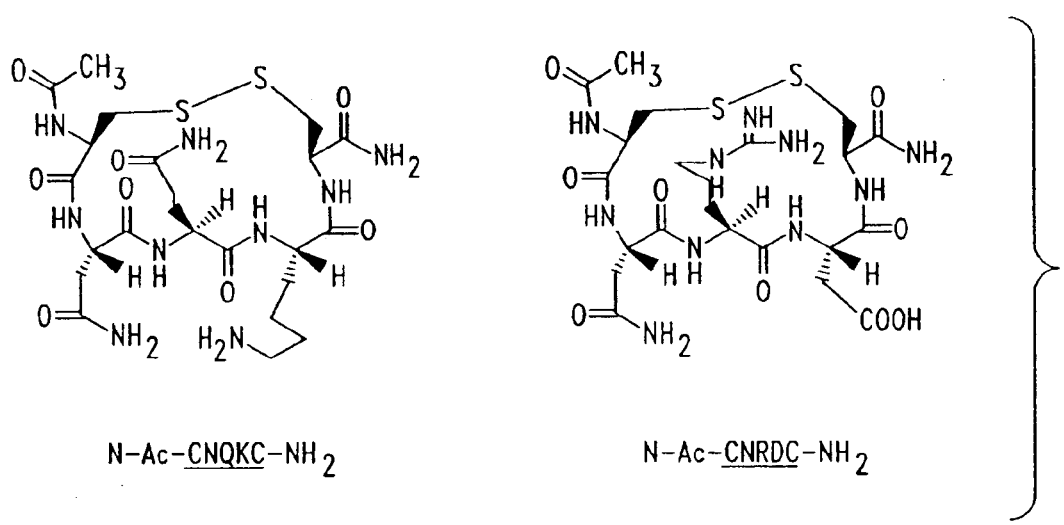

The resulting photographs are presented in FIGS. 6A–6F. FIGS. 6A and 6B are control cells. The cells in FIGS. 6C and 6D were exposed to 75 µg/mL of H-VFRVDAETGD-OH (SEQ ID NO:64) and the cells in FIGS. 6E and 6F were exposed to 75 µg/mL of the linear peptide modulating agent N-Ac-VFRVDAETGD-NH$_2$ (SEQ ID NO:64). These results indicate that the linear peptide modulating agent N-Ac-VFRVDAETGD-NH$_2$ (SEQ ID NO:64) disrupts endothelial cell adhesion, with an activity that is substantially greater that that of a similar peptide without the N- and C-terminal functional groups.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

The patent contains a lengthy "Sequence Listing" section. A copy of the "Sequence Listing" is available in electronic form from the USPTO web site (http://seqdata.uspto.gov/sequence.html?DocID=6962969B2). An electronic copy of the "Sequence Listing" will also be available from the USPTO upon request and payment of the fee set forth in 37 CFR 1.19(b)(3).

What is claimed is:

1. A cyclic peptide modulating agent comprising the formula:

(C)-(D)-(A)-(E)-(C)

wherein the agent can modulate cadherin-5-mediated endothelial cell adhesion.

2. The modulating agent according to claim 1 linked to a drug.

3. The modulating agent according to claim 1 linked to a detectable marker.

4. The modulating agent according to claim 1 linked to a targeting agent.

5. The modulating agent according to claim 1 linked to a support material.

6. The modulating agent according to claim 5, wherein the support material is a polymeric matrix.

7. The modulating agent according to claim 5, wherein the support material is selected from the group consisting plastic dishes, plastic tubes, sutures, membranes, ultra thin films, bioreactors and microparticles.

8. The modulating agent according to claim 1, further comprising one or more of:
    (a) a CAR sequence that is specifically recognized by an adhesion molecule other than cadherin-5; and/or
    (b) an antibody or antigen-binding fragment thereof that specifically binds to a CAR sequence that is specifically recognized by an adhesion molecule other than cadherin-5.

9. The modulating agent according to claim 8, wherein the adhesion molecule is selected from the group consisting of cadherins, integrins, occludin, claudins, desmogleins, desmocollins, protocadherins, cadherin-related neuronal receptors, fibronectin, laminin, claudins and other extracellular matrix proteins.

10. A composition comprising a modulating agent according to claim 1 in combination with a pharmaceutically acceptable carrier.

11. The composition according to claim 10, further comprising a drug.

12. The composition according to claim 10, wherein the modulating agent is present within a sustained-release formulation.

13. The pharmaceutical composition according to claim 12, further comprising a modulator of cell adhesion that comprises one or more of:
    (a) a CAR sequence that is specifically recognized by an adhesion molecule other than cadherin-5; and/or
    (b) an antibody or antigen-binding fragment thereof that specifically binds to a CAR sequence that is specifically recognized by an adhesion molecule other than cadherin-5.

14. The pharmaceutical composition according to claim 13, wherein the adhesion molecule is selected from the group consisting of cadherins, integrins, occludin, claudins, desmogleins, desmocollins, protocadherins, cadherin-related neuronal receptors, fibronectin, laminin and other extracellular matrix proteins.

* * * * *

UNITED STATES PATENT AND TRADEMARK OFFICE
CERTIFICATE OF CORRECTION

PATENT NO. : 6,962,969 B2  
DATED : November 8, 2005  
INVENTOR(S) : Orest W. Blaschuk It is certified that error appears in the above-identified patent and that said Letters Patent is hereby corrected as shown below:

Column 95,  
Line 46, "consisting plastic" should read -- consisting of plastic --.

Signed and Sealed this

Fourth Day of April, 2006

JON W. DUDAS  
*Director of the United States Patent and Trademark Office*